(12) United States Patent
Vogelstein et al.

(10) Patent No.: US 8,709,723 B2
(45) Date of Patent: Apr. 29, 2014

(54) INTEGRATED ANALYSES OF BREAST AND COLORECTAL CANCERS

(75) Inventors: Bert Vogelstein, Baltimore, MD (US); Kenneth W. Kinzler, Baltimore, MD (US); Rebecca J. Leary, Baltimore, MD (US); Victor E. Velculescu, Dayton, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 13/461,268

(22) Filed: May 1, 2012

(65) Prior Publication Data
US 2013/0035404 A1    Feb. 7, 2013

Related U.S. Application Data

(62) Division of application No. 12/619,726, filed on Nov. 17, 2009, now abandoned.

(60) Provisional application No. 61/119,103, filed on Dec. 2, 2008.

(51) Int. Cl.
*C12Q 1/66* (2006.01)
*C12P 19/34* (2006.01)
*C07H 21/02* (2006.01)

(52) U.S. Cl.
USPC .................. 435/6.11; 435/91.1; 536/23.1

(58) Field of Classification Search
None
See application file for complete search history.

(56) References Cited

FOREIGN PATENT DOCUMENTS

WO    2007-134210 A2    11/2007
WO    WO 2007/134210    * 11/2007

OTHER PUBLICATIONS

Wang, Tian-Li et al. Digital karyotyping. Dec. 10, 2002 PNAS vol. 99 No. 25 pp. 16156-16161.*
Leary et al. PNAS Oct. 21, 2008 vol. 105 No. 42 pp. 16224-16229 pre-pub online Oct. 13, 2008.*
Wang, Tian-Li et al. "Digital karyotyping," Dec. 10, 2002 PNAS vol. 99 No. 25 pp. 16156-16161.
R. J. Leary et al., "Integrated Analysis of Homozygous Deletions, Focal Amplifications, and Sequence Alterations in Breast and Colorectal Cancers," PNAS, Oct. 21, 2008, vol. 105, No. 42, pp. 16224-16229.

* cited by examiner

*Primary Examiner* — Amanda Haney
(74) *Attorney, Agent, or Firm* — Banner & Witcoff, Ltd.

(57) ABSTRACT

Genome-wide analysis of copy number changes in breast and colorectal tumors used approaches that can reliably detect homozygous deletions and amplifications. The number of genes altered by major copy number changes—deletion of all copies or amplification of at least twelve copies per cell—averaged thirteen per tumor. These data were integrated with previous mutation analysis of the Reference Sequence genes in these same tumor types to identify genes and cellular pathways affected by both copy number changes and point alterations. Pathways enriched for genetic alterations include those controlling cell adhesion, intracellular signaling, DNA topological change, and cell cycle control. These analysis provide an integrated view of copy number and sequencing alterations on a genome-wide scale and identify genes and pathways that are useful for cancer diagnosis and therapy.

4 Claims, 65 Drawing Sheets

Fig. 4
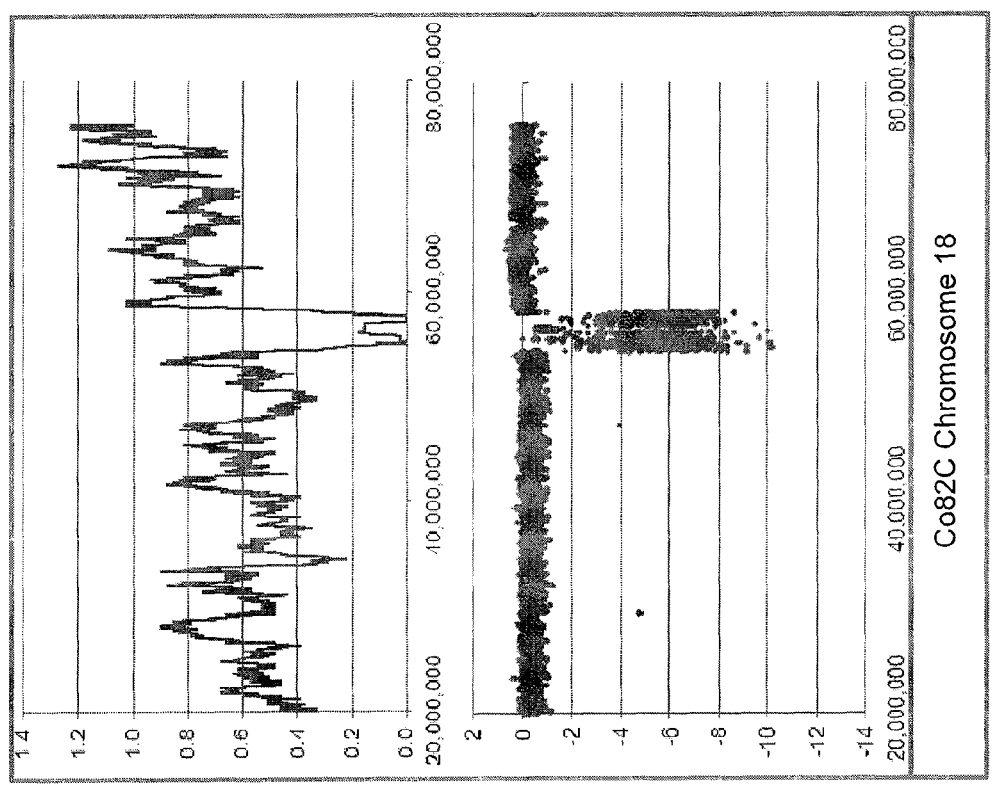
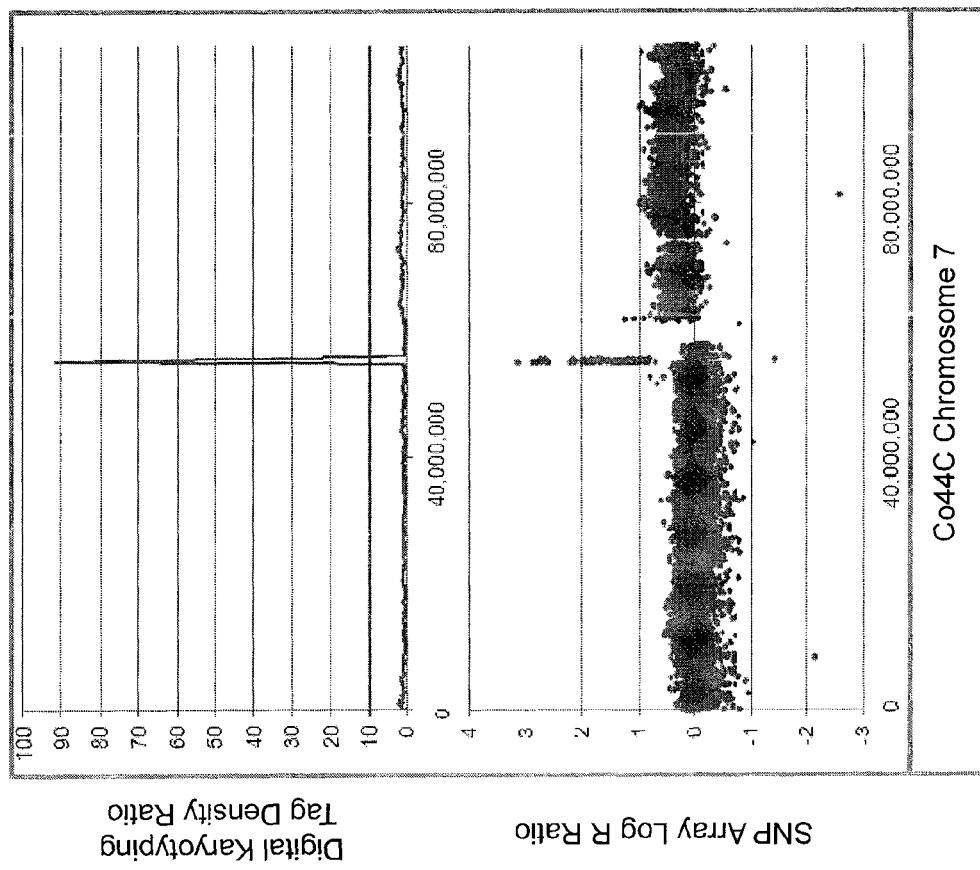

Fig. 5

Table 1. Top candidate cancer genes in breast and colorectal cancer amplifications

| Tumor type | Minimal affected region | | | Candidate cancer gene | Total number of amplifications | Total number of point mutations | Passenger probability |
|---|---|---|---|---|---|---|---|
| | Chr | Left boundary | Right boundary | | | | |
| Breast | | | | | | | |
| | 19 | 34,933,380 | 35,097,525 | CCNE1 | 4 (5) | 0 | <0.01 |
| | 17 | 34,634,168 | 35,387,448 | ERBB2 | 4 (8) | 0 | <0.01 |
| | 11 | 68,626,681 | 69,411,832 | CCND1 | 3 | 0 | <0.01 |
| | 11 | 93,740,661 | 93,972,379 | MRE11A | 1 | 2 | 0.01 |
| | 7 | 25,728,296 | 27,195,245 | HOXA3 | 1 | 2 | 0.01 |
| | 6 | 40,917,990 | 43,889,896 | TREM1 | 1 | 1 | 0.01 |
| | 1 | 149,032,752 | 149,156,966 | FLG2 | 1 (2) | 1 | 0.02 |
| Colon | | | | | | | |
| | 8 | 128,750,181 | 128,848,183 | MYC | 2 | 0 | <0.01 |
| | 17 | 19,136,024 | 19,211,040 | EPPB9 | 2 | 0 | <0.01 |
| | 7 | 54,862,624 | 55,406,733 | EGFR | 2 | 0 | <0.01 |
| | 13 | 109,108,212 | 109,557,712 | IRS2 | 1 | 1 | <0.01 |
| | 19 | 57,427,110 | 57,619,851 | ZNF480 | 1 | 1 | <0.01 |
| | 19 | 49,127,007 | 49,207,192 | ZNF155 | 1 | 1 | 0.01 |
| | 15 | 88,561,995 | 89,253,599 | NEUGRIN | 1 | 1 | 0.01 |
| Combined Breast and Colon | | | | | | | |
| | 19 | 34,933,380 | 35,097,525 | CCNE1 | 5 (6) | 0 | <0.01 |
| | 17 | 34,634,168 | 35,387,448 | ERBB2 | 5 (9) | 0 | <0.01 |
| | 6 | 41,419,345 | 42,485,546 | FOXP4 | 2 | 1 | <0.01 |
| | 8 | 37,767,164 | 40,003,731 | GPR124 | 2 (5) | 1 | <0.01 |
| | 20 | 61,788,664 | 61,840,441 | ARFRP1 | 1 (4) | 1 | 0.01 |
| | 10 | 123,231,784 | 123,471,190 | FGFR2 | 1 | 1 | 0.02 |
| | 20 | 29,297,270 | 29,721,415 | HM13 | 1 (4) | 1 | 0.03 |

* Top 7 candidate cancer genes for each tumor type are indicated. The "combined" group indicates genes that are altered in both tumor types, with at least one observed amplification. Minimal affected region is defined as the smallest overlapping interval affecting candidate cancer gene. Total number of amplifications indicates the number of focal amplifications or the number of focal and complex amplifications (in parentheses) in the indicated tumor type(s). Candidate cancer gene refers to either known cancer genes or the gene with the highest driver probability within the minimal affected region. Candidate genes were required to be entirely contained within the minimal affected region. The passenger probability provides a combined probability that the number of amplifications and point mutations observed were passengers alterations; these analyses used the intermediate passenger rate for point alterations (see Methods for additional information). All amplified genes and their passenger probabilities are indicated in SI Table 6.

Fig. 6

Table 2. Top candidate cancer genes in breast and colorectal cancer homozygous deletions

| Tumor type | Minimal affected region | | | Candidate cancer gene | Total number of homozygous deletions | Total number of point mutations | Passenger probability |
|---|---|---|---|---|---|---|---|
| | Chr | Left boundary | Right boundary | | | | |
| Breast | | | | | | | |
| | 9 | 21,963,422 | 21,974,661 | CDKN2A | 6 | 0 | <0.01 |
| | X | 41,487,365 | 46,563,031 | ZNF674 | 1 | 2 | 0.01 |
| | X | 82,896,749 | 84,431,661 | SATL1 | 1 | 1 | 0.05 |
| | 6 | 95,085,197 | 96,939,216 | MANEA | 1 | 1 | 0.05 |
| | 13 | 52,176,068 | 60,428,304 | PCDH8 | 1 | 1 | 0.05 |
| | 22 | 17,252,341 | 17,382,662 | PRODH | 1 | 1 | 0.07 |
| | X | 31,030,131 | 31,430,208 | DMD | 1 | 2 | 0.13 |
| Colon | | | | | | | |
| | 10 | 89,635,453 | 89,993,748 | PTEN | 2 | 3 | <0.01 |
| | 17 | 7,518,132 | 7,519,370 | TP53 | 1 | 18 | <0.01 |
| | 17 | 10,910,683 | 12,755,698 | MAP2K4 | 3 | 0 | <0.01 |
| | 18 | 43,490,500 | 44,141,990 | SMAD2 | 1 | 3 | <0.01 |
| | 15 | 65,239,008 | 65,323,050 | SMAD3 | 1 | 2 | 0.01 |
| | 18 | 20,178,701 | 21,064,617 | ZNF521 | 1 | 2 | 0.01 |
| | 1 | 57,175,347 | 57,297,452 | OMA1 | 1 | 1 | 0.01 |
| Combined Breast and Colon | | | | | | | |
| | 10 | 89,697,245 | 89,721,850 | PTEN | 4 | 3 | <0.01 |
| | 17 | 7,518,132 | 7,519,370 | TP53 | 1 | 36 | <0.01 |
| | 18 | 56,875,085 | 58,225,845 | CDH20 | 2 | 2 | <0.01 |
| | 1 | 55,485,777 | 57,152,356 | PRKAA2 | 1 | 2 | 0.04 |
| | 18 | 32,281,094 | 32,360,816 | FHOD3 | 1 | 3 | 0.05 |
| | 1 | 6,051,437 | 6,464,455 | CHD5 | 1 | 2 | 0.05 |
| | 6 | 159,338,933 | 159,632,547 | FNDC1 | 1 | 3 | 0.08 |

* Top 7 candidate cancer genes for each tumor type are indicated. The "combined" group indicates genes that are altered in both tumor types, with at least one observed homozyous deletion Minimal affected region is defined as the smallest overlapping interval affecting candidate cancer gene. Candidate cancer gene refers to either known cancer genes or the gene with the highest driver probability within the minimal affected region. Part of the coding sequence of the indicated candidate cancer gene was required to be contained within the minimal deleted region. The passenger probability provides a combined probability that the number of homozygous deletions and point mutations observed were passengers alterations; these analyses used the intermediate passenger rate for point alterations (see Methods for additional information). All deleted genes and their passenger probabilities are indicated in SI Table 7.

Table 3. Candidate cancer pathways altered in breast and colorectal cancers

| Pathways | Category | Total number of genes in pathway |
|---|---|---|
| Breast | | |
| Cell cycle_ATM/ATR regulation of G1/S checkpoint | MA | 37 |
| DNA topological change | GO | 10 |
| Development_EGFR signaling via PIP3 | MA | 23 |
| Cell-cell adhesion | GO | 67 |
| Signal transduction_AKT signaling | MA | 50 |
| T cell proliferation | GO | 10 |
| Cell cycle_G1-S Growth factor regulation | GG | 153 |
| Signal transduction_ERBB-family signaling | GG | 74 |
| Development_Leptin signaling via PI3K-dependent pathway | MA | 48 |
| Cell adhesion_Role of CDK5 in cell adhesion | MA | 12 |
| Regulation of angiogenesis | GO | 11 |
| Development_ERBB-family signaling | MA | 44 |
| Regulation of cell migration | GO | 30 |
| Cell cycle_Brca 1 as a transcription regulator | MA | 26 |
| Cell differentiation | GO | 391 |
| Cell adhesion_Endothelial cell contacts by non-junctional mechanisms | MA | 34 |
| Cell projection organization and biogenesis | GO | 21 |
| Signal transduction_NOTCH signaling | GG | 197 |
| Development_Hemopoiesis, Erythropoietin pathway | GG | 146 |
| Signal transduction_Leptin signaling | GG | 101 |
| Colon | | |
| Development_EGFR signaling via PIP3 | MA | 23 |
| Negative regulation of cell cycle | GO | 105 |
| Development_EGFR signaling via small GTPases | MA | 34 |
| Cell cycle_G1-S Growth factor regulation | GG | 153 |
| p38-MAPK cascade activation via IGF1R and EGFR | MA | 17 |
| Cell adhesion_Cadherins | GG | 210 |
| Defense response to bacterium | GO | 70 |
| Development_CNTF receptor signaling | MA | 33 |
| Cytoskeleton remodeling_Role of PDGFs in cell migration | MA | 20 |
| T cell proliferation | GO | 10 |
| Regulation of angiogenesis | GO | 11 |
| Signal transduction_AKT signaling | MA | 50 |
| DNA fragmentation during apoptosis | GO | 15 |
| Proteolysis | GO | 400 |
| Signal transduction_NOTCH signaling | GG | 197 |
| Signal transduction_ERBB-family signaling | GG | 74 |
| Cell adhesion_Cell-matrix interactions | GG | 158 |
| Cytoskeleton remodeling_Role Activin A in cytoskeleton remodeling | MA | 18 |
| Transcription_Receptor-mediated HIF regulation | MA | 28 |
| Signal transduction Androgen receptor signaling cross-talk | GG | 91 |

TO FIG. 7B

*Pathways correspond to GeneGO MetaCore pathway maps (MA), Gene Ontology groups (GO), or GeneGo groups (GG). The top twenty genes are included in this table. "Alterations in other tumor type" corresponds to the number of copy number changes and point mutations enriched for alterations in colorectal cancer. "Q value" corresponds to the probability of obtaining the observed enrichment of alterations in

FIG. 7A

| Number of altered genes | Number of point mutations | Number of amplifications | Number of homozygous deletions | Alterations in other tumor type | Q value |
|---|---|---|---|---|---|
| 10 | 26 | 8 | 0 | 26 | 1.13E-04 |
| 7 | 5 | 2 | 0 | 0 | 4.50E-04 |
| 5 | 8 | 4 | 2 | 23 | 1.38E-03 |
| 16 | 20 | 1 | 5 | 10 | 1.67E-03 |
| 12 | 31 | 6 | 2 | 36 | 3.00E-03 |
| 4 | 2 | 3 | 0 | 3 | 3.57E-03 |
| 27 | 19 | 21 | 13 | 67 | 3.59E-03 |
| 13 | 15 | 9 | 2 | 45 | 9.79E-03 |
| 11 | 12 | 5 | 0 | 11 | 1.40E-02 |
| 5 | 3 | 4 | 2 | 4 | 1.42E-02 |
| 3 | 2 | 4 | 1 | 5 | 1.42E-02 |
| 10 | 13 | 8 | 0 | 13 | 1.47E-02 |
| 9 | 8 | 4 | 1 | 7 | 1.47E-02 |
| 7 | 22 | 4 | 1 | 21 | 1.58E-02 |
| 59 | 69 | 22 | 9 | 64 | 1.58E-02 |
| 10 | 10 | 2 | 0 | 9 | 1.65E-02 |
| 7 | 6 | 3 | 0 | 3 | 1.65E-02 |
| 27 | 46 | 11 | 2 | 68 | 1.79E-02 |
| 25 | 28 | 14 | 0 | 41 | 1.99E-02 |
| 20 | 16 | 11 | 0 | 18 | 2.10E-02 |
| 9 | 12 | 5 | 6 | 14 | 8.79E-05 |
| 17 | 64 | 3 | 5 | 44 | 5.66E-04 |
| 9 | 25 | 6 | 4 | 11 | 1.20E-03 |
| 20 | 52 | 10 | 5 | 53 | 1.65E-03 |
| 6 | 9 | 0 | 4 | 6 | 3.69E-03 |
| 29 | 65 | 3 | 6 | 35 | 7.98E-03 |
| 14 | 9 | 7 | 0 | 9 | 9.24E-03 |
| 7 | 9 | 0 | 2 | 9 | 1.12E-02 |
| 5 | 8 | 1 | 1 | 8 | 1.98E-02 |
| 2 | 0 | 1 | 2 | 5 | 2.00E-02 |
| 4 | 2 | 3 | 0 | 7 | 2.03E-02 |
| 9 | 28 | 4 | 4 | 39 | 2.09E-02 |
| 3 | 1 | 3 | 0 | 9 | 2.18E-02 |
| 40 | 55 | 3 | 3 | 56 | 2.32E-02 |
| 26 | 50 | 8 | 10 | 59 | 3.02E-02 |
| 13 | 30 | 9 | 6 | 26 | 3.02E-02 |
| 19 | 31 | 4 | 0 | 31 | 3.02E-02 |
| 5 | 10 | 0 | 5 | 1 | 3.85E-02 |
| 6 | 11 | 0 | 3 | 10 | 3.89E-02 |
| 15 | 20 | 3 | 2 | 12 | 4.60E-02 |

FROM FIG. 7A entries having at least two copy number alterations are indicated for each tumor type. Only pathways containing between 10 and 500 observed in colorectal cancer when considering the pathways enriched for alterations in breast cancer and vice-versa for the pathways each pathway through passenger alterations alone as described in the SI Methods.

FIG. 7B

Fig. 8
SI Table 1. Comparison between Illumina array and Digital Karyotyping copy number analyses

| Alteration Type | Tumor Sample | Chr | Digital Karyotyping | | | | Illumina SNP Arrays | | | |
|---|---|---|---|---|---|---|---|---|---|---|
| | | | Left Boundary | Right Boundary | Size (bp) | Tag Density Ratio[#] | Left Boundary | Right Boundary | Size (bp) | Log R Ratio[#] |
| HD | Co44C | 5 | 59,059,409 | 59,807,807 | 748,399 | 0.0 | 59,109,232 | 59,522,525 | 413,294 | -8.3 |
| Amplification | Co84C | 6 | 41,273,307 | 43,008,812 | 1,735,506 | 9.1 | 41,419,345 | 42,485,546 | 1,066,202 | 1.9 |
| Amplification | Co44C | 7 | 54,856,760 | 55,409,704 | 552,945 | 92.5 | 54,862,624 | 55,406,733 | 544,110 | 3.1 |
| Amplification | Co84C | 8 | 127,618,526 | 128,009,287 | 390,762 | 19.2 | 127,621,008 | 127,995,012 | 374,005 | 2.7 |
| Amplification* | Co84C | 8 | 128,750,189 | 128,857,861 | 107,673 | 8.3 | 128,750,181 | 128,848,183 | 98,003 | 2.0 |
| Amplification | Co84C | 8 | 129,473,672 | 129,667,129 | 193,458 | 13.8 | 129,472,209 | 129,677,099 | 204,891 | 3.4 |
| Amplification | Co84C | 11 | 34,337,207 | 35,266,401 | 929,195 | 33.0 | 34,359,268 | 35,265,359 | 906,092 | 3.0 |
| Amplification* | Co82C | 12 | 30,734,351 | 32,018,350 | 1,284,000 | 6.2 | 30,702,093 | 32,036,123 | 1,334,031 | 2.2 |
| Amplification | Co84C | 13 | 109,096,557 | 109,553,930 | 457,374 | 9.2 | 109,108,212 | 109,557,712 | 449,501 | 2.3 |
| Amplification | Co84C | 15 | 88,545,070 | 89,258,106 | 713,037 | 26.2 | 88,561,995 | 89,253,599 | 691,605 | 3.6 |
| HD | Co82C | 18 | 54,490,515 | 56,426,158 | 1,935,644 | 0.0 | 54,517,561 | 56,407,631 | 1,890,071 | -10.1 |
| HD | Co82C | 18 | 56,629,615 | 58,250,812 | 1,621,198 | 0.0 | 56,875,085 | 58,225,845 | 1,350,761 | -9.5 |
| Amplification | Co84C | 19 | 34,570,450 | 34,641,949 | 71,500 | 7.9 | 34,561,976 | 34,641,548 | 79,573 | 2.2 |
| Amplification | Co84C | 19 | 34,956,853 | 35,344,522 | 387,670 | 14.3 | 34,966,463 | 35,321,409 | 354,947 | 2.6 |
| Amplification | Co84C | 19 | 36,274,262 | 36,388,331 | 114,070 | 6.2 | 36,281,540 | 36,385,232 | 103,693 | 2.5 |
| Amplification* | Co82C | 19 | 43,386,048 | 45,698,030 | 2,311,983 | 8.4 | 43,834,169 | 45,620,784 | 1,786,616 | 2.4 |
| Amplification* | Co84C | 19 | 54,500,237 | 54,643,655 | 143,419 | 8.4 | 54,520,709 | 54,622,533 | 101,825 | 2.1 |

* Starred alterations indicate those that are identified by Digital karyotyping which are represented by multiple smaller amplifications on the Illumina arrays.

[#] Values for Tag Density Ratios and Log R Ratios represent observed maximum values for amplifications and minimum values for homozygous deletions.

Fig. 9
SI Table 2. Copy number changes detected by Digital Karyotyping in colorectal cancer

| Sample | Tags analyzed | Type of alteration | Chr | Left boundary (bp) | Right boundary (bp) | Size | Window size (tags) | Tag density ratio[#] | Number of affected genes |
|---|---|---|---|---|---|---|---|---|---|
| M10-23 | 113,163 | Amplification | 1 | 142,456,410 | 142,686,517 | 230,108 | 50 | 7.1 | 1 |
| M12-05 | 60,438 | HD | 4 | 166,843,261 | 168,228,892 | 1,385,632 | 300 | 0.0 | 2 |
| Co44C | 114,462 | HD | 5 | 59,059,409 | 59,807,807 | 748,399 | 175 | 0.0 | 0 |
| Co84C | 441,113 | Amplification | 6 | 41,273,307 | 43,008,812 | 1,735,506 | 50 | 9.1 | 26 |
| Co44C | 114,462 | Amplification | 7 | 54,856,760 | 55,409,704 | 552,945 | 50 | 92.5 | 3 |
| Co37C | 74,314 | Amplification | 7 | 99,594,694 | 99,864,037 | 269,344 | 50 | 6.8 | 13 |
| Co84C | 441,113 | Amplification | 8 | 127,618,526 | 128,009,287 | 390,762 | 50 | 19.2 | 1 |
| Co37C | 74,314 | Amplification | 8 | 128,148,391 | 128,420,136 | 271,746 | 50 | 6.6 | 0 |
| Co37C | 74,314 | Amplification | 8 | 128,667,420 | 129,170,226 | 502,807 | 50 | 8.6 | 2 |
| Co84C | 441,113 | Amplification | 8 | 128,750,189 | 128,857,861 | 107,673 | 50 | 8.3 | 1 |
| Co84C | 441,113 | Amplification | 8 | 129,473,672 | 129,667,129 | 193,458 | 50 | 13.8 | 0 |
| M11-1 | 110,884 | Amplification | 8 | 142,414,288 | 142,454,841 | 40,554 | 50 | 7.1 | 1 |
| M11-1 | 110,884 | Amplification | 8 | 144,356,733 | 144,478,642 | 121,910 | 50 | 6.4 | 4 |
| Co84C | 441,113 | Amplification | 11 | 34,337,207 | 35,266,401 | 929,195 | 50 | 33.0 | 6 |
| Co82C | 128,368 | Amplification | 12 | 30,734,351 | 32,018,350 | 1,284,000 | 50 | 6.2 | 7 |
| Co84C | 441,113 | Amplification | 13 | 109,096,557 | 109,553,930 | 457,374 | 50 | 9.2 | 1 |
| Co84C | 441,113 | Amplification | 15 | 88,545,070 | 89,258,106 | 713,037 | 50 | 26.2 | 11 |
| M12-02 | 132,232 | Amplification | 16 | 50,791,506 | 51,506,000 | 714,495 | 50 | 16.9 | 0 |
| Co82C | 128,368 | HD | 18 | 54,490,515 | 56,426,158 | 1,935,644 | 175 | 0.0 | 10 |
| Co82C | 128,368 | HD | 18 | 56,629,615 | 58,250,812 | 1,621,198 | 175 | 0.0 | 5 |
| Co84C | 441,113 | Amplification | 19 | 34,570,450 | 34,641,949 | 71,500 | 50 | 7.9 | 0 |
| Co84C | 441,113 | Amplification | 19 | 34,956,853 | 35,344,522 | 387,670 | 50 | 14.3 | 2 |
| Co84C | 441,113 | Amplification | 19 | 36,274,262 | 36,388,331 | 114,070 | 50 | 6.2 | 0 |
| Co82C | 128,368 | Amplification | 19 | 43,386,048 | 45,698,030 | 2,311,983 | 50 | 8.4 | 70 |
| Co84C | 441,113 | Amplification | 19 | 54,500,237 | 54,643,655 | 143,419 | 50 | 8.4 | 5 |

[#] Values for tag density ratios represent observed maximum values for amplifications and minimum values for homozygous deletions.

SI Table 3. Amplifications and homozygous deletions detected by Illumina arrays in breast and colorectal cancers

| Alteration # | Sample | Array Type | Tissue | Chromosome | Left Boundary (bp) | Right Boundary (bp) | Candidate target of alteration | Evidence for candidate target* | Other Genes** |
|---|---|---|---|---|---|---|---|---|---|
| Amplification | B6C | 317k | Breast | 1 | 2,179,128 | 2,263,625 | Unknown | | |
| Amplification | B2C | 317k | Breast | 1 | 2,179,128 | 2,296,050 | Unknown | | SKI |
| HD | Mx27x | 317k | Colon | 1 | 6,051,437 | 6,464,455 | CHD5 | 8 | BACH, ESPN, FLJ32096, FLJ46380, GPR153, HES2, HES3, ICMT, KCNAB2, KIAA0720, MGC40168, RPL22, TNFRSF25 |
| HD | B7C | 317k | Breast | 1 | 9,353,556 | 9,366,656 | Unknown | | SSB1 |
| HD | Bx13 | 550k | Breast | 1 | 9,483,594 | 9,541,307 | Unknown | | MGC4399 |
| HD | Bx25 | 550k | Breast | 1 | 12,846,354 | 12,848,162 | Unknown | | |
| HD | Bx35 | 550k | Breast | 1 | 16,385,378 | 16,436,329 | Unknown | | FBXO42 |
| Amplification | B2C | 317k | Breast | 1 | 28,959,591 | 28,982,225 | Unknown | | |
| HD | Bx13 | 550k | Breast | 1 | 40,691,069 | 40,695,842 | Unknown | | |
| Amplification | B10C | 317k | Breast | 1 | 40,922,278 | 41,122,546 | Unknown | | CITED4 |
| HD | T47D | 550k | Breast | 1 | 40,941,626 | 40,966,504 | Unknown | | KCNQ4 |
| Amplification | B2C | 317k | Breast | 1 | 44,138,124 | 44,156,373 | Unknown | | |
| HD | Mx27x | 317k | Colon | 1 | 49,731,869 | 50,084,052 | Unknown | | |
| HD | Hx190 | 550k | Colon | 1 | 49,765,905 | 49,904,170 | Unknown | | |
| HD | Bx13 | 550k | Breast | 1 | 54,098,292 | 54,101,221 | Unknown | | C1orf41 |
| Amplification | Bx28 | 550k | Breast | 1 | 54,488,072 | 54,488,196 | Unknown | | |
| HD | Mx31x | 550k | Colon | 1 | 55,485,777 | 57,152,356 | PRKAA2 | 8 | C1orf168, C8A, PPAP2B, FLJ45337 |
| Amplification | Bx22 | 550k | Breast | 1 | 56,869,565 | 56,913,892 | Unknown | | |
| HD | Mx31x | 550k | Colon | 1 | 57,175,347 | 67,534,398 | OMA1 | 8 | AK3, ALG6, ANGPTL3, APG4C, C1orf141, CYP2J2, DAB1, DNAJC6, DOCK7, FLJ10884, FLJ10986, FLJ23129, FLJ40873, FOXD3, HOOK1, IL12RB2, IL23R, INADL, INSL5, ITGB3BP, JAK1, KIAA1573, KIAA1799, LEPR, LEPROT, LOC163782, MGC34837, MGC35130, MIER1, NFIA, PDE4B, PGM1, RAVER2, ROR1, SGIP1, SLC35D1, TACSTD2, TM2D1, USP1 |
| Amplification | Bx22 | 550k | Breast | 1 | 60,455,133 | 60,470,190 | Unknown | | |
| Amplification | Bx22 | 550k | Breast | 1 | 69,134,701 | 69,139,297 | Unknown | | |
| HD | Mx31x | 550k | Colon | 1 | 72,665,272 | 72,676,338 | Unknown | | |
| HD | Mx27x | 317k | Colon | 1 | 104,329,193 | 104,384,073 | Unknown | | |
| Amplification | MCF7 | 550k | Breast | 1 | 106,454,323 | 107,642,407 | Unknown | | PRMT6 |
| HD | Bx38 | 550k | Breast | 1 | 107,368,398 | 107,370,904 | Unknown | | |
| Amplification | BT483 | 550k | Breast | 1 | 109,042,399 | 109,055,236 | Unknown | | |
| HD | Bx12 | 550k | Breast | 1 | 109,079,986 | 109,083,916 | Unknown | | |
| Amplification | MCF7 | 550k | Breast | 1 | 112,088,163 | 112,155,323 | Unknown | | |
| Amplification | MCF7 | 550k | Breast | 1 | 112,229,586 | 112,267,465 | Unknown | | |
| Amplification | MCF7 | 550k | Breast | 1 | 114,050,631 | 115,354,860 | Unknown | | AMPD1, AP4B1, BCAS2, C1orf178, CSDE1, DCLRE1B, FLJ21168, FLJ37099, HIPK1, NRAS, OLFML3, PTPN22, SYCP1, SYT6, TRIM33, TSHB, TSPAN2 |
| Amplification | Bx8 | 550k | Breast | 1 | 117,604,837 | 117,766,408 | Unknown | | |
| Amplification | Bx8 | 550k | Breast | 1 | 117,956,681 | 118,005,135 | Unknown | | |
| Amplification | B8C | 550k | Breast | 1 | 144,369,065 | 144,392,841 | Unknown | | |
| Amplification | Bx27 | 550k | Breast | 1 | 145,822,267 | 145,840,274 | Unknown | | |

FROM FIG. 10A

| | | | | | | | |
|---|---|---|---|---|---|---|---|
| Amplification | B6C | 317k | Breast | 1 | 146,956,266 | 147,037,200 | Unknown | ANP32E |
| Amplification | B6C | 317k | Breast | 1 | 147,349,422 | 147,421,967 | Unknown | ENSA, MCL1 |
| Amplification | Bx28 | 550k | Breast | 1 | 147,697,849 | 148,151,643 | ANXA9 | 4 | AF1Q, BNIPL, CDC42SE1, FLJ11280, FLJ20519, FLJ23467, KIAA1441, LASS2, MGC29891, PIK4CB, PIP5K1A, PRUNE, PSMD4, RFX5, SB145, SCNM1, SEMA6C, SETDB1, TCFL1, TMOD4 |
| Amplification | B6C | 317k | Breast | 1 | 147,753,698 | 147,787,235 | ANXA9 | 4 | |
| Amplification | MCF7 | 550k | Breast | 1 | 148,656,117 | 148,960,378 | CTMP | 4 | S100A10, S100A11, TCHHL1 |
| Amplification | MCF7 | 550k | Breast | 1 | 149,032,752 | 149,156,966 | FLG2 | 3 | FLG |
| Amplification | B8C | 550k | Breast | 1 | 150,071,673 | 150,218,699 | CTMP | 4 | |
| Amplification | Bx25 | 550k | Breast | 1 | 150,805,807 | 150,881,269 | Unknown | |
| Amplification | B8C | 550k | Breast | 1 | 152,558,785 | 152,570,600 | Unknown | AQP10 |
| Amplification | Bx29 | 550k | Breast | 1 | 156,412,487 | 156,530,235 | Unknown | CRP |
| Amplification | Bx29 | 550k | Breast | 1 | 156,587,481 | 156,673,990 | Unknown | LOC391123, SLAMF8 |
| Amplification | Bx29 | 550k | Breast | 1 | 161,812,399 | 161,907,032 | Unknown | |
| Amplification | Bx29 | 550k | Breast | 1 | 161,946,764 | 162,179,815 | Unknown | RXRG |
| Amplification | B8C | 550k | Breast | 1 | 162,183,133 | 162,187,421 | Unknown | |
| Amplification | Bx29 | 550k | Breast | 1 | 162,457,936 | 163,789,383 | Unknown | C1orf32, FAM78B, FLJ14904, LOC116123, POGK, STAF42, UCK2 |
| Amplification | Bx25 | 550k | Breast | 1 | 162,464,140 | 162,465,746 | Unknown | |
| Amplification | Bx29 | 550k | Breast | 1 | 165,283,850 | 165,396,108 | Unknown | |
| Amplification | Bx29 | 550k | Breast | 1 | 165,422,951 | 165,794,755 | Unknown | |
| Amplification | Bx29 | 550k | Breast | 1 | 166,193,064 | 166,236,816 | Unknown | |
| Amplification | Bx29 | 550k | Breast | 1 | 168,792,420 | 168,833,323 | Unknown | |
| Amplification | Bx29 | 550k | Breast | 1 | 168,896,156 | 169,120,098 | Unknown | |
| Amplification | ZR7530 | 550k | Breast | 1 | 185,801,194 | 185,878,783 | Unknown | |
| Amplification | ZR7530 | 550k | Breast | 1 | 186,468,490 | 186,483,957 | Unknown | |
| Amplification | ZR7530 | 550k | Breast | 1 | 188,342,417 | 188,350,822 | Unknown | |
| Amplification | B8C | 550k | Breast | 1 | 193,041,961 | 193,119,795 | Unknown | |
| Amplification | ZR7530 | 550k | Breast | 1 | 195,744,135 | 195,751,512 | Unknown | |
| HD | Bx19 | 550k | Breast | 1 | 216,142,036 | 216,237,023 | Unknown | |
| Amplification | Bx28 | 550k | Breast | 1 | 221,800,953 | 221,801,303 | Unknown | |
| Amplification | B10C | 317k | Breast | 1 | 223,090,923 | 223,134,773 | Unknown | |
| Amplification | B10C | 317k | Breast | 1 | 224,242,179 | 224,242,497 | Unknown | |
| Amplification | B10C | 317k | Breast | 1 | 224,410,516 | 224,416,799 | Unknown | |
| Amplification | B10C | 317k | Breast | 1 | 224,801,525 | 224,923,798 | Unknown | HIST3H3, TRIM11, TRIM17 |
| Amplification | Bx25 | 550k | Breast | 1 | 229,588,945 | 229,639,082 | Unknown | |
| Amplification | Bx25 | 550k | Breast | 1 | 230,008,031 | 230,025,386 | Unknown | |
| Amplification | Bx25 | 550k | Breast | 1 | 231,010,781 | 231,046,876 | Unknown | |
| Amplification | Bx28 | 550k | Breast | 1 | 234,319,457 | 234,329,383 | Unknown | |
| Amplification | Bx28 | 550k | Breast | 1 | 234,791,496 | 234,800,635 | Unknown | |
| Amplification | Bx28 | 550k | Breast | 1 | 235,643,176 | 235,643,279 | Unknown | |
| Amplification | Bx28 | 550k | Breast | 1 | 236,499,524 | 236,509,990 | Unknown | |
| Amplification | ZR7530 | 550k | Breast | 1 | 237,394,893 | 237,452,031 | Unknown | |
| Amplification | ZR7530 | 550k | Breast | 1 | 238,879,022 | 238,879,199 | Unknown | |
| Amplification | Bx28 | 550k | Breast | 1 | 241,846,623 | 241,854,821 | Unknown | |
| Amplification | Mx41x | 317k | Colon | 1 | 242,176,136 | 242,178,429 | Unknown | |

FROM FIG. 10B

| | | | | | | | | | |
|---|---|---|---|---|---|---|---|---|---|
| Amplification | B2C | 317k | Breast | 1 | 243,280,338 | 243,299,135 | Unknown | | |
| HD | BT483 | 550k | Breast | 2 | 3,706,747 | 3,715,513 | Unknown | | |
| Amplification | Bx28 | 550k | Breast | 2 | 20,865,370 | 20,907,156 | Unknown | | |
| Amplification | B9C | 317k | Breast | 2 | 26,444,386 | 26,448,345 | Unknown | | |
| Amplification | Bx28 | 550k | Breast | 2 | 29,712,133 | 29,713,300 | Unknown | | |
| Amplification | Bx28 | 550k | Breast | 2 | 29,735,303 | 29,821,177 | Unknown | | |
| Amplification | Bx28 | 550k | Breast | 2 | 29,900,854 | 30,048,181 | Unknown | | |
| Amplification | Bx28 | 550k | Breast | 2 | 31,179,042 | 31,209,175 | Unknown | | |
| HD | B6C | 317k | Breast | 2 | 33,110,131 | 33,154,206 | Unknown | | |
| Amplification | UACC893 | 550k | Breast | 2 | 34,318,182 | 34,321,891 | Unknown | | |
| HD | Bx25 | 550k | Breast | 2 | 36,496,975 | 36,664,773 | Unknown | | CRIM1 |
| Amplification | UACC893 | 550k | Breast | 2 | 42,771,365 | 42,858,536 | Unknown | | |
| HD | Mx27x | 317k | Colon | 2 | 43,372,165 | 43,408,637 | Unknown | | |
| Amplification | B8C | 550k | Breast | 2 | 48,891,658 | 48,905,797 | Unknown | | |
| Amplification | Bx39 | 550k | Breast | 2 | 49,580,624 | 49,651,012 | Unknown | | |
| Amplification | B8C | 550k | Breast | 2 | 51,898,724 | 51,913,735 | Unknown | | |
| Amplification | B8C | 550k | Breast | 2 | 51,927,265 | 51,937,820 | Unknown | | |
| Amplification | UACC893 | 550k | Breast | 2 | 56,685,894 | 57,142,761 | Unknown | | |
| Amplification | B8C | 550k | Breast | 2 | 57,530,920 | 57,546,267 | Unknown | | |
| Amplification | B8C | 550k | Breast | 2 | 57,870,383 | 57,895,745 | Unknown | | |
| Amplification | B8C | 550k | Breast | 2 | 61,415,162 | 61,656,813 | Unknown | | XPO1 |
| Amplification | Bx27 | 550k | Breast | 2 | 71,202,713 | 71,306,891 | Unknown | | MCEE, MPHOSPH10, NAGK |
| Amplification | B8C | 550k | Breast | 2 | 76,882,831 | 76,902,804 | Unknown | | |
| Amplification | Bx27 | 550k | Breast | 2 | 78,379,067 | 78,602,723 | Unknown | | |
| HD | Bx19 | 550k | Breast | 2 | 84,087,184 | 84,107,642 | Unknown | | |
| Amplification | Bx39 | 550k | Breast | 2 | 98,159,561 | 98,915,379 | MGC26733 | 3 | CNGA3, INPP4A, MGAT4A, MGC52110, UNC50 |
| HD | Co44C | 317k | Colon | 2 | 129,500,953 | 129,501,437 | Unknown | | |
| HD | Bx22 | 550k | Breast | 2 | 132,144,820 | 132,156,743 | Unknown | | |
| HD | B7C | 317k | Breast | 2 | 134,609,076 | 134,611,862 | Unknown | | |
| HD | Bx20 | 550k | Breast | 2 | 141,415,064 | 141,615,805 | Unknown | | |
| HD | Bx10 | 550k | Breast | 2 | 141,643,469 | 141,695,642 | Unknown | | |
| HD | Bx20 | 550k | Breast | 2 | 141,646,948 | 141,815,864 | Unknown | | |
| HD | Bx34 | 550k | Breast | 2 | 141,666,071 | 141,822,860 | Unknown | | |
| HD | B4C | 317k | Breast | 2 | 141,723,484 | 141,730,744 | Unknown | | |
| HD | Bx20 | 550k | Breast | 2 | 141,853,329 | 141,992,699 | Unknown | | |
| HD | Bx20 | 550k | Breast | 2 | 142,185,694 | 142,226,087 | Unknown | | |
| HD | B6C | 317k | Breast | 2 | 166,682,507 | 166,767,280 | SCN1A | 8 | |
| HD | Co109C | 550k | Colon | 2 | 171,072,899 | 171,074,600 | Unknown | | MYO3B |
| HD | B6C | 317k | Breast | 2 | 183,911,294 | 183,914,755 | Unknown | | |
| HD | Mx41x | 317k | Colon | 2 | 187,248,804 | 187,272,535 | Unknown | | |
| HD | Bx35 | 550k | Breast | 2 | 191,052,248 | 191,058,681 | Unknown | | INPP1 |
| Amplification | B9C | 317k | Breast | 2 | 193,165,783 | 193,221,398 | Unknown | | |
| HD | Bx20 | 550k | Breast | 2 | 205,412,928 | 205,456,124 | Unknown | | |
| HD | B8C | 550k | Breast | 2 | 212,305,160 | 212,307,474 | Unknown | | |
| HD | Bx34 | 550k | Breast | 2 | 213,381,070 | 213,812,201 | Unknown | | ZNFN1A2 |
| HD | B9C | 317k | Breast | 2 | 213,488,445 | 213,594,929 | Unknown | | |
| HD | B9C | 317k | Breast | 2 | 236,125,827 | 236,234,412 | Unknown | | CENTG2 |

FROM FIG. 10C

| | | | | | | | | | |
|---|---|---|---|---|---|---|---|---|---|
| Amplification | B7C | 317k | Breast | 2 | 238,225,226 | 238,231,007 | Unknown | | |
| Amplification | B7C | 317k | Breast | 2 | 238,841,464 | 238,857,812 | Unknown | | C2orf19 |
| HD | T47D | 550k | Breast | 2 | 242,633,058 | 242,723,120 | Unknown | | FLJ41327 |
| Amplification | Bx19 | 550k | Breast | 3 | 1,825,547 | 1,936,623 | Unknown | | |
| HD | UACC893 | 550k | Breast | 3 | 2,434,320 | 2,439,738 | Unknown | | |
| Amplification | Bx17 | 550k | Breast | 3 | 4,688,504 | 4,707,040 | Unknown | | |
| Amplification | Bx17 | 550k | Breast | 3 | 4,725,674 | 4,752,544 | Unknown | | |
| Amplification | Bx17 | 550k | Breast | 3 | 4,966,139 | 5,010,285 | Unknown | | BHLHB2 |
| Amplification | Bx17 | 550k | Breast | 3 | 5,110,571 | 5,265,450 | EDEM1 | 3 | ARL10C |
| HD | Hx130 | 550k | Colon | 3 | 5,572,285 | 5,573,666 | Unknown | | |
| HD | Bx26 | 550k | Breast | 3 | 6,354,792 | 6,355,289 | Unknown | | |
| HD | Co111C | 550k | Colon | 3 | 28,786,333 | 28,789,921 | Unknown | | |
| Amplification | Bx17 | 550k | Breast | 3 | 30,027,403 | 30,679,623 | Unknown | | |
| HD | Bx17 | 550k | Breast | 3 | 31,837,685 | 31,838,437 | Unknown | | |
| HD | UACC893 | 550k | Breast | 3 | 47,724,712 | 47,821,570 | Unknown | | SMARCC1 |
| HD | Hx130 | 550k | Colon | 3 | 56,866,486 | 56,871,425 | Unknown | | |
| HD | Bx13 | 550k | Breast | 3 | 59,961,337 | 59,961,969 | Unknown | | |
| HD | Bx20 | 550k | Breast | 3 | 60,263,468 | 60,467,176 | Unknown | | |
| HD | Co44C | 317k | Colon | 3 | 60,305,396 | 60,421,098 | Unknown | | |
| HD | Co108C | 317k | Colon | 3 | 60,325,749 | 60,332,713 | Unknown | | |
| HD | Hx132 | 550k | Colon | 3 | 60,339,870 | 60,407,332 | Unknown | | |
| HD | Co108C | 317k | Colon | 3 | 60,407,332 | 60,421,098 | Unknown | | |
| HD | Co108C | 317k | Colon | 3 | 60,475,589 | 60,498,370 | Unknown | | FHIT |
| HD | Hx132 | 550k | Colon | 3 | 60,548,809 | 60,551,809 | Unknown | | |
| HD | Hx130 | 550k | Colon | 3 | 60,567,388 | 60,683,929 | Unknown | | |
| HD | Bx20 | 550k | Breast | 3 | 60,708,577 | 60,851,688 | Unknown | | |
| HD | Bx20 | 550k | Breast | 3 | 60,908,760 | 61,020,132 | Unknown | | |
| HD | Hx130 | 550k | Colon | 3 | 60,996,228 | 61,165,273 | Unknown | | |
| HD | UACC893 | 550k | Breast | 3 | 68,225,041 | 68,231,965 | Unknown | | |
| HD | Bx34 | 550k | Breast | 3 | 75,511,365 | 75,540,548 | Unknown | | |
| HD | Co111C | 550k | Colon | 3 | 75,511,365 | 75,613,585 | Unknown | | |
| HD | B4C | 317k | Breast | 3 | 76,892,524 | 81,005,517 | ROBO1 | 8 | ROBO2 |
| HD | Co111C | 550k | Colon | 3 | 82,633,832 | 82,685,655 | Unknown | | |
| Amplification | Hx152 | 550k | Colon | 3 | 83,033,092 | 85,444,335 | Unknown | | |
| Amplification | Bx23 | 550k | Breast | 3 | 87,993,078 | 87,993,621 | Unknown | | |
| HD | SKBR3 | 550k | Breast | 3 | 100,595,918 | 100,631,223 | Unknown | | |
| HD | B7C | 317k | Breast | 3 | 115,586,437 | 115,645,413 | Unknown | | |
| HD | Co44C | 317k | Colon | 3 | 117,711,926 | 117,954,984 | Unknown | | |
| HD | Co44C | 317k | Colon | 3 | 118,293,883 | 118,321,694 | Unknown | | |
| HD | Co44C | 317k | Colon | 3 | 118,452,943 | 118,482,818 | Unknown | | |
| HD | Bx26 | 550k | Breast | 3 | 123,470,622 | 123,472,947 | Unknown | | |
| HD | Bx20 | 550k | Breast | 3 | 142,886,150 | 142,886,908 | Unknown | | |
| Amplification | B8C | 550k | Breast | 3 | 147,849,203 | 147,881,807 | Unknown | | |
| Amplification | B8C | 550k | Breast | 3 | 148,918,493 | 148,969,680 | Unknown | | |
| Amplification | B8C | 550k | Breast | 3 | 149,441,814 | 149,465,467 | Unknown | | |
| Amplification | MCF7 | 550k | Breast | 3 | 150,446,093 | 150,447,390 | Unknown | | |
| Amplification | B4C | 317k | Breast | 3 | 150,971,007 | 151,208,632 | Unknown | | PFN2, RNF13 |

FROM FIG. 10D

| | | | | | | | | |
|---|---|---|---|---|---|---|---|---|
| Amplification | SKBR3 | 550k | Breast | 3 | 152,571,924 | 153,122,463 | Unknown | AADAC, IGSF10, MGC72001, SUCNR1 |
| HD | Bx30 | 550k | Breast | 3 | 152,997,288 | 153,028,739 | Unknown | AADAC |
| Amplification | MCF7 | 550k | Breast | 3 | 162,903,824 | 162,937,897 | Unknown | |
| Amplification | T47D | 550k | Breast | 3 | 175,708,047 | 175,781,075 | Unknown | |
| Amplification | T47D | 550k | Breast | 3 | 175,908,513 | 175,909,411 | Unknown | |
| Amplification | T47D | 550k | Breast | 3 | 175,993,716 | 176,057,894 | Unknown | |
| HD | Co44C | 317k | Colon | 3 | 176,238,853 | 176,245,849 | Unknown | |
| HD | Co44C | 317k | Colon | 3 | 176,376,499 | 176,380,692 | Unknown | |
| Amplification | Bx34 | 550k | Breast | 3 | 176,707,161 | 176,720,319 | Unknown | |
| Amplification | Bx34 | 550k | Breast | 3 | 178,039,372 | 178,042,461 | Unknown | |
| Amplification | B8C | 550k | Breast | 3 | 180,122,148 | 180,148,166 | Unknown | |
| Amplification | B8C | 550k | Breast | 3 | 181,428,045 | 181,466,551 | Unknown | |
| Amplification | T47D | 550k | Breast | 3 | 182,128,962 | 182,173,794 | Unknown | |
| Amplification | T47D | 550k | Breast | 3 | 184,242,775 | 184,269,747 | Unknown | |
| Amplification | Bx27 | 550k | Breast | 3 | 190,496,921 | 190,547,858 | Unknown | |
| Amplification | Bx13 | 550k | Breast | 3 | 195,020,693 | 195,050,218 | Unknown | |
| Amplification | T47D | 550k | Breast | 3 | 195,706,952 | 195,734,790 | Unknown | |
| HD | B2C | 317k | Breast | 3 | 195,726,019 | 195,727,228 | Unknown | |
| Amplification | T47D | 550k | Breast | 3 | 197,226,716 | 197,304,505 | Unknown | TFRC |
| Amplification | T47D | 550k | Breast | 3 | 197,930,442 | 197,973,277 | Unknown | PIGX |
| Amplification | Bx13 | 550k | Breast | 3 | 199,177,520 | 199,183,933 | Unknown | |
| HD | B7C | 317k | Breast | 4 | 734,802 | 780,587 | Unknown | PCGF3 |
| HD | Hx152 | 550k | Colon | 4 | 4,041,825 | 4,098,205 | Unknown | |
| HD | B5C | 317k | Breast | 4 | 7,447,498 | 7,451,224 | Unknown | |
| HD | Co84C | 317k | Colon | 4 | 9,870,773 | 9,873,122 | Unkown | |
| HD | MDAMB175VII | 550k | Breast | 4 | 14,021,874 | 14,025,782 | Unknown | |
| HD | B9C | 317k | Breast | 4 | 15,687,480 | 15,749,490 | Unknown | PROM1 |
| HD | B4C | 317k | Breast | 4 | 19,459,421 | 19,549,340 | Unknown | |
| Amplification | Bx22 | 550k | Breast | 4 | 26,293,707 | 27,267,586 | Unknown | FLJ45721, STIM2 |
| Amplification | MDAMB175VII | 550k | Breast | 4 | 30,363,321 | 30,742,939 | Unknown | PCDH7 |
| HD | Bx8 | 550k | Breast | 4 | 34,972,226 | 34,972,759 | Unknown | |
| HD | Mx43x | 317k | Colon | 4 | 42,367,964 | 43,820,536 | Unknown | ATP8A1 |
| HD | Hx152 | 550k | Colon | 4 | 58,391,218 | 58,702,891 | Unknown | |
| Amplification | Bx37 | 550k | Breast | 4 | 58,787,874 | 59,447,552 | Unknown | |
| HD | Bx27 | 550k | Breast | 4 | 63,967,107 | 63,978,153 | Unknown | |
| HD | B8C | 550k | Breast | 4 | 64,381,774 | 64,392,223 | Unknown | |
| HD | B10C | 317k | Breast | 4 | 66,778,241 | 66,799,164 | Unknown | |
| Amplification | Bx34 | 550k | Breast | 4 | 70,855,398 | 70,857,096 | Unknown | |
| Amplification | Bx39 | 550k | Breast | 4 | 75,123,474 | 75,328,084 | Unknown | CXCL3, CXCL5, PF4, PPBP |
| HD | Bx28 | 550k | Breast | 4 | 86,457,943 | 86,466,799 | Unknown | |
| HD | Bx19 | 550k | Breast | 4 | 87,465,689 | 87,548,009 | Unknown | |
| HD | Co108C | 317k | Colon | 4 | 92,282,658 | 92,318,446 | Unknown | |
| HD | Bx26 | 550k | Breast | 4 | 92,638,111 | 92,640,949 | Unknown | |
| HD | B5C | 317k | Breast | 4 | 92,679,511 | 93,240,391 | Unknown | |
| Amplification | Bx17 | 550k | Breast | 4 | 109,013,438 | 109,176,361 | Unknown | |
| Amplification | Bx17 | 550k | Breast | 4 | 110,062,842 | 110,076,930 | Unknown | |
| HD | Bx37 | 550k | Breast | 4 | 113,815,122 | 113,818,531 | Unknown | LOC91431 |

FROM FIG. 10E

| | | | | | | | | |
|---|---|---|---|---|---|---|---|---|
| HD | Bx19 | 550k | Breast | 4 | 124,447,868 | 124,493,983 | Unknown | |
| HD | Bx19 | 550k | Breast | 4 | 133,958,222 | 134,424,311 | Unknown | |
| HD | B6C | 317k | Breast | 4 | 138,151,926 | 138,174,620 | Unknown | |
| HD | MDAMB175VII | 550k | Breast | 4 | 147,260,816 | 147,261,909 | Unknown | |
| HD | Bx34 | 550k | Breast | 4 | 149,393,054 | 149,399,939 | NR3C2 | 8 |
| Amplification | Bx17 | 550k | Breast | 4 | 149,461,059 | 150,018,516 | Unknown | |
| Amplification | Bx17 | 550k | Breast | 4 | 150,069,646 | 150,189,759 | Unknown | |
| HD | Bx25 | 550k | Breast | 4 | 158,992,374 | 158,998,287 | Unknown | |
| Amplification | Bx35 | 550k | Breast | 4 | 162,581,086 | 162,581,104 | Unknown | |
| HD | Mx43x | 317k | Colon | 4 | 165,246,977 | 165,466,669 | Unknown | |
| HD | Hx130 | 550k | Colon | 4 | 172,125,789 | 172,168,306 | Unknown | |
| HD | Hx130 | 550k | Colon | 4 | 175,804,538 | 175,957,714 | Unknown | GLRA3, HPGD |
| HD | Co111C | 550k | Colon | 4 | 180,902,755 | 181,693,987 | Unknown | |
| HD | MDAMB175VII | 550k | Breast | 4 | 181,510,452 | 181,510,834 | Unknown | |
| HD | MCF7 | 550k | Breast | 4 | 182,176,201 | 182,219,623 | Unknown | |
| HD | MCF7 | 550k | Breast | 4 | 182,295,446 | 182,697,954 | Unknown | |
| HD | MCF7 | 550k | Breast | 4 | 183,756,101 | 183,851,396 | Unknown | |
| Amplification | Bx37 | 550k | Breast | 4 | 185,835,471 | 186,019,666 | Unknown | CASP3, FLJ33167 |
| Amplification | Bx37 | 550k | Breast | 4 | 186,324,145 | 187,336,164 | SNX25 | 3 ARGBP2, DKFZp761O00113, FLJ11200, KM-HN-1, Lrp2bp, PDLIM3, SLC25A4 |
| HD | B8C | 550k | Breast | 4 | 186,859,173 | 187,608,313 | Unknown | CYP4V2, F11, KLKB1, TLR3 |
| HD | B8C | 550k | Breast | 4 | 187,617,051 | 187,794,887 | FAT | 9 MTNR1A |
| HD | B8C | 550k | Breast | 4 | 187,810,912 | 188,357,094 | FAT | 9 |
| HD | B8C | 550k | Breast | 4 | 188,369,818 | 190,493,294 | Unknown | FLJ25801, TRIML1, ZFP42 |
| HD | HX152 | 550k | Colon | 4 | 189,040,763 | 189,056,015 | Unknown | |
| HD | Mx43x | 317k | Colon | 4 | 189,808,439 | 189,941,577 | Unknown | |
| HD | B8C | 550k | Breast | 4 | 190,503,525 | 191,164,126 | Unknown | TUBB4Q |
| Amplification | B7C | 317k | Breast | 5 | 362,096 | 409,381 | Unknown | |
| Amplification | Bx20 | 550k | Breast | 5 | 463,980 | 464,047 | Unknown | |
| Amplification | B10C | 317k | Breast | 5 | 726,408 | 727,921 | Unknown | |
| Amplification | B2C | 317k | Breast | 5 | 727,921 | 738,748 | Unknown | |
| HD | Hx134 | 550k | Colon | 5 | 8,312,322 | 8,313,550 | Unknown | |
| Amplification | Hx152 | 550k | Colon | 5 | 9,711,482 | 9,720,062 | Unknown | |
| HD | B8C | 550k | Breast | 5 | 16,867,274 | 16,911,282 | Unknown | |
| Amplification | Hx152 | 550k | Colon | 5 | 24,707,842 | 24,732,750 | Unknown | |
| Amplification | B8C | 550k | Breast | 5 | 26,792,147 | 26,868,451 | Unknown | |
| Amplification | Bx20 | 550k | Breast | 5 | 28,118,128 | 28,137,865 | Unknown | |
| Amplification | B8C | 550k | Breast | 5 | 28,842,013 | 29,152,463 | Unknown | |
| Amplification | ZR7530 | 550k | Breast | 5 | 35,667,809 | 35,669,190 | Unknown | |
| Amplification | Bx20 | 550k | Breast | 5 | 39,031,440 | 39,176,845 | Unknown | |
| Amplification | Mx31x | 550k | Colon | 5 | 39,694,775 | 39,773,113 | Unknown | C6, C7, CARD6, FLJ40243, RPL37 |
| Amplification | Bx17 | 550k | Breast | 5 | 40,819,020 | 41,399,645 | Unknown | |
| HD | Bx12 | 550k | Breast | 5 | 41,000,314 | 41,000,352 | Unknown | |
| HD | Bx24 | 550k | Breast | 5 | 45,996,650 | 46,004,619 | Unknown | |
| HD | Mx43x | 317k | Colon | 5 | 51,244,867 | 51,268,842 | Unknown | |
| Amplification | Bx22 | 550k | Breast | 5 | 56,360,131 | 56,689,628 | GPBP1 | 3 |
| Amplification | Bx22 | 550k | Breast | 5 | 58,868,626 | 59,290,535 | Unknown | |

FROM FIG. 10F

| | | | | | | | | | |
|---|---|---|---|---|---|---|---|---|---|
| HD | Co44C | 317k | Colon | 5 | 59,109,232 | 59,522,525 | Unknown | | |
| HD | Bx22 | 550k | Breast | 5 | 62,509,099 | 62,509,123 | Unknown | | |
| HD | Mx43x | 317k | Colon | 5 | 67,486,255 | 67,649,557 | PIK3R1 | 8 | |
| HD | Bx24 | 550k | Breast | 5 | 73,486,196 | 73,755,987 | Unknown | | |
| HD | Bx15 | 550k | Breast | 5 | 73,486,196 | 74,015,867 | ENC1 | 9 | |
| HD | Bx24 | 550k | Breast | 5 | 73,780,322 | 74,015,867 | ENC1 | 9 | |
| HD | Bx12 | 550k | Breast | 5 | 74,953,618 | 74,962,534 | Unknown | | |
| HD | Bx19 | 550k | Breast | 5 | 84,248,096 | 84,251,842 | Unknown | | |
| HD | B5C | 317k | Breast | 5 | 86,375,643 | 86,386,634 | Unknown | | |
| HD | Bx15 | 550k | Breast | 5 | 104,897,405 | 105,210,499 | Unknown | | |
| HD | Bx24 | 550k | Breast | 5 | 104,897,405 | 105,224,327 | Unknown | | |
| HD | Bx19 | 550k | Breast | 5 | 105,667,441 | 107,403,356 | FBXL17 | 9 | EFNA5 |
| HD | Bx8 | 550k | Breast | 5 | 106,924,383 | 106,972,172 | Unknown | | |
| HD | B7C | 317k | Breast | 5 | 107,233,866 | 107,386,611 | FBXL17 | 9 | |
| HD | B8C | 550k | Breast | 5 | 109,391,074 | 109,403,379 | Unknown | | |
| HD | Bx17 | 550k | Breast | 5 | 109,649,181 | 109,778,421 | Unknown | | FLJ43080 |
| HD | Co82C | 550k | Colon | 5 | 111,970,668 | 111,971,451 | Unknown | | |
| HD | Mx26x | 317k | Colon | 5 | 113,188,408 | 113,197,319 | Unknown | | |
| HD | Bx34 | 550k | Breast | 5 | 113,355,460 | 113,363,129 | Unknown | | |
| HD | Bx28 | 550k | Breast | 5 | 114,310,941 | 114,330,486 | Unknown | | |
| HD | B7C | 317k | Breast | 5 | 126,153,108 | 126,158,000 | Unknown | | |
| HD | Mx31x | 550k | Colon | 5 | 143,313,087 | 143,325,293 | Unknown | | |
| HD | SKBR3 | 550k | Breast | 5 | 164,932,080 | 164,934,912 | Unknown | | |
| Amplification | B8C | 550k | Breast | 5 | 170,658,594 | 170,658,676 | Unknown | | |
| HD | Bx22 | 550k | Breast | 5 | 171,318,696 | 171,339,258 | Unknown | | |
| HD | Bx17 | 550k | Breast | 5 | 177,539,025 | 177,540,801 | Unknown | | |
| Amplification | Bx20 | 550k | Breast | 6 | 2,771,716 | 2,776,190 | Unknown | | |
| Amplification | Bx22 | 550k | Breast | 6 | 3,956,911 | 3,958,740 | Unknown | | |
| HD | Bx38 | 550k | Breast | 6 | 4,744,646 | 4,769,197 | Unknown | | |
| Amplification | Bx17 | 550k | Breast | 6 | 19,936,192 | 19,958,854 | Unknown | | ID4 |
| HD | B4C | 317k | Breast | 6 | 21,837,941 | 21,848,861 | Unknown | | |
| Amplification | Bx17 | 550k | Breast | 6 | 24,627,865 | 24,634,969 | Unknown | | |
| Amplification | Bx28 | 550k | Breast | 6 | 29,994,143 | 30,052,137 | Unknown | | HCG9, HLA-A |
| Amplification | B6C | 317k | Breast | 6 | 31,648,535 | 31,648,736 | Unknown | | |
| Amplification | B6C | 317k | Breast | 6 | 36,818,247 | 36,820,940 | Unknown | | |
| Amplification | MDAMB231 | 550k | Breast | 6 | 37,468,535 | 37,507,239 | Unknown | | |
| Amplification | Bx22 | 550k | Breast | 6 | 40,917,990 | 43,889,896 | FOXP4 | 2 | ABCC10, APOBEC2, BYSL, BZRPL1, C6orf108, C6orf109, C6orf130, C6orf153, C6orf154, C6orf206, C6orf49, CCND3, CRIP3, CUL7, EGFL9, FRS3, GNMT, GTPBP2, GUCA1A, GUCA1B, KIAA0240, KLHDC3, KNSL8, LOC441150, MAD2L1BP, MDFI, MEA, MGC20741, MRPL2, MRPS10, MRPS18A, NCR2, NFYA, PARC, PEX6, PGC, POLH, POLR1C, PPP2R5D, PTCRA, PTK7, RDS, RPL7L1, SLC22A7, SRF, TBCC, TBN, TFEB, TJP4, TNRC5, TREM1, TREM2, TREML1, TREML2, TREML4, TRERF1, TTBK1, UBR2, UNC5CL, USP49, VEGF, XPO5, ZNF318 |

FROM FIG. 10G

| | | | | | | | | | |
|---|---|---|---|---|---|---|---|---|---|
| Amplification | Co84C | 317k | Colon | 6 | 41,419,345 | 42,485,546 | FOXP4 | 2 | BYSL, C6orf49, CCND3, FRS3, GUCA1A, GUCA1B, MDFI, MGC20741, MRPS10, PGC, TBN, TFEB, TRERF1, USP49 |
| Amplification | B6C | 317k | Breast | 6 | 42,182,084 | 42,234,507 | Unknown | | |
| Amplification | MDAMB231 | 550k | Breast | 6 | 42,567,096 | 42,767,957 | Unknown | | UBR2 |
| Amplification | Bx20 | 550k | Breast | 6 | 44,271,508 | 44,271,602 | Unknown | | |
| Amplification | Bx20 | 550k | Breast | 6 | 44,396,825 | 44,401,844 | Unknown | | |
| Amplification | Bx22 | 550k | Breast | 6 | 52,586,323 | 53,614,446 | Unknown | | ELOVL5, FBXO9, GCLC, GCM1, GSTA1, GSTA2, GSTA3, GSTA4, GSTA5, ICK, TMEM14A |
| Amplification | Bx37 | 550k | Breast | 6 | 54,404,623 | 54,779,049 | Unknown | | |
| Amplification | Bx22 | 550k | Breast | 6 | 55,263,663 | 55,332,066 | Unknown | | |
| HD | Bx20 | 550k | Breast | 6 | 58,412,859 | 58,416,914 | Unknown | | |
| Amplification | Bx14 | 550k | Breast | 6 | 63,127,022 | 63,385,934 | Unknown | | |
| Amplification | Bx23 | 550k | Breast | 6 | 66,302,704 | 66,321,652 | Unknown | | |
| HD | BT483 | 550k | Breast | 6 | 67,075,448 | 67,105,019 | Unknown | | |
| HD | B7C | 317k | Breast | 6 | 67,736,572 | 67,738,293 | Unknown | | |
| HD | Bx20 | 550k | Breast | 6 | 69,298,741 | 69,306,105 | Unknown | | |
| HD | Co84C | 317k | Colon | 6 | 69,744,886 | 69,747,288 | Unknown | | |
| HD | Bx20 | 550k | Breast | 6 | 70,071,329 | 70,074,971 | Unknown | | |
| HD | Co111C | 550k | Colon | 6 | 78,527,050 | 79,316,009 | Unknown | | |
| HD | Bx22 | 550k | Breast | 6 | 78,938,928 | 78,945,635 | Unknown | | |
| HD | Mx40x | 550k | Colon | 6 | 81,341,226 | 81,344,394 | Unknown | | |
| HD | Bx13 | 550k | Breast | 6 | 94,093,451 | 94,097,830 | Unknown | | |
| HD | Bx28 | 550k | Breast | 6 | 94,537,883 | 94,638,804 | Unknown | | |
| HD | B7C | 317k | Breast | 6 | 94,961,207 | 95,068,944 | Unknown | | |
| HD | B7C | 317k | Breast | 6 | 95,085,197 | 96,939,216 | MANEA | 8 | FUT9 |
| HD | B7C | 317k | Breast | 6 | 102,449,771 | 106,399,123 | GRIK2 | 8 | BVES, HACE1, LIN28B, POPDC3, PREP |
| HD | B7C | 317k | Breast | 6 | 106,910,018 | 106,911,439 | Unknown | | |
| Amplification | B8C | 550k | Breast | 6 | 132,423,548 | 132,449,997 | Unknown | | |
| HD | Mx31x | 550k | Colon | 6 | 133,998,544 | 134,098,765 | Unknown | | |
| HD | B6C | 317k | Breast | 6 | 134,372,751 | 134,562,589 | Unknown | | SLC2A12, SGK |
| HD | Mx26x | 317k | Colon | 6 | 148,150,583 | 148,250,828 | Unknown | | |
| HD | Bx22 | 550k | Breast | 6 | 149,451,553 | 149,451,825 | Unknown | | |
| HD | Mx31x | 550k | Colon | 6 | 150,477,589 | 150,478,000 | Unknown | | ULBP3 |
| HD | B4C | 317k | Breast | 6 | 159,338,933 | 159,632,547 | FNDC1 | 8 | RSHL2, TAGAP |
| HD | Bx13 | 550k | Breast | 6 | 163,590,820 | 163,592,528 | Unknown | | |
| HD | B10C | 317k | Breast | 6 | 163,877,652 | 163,878,296 | Unknown | | |
| HD | Co111C | 550k | Colon | 6 | 167,879,612 | 168,358,411 | Unknown | | C6orf54, MLLT4, KIF25, FRMD1 |
| HD | Bx26 | 550k | Breast | 6 | 168,350,007 | 168,352,007 | Unknown | | |
| HD | Co111C | 550k | Colon | 6 | 168,365,408 | 168,447,937 | Unknown | | |
| Amplification | Bx22 | 550k | Breast | 7 | 190,756 | 293,986 | Unknown | | FLJ36840 |
| Amplification | Bx22 | 550k | Breast | 7 | 2,221,734 | 2,225,902 | Unknown | | |
| Amplification | Bx28 | 550k | Breast | 7 | 2,739,379 | 2,895,070 | Unknown | | |
| HD | Bx20 | 550k | Breast | 7 | 2,909,011 | 2,910,918 | Unknown | | |
| Amplification | Bx28 | 550k | Breast | 7 | 3,147,061 | 3,189,187 | Unknown | | |
| HD | Bx20 | 550k | Breast | 7 | 4,191,960 | 4,192,528 | Unknown | | |
| Amplification | Bx22 | 550k | Breast | 7 | 4,333,922 | 4,343,462 | Unknown | | |

FROM FIG. 10H

| | | | | | | | | | |
|---|---|---|---|---|---|---|---|---|---|
| Amplification | Mx32x | 317k | Colon | 7 | 4,601,834 | 4,649,298 | Unknown | | |
| Amplification | Co109C | 550k | Colon | 7 | 14,919,353 | 14,956,938 | Unknown | | |
| Amplification | Bx19 | 550k | Breast | 7 | 16,597,902 | 16,616,705 | Unknown | | AGR2 |
| Amplification | Bx19 | 550k | Breast | 7 | 16,672,437 | 16,699,513 | Unknown | | BCMP11 |
| HD | B4C | 317k | Breast | 7 | 16,782,852 | 16,827,280 | Unknown | | |
| HD | Bx17 | 550k | Breast | 7 | 17,344,380 | 17,449,545 | Unknown | | |
| Amplification | B2C | 317k | Breast | 7 | 25,728,296 | 27,195,245 | HOXA3 | 3 | CBX3, EVX1, HNRPA2B1, HOXA1, HOXA10, HOXA11, HOXA13, HOXA2, HOXA4, HOXA5, HOXA6, HOXA7, HOXA9, NFE2L3, SCAP2, SNX10 |
| Amplification | B2C | 317k | Breast | 7 | 27,221,519 | 27,226,952 | Unknown | | |
| Amplification | Bx19 | 550k | Breast | 7 | 27,783,221 | 27,794,585 | Unknown | | |
| Amplification | Bx19 | 550k | Breast | 7 | 27,843,551 | 27,848,825 | Unknown | | |
| Amplification | B2C | 317k | Breast | 7 | 28,341,259 | 28,343,927 | Unknown | | |
| HD | Bx25 | 550k | Breast | 7 | 34,672,475 | 34,681,026 | Unknown | | |
| HD | Bx22 | 550k | Breast | 7 | 45,887,074 | 45,887,123 | Unknown | | |
| HD | Bx23 | 550k | Breast | 7 | 51,573,097 | 51,610,221 | Unknown | | |
| Amplification | Mx42x | 317k | Colon | 7 | 53,308,318 | 55,836,044 | EGFR | 1 | ECOP, FKBP9L, FLJ44060, FLJ45974, LANCL2, MGC33530, MRPS17, SEC61G, ZNF713 |
| Amplification | Co44C | 317k | Colon | 7 | 54,862,624 | 55,406,733 | EGFR | 1 | LANCL2 |
| Amplification | B7C | 317k | Breast | 7 | 57,228,226 | 57,372,639 | Unknown | | |
| HD | Bx14 | 550K | Breast | 7 | 67,009,649 | 67,011,579 | Unknown | | |
| HD | BX10 | 550k | Breast | 7 | 69,305,364 | 69,337,913 | Unknown | | |
| HD | BX13 | 550k | Breast | 7 | 73,512,818 | 73,543,600 | Unknown | | |
| Amplification | BX19 | 550k | Breast | 7 | 77,798,670 | 77,806,756 | Unknown | | |
| Amplification | HX107 | 550k | Colon | 7 | 78,967,741 | 78,986,327 | Unknown | | |
| Amplification | Bx17 | 550k | Breast | 7 | 83,200,545 | 83,229,743 | Unknown | | |
| Amplification | Bx17 | 550k | Breast | 7 | 83,291,467 | 83,471,446 | Unknown | | |
| Amplification | Bx25 | 550k | Breast | 7 | 83,311,824 | 83,344,384 | Unknown | | |
| HD | Hx130 | 550k | Colon | 7 | 88,549,325 | 88,549,428 | Unknown | | |
| HD | Bx13 | 550k | Breast | 7 | 89,165,554 | 89,169,524 | Unknown | | |
| Amplification | Bx26 | 550k | Breast | 7 | 95,017,953 | 95,033,345 | Unknown | | |
| HD | Mx08x | 550k | Colon | 7 | 96,884,008 | 96,886,905 | Unknown | | |
| Amplification | B7C | 317k | Breast | 7 | 99,709,370 | 99,736,446 | Unknown | | FLJ37538 |
| HD | Co111C | 550k | Colon | 7 | 109,776,365 | 109,786,112 | Unknown | | |
| HD | Bx13 | 550k | Breast | 7 | 112,712,975 | 112,724,935 | Unknown | | |
| HD | Hx130 | 550k | Colon | 7 | 118,369,052 | 118,372,753 | Unknown | | |
| Amplification | Bx14 | 550k | Breast | 7 | 130,232,521 | 130,240,376 | Unknown | | |
| HD | Bx13 | 550k | Breast | 7 | 131,233,002 | 131,237,510 | Unknown | | |
| HD | Hx130 | 550k | Colon | 7 | 134,291,125 | 134,291,754 | Unknown | | |
| HD | SKBR3 | 550k | Breast | 7 | 141,227,574 | 141,241,903 | Unknown | | |
| HD | Hx130 | 550k | Colon | 7 | 151,627,443 | 151,629,769 | Unknown | | |
| Amplification | B7C | 317k | Breast | 7 | 153,309,611 | 153,316,479 | Unknown | | |
| Amplification | B7C | 317k | Breast | 7 | 154,746,368 | 154,757,370 | Unknown | | EN2 |
| HD | B10C | 317k | Breast | 8 | 271,572 | 325,646 | Unknown | | |
| HD | ZR7530 | 550k | Breast | 8 | 2,118,532 | 2,120,745 | Unknown | | |
| HD | Mx43x | 317k | Colon | 8 | 2,128,549 | 2,145,944 | Unknown | | |
| HD | Bx38 | 550k | Breast | 8 | 3,442,144 | 3,948,393 | CSMD1 | 7 | |

FROM FIG. 10I

| | | | | | | | | |
|---|---|---|---|---|---|---|---|---|
| HD | Bx34 | 550k | Breast | 8 | 3,705,343 | 3,885,567 | CSMD1 | 7 |
| HD | B4C | 317k | Breast | 8 | 3,765,863 | 3,793,246 | Unknown | |
| HD | Bx34 | 550k | Breast | 8 | 3,951,430 | 4,488,686 | CSMD1 | 7 |
| HD | Bx38 | 550k | Breast | 8 | 3,963,273 | 4,030,923 | Unknown | |
| HD | Hx130 | 550k | Colon | 8 | 4,038,651 | 4,039,963 | Unknown | |
| HD | B2C | 317k | Breast | 8 | 4,569,650 | 4,576,576 | Unknown | |
| HD | BT483 | 550k | Breast | 8 | 6,143,066 | 6,158,732 | Unknown | |
| HD | Mx41x | 317k | Colon | 8 | 9,352,194 | 9,352,928 | Unknown | |
| HD | Mx35x | 550k | Colon | 8 | 10,054,044 | 10,331,740 | Unknown | MSRA |
| HD | Co108C | 317k | Colon | 8 | 12,747,634 | 13,403,871 | Unknown | DLC1, FLJ36980, KIAA1456 |
| HD | Hx130 | 550k | Colon | 8 | 14,377,004 | 14,378,681 | Unknown | |
| HD | Mx34x | 550k | Colon | 8 | 15,014,342 | 15,027,349 | Unknown | |
| HD | Bx39 | 550k | Breast | 8 | 17,038,314 | 17,040,806 | Unknown | |
| HD | MDAMB415 | 550k | Breast | 8 | 17,625,071 | 17,625,980 | Unknown | MTUS1 |
| HD | B8C | 550k | Breast | 8 | 18,578,565 | 18,584,048 | PSD3 | 9 |
| HD | Bx28 | 550k | Breast | 8 | 18,656,744 | 18,656,892 | Unknown | |
| HD | Bx38 | 550k | Breast | 8 | 18,656,744 | 18,786,993 | PSD3 | 9 |
| HD | Co109C | 550k | Colon | 8 | 18,898,220 | 18,905,763 | Unknown | |
| HD | Mx08x | 550k | Colon | 8 | 23,105,237 | 23,117,578 | Unknown | TNFRSF10A |
| HD | Bx34 | 550k | Breast | 8 | 23,312,037 | 23,479,614 | Unknown | ENTPD4, SLC25A37 |
| HD | B8C | 550k | Breast | 8 | 23,884,120 | 23,983,658 | Unknown | |
| HD | UACC893 | 550k | Breast | 8 | 25,157,853 | 25,391,271 | Unknown | CDCA2, DOCK5, KCTD9 |
| HD | B9C | 317k | Breast | 8 | 31,923,000 | 31,925,590 | Unknown | |
| HD | BT483 | 550k | Breast | 8 | 32,517,664 | 32,520,170 | Unknown | |
| HD | Bx19 | 550k | Breast | 8 | 32,606,434 | 32,619,282 | Unknown | |
| Amplification | Bx24 | 550k | Breast | 8 | 37,767,164 | 40,003,731 | GPR124 | 2 ADAM18, ADAM2, ADAM32, ADAM9, ADRB3, ASH2L, BAG4, BLP1, BRF2, DDHD2, EIF4EBP1, FGFR1, FLJ43582, GOT1L1, HTRA4, INDO, LETM2, LOC169355, LSM1, PPAPDC1B, RAB11FIP1, STAR, TACC1, WHSC1L1 |
| Amplification | Bx15 | 550k | Breast | 8 | 37,767,164 | 40,291,664 | GPR124 | 2 ADAM18, ADAM2, ADAM32, ADAM9, ADRB3, ASH2L, BAG4, BLP1, BRF2, C8orf4, DDHD2, EIF4EBP1, FGFR1, FLJ43582, GOT1L1, HTRA4, INDO, LETM2, LOC169355, LSM1, PPAPDC1B, RAB11FIP1, STAR, TACC1, WHSC1L1 |
| Amplification | Bx24 | 550k | Breast | 8 | 40,053,601 | 40,291,664 | Unknown | |
| Amplification | ZR751 | 550k | Breast | 8 | 40,755,199 | 40,793,444 | Unknown | |
| HD | B7C | 317k | Breast | 8 | 50,801,846 | 52,587,262 | Unknown | SNTG1, PXDNL |
| Amplification | B11C | 317k | Breast | 8 | 51,298,097 | 51,713,938 | Unknown | |
| Amplification | Mx42x | 317k | Colon | 8 | 53,535,549 | 53,552,669 | Unknown | |
| Amplification | B11C | 317k | Breast | 8 | 58,428,893 | 58,458,313 | Unknown | |
| Amplification | Bx19 | 550k | Breast | 8 | 59,040,943 | 59,060,510 | Unknown | |
| Amplification | Hx152 | 550k | Colon | 8 | 61,164,389 | 61,166,451 | Unknown | |
| Amplification | Mx42x | 317k | Colon | 8 | 63,952,637 | 63,970,203 | Unknown | |
| Amplification | Bx19 | 550k | Breast | 8 | 69,102,194 | 69,127,494 | Unknown | |
| Amplification | Bx15 | 550k | Breast | 8 | 69,750,301 | 69,767,325 | Unknown | |
| Amplification | Bx19 | 550k | Breast | 8 | 72,765,387 | 72,767,224 | Unknown | |

FROM FIG. 10J

| | | | | | | | |
|---|---|---|---|---|---|---|---|
| Amplification | Bx17 | 550k | Breast | 8 | 72,825,118 | 72,881,221 | Unknown | |
| Amplification | Bx24 | 550k | Breast | 8 | 72,926,615 | 72,547,487 | Unknown | TRPA1 |
| Amplification | Bx17 | 550k | Breast | 8 | 73,062,120 | 73,072,234 | Unknown | |
| Amplification | Bx15 | 550k | Breast | 8 | 73,096,586 | 73,547,487 | Unknown | |
| Amplification | Bx24 | 550k | Breast | 8 | 73,653,731 | 73,839,615 | Unknown | |
| Amplification | Bx15 | 550k | Breast | 8 | 73,653,731 | 73,880,530 | Unknown | |
| Amplification | Bx24 | 550k | Breast | 8 | 74,069,184 | 74,236,815 | Unknown | RPESP, TERF1 |
| Amplification | Bx15 | 550k | Breast | 8 | 74,069,184 | 74,278,433 | Unknown | RPESP, TERF1 |
| Amplification | Bx17 | 550k | Breast | 8 | 74,345,111 | 74,381,873 | Unknown | RPL7 |
| Amplification | Bx15 | 550k | Breast | 8 | 74,524,905 | 74,587,539 | Unknown | |
| Amplification | Bx17 | 550k | Breast | 8 | 77,029,752 | 77,230,241 | Unknown | |
| Amplification | Bx17 | 550k | Breast | 8 | 78,059,400 | 78,083,037 | Unknown | |
| Amplification | Bx17 | 550k | Breast | 8 | 78,715,231 | 78,887,224 | Unknown | |
| Amplification | Bx17 | 550k | Breast | 8 | 79,107,885 | 79,479,575 | Unknown | |
| Amplification | Bx17 | 550k | Breast | 8 | 79,660,454 | 79,734,777 | Unknown | PKIA |
| Amplification | B4C | 317k | Breast | 8 | 81,839,021 | 82,024,901 | Unknown | |
| HD | Bx26 | 550k | Breast | 8 | 82,153,904 | 82,155,012 | Unknown | |
| Amplification | MCF7 | 550k | Breast | 8 | 87,674,247 | 87,868,123 | Unknown | |
| Amplification | Bx25 | 550k | Breast | 8 | 87,824,228 | 87,873,283 | Unknown | |
| Amplification | Bx25 | 550k | Breast | 8 | 87,913,119 | 87,990,792 | Unknown | |
| Amplification | MCF7 | 550k | Breast | 8 | 89,933,336 | 90,075,430 | Unknown | |
| Amplification | MCF7 | 550k | Breast | 8 | 90,442,285 | 91,408,755 | Unknown | C8orf1, CALB1, DECR1, NBS1, RIPK2 |
| HD | Co44C | 317k | Colon | 8 | 90,544,491 | 90,546,041 | Unknown | |
| Amplification | Mx42x | 317k | Colon | 8 | 102,200,330 | 102,201,806 | Unknown | |
| Amplification | B11C | 317k | Breast | 8 | 103,781,255 | 103,784,479 | Unknown | |
| Amplification | MCF7 | 550k | Breast | 8 | 104,665,927 | 104,909,676 | Unknown | |
| Amplification | Bx22 | 550k | Breast | 8 | 105,617,757 | 105,652,494 | Unknown | |
| Amplification | Bx22 | 550k | Breast | 8 | 105,911,442 | 105,920,571 | Unknown | |
| Amplification | Bx39 | 550k | Breast | 8 | 105,947,823 | 105,953,781 | Unknown | |
| Amplification | Bx27 | 550k | Breast | 8 | 106,587,993 | 106,591,021 | Unknown | |
| Amplification | Bx27 | 550k | Breast | 8 | 106,660,978 | 106,696,752 | Unknown | |
| Amplification | Mx35x | 550k | Colon | 8 | 112,524,840 | 112,685,591 | Unknown | |
| Amplification | Bx25 | 550k | Breast | 8 | 113,830,318 | 114,024,371 | Unknown | |
| Amplification | Bx17 | 550k | Breast | 8 | 113,830,319 | 114,028,444 | Unknown | |
| Amplification | Bx22 | 550k | Breast | 8 | 117,363,283 | 117,391,083 | Unknown | |
| Amplification | Bx25 | 550k | Breast | 8 | 118,353,561 | 118,357,069 | Unknown | |
| Amplification | Bx25 | 550k | Breast | 8 | 118,435,498 | 118,468,837 | Unknown | |
| Amplification | Bx25 | 550k | Breast | 8 | 121,516,434 | 121,640,447 | Unknown | MTBP |
| Amplification | Bx25 | 550k | Breast | 8 | 121,787,847 | 121,790,067 | Unknown | |
| Amplification | Bx34 | 550k | Breast | 8 | 122,266,575 | 122,531,470 | Unknown | |
| Amplification | Bx34 | 550k | Breast | 8 | 122,566,566 | 122,781,672 | Unknown | HAS2 |
| Amplification | MCF7 | 550k | Breast | 8 | 122,781,672 | 122,794,401 | Unknown | |
| Amplification | Bx34 | 550k | Breast | 8 | 122,830,368 | 123,350,555 | Unknown | |
| Amplification | Bx34 | 550k | Breast | 8 | 123,399,264 | 123,639,417 | Unknown | |
| Amplification | Bx34 | 550k | Breast | 8 | 123,873,449 | 123,886,375 | Unknown | |
| Amplification | Bx22 | 550k | Breast | 8 | 124,614,328 | 124,624,416 | Unknown | |
| Amplification | Bx34 | 550k | Breast | 8 | 124,788,840 | 124,862,224 | Unknown | |

FROM FIG. 10K

| | | | | | | | | |
|---|---|---|---|---|---|---|---|---|
| Amplification | Bx34 | 550k | Breast | 8 | 126,117,468 | 126,187,341 | Unknown | |
| Amplification | MCF7 | 550k | Breast | 8 | 126,117,468 | 126,219,985 | Unknown | |
| Amplification | Bx10 | 550k | Breast | 8 | 126,899,192 | 127,321,302 | Unknown | |
| Amplification | Bx34 | 550k | Breast | 8 | 126,899,192 | 127,506,287 | Unknown | |
| Amplification | Bx37 | 550k | Breast | 8 | 127,469,169 | 127,485,749 | Unknown | |
| Amplification | Bx34 | 550k | Breast | 8 | 127,547,507 | 128,150,703 | Unknown | NSE2 |
| Amplification | Co84C | 317k | Colon | 8 | 127,621,008 | 127,995,012 | Unknown | NSE2 |
| Amplification | Hx110 | 550k | Colon | 8 | 128,074,016 | 130,290,041 | MYC | 1 TMEM75 |
| Amplification | Bx37 | 550k | Breast | 8 | 128,164,338 | 128,173,119 | Unknown | |
| Amplification | Bx34 | 550k | Breast | 8 | 128,173,119 | 128,414,645 | Unknown | |
| Amplification | Bx20 | 550k | Breast | 8 | 128,309,583 | 128,358,773 | Unknown | |
| Amplification | Co84C | 317k | Colon | 8 | 128,437,695 | 128,493,974 | Unknown | |
| Amplification | Bx34 | 550k | Breast | 8 | 128,530,060 | 128,617,860 | Unknown | |
| Amplification | Co84C | 317k | Colon | 8 | 128,750,181 | 128,848,183 | MYC | 1 |
| Amplification | Bx22 | 550k | Breast | 8 | 128,989,309 | 129,004,408 | Unknown | |
| Amplification | Co84C | 317k | Colon | 8 | 129,472,209 | 129,677,099 | Unknown | |
| Amplification | Bx22 | 550k | Breast | 8 | 129,617,375 | 129,637,260 | Unknown | |
| Amplification | Bx22 | 550k | Breast | 8 | 130,801,477 | 130,855,919 | Unknown | |
| HD | B3C | 317k | Breast | 8 | 135,133,983 | 135,135,129 | Unknown | |
| HD | Bx13 | 550k | Breast | 8 | 141,613,930 | 141,615,136 | Unknown | EIF2C2 |
| Amplification | B7C | 317k | Breast | 8 | 142,512,371 | 142,529,990 | Unknown | |
| Amplification | B7C | 317k | Breast | 8 | 142,582,314 | 142,586,404 | Unknown | |
| Amplification | B7C | 317k | Breast | 8 | 142,805,713 | 142,815,249 | Unknown | |
| Amplification | B7C | 317k | Breast | 8 | 144,886,230 | 144,923,639 | Unknown | |
| Amplification | B6C | 317k | Breast | 8 | 145,028,388 | 145,817,378 | KIAA1875 | 2 ADCK5, BOP1, CPSF1, CYC1, CYHR1, DGAT1, EXOSC4, F8XL6, FOXH1, GPAA1, GPR172A, GPT, GRINA, HSF1, KIAA1688, KIFC2, LOC113655, LOC51236, LRRC14, LRRC24, MAF1, MGC70857, NFKBIL2, OPLAH, PARP10, PLEC1, PPP1R16A, RECQL4, SCRT1, SHARPIN, SLC39A4, SPATC1, VPS28 |
| Amplification | B7C | 317k | Breast | 8 | 145,064,091 | 145,484,561 | KIAA1875 | 2 CYC1, EXOSC4, GPAA1, GRINA, LOC51236, MAF1, OPLAH, PARP10, SHARPIN, SPATC1 |
| HD | Bx29 | 550k | Breast | 9 | 1,437,011 | 1,440,428 | Unknown | |
| Amplification | Co109C | 550k | Colon | 9 | 9,239,795 | 9,239,912 | Unknown | |
| HD | MCF7 | 550k | Breast | 9 | 9,459,877 | 9,581,059 | Unknown | |
| Amplification | Bx19 | 550k | Breast | 9 | 9,530,141 | 9,589,879 | Unknown | |
| Amplification | Hx110 | 550k | Colon | 9 | 11,501,860 | 11,509,008 | Unknown | |
| Amplification | B4C | 317k | Breast | 9 | 12,894,064 | 12,917,973 | Unknown | |
| HD | ZR751 | 550k | Breast | 9 | 13,561,341 | 13,561,933 | Unknown | |
| Amplification | Bx19 | 550k | Breast | 9 | 13,800,014 | 13,902,195 | Unknown | |
| HD | B8C | 550k | Breast | 9 | 14,234,376 | 14,235,551 | Unknown | |
| HD | MDAMB231 | 550k | Breast | 9 | 16,463,118 | 18,065,847 | Unknown | BNC2, C9orf39, SH3GL2 |
| HD | Bx34 | 550k | Breast | 9 | 16,961,165 | 17,137,191 | Unknown | |
| HD | MDAMB231 | 550k | Breast | 9 | 20,830,838 | 24,873,440 | CDKN2A | 6 CDKN2B, DMRTA1, ELAVL2, IFNA1, IFNA10, IFNA13, IFNA14, IFNA16, IFNA17, IFNA2, IFNA21, IFNA4, IFNA5, IFNA6, IFNA7, IFNA8, IFNB1, IFNE1, IFNW1, KLHL9, MTAP, |

FROM FIG. 10L

| | | | | | | | | | |
|---|---|---|---|---|---|---|---|---|---|
| HD | Bx26 | 550k | Breast | 9 | 21,139,963 | 26,374,371 | CDKN2A | 6 | PTPLAD2 CDKN2B, DMRTA1, ELAVL2, FLJ16323, IFNA1, IFNA10, IFNA13, IFNA14, IFNA16, IFNA17, IFNA2, IFNA21, IFNA4, IFNA5, IFNA6, IFNA7, IFNA8, IFNE1, KLHL9, MTAP, TUSC1 |
| HD | B7C | 317k | Breast | 9 | 21,796,564 | 21,998,026 | CDKN2A | 6 | CDKN2B, MTAP |
| HD | MCF7 | 550k | Breast | 9 | 21,830,298 | 21,974,661 | CDKN2A | 6 | MTAP |
| HD | B4C | 317k | Breast | 9 | 21,884,495 | 32,193,380 | CDKN2A | 6 | C9orf11, C9orf72, C9orf82, CDKN2B, DMRTA1, ELAVL2, FLJ16323, FLJ31810, IFNK, IFT74, LRRC19, MOBKL2B, PLAA, TEK, TUSC1 |
| HD | B1C | 317k | Breast | 9 | 21,963,422 | 21,964,218 | Unknown | | |
| HD | Bx12 | 550k | Breast | 9 | 21,963,422 | 22,024,719 | CDKN2A | 6 | CDKN2B |
| Amplification | Bx34 | 550k | Breast | 9 | 28,499,969 | 29,182,125 | Unknown | | |
| Amplification | Bx10 | 550k | Breast | 9 | 31,337,460 | 31,659,518 | Unknown | | |
| Amplification | Bx10 | 550k | Breast | 9 | 31,738,036 | 31,869,919 | Unknown | | |
| Amplification | Bx10 | 550k | Breast | 9 | 31,967,623 | 32,321,414 | Unknown | | |
| Amplification | Bx10 | 550k | Breast | 9 | 33,919,685 | 34,639,442 | KIAA1161 | 3 | ARID3C, C9orf165, C9orf23, C9orf24, C9orf25, C9orf48, CNTFR, DCTN3, DNAI1, GALT, NUDT2, OPRS1, UBAP1, WDR40A |
| Amplification | Bx34 | 550k | Breast | 9 | 37,035,825 | 37,372,099 | Unknown | | ZCCHC7 |
| Amplification | Bx34 | 550k | Breast | 9 | 37,512,372 | 37,682,108 | Unknown | | |
| Amplification | Bx34 | 550k | Breast | 9 | 37,709,011 | 37,891,883 | Unknown | | EXOSC3, MCART1, RG9MTD3, WDR32 |
| HD | B9C | 317k | Breast | 9 | 38,626,463 | 38,631,335 | Unknown | | |
| HD | B2C | 317k | Breast | 9 | 43,943,791 | 43,944,793 | Unknown | | |
| HD | Co109C | 550k | Colon | 9 | 68,625,793 | 68,636,392 | Unknown | | |
| Amplification | Bx35 | 550k | Breast | 9 | 69,742,452 | 69,749,824 | Unknown | | |
| Amplification | Bx22 | 550k | Breast | 9 | 76,767,425 | 77,847,928 | VPS13A | 3 | GNA14, LOC442425 |
| Amplification | Bx35 | 550k | Breast | 9 | 79,775,742 | 79,776,984 | Unknown | | |
| Amplification | B9C | 317k | Breast | 9 | 89,272,738 | 89,299,225 | Unknown | | |
| Amplification | Bx35 | 550k | Breast | 9 | 102,574,762 | 102,613,932 | Unknown | | |
| HD | Bx34 | 550k | Breast | 9 | 116,306,284 | 116,332,183 | ASTN2 | 8 | |
| Amplification | Bx17 | 550k | Breast | 9 | 116,446,862 | 116,484,277 | Unknown | | |
| Amplification | B2C | 317k | Breast | 9 | 126,339,811 | 126,345,695 | Unknown | | |
| Amplification | B2C | 317k | Breast | 9 | 127,321,720 | 127,351,220 | Unknown | | |
| Amplification | Co74C | 317k | Colon | 9 | 135,842,003 | 135,854,761 | Unknown | | |
| Amplification | Bx22 | 550k | Breast | 10 | 242,693 | 328,553 | Unknown | | ZMYND11 |
| Amplification | Bx28 | 550k | Breast | 10 | 269,248 | 328,553 | Unknown | | |
| Amplification | Bx22 | 550k | Breast | 10 | 578,126 | 623,495 | Unknown | | |
| Amplification | B6C | 317k | Breast | 10 | 1,706,614 | 1,708,040 | Unknown | | |
| Amplification | Bx22 | 550k | Breast | 10 | 4,560,425 | 4,576,302 | Unknown | | |
| Amplification | Bx17 | 550k | Breast | 10 | 4,747,822 | 4,748,119 | Unknown | | |
| Amplification | B10C | 317k | Breast | 10 | 6,285,323 | 6,293,989 | Unknown | | |
| Amplification | Bx22 | 550k | Breast | 10 | 10,361,880 | 10,380,715 | Unknown | | |
| HD | Bx19 | 550k | Breast | 10 | 19,988,833 | 20,447,496 | Unknown | | PLXDC2 |
| HD | Bx34 | 550k | Breast | 10 | 27,656,549 | 27,745,861 | Unknown | | PTCHD3 |
| Amplification | B7C | 317k | Breast | 10 | 39,137,918 | 41,934,567 | Unknown | | |
| Amplification | SKBR3 | 550k | Breast | 10 | 57,417,982 | 58,227,959 | Unknown | | ZWINT |

FROM FIG. 10M

| | | | | | | | | | |
|---|---|---|---|---|---|---|---|---|---|
| Amplification | B4C | 317k | Breast | 10 | 61,983,247 | 62,080,511 | Unknown | | |
| HD | Bx38 | 550k | Breast | 10 | 64,728,230 | 64,886,250 | Unknown | | |
| Amplification | Bx19 | 550k | Breast | 10 | 65,131,799 | 65,149,421 | Unknown | | |
| HD | Mx35x | 550k | Colon | 10 | 65,303,906 | 65,304,118 | Unknown | | |
| HD | B9C | 317k | Breast | 10 | 65,855,381 | 67,299,558 | Unknown | | |
| HD | Bx19 | 550k | Breast | 10 | 69,681,844 | 69,682,295 | Unknown | | |
| HD | B2C | 317k | Breast | 10 | 70,728,020 | 70,728,021 | Unknown | | |
| HD | Bx20 | 550k | Breast | 10 | 77,520,704 | 77,539,824 | Unknown | | |
| Amplification | Bx28 | 550k | Breast | 10 | 79,322,160 | 79,343,486 | Unknown | | |
| Amplification | B6C | 317k | Breast | 10 | 80,233,525 | 80,261,070 | Unknown | | |
| Amplification | B6C | 317k | Breast | 10 | 80,363,731 | 80,423,609 | Unknown | | |
| Amplification | B6C | 317k | Breast | 10 | 80,728,033 | 81,697,593 | C10orf56 | 3 | PPIF, SFTPA1, SFTPA2, SFTPD |
| HD | B1C | 317k | Breast | 10 | 82,869,699 | 82,875,955 | Unknown | | |
| HD | Co82C | 550k | Colon | 10 | 84,611,296 | 84,613,706 | Unknown | | |
| HD | Bx25 | 550k | Breast | 10 | 88,445,859 | 88,451,679 | Unknown | | |
| HD | B9C | 317k | Breast | 10 | 88,706,557 | 88,896,905 | MMRN2 | 8 | C10orf116, SNCG, GLUD1 |
| HD | B9C | 317k | Breast | 10 | 89,165,616 | 89,921,163 | PTEN | 6 | MINPP1, PAPSS2, ATAD1 |
| HD | Mx22x | 317k | Colon | 10 | 89,252,967 | 90,241,482 | PTEN | 6 | ATAD1, C10orf59, MINPP1, PAPSS2 |
| HD | Co111C | 550k | Colon | 10 | 89,635,453 | 89,993,748 | PTEN | 6 | |
| HD | Bx38 | 550k | Breast | 10 | 89,697,245 | 89,721,850 | PTEN | 6 | |
| HD | B7C | 317k | Breast | 10 | 89,721,850 | 89,758,564 | Unknown | | |
| HD | Hx152 | 550k | Colon | 10 | 102,350,845 | 102,352,105 | Unknown | | |
| Amplification | Hx110 | 550k | Colon | 10 | 121,732,421 | 121,774,052 | Unknown | | |
| Amplification | Hx110 | 550k | Colon | 10 | 121,928,609 | 121,973,116 | Unknown | | |
| Amplification | Hx110 | 550k | Colon | 10 | 122,304,898 | 122,317,553 | Unknown | | |
| Amplification | Hx110 | 550k | Colon | 10 | 122,431,376 | 122,479,308 | Unknown | | |
| Amplification | Hx110 | 550k | Colon | 10 | 122,520,128 | 122,526,602 | Unknown | | |
| Amplification | Hx110 | 550k | Colon | 10 | 122,878,545 | 122,994,629 | Unknown | | |
| Amplification | Hx110 | 550k | Colon | 10 | 123,231,784 | 123,471,190 | FGFR2 | 3 | |
| Amplification | Hx110 | 550k | Colon | 10 | 123,980,184 | 123,992,886 | Unknown | | |
| Amplification | Hx110 | 550k | Colon | 10 | 124,122,178 | 124,220,602 | Unknown | | PLEKHA1 |
| Amplification | Hx110 | 550k | Colon | 10 | 124,245,330 | 124,600,017 | Unknown | | C10orf120, CUZD1, DMBT1 |
| HD | Bx38 | 550k | Breast | 10 | 126,721,726 | 126,754,403 | Unknown | | |
| HD | Bx19 | 550k | Breast | 10 | 127,774,874 | 127,774,926 | Unknown | | |
| Amplification | B4C | 317k | Breast | 10 | 134,155,653 | 134,235,604 | Unknown | | |
| Amplification | Mx43x | 317k | Colon | 11 | 399,815 | 409,906 | Unknown | | |
| HD | Bx39 | 550k | Breast | 11 | 419,659 | 422,436 | Unknown | | TMEM16J |
| Amplification | Mx32x | 317k | Colon | 11 | 548,884 | 557,391 | Unknown | | C11orf13 |
| Amplification | B10C | 317k | Breast | 11 | 692,250 | 695,404 | Unknown | | |
| Amplification | Mx38x | 317k | Colon | 11 | 1,375,453 | 1,386,192 | Unknown | | |
| HD | Co111C | 550k | Colon | 11 | 4,650,884 | 4,699,502 | Unknown | | OR51E2 |
| HD | B7C | 317k | Breast | 11 | 6,440,086 | 6,516,717 | TRIM3 | 8 | ARFIP2, FXC1, FLJ35709 |
| Amplification | Bx22 | 550k | Breast | 11 | 13,513,831 | 13,867,871 | Unknown | | MLSTD2 |
| Amplification | Bx39 | 550k | Breast | 11 | 16,532,125 | 17,543,098 | Unknown | | ABCC8, KCNJ11, NUCB2, PIK3C2A, PLEKHA7, RPS13, SMAP, USH1C |
| HD | B9C | 317k | Breast | 11 | 19,186,741 | 19,206,740 | Unknown | | FLJ23311 |
| HD | Bx38 | 550k | Breast | 11 | 20,711,016 | 20,723,082 | Unknown | | |

FROM FIG. 10N

| Type | Sample | Array | Tissue | Chr | Start | End | Gene | Count | Other Genes |
|---|---|---|---|---|---|---|---|---|---|
| HD | Bx38 | 550k | Breast | 11 | 20,796,450 | 20,828,374 | NELL1 | 8 | |
| HD | Bx17 | 550k | Breast | 11 | 22,200,524 | 22,209,226 | Unknown | | TMEM16E |
| HD | B4C | 317k | Breast | 11 | 28,121,437 | 28,332,525 | Unknown | | METT5D1 |
| HD | Bx28 | 550k | Breast | 11 | 32,021,832 | 32,046,769 | Unknown | | |
| Amplification | Co84C | 317k | Colon | 11 | 34,359,268 | 35,265,359 | Unknown | | CAT, CD44, EHF, ELF5, MMRP19, PDHX |
| HD | B7C | 317k | Breast | 11 | 36,112,154 | 36,292,839 | Unknown | | COMMD9, FLJ45212, LDLRAD3 |
| Amplification | B6C | 317k | Breast | 11 | 47,391,562 | 47,425,145 | Unknown | | PSMC3 |
| HD | Bx23 | 550k | Breast | 11 | 55,165,240 | 55,198,944 | Unknown | | OR4C6, OR4S2 |
| Amplification | Bx39 | 550k | Breast | 11 | 57,177,356 | 58,184,159 | CTNND1 | 3 | C11orf31, CNTF, HEAB, LPXN, MED19, OR10Q1, OR1S1, OR1S2, OR5B12, OR5B17, OR5B2, OR5B21, OR5B3, OR6Q1, OR9I1, OR9Q1, OR9Q2, TMX2, UNQ6469, ZDHHC5, ZFP91 |
| Amplification | B9C | 317k | Breast | 11 | 61,270,661 | 61,293,159 | Unknown | | |
| HD | Bx20 | 550k | Breast | 11 | 65,691,125 | 65,691,765 | Unknown | | |
| Amplification | Bx37 | 550k | Breast | 11 | 66,272,625 | 66,336,148 | Unknown | | |
| Amplification | MDAMB415 | 550k | Breast | 11 | 66,523,330 | 66,769,773 | Unknown | | RHOD, SYT12 |
| Amplification | B6C | 317k | Breast | 11 | 67,158,938 | 67,190,445 | Unknown | | ACY3 |
| Amplification | Bx22 | 550k | Breast | 11 | 67,217,488 | 67,306,971 | Unknown | | |
| Amplification | Bx22 | 550k | Breast | 11 | 68,055,088 | 68,633,163 | Unknown | | C11orf23, CPT1A, GAL, IGHMBP2, MRGPRD, MRGPRF, MRPL21, MTL5, TPCN2 |
| Amplification | MDAMB415 | 550k | Breast | 11 | 68,055,088 | 70,314,702 | CCND1 | 1 | C11orf23, CPT1A, CTTN, FADD, FGF19, FGF3, FGF4, FLJ42258, GAL, IGHMBP2, MRGPRD, MRGPRF, MRPL21, MTL5, MYEOV, ORAOV1, PPFIA1, SHANK2, TMEM16A, TPCN2 |
| Amplification | B9C | 317k | Breast | 11 | 68,613,492 | 68,617,234 | Unknown | | |
| Amplification | B3C | 317k | Breast | 11 | 68,617,234 | 69,411,832 | CCND1 | 1 | FGF19, FGF3, FGF4, FLJ42258, MYEOV, ORAOV1 |
| Amplification | B5C | 317k | Breast | 11 | 68,626,681 | 69,796,137 | CCND1 | 1 | FADD, FGF19, FGF3, FGF4, FLJ42258, MYEOV, ORAOV1, TMEM16A |
| Amplification | Bx10 | 550k | Breast | 11 | 68,840,719 | 68,940,977 | Unknown | | |
| Amplification | Bx10 | 550k | Breast | 11 | 68,984,727 | 69,027,272 | Unknown | | |
| Amplification | B3C | 317k | Breast | 11 | 69,601,186 | 70,341,866 | Unknown | | CTTN, FADD, PPFIA1, SHANK2, TMEM16A |
| Amplification | Bx28 | 550k | Breast | 11 | 70,326,821 | 70,520,567 | Unknown | | LOC220070 |
| Amplification | Bx28 | 550k | Breast | 11 | 70,604,711 | 70,827,944 | Unknown | | |
| Amplification | Bx22 | 550k | Breast | 11 | 70,644,511 | 70,659,973 | Unknown | | |
| Amplification | Bx22 | 550k | Breast | 11 | 77,001,909 | 78,769,253 | Unknown | | ALG8, CLNS1A, FLJ23441, GAB2, HBXAP, INTS4, KCTD14, LOC283219, NDUFC2, PTD015, THRSP |
| Amplification | MDAMB175VII | 550k | Breast | 11 | 78,369,205 | 78,382,351 | Unknown | | |
| Amplification | MDAMB175VII | 550k | Breast | 11 | 78,406,142 | 78,422,927 | Unknown | | |
| HD | B2C | 317k | Breast | 11 | 79,655,019 | 79,659,821 | Unknown | | |
| HD | MDAMB415 | 550k | Breast | 11 | 81,181,640 | 81,194,909 | Unknown | | |
| HD | Bx10 | 550k | Breast | 11 | 81,378,024 | 81,378,074 | Unknown | | |
| HD | MDAMB175VII | 550k | Breast | 11 | 84,943,969 | 84,944,441 | Unknown | | |
| HD | Mx31x | 550k | Colon | 11 | 88,228,289 | 88,303,300 | Unknown | | |
| HD | Mx31x | 550k | Colon | 11 | 88,336,310 | 88,441,929 | Unknown | | GRM5 |
| HD | Mx31x | 550k | Colon | 11 | 88,498,045 | 88,498,127 | Unknown | | |
| Amplification | B3C | 317k | Breast | 11 | 93,740,661 | 93,972,379 | MRE11A | 3 | FGIF, FUT4, GPR83 |
| Amplification | B3C | 317k | Breast | 11 | 94,031,493 | 94,607,785 | Unknown | | AMOTL1, HSPC148, JMJD2D, SESN3, SRP46 |

FROM FIG. 10O

| | | | | | | | |
|---|---|---|---|---|---|---|---|
| HD | Bx26 | 550k | Breast | 11 | 97,023,895 | 97,025,197 | Unknown |
| Amplification | Bx19 | 550k | Breast | 11 | 98,000,484 | 98,457,427 | Unknown |
| Amplification | B3C | 317k | Breast | 11 | 103,202,627 | 103,250,270 | Unknown |
| Amplification | B3C | 317k | Breast | 11 | 103,441,679 | 103,481,503 | Unknown |
| HD | Bx19 | 550k | Breast | 11 | 103,515,175 | 103,522,247 | Unknown |
| HD | B7C | 317k | Breast | 11 | 105,784,821 | 105,793,764 | Unknown |
| Amplification | B9C | 317k | Breast | 11 | 116,768,313 | 116,773,094 | Unknown |
| HD | ZR7530 | 550k | Breast | 11 | 118,407,959 | 118,408,051 | Unknown |
| Amplification | T47D | 550k | Breast | 11 | 124,379,592 | 124,415,988 | Unknown |
| Amplification | B6C | 317k | Breast | 11 | 125,701,385 | 125,713,969 | Unknown |
| Amplification | T47D | 550k | Breast | 11 | 127,472,564 | 127,482,649 | Unknown |
| Amplification | T47D | 550k | Breast | 11 | 131,154,656 | 131,163,337 | Unknown |
| Amplification | T47D | 550k | Breast | 11 | 131,312,381 | 131,322,059 | Unknown |
| Amplification | T47D | 550k | Breast | 11 | 132,003,494 | 132,005,975 | Unknown |
| HD | Co111C | 550k | Colon | 11 | 134,043,708 | 134,445,626 | Unknown |
| Amplification | Bx26 | 550k | Breast | 12 | 1,957,306 | 1,999,243 | Unknown |
| Amplification | Bx26 | 550k | Breast | 12 | 2,306,783 | 2,322,880 | Unknown |
| HD | Mx22x | 317k | Colon | 12 | 14,366,359 | 14,439,581 | Unknown |
| Amplification | Co82C | 550k | Colon | 12 | 29,861,177 | 30,173,555 | Unknown |
| Amplification | Co82C | 550k | Colon | 12 | 30,209,755 | 30,231,798 | Unknown |
| Amplification | Co82C | 550k | Colon | 12 | 30,702,093 | 31,275,324 | Unknown | C1QDC1, DDX11 |
| Amplification | Co82C | 550k | Colon | 12 | 31,296,067 | 32,036,123 | Unknown | C12orf14, LOC196394, LOC440093, MGC24039, MGC50559 |
| HD | Mx34x | 550k | Colon | 12 | 32,465,875 | 32,508,065 | Unknown |
| Amplification | B3C | 317k | Breast | 12 | 34,480,677 | 34,692,538 | Unknown |
| HD | Mx43x | 317k | Colon | 12 | 36,718,276 | 36,733,128 | Unknown |
| Amplification | B3C | 317k | Breast | 12 | 38,689,229 | 41,159,574 | Unknown | CNTN1, LRRK2, MADP-1, PDZRN4, PPHLN1, PRICKLE1, YAF2 |
| Amplification | B3C | 317k | Breast | 12 | 43,755,016 | 44,049,336 | Unknown | PLEKHA9 |
| HD | Bx28 | 550k | Breast | 12 | 51,372,912 | 51,373,716 | Unknown | KRT1B |
| HD | Mx03x | 550k | Colon | 12 | 63,304,111 | 63,304,459 | Unknown |
| Amplification | Bx13 | 550k | Breast | 12 | 68,118,736 | 69,826,182 | Unknown | C12orf28, CCT2, CNOT2, FRS2, KCNMB4, LRRC10, MGC13168, PTPRB, PTPRR, RAB3IP, VMD2L3 |
| HD | Mx43x | 317k | Colon | 12 | 74,672,072 | 75,591,349 | Unknown | NAP1L1, PHLDA1, FLJ23560, OSBPL8 |
| HD | Bx25 | 550k | Breast | 12 | 76,383,442 | 76,592,708 | Unknown |
| Amplification | B2C | 317k | Breast | 12 | 80,902,125 | 80,949,903 | Unknown |
| HD | Mx22x | 317k | Colon | 12 | 83,514,781 | 85,794,805 | Unknown | CART1, HGNT-IV-H, LRRIQ1, NTS, PAMCI, SLC6A15 |
| HD | Bx19 | 550k | Breast | 12 | 85,123,178 | 85,141,692 | Unknown |
| HD | B5C | 317k | Breast | 12 | 101,675,983 | 101,677,726 | Unknown |
| Amplification | B5C | 317k | Breast | 12 | 111,233,783 | 111,257,434 | Unknown |
| HD | B1C | 317k | Breast | 12 | 127,755,956 | 127,757,177 | Unknown |
| HD | B2C | 317k | Breast | 12 | 127,913,143 | 127,913,857 | Unknown |
| HD | B6C | 317k | Breast | 12 | 130,255,197 | 130,339,814 | Unknown |
| HD | Bx19 | 550k | Breast | 12 | 131,951,694 | 131,972,193 | Unknown | GOLGA3 |
| Amplification | Mx38x | 317k | Colon | 13 | 22,864,145 | 22,905,495 | Unknown |
| Amplification | Hx152 | 550k | Colon | 13 | 23,387,695 | 23,388,921 | Unknown |
| Amplification | Mx38x | 317k | Colon | 13 | 23,419,485 | 23,427,399 | Unknown |

FROM FIG. 10P

| | | | | | | | | | |
|---|---|---|---|---|---|---|---|---|---|
| HD | Mx43x | 317k | Colon | 13 | 26,945,269 | 26,982,069 | Unknown | | |
| Amplification | Hx110 | 550k | Colon | 13 | 27,076,525 | 27,602,081 | Unknown | | CDX2, FLT3, GSH1, IPF1, MGC9850, POLR1D |
| Amplification | Hx110 | 550k | Colon | 13 | 29,124,924 | 29,278,407 | Unknown | | |
| Amplification | Co110C | 550k | Colon | 13 | 37,724,809 | 37,728,641 | Unknown | | |
| Amplification | Co110C | 550k | Colon | 13 | 43,636,069 | 43,643,719 | Unknown | | |
| Amplification | MCF7 | 550k | Breast | 13 | 46,002,437 | 46,213,526 | Unknown | | |
| Amplification | MCF7 | 550k | Breast | 13 | 46,253,525 | 46,555,923 | Unknown | | HTR2A |
| Amplification | Bx19 | 550k | Breast | 13 | 46,371,221 | 46,371,551 | Unknown | | |
| Amplification | MCF7 | 550k | Breast | 13 | 46,601,653 | 47,001,519 | Unknown | | |
| Amplification | Hx129 | 550k | Colon | 13 | 46,708,395 | 46,721,736 | Unknown | | |
| HD | Bx27 | 550k | Breast | 13 | 47,726,532 | 47,846,570 | RB1 | 5 | ITM2B |
| Amplification | Hx152 | 550k | Colon | 13 | 49,004,562 | 49,005,290 | Unknown | | |
| HD | B7C | 317k | Breast | 13 | 52,176,068 | 60,428,304 | PCDH8 | 8 | DIAPH3, LECT1, OLFM4, PCDH17, TDRD3 |
| HD | B1C | 317k | Breast | 13 | 52,593,780 | 52,815,866 | Unknown | | |
| HD | Bx35 | 550k | Breast | 13 | 57,491,658 | 57,497,032 | Unknown | | |
| HD | B4C | 317k | Breast | 13 | 65,896,579 | 65,929,479 | Unknown | | |
| Amplification | Hx129 | 550k | Colon | 13 | 71,666,710 | 71,688,350 | Unknown | | |
| Amplification | Hx129 | 550k | Colon | 13 | 71,788,604 | 71,826,381 | Unknown | | |
| HD | Mx43x | 317k | Colon | 13 | 76,909,656 | 77,168,955 | Unknown | | SCEL |
| HD | Bx27 | 550k | Breast | 13 | 77,665,412 | 77,665,502 | Unknown | | |
| HD | Bx34 | 550k | Breast | 13 | 81,394,402 | 84,550,996 | Unknown | | SLITRK1 |
| HD | Bx39 | 550k | Breast | 13 | 83,000,441 | 83,045,171 | Unknown | | |
| Amplification | Hx129 | 550k | Colon | 13 | 89,431,424 | 89,440,786 | Unknown | | |
| Amplification | B9C | 317k | Breast | 13 | 93,666,585 | 93,666,905 | Unknown | | |
| Amplification | Co110C | 550k | Colon | 13 | 98,189,347 | 98,196,933 | Unknown | | |
| Amplification | Hx152 | 550k | Colon | 13 | 103,438,450 | 103,439,204 | Unknown | | |
| HD | B9C | 317k | Breast | 13 | 106,979,630 | 106,979,661 | Unknown | | |
| Amplification | Co84C | 317k | Colon | 13 | 109,108,212 | 109,557,712 | IRS2 | 3 | |
| Amplification | Mx38x | 317k | Colon | 13 | 109,233,954 | 109,260,023 | Unknown | | |
| HD | UACC812 | 550k | Breast | 13 | 110,903,823 | 110,957,774 | Unknown | | |
| Amplification | Mx38x | 317k | Colon | 13 | 110,957,774 | 111,001,762 | Unknown | | |
| Amplification | Mx38x | 317k | Colon | 13 | 111,883,255 | 111,885,504 | Unknown | | |
| Amplification | Mx38x | 317k | Colon | 13 | 111,979,651 | 112,029,555 | Unknown | | |
| Amplification | Mx38x | 317k | Colon | 13 | 113,485,357 | 113,927,626 | Unknown | | FLJ41484, GAS6, MGC20579, RASA3 |
| Amplification | B2C | 317k | Breast | 14 | 22,675,813 | 22,793,634 | Unknown | | |
| Amplification | B2C | 317k | Breast | 14 | 22,901,017 | 22,936,553 | Unknown | | CKLFSF5, IL17E |
| Amplification | B2C | 317k | Breast | 14 | 23,060,945 | 23,072,727 | Unknown | | |
| HD | Mx08x | 550k | Colon | 14 | 26,494,184 | 26,699,160 | Unknown | | |
| HD | B2C | 317k | Breast | 14 | 26,744,449 | 26,751,374 | Unknown | | |
| Amplification | Bx27 | 550k | Breast | 14 | 29,559,374 | 29,599,580 | Unknown | | |
| Amplification | BT483 | 550k | Breast | 14 | 32,038,777 | 32,076,550 | Unknown | | |
| HD | B5C | 317k | Breast | 14 | 32,503,328 | 32,505,285 | Unknown | | |
| Amplification | BT483 | 550k | Breast | 14 | 40,613,181 | 40,625,514 | Unknown | | |
| Amplification | Bx13 | 550k | Breast | 14 | 42,565,032 | 42,843,401 | Unknown | | |
| HD | Hx152 | 550k | Colon | 14 | 45,671,842 | 45,677,824 | Unknown | | |
| HD | B9C | 317k | Breast | 14 | 46,778,147 | 46,785,371 | Unknown | | |
| Amplification | Bx10 | 550k | Breast | 14 | 47,185,921 | 47,366,743 | Unknown | | |

FROM FIG. 10Q

| | | | | | | | | | |
|---|---|---|---|---|---|---|---|---|---|
| Amplification | Bx10 | 550k | Breast | 14 | 48,854,983 | 49,532,182 | Unknown | | ARF6, C14orf104, KLHDC1, KLHDC2, MGAT2, POLE2, PPIL5, RPL36AL, RPS29, SDCCAG1. |
| Amplification | Bx10 | 550k | Breast | 14 | 50,593,169 | 50,666,679 | Unknown | | |
| Amplification | BT483 | 550k | Breast | 14 | 61,631,948 | 61,632,399 | Unknown | | |
| HD | B6C | 317k | Breast | 14 | 62,776,535 | 63,406,232 | Unknown | | C14orf150, PPP2R5E, SGPP1, RHOJ |
| HD | Hx132 | 550k | Colon | 14 | 66,596,886 | 66,629,423 | Unknown | | GPHN |
| HD | Co110C | 550k | Colon | 14 | 73,311,441 | 73,312,722 | Unknown | | |
| HD | Bx38 | 550k | Breast | 14 | 77,278,047 | 77,280,978 | Unknown | | |
| HD | Hx152 | 550k | Colon | 14 | 77,858,841 | 77,861,378 | Unknown | | |
| HD | Mx08x | 550k | Colon | 14 | 78,933,086 | 79,209,665 | NRXN3 | 8 | |
| HD | Bx13 | 550k | Breast | 14 | 83,114,478 | 83,116,313 | Unknown | | |
| Amplification | Bx39 | 550k | Breast | 14 | 85,134,120 | 85,138,393 | Unknown | | |
| HD | Bx39 | 550k | Breast | 14 | 85,357,100 | 85,379,917 | Unknown | | |
| HD | Bx29 | 550k | Breast | 14 | 85,533,951 | 85,557,882 | Unknown | | |
| HD | Bx8 | 550k | Breast | 14 | 90,327,494 | 90,331,937 | Unknown | | |
| HD | Bx13 | 550k | Breast | 14 | 91,952,579 | 91,952,754 | Unknown | | |
| HD | Bx38 | 550k | Breast | 14 | 94,735,334 | 94,736,013 | Unknown | | |
| HD | B2C | 317k | Breast | 14 | 95,753,951 | 95,754,523 | Unknown | | |
| Amplification | B5C | 317k | Breast | 14 | 103,956,015 | 104,271,422 | Unknown | | C14orf151, C14orf173, FLJ42486, LOC400258 |
| HD | Bx22 | 550k | Breast | 15 | 21,609,833 | 21,612,590 | Unknown | | |
| HD | MDAMB231 | 550k | Breast | 15 | 21,948,712 | 21,985,041 | Unknown | | |
| HD | Bx26 | 550k | Breast | 15 | 22,974,169 | 22,978,970 | Unknown | | |
| HD | Bx26 | 550k | Breast | 15 | 23,474,580 | 23,475,632 | ATP10A | 8 | |
| Amplification | B3C | 317k | Breast | 15 | 24,604,699 | 25,347,771 | Unknown | | GABRA5 |
| HD | B10C | 317k | Breast | 15 | 27,014,674 | 27,091,095 | Unknown | | |
| HD | Bx38 | 550k | Breast | 15 | 27,025,865 | 27,091,095 | Unknown | | |
| HD | MCF7 | 550k | Breast | 15 | 32,505,886 | 32,543,717 | Unknown | | |
| HD | Mx40x | 550k | Colon | 15 | 50,054,170 | 50,057,972 | Unknown | | |
| HD | B2C | 317k | Breast | 15 | 58,855,240 | 59,142,548 | Unknown | | |
| HD | Bx19 | 550k | Breast | 15 | 61,628,728 | 61,647,753 | Unknown | | USP3 |
| HD | Mx31x | 550k | Colon | 15 | 65,239,008 | 65,323,050 | SMAD3 | 8 | FLJ11506 |
| HD | Bx22 | 550k | Breast | 15 | 67,192,239 | 67,205,778 | Unknown | | |
| HD | B6C | 317k | Breast | 15 | 69,972,022 | 70,217,488 | Unknown | | MYO9A |
| Amplification | Bx28 | 550k | Breast | 15 | 76,274,638 | 76,297,874 | Unknown | | |
| Amplification | B7C | 317k | Breast | 15 | 81,302,316 | 81,331,475 | Unknown | | |
| Amplification | Co84C | 317k | Colon | 15 | 88,561,995 | 89,253,599 | NEUGRIN | 8 | BLM, CIB1, CRTC3, FES, FURIN, IQGAP1, LOC390637, MGC75360, TTLL13 |
| Amplification | Bx34 | 550k | Breast | 15 | 88,624,043 | 88,685,795 | Unknown | | |
| Amplification | B7C | 317k | Breast | 15 | 89,181,003 | 89,201,212 | Unknown | | |
| Amplification | B7C | 317k | Breast | 15 | 91,356,254 | 91,394,651 | Unknown | | |
| Amplification | Co74C | 317k | Colon | 15 | 91,388,106 | 91,389,084 | Unknown | | |
| Amplification | B7C | 317k | Breast | 15 | 92,067,571 | 92,118,937 | Unknown | | |
| HD | B6C | 317k | Breast | 15 | 92,916,997 | 92,917,093 | Unknown | | |
| Amplification | B7C | 317k | Breast | 15 | 95,372,545 | 95,377,508 | Unknown | | |
| Amplification | B7C | 317k | Breast | 15 | 95,446,131 | 95,477,520 | Unknown | | |
| HD | Bx28 | 550k | Breast | 15 | 95,616,714 | 95,632,771 | Unknown | | |
| Amplification | B2C | 317k | Breast | 15 | 98,499,391 | 98,507,671 | Unknown | | |

FROM FIG. 10R

| | | | | | | | |
|---|---|---|---|---|---|---|---|
| Amplification | B2C | 317k | Breast | 16 | 1,071,696 | 1,541,288 | Unknown | BAIAP3, C16orf28, C1QTNF8, CACNA1H, CLCN7, GNPTG, KIAA0590, KIAA0683, LOC283951, LOC390667, MGC24381, TPSAB1, TPSB2, TPSD1, TPSG1, UBE2I, UNKL |
| Amplification | Mx42x | 317k | Colon | 16 | 1,747,781 | 1,766,303 | Unknown | EME2, MRPS34, NME3 |
| Amplification | B7C | 317k | Breast | 16 | 1,754,392 | 1,766,303 | Unknown | EME2, MRPS34, NME3 |
| Amplification | B2C | 317k | Breast | 16 | 1,945,564 | 2,010,569 | Unknown | GFER, NDUFB10, NOXO1, RNF151, RPS2, SYNGR3, TBL3, ZNF598 |
| Amplification | B2C | 317k | Breast | 16 | 4,344,621 | 4,372,030 | Unknown | |
| Amplification | Mx32x | 317k | Colon | 16 | 4,647,433 | 4,674,514 | Unknown | |
| HD | Mx35x | 550k | Colon | 16 | 6,207,058 | 6,254,859 | Unknown | |
| HD | Co84C | 317k | Colon | 16 | 6,365,753 | 6,377,673 | Unknown | LOC440337 |
| HD | Hx134 | 550k | Colon | 16 | 6,387,772 | 6,550,704 | Unknown | |
| HD | Mx41x | 317k | Colon | 16 | 6,463,143 | 6,616,448 | Unknown | |
| HD | Mx35x | 550k | Colon | 16 | 6,463,143 | 6,657,519 | Unknown | |
| HD | Hx129 | 550k | Colon | 16 | 6,494,254 | 6,589,736 | Unknown | |
| HD | Hx129 | 550k | Colon | 16 | 6,594,148 | 6,699,607 | Unknown | |
| HD | Mx31x | 550k | Colon | 16 | 6,674,599 | 6,707,301 | Unknown | |
| HD | Mx35x | 550k | Colon | 16 | 6,783,832 | 6,899,490 | Unknown | |
| HD | Hx129 | 550k | Colon | 16 | 6,838,384 | 6,866,262 | Unknown | |
| HD | Mx35x | 550k | Colon | 16 | 6,928,412 | 6,967,720 | Unknown | |
| Amplification | B7C | 317k | Breast | 16 | 11,317,342 | 11,336,128 | Unknown | |
| Amplification | B7C | 317k | Breast | 16 | 14,031,238 | 14,053,599 | Unknown | |
| HD | Mx43x | 317k | Colon | 16 | 27,825,670 | 27,826,687 | Unknown | |
| Amplification | Hx130 | 550k | Colon | 16 | 32,045,466 | 33,744,011 | Unknown | FLJ43855, TP53TG3 |
| Amplification | Bx28 | 550k | Breast | 16 | 34,393,084 | 35,106,851 | Unknown | |
| HD | Bx26 | 550k | Breast | 16 | 45,627,130 | 45,631,736 | Unknown | |
| HD | Co111C | 550k | Colon | 16 | 50,451,735 | 50,460,971 | Unknown | |
| Amplification | Bx22 | 550k | Breast | 16 | 52,917,351 | 52,919,768 | Unknown | |
| HD | Bx13 | 550k | Breast | 16 | 57,364,537 | 57,365,043 | Unknown | |
| HD | Bx28 | 550k | Breast | 16 | 57,390,260 | 57,398,356 | Unknown | |
| Amplification | Bx14 | 550k | Breast | 16 | 60,819,575 | 60,830,344 | Unknown | |
| Amplification | Mx26x | 317k | Colon | 16 | 66,240,081 | 66,257,449 | Unknown | ACD, PARD6A |
| HD | SKBR3 | 550k | Breast | 16 | 67,196,839 | 67,411,172 | CDH1 | 9 | CDH3 |
| HD | B11C | 317k | Breast | 16 | 67,255,962 | 67,408,284 | CDH1 | 9 | CDH3 |
| HD | Co44C | 317k | Colon | 16 | 67,414,790 | 67,420,815 | CDH1 | 9 | |
| HD | Bx35 | 550k | Breast | 16 | 68,673,020 | 68,693,706 | Unknown | |
| HD | Bx29 | 550k | Breast | 16 | 69,913,636 | 69,916,438 | Unknown | |
| HD | Bx20 | 550k | Breast | 16 | 77,021,013 | 77,159,207 | Unknown | WWOX |
| HD | Bx20 | 550k | Breast | 16 | 77,199,241 | 77,214,539 | Unknown | |
| HD | Bx20 | 550k | Breast | 16 | 77,234,640 | 77,253,758 | Unknown | |
| HD | Bx20 | 550k | Breast | 16 | 77,312,188 | 77,376,728 | Unknown | |
| HD | Bx20 | 550k | Breast | 16 | 77,410,183 | 77,435,119 | Unknown | |
| HD | Bx26 | 550k | Breast | 16 | 77,824,930 | 77,831,740 | Unknown | |
| HD | Bx22 | 550k | Breast | 16 | 79,461,910 | 79,471,170 | Unknown | |
| Amplification | B9C | 317k | Breast | 16 | 79,992,878 | 80,000,314 | Unknown | |
| HD | Bx27 | 550k | Breast | 16 | 84,516,666 | 84,517,780 | Unknown | |

FROM FIG. 10S

| | | | | | | | | |
|---|---|---|---|---|---|---|---|---|
| Amplification | MCF7 | 550k | Breast | 16 | 84,978,318 | 84,980,187 | Unknown | |
| HD | Bx13 | 550k | Breast | 16 | 85,622,534 | 85,627,484 | Unknown | |
| Amplification | Mx32x | 317k | Colon | 16 | 86,235,645 | 86,235,666 | Unknown | |
| Amplification | Mx42x | 317k | Colon | 16 | 86,906,435 | 86,924,174 | Unknown | |
| Amplification | Mx32x | 317k | Colon | 16 | 87,079,871 | 87,082,060 | Unknown | |
| Amplification | Mx38x | 317k | Colon | 16 | 87,079,871 | 87,097,884 | Unknown | |
| HD | B8C | 550k | Breast | 16 | 88,019,550 | 88,072,257 | Unknown | |
| HD | Bx10 | 550k | Breast | 17 | 917,163 | 1,051,470 | Unknown | ABR |
| HD | Mx38x | 317k | Colon | 17 | 3,249,738 | 3,271,560 | Unknown | OR3A3 |
| HD | Mx43x | 317k | Colon | 17 | 7,518,132 | 7,519,370 | TP53 | 6 |
| HD | Bx17 | 550k | Breast | 17 | 10,832,202 | 10,836,404 | Unknown | |
| HD | Mx27x | 317k | Colon | 17 | 10,910,683 | 12,755,698 | MAP2K4 | 6  DNAH9, FLJ45455, MYOCD, ZNF18 |
| HD | Mx45x | 550k | Colon | 17 | 11,496,715 | 12,155,589 | MAP2K4 | 6  ZNF18, DNAH9 |
| HD | Mx22x | 317k | Colon | 17 | 11,806,187 | 12,377,210 | MAP2K4 | 6  DNAH9, ZNF18 |
| Amplification | UACC812 | 550k | Breast | 17 | 12,323,188 | 12,547,401 | Unknown | |
| Amplification | UACC812 | 550k | Breast | 17 | 13,070,369 | 13,150,573 | Unknown | |
| Amplification | B2C | 317k | Breast | 17 | 17,063,052 | 17,102,612 | Unknown | FLCN |
| Amplification | B2C | 317k | Breast | 17 | 17,190,331 | 18,216,572 | Unknown | ALKBH5, ATPAF2, C17orf39, DRG2, FLII, LLGL1, LRRC48, MED9, MYO15A, PEMT, RAI1, RASD1, SHMT1, SMCR7, SMCR8, SREBF1, TOM1L2, TOP3A |
| Amplification | Hx130 | 550k | Colon | 17 | 19,136,024 | 19,211,040 | EPPB9 | 4 |
| Amplification | Mx32x | 317k | Colon | 17 | 19,136,024 | 19,313,429 | EPPB9 | 4  MAPK7, MFAP4, ZNF179 |
| Amplification | Hx130 | 550k | Colon | 17 | 19,414,112 | 19,750,341 | Unknown | ALDH3A1, ALDH3A2, FLJ31196, ULK2 |
| HD | B1C | 317k | Breast | 17 | 21,641,854 | 22,166,482 | FAM27L | 9 |
| HD | Mx27x | 317k | Colon | 17 | 21,654,390 | 22,166,482 | FAM27L | 9 |
| Amplification | Bx28 | 550k | Breast | 17 | 23,533,941 | 24,185,264 | PIGS | 3  ALDOC, C17orf32, FLJ25006, FLJ40504, FOXN1, HCP1, IFT20, KIAA0100, LOC116238, MAC30, NEK8, POLDIP2, PROCA1, PYY2, RAB34, RPL23A, SARM1, SDF2, SLC13A2, SPAG5, SUPT6H, TNFAIP1, TRAF4, UNC119, VTN |
| Amplification | UACC812 | 550k | Breast | 17 | 24455551 | 24900687 | NUFIP2 | 3  CRYBA1, TAOK1, |
| Amplification | UACC812 | 550k | Breast | 17 | 25,116,079 | 25,532,524 | Unknown | FLJ46247 |
| Amplification | Hx152 | 550k | Colon | 17 | 33,058,523 | 33,077,948 | Unknown | |
| Amplification | Bx22 | 550k | Breast | 17 | 33,914,210 | 35,658,563 | ERBB2 | 1  C17orf37, CACNB1, CASC3, CCDC49, CRK7, CSF3, FBXL20, FBXO47, FLJ43826, GRB7, GSDM1, GSDML, LASP1, MLLT6, NEUROD2, NR1D1, ORMDL3, PCGF2, PERLD1, PIP5K2B, PLXDC1, PNMT, PPARBP, PPP1R1B, PSMB3, PSMD3, RAPGEFL1, RPL19, RPL23, SNIP, STAC2, STARD3, TCAP, THRA, THRAP4, ZNFN1A3, ZPBP2 |
| Amplification | UACC812 | 550k | Breast | 17 | 33,967,529 | 36,194,010 | ERBB2 | C17orf37, CACNB1, CASC3, CCDC49, CCR7, CDC6, CRK7, CSF3, CTEN, FBXL20, FBXO47, FLJ43826, GJC1, GRB7, GSDM1, GSDML, IGFBP4, KRT24, KRT25A, KRT25B, KRT25C, LASP1, MGC45562, MLLT6, NEUROD2, NR1D1, ORMDL3, PCGF2, PERLD1, PIP5K2B, PLXDC1, PNMT, PPARBP, PPP1R1B, PSMB3, PSMD3, RAPGEFL1, RARA, RPL19, RPL23, SMARCE1, STAC2, STARD3, TCAP, THRA, |

FROM FIG. 10T

| | | | | | | | | |
|---|---|---|---|---|---|---|---|---|
| | | | | | | | | THRAP4, TOP2A, WIRE, ZNFN1A3, ZPBP2 |
| Amplification | SKBR3 | 550k | Breast | 17 | 34,536,896 | 35,392,550 | ERBB2 | 1 | C17orf37, CACNB1, CRK7, FBXL20, GRB7, GSDM1, GSDML, NEUROD2, ORMDL3, PERLD1, PNMT, PPARBP, PPP1R1B, RPL19, STAC2, STARD3, TCAP, ZNFN1A3, ZPBP2 |
| Amplification | Mx38x | 317k | Colon | 17 | 34,594,761 | 34,603,181 | Unknown | | |
| Amplification | B3C | 317k | Breast | 17 | 34,634,168 | 35,387,448 | ERBB2 | 1 | C17orf37, CRK7, FBXL20, GRB7, GSDML, NEUROD2, ORMDL3, PERLD1, PNMT, PPARBP, PPP1R1B, STARD3, TCAP, ZNFN1A3, ZPBP2 |
| Amplification | Hx152 | 550k | Colon | 17 | 34,862,646 | 35,710,677 | ERBB2 | 1 | C17orf37, CASC3, CRK7, CSF3, GRB7, GSDM1, GSDML, NEUROD2, NR1D1, ORMDL3, PERLD1, PNMT, PPP1R1B, PSMD3, RAPGEFL1, STARD3, TCAP, THRA, THRAP4, WIRE, ZNFN1A3, ZPBP2 |
| Amplification | SKBR3 | 550k | Breast | 17 | 35,517,723 | 35,798,150 | Unknown | | CASC3, CDC6, GJC1, RAPGEFL1, RARA, WIRE |
| HD | Bx28 | 550k | Breast | 17 | 51,515,464 | 51,527,276 | Unknown | | |
| Amplification | B2C | 317k | Breast | 17 | 53,743,926 | 53,751,608 | Unknown | | |
| HD | Co84C | 317k | Colon | 17 | 53,803,296 | 53,827,118 | Unknown | | FLJ20315 |
| Amplification | Mx38x | 317k | Colon | 17 | 58,101,711 | 58,120,747 | Unknown | | |
| Amplification | B7C | 317k | Breast | 17 | 73,785,521 | 73,808,867 | Unknown | | |
| HD | Bx34 | 550k | Breast | 17 | 73,799,302 | 73,799,603 | Unknown | | |
| Amplification | B7C | 317k | Breast | 17 | 74,071,972 | 74,084,911 | Unknown | | |
| Amplification | B7C | 317k | Breast | 17 | 74,642,689 | 74,662,402 | Unknown | | |
| Amplification | Mx38x | 317k | Colon | 17 | 76,704,933 | 76,778,244 | Unknown | | FLJ44861 |
| Amplification | Bx8 | 550k | Breast | 18 | 59,836 | 285,046 | Unknown | | THOC1, USP14 |
| Amplification | Bx17 | 550k | Breast | 18 | 2,313,411 | 2,852,368 | Unknown | | KNTC2, METTL4 |
| Amplification | MCF7 | 550k | Breast | 18 | 2,343,856 | 2,358,597 | Unknown | | |
| HD | T47D | 550k | Breast | 18 | 2,846,482 | 3,013,264 | Unknown | | EMILIN2, LPIN2 |
| Amplification | Bx17 | 550k | Breast | 18 | 2,992,230 | 3,322,667 | MRCL3 | 4 | MRLC2, MYOM1 |
| Amplification | MCF7 | 550k | Breast | 18 | 3,197,370 | 3,260,397 | MRCL3 | 4 | |
| Amplification | Bx17 | 550k | Breast | 18 | 4,188,603 | 4,320,954 | Unknown | | |
| Amplification | Bx17 | 550k | Breast | 18 | 4,364,408 | 4,626,537 | Unknown | | |
| HD | BT483 | 550k | Breast | 18 | 8,202,420 | 8,203,200 | Unknown | | |
| HD | B7C | 317k | Breast | 18 | 8,798,464 | 8,807,441 | Unknown | | KIAA0802 |
| Amplification | B5C | 317k | Breast | 18 | 9,431,020 | 9,702,098 | Unknown | | PPP4R1, RALBP1 |
| Amplification | B2C | 317k | Breast | 18 | 12,047,117 | 12,099,597 | Unknown | | |
| HD | B2C | 317k | Breast | 18 | 18,308,209 | 18,317,202 | Unknown | | |
| HD | Co82C | 550k | Colon | 18 | 19,036,044 | 19,151,312 | Unknown | | CABLES1 |
| HD | Co111C | 550k | Colon | 18 | 20,178,701 | 21,064,617 | ZNF521 | 8 | HRH4, IMPACT, OSBPL1A |
| Amplification | Bx37 | 550k | Breast | 18 | 30,710,352 | 30,770,342 | Unknown | | |
| HD | Co44C | 317k | Colon | 18 | 32,281,094 | 32,360,816 | FHOD3 | 8 | |
| HD | Hx130 | 550k | Colon | 18 | 35,338,454 | 35,409,444 | Unknown | | |
| HD | B9C | 317k | Breast | 18 | 43,110,527 | 43,219,964 | Unknown | | |
| HD | Co111C | 550k | Colon | 18 | 43,490,500 | 44,141,990 | SMAD2 | 8 | ZBTB7C |
| HD | Co111C | 550k | Colon | 18 | 44,391,897 | 44,523,898 | KIAA0427 | 8 | |
| Amplification | Bx39 | 550k | Breast | 18 | 44,573,683 | 44,612,905 | Unknown | | |
| Amplification | Bx39 | 550k | Breast | 18 | 44,782,268 | 45,222,601 | Unknown | | DYM |

FROM FIG. 10U

| | | | | | | | | | |
|---|---|---|---|---|---|---|---|---|---|
| HD | ZR7530 | 550k | Breast | 18 | 50,654,311 | 50,654,587 | Unknown | | |
| HD | Co108C | 317k | Colon | 18 | 53,578,381 | 58,240,624 | CDH20 | 7 | ALPK2, CCBE1, CPLX4, GRP, KIAA1468, LMAN1, MALT1, MC4R, NEDD4L, PMAIP1, RAX, RNF152, SEC11L3, TNFRS11A, ZNF532 |
| HD | Bx39 | 550k | Breast | 18 | 54,087,084 | 54,088,089 | Unknown | | |
| HD | Co82C | 550k | Colon | 18 | 54,517,561 | 55,649,208 | Unknown | | CCBE1, CPLX4, GRP, LMAN1, MALT1, RAX, SEC11L3, ZNF532 |
| HD | Co82C | 550k | Colon | 18 | 55,688,923 | 56,407,631 | Unknown | | PMAIP1, MC4R |
| HD | Co82C | 550k | Colon | 18 | 56,875,085 | 58,225,845 | CDH20 | 7 | RNF152, TNFRSF11A, KIAA1468 |
| HD | Mx31x | 550k | Colon | 18 | 61,125,703 | 61,162,474 | Unknown | | |
| Amplification | Bx19 | 550k | Breast | 18 | 64,302,055 | 64,323,734 | Unknown | | |
| HD | B4C | 317k | Breast | 18 | 64,897,188 | 64,906,488 | Unknown | | |
| Amplification | Bx19 | 550k | Breast | 18 | 65,017,202 | 65,032,392 | Unknown | | |
| HD | Bx27 | 550k | Breast | 18 | 65,359,372 | 65,367,619 | Unknown | | |
| HD | MDAMB415 | 550k | Breast | 18 | 66,538,998 | 66,553,573 | Unknown | | |
| Amplification | Bx19 | 550k | Breast | 18 | 67,708,906 | 67,905,592 | Unknown | | |
| Amplification | Bx19 | 550k | Breast | 18 | 71,860,296 | 71,876,148 | Unknown | | |
| Amplification | Bx19 | 550k | Breast | 18 | 71,944,229 | 71,955,466 | Unknown | | |
| HD | Hx130 | 550k | Colon | 18 | 74,122,846 | 74,126,111 | Unknown | | |
| HD | Bx28 | 550k | Breast | 18 | 74,763,702 | 74,766,163 | Unknown | | |
| Amplification | B2C | 317k | Breast | 19 | 2,428,316 | 2,456,737 | Unknown | | |
| Amplification | B6C | 317k | Breast | 19 | 12,007,370 | 12,049,266 | Unknown | | |
| Amplification | B2C | 317k | Breast | 19 | 12,782,186 | 12,824,143 | Unknown | | RTBDN |
| Amplification | B5C | 317k | Breast | 19 | 14,667,162 | 15,645,116 | AKAP8 | 3 | 7h3, ABHD9, AKAP8L, BRD4, CASP14, CYP4F3, CYP4F8, EMR2, FLJ39501, FLJ40365, ILVBL, NOTCH3, OR1I1, OR7A10, OR7A17, OR7A5, OR7C1, OR7C2, PGLYRP2, SLC1A6 |
| Amplification | B6C | 317k | Breast | 19 | 16,837,289 | 16,865,049 | Unknown | | F2RL3 |
| Amplification | B5C | 317k | Breast | 19 | 20,136,047 | 20,439,390 | Unknown | | FLJ44894 |
| HD | SKBR3 | 550k | Breast | 19 | 20,222,848 | 23,278,680 | Unknown | | FLJ44894, LOC115648, ZNF100, ZNF257, ZNF43, ZNF430, ZNF431, ZNF493, ZNF626, ZNF676, ZNF708, ZNF714, ZNF85 |
| HD | T47D | 550k | Breast | 19 | 20,422,200 | 20,473,895 | Unknown | | |
| HD | Co74C | 317k | Colon | 19 | 20,423,788 | 20,473,895 | Unknown | | |
| HD | SKBR3 | 550k | Breast | 19 | 23,332,057 | 24,282,139 | Unknown | | LOC148213, ZNF254, ZNF539, ZNF675, ZNF91 |
| HD | Co111C | 550k | Colon | 19 | 32,615,675 | 33,724,034 | Unknown | | |
| Amplification | B2C | 317k | Breast | 19 | 32,640,702 | 34,056,748 | Unknown | | |
| Amplification | Bx22 | 550k | Breast | 19 | 33,642,044 | 35,612,519 | CCNE1 | 1 | C19orf12, C19orf2, PLEKHF1, POP4, UQCRFS1 |
| Amplification | Bx39 | 550k | Breast | 19 | 34,277,090 | 34,279,795 | Unknown | | |
| Amplification | B2C | 317k | Breast | 19 | 34,395,850 | 35,097,525 | CCNE1 | 1 | C19orf12, PLEKHF1, POP4 |
| Amplification | Co84C | 317k | Colon | 19 | 34,561,976 | 34,641,548 | Unknown | | |
| Amplification | Bx24 | 550k | Breast | 19 | 34,806,368 | 35,170,271 | CCNE1 | 1 | C19orf12, PLEKHF1 |
| Amplification | Bx15 | 550k | Breast | 19 | 34,809,282 | 34,907,651 | Unknown | | C19orf12, PLEKHF1 |
| Amplification | Bx15 | 550k | Breast | 19 | 34,933,380 | 35,170,271 | CCNE1 | 1 | |
| Amplification | Co84C | 317k | Colon | 19 | 34,966,463 | 35,321,409 | CCNE1 | 1 | C19orf12 |
| Amplification | Mx41x | 317k | Colon | 19 | 35,644,646 | 35,653,314 | Unknown | | |
| Amplification | Co84C | 317k | Colon | 19 | 36,281,540 | 36,385,232 | Unknown | | |

FROM FIG. 10V

| | | | | | | | | |
|---|---|---|---|---|---|---|---|---|
| Amplification | Bx17 | 550k | Breast | 19 | 37,028,650 | 37,085,651 | Unknown | |
| Amplification | Bx17 | 550k | Breast | 19 | 37,543,985 | 38,024,995 | Unknown | ANKRD27, FLJ45744, LOC147991, PDCD5 |
| Amplification | Mx43x | 317k | Colon | 19 | 38,570,677 | 38,594,649 | Unknown | |
| Amplification | Co82C | 550k | Colon | 19 | 43,834,169 | 44,470,224 | Unknown | CAPN12, ECH1, FBXO17, FBXO27, FLJ16165, FLJ45909, HNRPL, IL28A, IL28B, LGALS4, LGALS7. LOC342897, MRPS12, NFKBIB, PAK4, SARS2, SIRT2 |
| Amplification | Co82C | 550k | Colon | 19 | 44,537,384 | 44,548,086 | Unknown | |
| Amplification | Bx22 | 550k | Breast | 19 | 44,640,619 | 44,651,359 | Unknown | |
| Amplification | Co82C | 550k | Colon | 19 | 44,926,848 | 45,620,784 | ZNF546 3 | AKT2, DYRK1B, FBL, FCGBP, FLJ13265, FLJ36888, HIPK4, LOC163131, LOC284323, MAP3K10, MGC33962, PLD3, PRX, PSMC4 |
| HD | Co111C | 550k | Colon | 19 | 46,291,894 | 46,294,310 | Unknown | CYP2A13 |
| HD | T47D | 550k | Breast | 19 | 48,388,970 | 48,387,680 | Unknown | PSG5 |
| Amplification | Co84C | 317k | Colon | 19 | 49,127,007 | 49,207,192 | ZNF155 3 | ZNF221 |
| Amplification | Bx26 | 550k | Breast | 19 | 49,837,943 | 49,857,752 | Unknown | PVR |
| HD | Bx26 | 550k | Breast | 19 | 51,377,690 | 51,385,102 | Unknown | |
| Amplification | Mx41x | 317k | Colon | 19 | 52,488,640 | 52,504,750 | Unknown | |
| Amplification | B9C | 317k | Breast | 19 | 54,134,745 | 54,137,629 | Unknown | |
| Amplification | Co84C | 317k | Colon | 19 | 54,520,709 | 54,622,533 | Unknown | CD37, DKKL1, TEAD2, TIP39 |
| HD | Bx26 | 550k | Breast | 19 | 56,237,863 | 56,238,454 | Unknown | |
| Amplification | Co84C | 317k | Colon | 19 | 57,427,110 | 57,619,851 | ZNF480 3 | LOC90321, ZNF528, ZNF610 |
| HD | Bx26 | 550k | Breast | 19 | 59,049,576 | 59,059,409 | Unknown | |
| HD | Hx152 | 550k | Colon | 19 | 59,993,623 | 60,018,551 | Unknown | |
| Amplification | Mx38x | 317k | Colon | 19 | 60,270,514 | 60,317,756 | Unknown | EPS8L1 |
| Amplification | Mx41x | 317k | Colon | 19 | 60,290,536 | 60,317,756 | Unknown | |
| Amplification | B2C | 317k | Breast | 19 | 60,431,327 | 60,448,792 | Unknown | |
| Amplification | B6C | 317k | Breast | 19 | 61,301,183 | 61,361,570 | Unknown | |
| Amplification | B9C | 317k | Breast | 19 | 61,301,183 | 61,443,594 | ZSCAN5 3 | GALP, ZNF444 |
| Amplification | B2C | 317k | Breast | 19 | 61,351,554 | 61,361,570 | Unknown | |
| Amplification | Mx26x | 317k | Colon | 19 | 63,583,872 | 63,612,114 | Unknown | RPS5 |
| Amplification | SKBR3 | 550k | Breast | 20 | 9,661,878 | 9,666,199 | Unknown | |
| Amplification | Mx08x | 550k | Colon | 20 | 9,752,835 | 9,829,109 | Unknown | |
| Amplification | UACC812 | 550k | Breast | 20 | 9,996,606 | 10,012,529 | Unknown | |
| HD | Hx130 | 550k | Colon | 20 | 14,690,886 | 14,712,611 | Unknown | |
| HD | Hx130 | 550k | Colon | 20 | 14,742,361 | 14,755,599 | Unknown | |
| HD | Hx130 | 550k | Colon | 20 | 14,770,129 | 15,294,624 | Unknown | |
| HD | Bx20 | 550k | Breast | 20 | 14,796,659 | 15,074,507 | Unknown | |
| HD | Mx29x | 550k | Colon | 20 | 14,873,275 | 14,897,763 | Unknown | |
| HD | Bx10 | 550k | Breast | 20 | 14,940,542 | 15,091,806 | Unknown | |
| HD | Co44C | 317k | Colon | 20 | 14,955,730 | 15,019,428 | Unknown | |
| HD | Mx29x | 550k | Colon | 20 | 14,980,845 | 15,235,316 | Unknown | |
| HD | Mx31x | 550k | Colon | 20 | 15,155,464 | 15,340,520 | Unknown | |
| HD | Bx20 | 550k | Breast | 20 | 15,167,500 | 15,194,701 | Unknown | |
| HD | Bx35 | 550k | Breast | 20 | 16,985,876 | 16,987,959 | Unknown | |
| Amplification | Hx152 | 550k | Colon | 20 | 21,887,656 | 21,933,498 | Unknown | |
| Amplification | Hx152 | 550k | Colon | 20 | 22,052,421 | 22,598,638 | Unknown | FOXA2 |
| Amplification | Co92C | 317k | Colon | 20 | 26,061,643 | 26,257,255 | Unknown | |

FROM FIG. 10W

| Type | Sample | Array | Tissue | Chr | Start | End | Gene | Count | Genes |
|---|---|---|---|---|---|---|---|---|---|
| Amplification | Mx31x | 550k | Colon | 20 | 29,297,270 | 29,721,415 | HM13 | 3 | COX4l2, DEFB115, DEFB116, DEFB118, DEFB119, DEFB121, DEFB123, DEFB124, ID1, REM1 |
| Amplification | Mx27x | 317k | Colon | 20 | 29,597,479 | 29,648,527 | Unknown | | |
| Amplification | Mx27x | 317k | Colon | 20 | 31,340,342 | 31,369,474 | Unknown | | |
| Amplification | UACC812 | 550k | Breast | 20 | 36,606,900 | 36,716,388 | Unknown | | SMAF1 |
| Amplification | Hx190 | 550k | Colon | 20 | 36,817,054 | 36,829,534 | Unknown | | |
| Amplification | Mx08x | 550k | Colon | 20 | 41,337,193 | 41,356,169 | Unknown | | |
| Amplification | Mx08x | 550k | Colon | 20 | 46,932,762 | 46,933,482 | Unknown | | |
| Amplification | UACC812 | 550k | Breast | 20 | 48,407,797 | 48,638,502 | Unknown | | PTPN1 |
| Amplification | UACC812 | 550k | Breast | 20 | 48,701,334 | 48,828,918 | Unknown | | PARD6B |
| Amplification | UACC812 | 550k | Breast | 20 | 48,907,998 | 49,208,846 | Unknown | | ADNP, DPM1, KCNG1, MOCS3 |
| Amplification | Bx14 | 550k | Breast | 20 | 49,535,610 | 49,600,874 | Unknown | | |
| Amplification | Bx14 | 550k | Breast | 20 | 49,999,729 | 50,174,874 | Unknown | | |
| Amplification | Bx23 | 550k | Breast | 20 | 50,031,593 | 50,065,689 | Unknown | | |
| Amplification | Bx14 | 550k | Breast | 20 | 50,218,585 | 50,458,788 | Unknown | | |
| HD | B6C | 317k | Breast | 20 | 52,274,441 | 52,277,689 | Unknown | | |
| Amplification | Bx14 | 550k | Breast | 20 | 53,492,481 | 53,492,826 | Unknown | | |
| Amplification | Bx14 | 550k | Breast | 20 | 56,877,832 | 53,943,150 | Unknown | | |
| Amplification | UACC812 | 550k | Breast | 20 | 55,538,936 | 56,379,407 | Unknown | | C20orf85, C20orf86, PCK1, PPP4R1L, RAB22A, TMEPAI, ZBP1 |
| Amplification | Mx08x | 550k | Colon | 20 | 55,756,135 | 55,756,368 | Unknown | | |
| Amplification | Bx14 | 550k | Breast | 20 | 56,070,883 | 56,153,079 | Unknown | | |
| Amplification | B2C | 317k | Breast | 20 | 56,478,180 | 56,482,644 | Unknown | | |
| Amplification | B2C | 317k | Breast | 20 | 57,338,114 | 57,351,084 | Unknown | | |
| Amplification | UACC812 | 550k | Breast | 20 | 57,788,233 | 58,580,091 | C20orf177 | 3 | CDH26, FLJ33860, LOC284757, PPP1R3D, SYCP2 |
| HD | Hx134 | 550k | Colon | 20 | 58,546,996 | 58,554,851 | Unknown | | |
| Amplification | B2C | 317k | Breast | 20 | 59,414,462 | 59,424,986 | Unknown | | |
| Amplification | B10C | 317k | Breast | 20 | 59,421,571 | 59,424,986 | Unknown | | |
| Amplification | B2C | 317k | Breast | 20 | 60,211,696 | 60,423,470 | Unknown | | ADRM1, CABLES2, FLJ44790, HRH3, LAMA5, OSBPL2, RPS21 |
| Amplification | B10C | 317k | Breast | 20 | 60,220,455 | 60,423,470 | Unknown | | ADRM1, CABLES2, FLJ44790, HRH3, LAMA5, OSBPL2, RPS21 |
| Amplification | B9C | 317k | Breast | 20 | 61,189,376 | 61,192,853 | Unknown | | |
| Amplification | B2C | 317k | Breast | 20 | 61,323,074 | 61,370,750 | Unknown | | BIRC7, C20orf58, |
| Amplification | Mx27x | 317k | Colon | 20 | 61,323,074 | 61,400,462 | Unknown | | ARFGAP1, BIRC7, C20orf58 |
| Amplification | Mx27x | 317k | Colon | 20 | 61,588,512 | 61,683,372 | Unknown | | C20orf149, EEF1A2, MGC5356, PRIC285, PTK6, SRMS |
| Amplification | Mx30x | 317k | Colon | 20 | 61,666,697 | 61,668,792 | Unknown | | |
| Amplification | Mx27x | 317k | Colon | 20 | 61,788,664 | 61,840,441 | ARFRP1 | 3 | TNFRSF6B, ZGPAT |
| Amplification | B5C | 317k | Breast | 21 | 14,557,744 | 15,309,774 | Unknown | | ABCC13, NRIP1, SAMSN1, STCH |
| Amplification | B5C | 317k | Breast | 21 | 15,364,175 | 16,150,021 | Unknown | | |
| Amplification | B5C | 317k | Breast | 21 | 17,799,662 | 18,272,253 | Unknown | | BTG3, C21orf91, CXADR |
| HD | B5C | 317k | Breast | 21 | 35,124,310 | 35,142,549 | Unknown | | RUNX1 |
| Amplification | Bx22 | 550k | Breast | 21 | 36,739,523 | 36,956,042 | Unknown | | CLDN14 |
| Amplification | Bx17 | 550k | Breast | 21 | 40,398,097 | 40,401,568 | Unknown | | |
| Amplification | B5C | 317k | Breast | 21 | 41,214,571 | 41,246,258 | Unknown | | |
| Amplification | B5C | 317k | Breast | 21 | 42,282,167 | 42,286,622 | Unknown | | |
| Amplification | B6C | 317k | Breast | 21 | 44,495,198 | 44,505,581 | Unknown | | |

FROM FIG. 10X

| | | | | | | | | | |
|---|---|---|---|---|---|---|---|---|---|
| HD | UACC893 | 550k | Breast | 22 | 17,001,191 | 17,003,582 | Unknown | | |
| HD | Bx28 | 550k | Breast | 22 | 17,252,341 | 17,382,662 | PRODH | 8 | DGCR6 |
| Amplification | B7C | 317k | Breast | 22 | 22,056,355 | 22,066,659 | Unknown | | |
| Amplification | Bx28 | 550k | Breast | 22 | 28,818,925 | 28,828,761 | Unknown | | |
| Amplification | Mx43x | 317k | Colon | 22 | 38,379,448 | 38,382,686 | Unknown | | |
| HD | UACC893 | 550k | Breast | 22 | 49,104,219 | 49,149,193 | Unknown | | SAPS2 |
| Amplification | Bx8 | 550k | Breast | X | 2,725,457 | 2,770,921 | Unknown | | |
| Amplification | Mx26x | 317k | Colon | X | 3,210,269 | 3,233,704 | Unknown | | |
| Amplification | MDAMB415 | 550k | Breast | X | 4,983,762 | 5,011,331 | Unknown | | |
| Amplification | Bx20 | 550k | Breast | X | 6,093,293 | 6,267,304 | Unknown | | |
| Amplification | Bx20 | 550k | Breast | X | 7,893,418 | 7,894,339 | Unknown | | |
| HD | Bx19 | 550k | Breast | X | 21,138,763 | 21,211,914 | CNKSR2 | 8 | |
| Amplification | Bx15 | 550k | Breast | X | 22,614,412 | 22,614,606 | Unknown | | |
| Amplification | Bx15 | 550k | Breast | X | 24,221,711 | 24,228,487 | Unknown | | |
| HD | Bx35 | 550k | Breast | X | 28,456,060 | 28,489,951 | Unknown | | |
| HD | B7C | 317k | Breast | X | 31,030,131 | 31,430,208 | DMD | 8 | |
| Amplification | MDAMB415 | 550k | Breast | X | 31,633,570 | 31,666,692 | Unknown | | |
| Amplification | MDAMB415 | 550k | Breast | X | 33,318,385 | 33,472,079 | Unknown | | |
| HD | Bx26 | 550k | Breast | X | 33,814,127 | 33,827,684 | Unknown | | |
| Amplification | Mx40x | 550k | Colon | X | 38,271,385 | 38,381,009 | Unknown | | |
| HD | B10C | 317k | Breast | X | 41,487,365 | 46,563,031 | ZNF674 | 8 | CASK, CHST7, CXorf36, DUSP21, EFHC2, FLJ20344, FUNDC1, MAOA, MAOB, NDP, RP2, SLC9A7, UTX |
| Amplification | B3C | 317k | Breast | X | 47,133,705 | 47,138,122 | Unknown | | |
| Amplification | Bx22 | 550k | Breast | X | 48,173,260 | 48,201,207 | Unknown | | RBM3 |
| Amplification | Bx22 | 550k | Breast | X | 48,930,475 | 49,963,580 | CCNB3 | 3 | AKAP4, CLCN5, GAGE1, GAGE2, GAGE4, LOC158572 PAGE1, PAGE4 |
| Amplification | Bx39 | 550k | Breast | X | 50,196,109 | 51,030,747 | Unknown | | BMP15, LOC340602, NUDT10 |
| Amplification | Mx45x | 550k | Colon | X | 50,760,197 | 50,800,476 | Unknown | | |
| Amplification | Bx39 | 550k | Breast | X | 51,185,071 | 51,833,006 | Unknown | | GSPT2, MAGED1, MAGED4 |
| Amplification | B6C | 317k | Breast | X | 51,831,404 | 51,836,733 | Unknown | | |
| HD | Mx43x | 317k | Colon | X | 51,831,404 | 51,900,253 | Unknown | | |
| Amplification | Bx15 | 550k | Breast | X | 54,081,339 | 54,105,666 | Unknown | | |
| Amplification | B4C | 317k | Breast | X | 55,218,064 | 56,892,727 | Unknown | | FOXR2, KLF8, MAGEH1, RRAGB, UBQLN2, USP51 |
| Amplification | Bx28 | 550k | Breast | X | 55,317,221 | 56,144,046 | Unknown | | FOXR2, MAGEH1, RRAGB, USP51 |
| Amplification | Bx45 | 550k | Breast | X | 67,037,602 | 67,639,440 | Unknown | | MGC21416, OPHN1 |
| HD | B2C | 317k | Breast | X | 68,685,785 | 68,708,340 | Unknown | | |
| HD | Hx107 | 550k | Colon | X | 68,708,340 | 68,954,842 | Unknown | | |
| Amplification | Mx26x | 317k | Colon | X | 69,261,796 | 69,261,963 | Unknown | | |
| HD | Hx107 | 550k | Colon | X | 74,606,867 | 74,610,992 | Unknown | | |
| HD | Co82C | 550k | Colon | X | 75,561,827 | 75,612,862 | Unknown | | |
| HD | Bx25 | 550k | Breast | X | 81,205,195 | 81,209,622 | Unknown | | |
| Amplification | Co108C | 317k | Colon | X | 81,368,660 | 81,381,788 | Unknown | | |
| HD | B9C | 317k | Breast | X | 81,875,667 | 81,917,042 | Unknown | | |
| Amplification | B4C | 317k | Breast | X | 82,667,340 | 82,760,635 | Unknown | | |
| HD | B7C | 317k | Breast | X | 82,896,749 | 84,431,661 | SALT1 | 8 | CXorf33, CXorf43, POF1B, RPS6KA6, ZNF6 CPXCR1 |
| Amplification | Bx17 | 550k | Breast | X | 87,458,632 | 87,858,743 | Unknown | | |
| HD | Co111C | 550k | Colon | X | 90,324,299 | 90,363,682 | Unknown | | |

FROM FIG. 10Y

| Type | Sample | Array | Tissue | Chr | Start | End | Gene | Class | Other Genes |
|---|---|---|---|---|---|---|---|---|---|
| Amplification | SKBR3 | 550k | Breast | X | 90,527,578 | 90,869,952 | Unknown | | |
| Amplification | Bx17 | 550k | Breast | X | 94,078,808 | 94,182,134 | Unknown | | |
| HD | Bx20 | 550k | Breast | X | 96,272,322 | 96,344,518 | Unknown | | |
| Amplification | B8C | 550k | Breast | X | 97,796,606 | 97,844,097 | Unknown | | |
| Amplification | B8C | 550k | Breast | X | 100,885,019 | 100,893,688 | Unknown | | |
| Amplification | B8C | 550k | Breast | X | 115,751,282 | 115,852,426 | Unknown | | |
| Amplification | B6C | 317k | Breast | X | 116,443,618 | 116,515,613 | Unknown | | |
| Amplification | B5C | 317k | Breast | X | 117,022,394 | 117,778,434 | Unknown | | DOCK11, IL13RA1, WDR44, ZCCHC12 |
| Amplification | B6C | 317k | Breast | X | 118,419,208 | 118,470,421 | Unknown | | |
| Amplification | B6C | 317k | Breast | X | 120,150,566 | 120,181,741 | Unknown | | |
| Amplification | UACC893 | 550k | Breast | X | 121,198,410 | 121,240,606 | Unknown | | |
| HD | B9C | 317k | Breast | X | 122,032,087 | 122,058,228 | Unknown | | GRIA3 |
| Amplification | UACC893 | 550k | Breast | X | 124,417,864 | 124,611,307 | Unknown | | |
| Amplification | Co108C | 317k | Colon | X | 124,467,889 | 124,940,997 | Unknown | | |
| Amplification | B2C | 317k | Breast | X | 128,272,178 | 128,597,113 | Unknown | | APLN, OCRL, SMARCA1 |
| Amplification | Bx28 | 550k | Breast | X | 130,635,164 | 131,057,127 | Unknown | | LOC90167, MST4 |
| Amplification | B8C | 550k | Breast | X | 130,741,174 | 130,760,288 | Unknown | | |
| Amplification | B2C | 317k | Breast | X | 133,713,773 | 135,083,327 | MOSPD1 | 3 | CT45-1, CT45-5, CXorf48, CXX1, DDX26B, FHL1, MGC27005, MGC39606, SAGE1, SLC9A6, TMEM32, ZNF449, ZNF75 |
| HD | Mx43x | 317k | Colon | X | 135,967,963 | 135,986,233 | Unknown | | |
| Amplification | Bx28 | 550k | Breast | X | 137,832,621 | 137,849,180 | Unknown | | |
| Amplification | Mx38x | 317k | Colon | X | 138,907,455 | 138,939,998 | Unknown | | |
| Amplification | Co19C | 550k | Colon | X | 139,602,340 | 139,612,611 | Unknown | | |
| Amplification | B8C | 550k | Breast | X | 143,701,181 | 143,720,033 | Unknown | | |
| HD | SKBR3 | 550k | Breast | X | 148,222,304 | 148,241,905 | Unknown | | |
| HD | Hx190 | 550k | Colon | X | 150,269,611 | 150,270,518 | Unknown | | |
| Amplification | Mx26x | 317k | Colon | X | 150,812,100 | 150,813,365 | Unknown | | |

Each alteration identified is labeled as either an amplification or homozygous deletion (HD). For each amplification only those genes entirely contained within the alteration are indicated. For each homozygous deletion, only those genes that have at least part of their coding region contained within the alteration are indicated.
*Classes of evidence for the indicated genes: 1: Gene in this amplification is a known oncogene, and mutated or amplified in other samples(s); 2: Gene in this amplification is mutated and amplified in other samples; 3: Gene in this amplification is mutated in other sample(s); 4: Gene in this amplification is amplified in other sample(s); 7: Gene in this homozygous deletion is mutated and deleted in other samples; 8: Gene in this homozygous deletion is mutated in other sample(s); 9: Gene in this homozygous deletion is deleted in other sample(s); **Indicates genes within the alteration in addition to the candidate target gene

FIG. 10Z

SI Table 4. Amplified genes in breast and colorectal cancers

| Gene | Breast Mutations | Breast Amplifications | Colon Mutations | Colon Amplifications | Passenger Probability ||||||||| 
| | | | | | Breast ||| Colon ||| Both tumor types combined |||
| | | | | | Low | Medium | High | Low | Medium | High | Low | Medium | High |
|---|---|---|---|---|---|---|---|---|---|---|---|---|---|
| 7h3 | 0 | 1 | 0 | 0 | 0.57 | 0.68 | 0.92 | 0.97 | 0.97 | 1.00 | 0.62 | 0.70 | 0.93 |
| AADAC | 0 | 1 | 0 | 0 | 0.55 | 0.66 | 0.95 | 0.97 | 0.97 | 1.00 | 0.60 | 0.68 | 0.94 |
| ABCC10 | 0 | 1 | 0 | 0 | 0.57 | 0.68 | 0.92 | 0.97 | 0.97 | 1.00 | 0.62 | 0.70 | 0.93 |
| ABCC13 | 0 | 1 | 0 | 0 | 0.46 | 0.58 | 0.92 | 0.97 | 0.97 | 1.00 | 0.51 | 0.60 | 0.92 |
| ABCC8 | 0 | 1 | 0 | 0 | 0.46 | 0.57 | 0.87 | 0.97 | 0.97 | 1.00 | 0.51 | 0.60 | 0.89 |
| ABHD9 | 0 | 1 | 0 | 0 | 0.57 | 0.68 | 0.95 | 0.97 | 0.97 | 1.00 | 0.62 | 0.70 | 0.95 |
| ACD | 0 | 0 | 0 | 1 | 0.95 | 0.97 | 1.00 | 0.19 | 0.23 | 0.64 | 0.15 | 0.20 | 0.65 |
| ACY3 | 0 | 1 | 0 | 0 | 0.56 | 0.67 | 0.95 | 0.97 | 0.97 | 1.00 | 0.61 | 0.69 | 0.94 |
| ADAM18 | 0 | 2 | 0 | 0 | 0.01 | 0.02 | 0.10 | 0.97 | 0.97 | 1.00 | 0.02 | 0.02 | 0.12 |
| ADAM2 | 0 | 2 | 0 | 0 | 0.01 | 0.02 | 0.10 | 0.97 | 0.97 | 1.00 | 0.02 | 0.02 | 0.12 |
| ADAM32 | 0 | 2 | 0 | 0 | 0.01 | 0.02 | 0.09 | 0.97 | 0.97 | 1.00 | 0.01 | 0.02 | 0.10 |
| ADAM9 | 0 | 2 | 0 | 0 | 0.01 | 0.02 | 0.10 | 0.97 | 0.97 | 1.00 | 0.02 | 0.02 | 0.11 |
| ADCK5 | 0 | 1 | 0 | 0 | 0.56 | 0.66 | 0.95 | 0.97 | 0.97 | 1.00 | 0.60 | 0.69 | 0.94 |
| ADNP | 0 | 1 | 0 | 0 | 0.58 | 0.69 | 0.92 | 0.97 | 0.97 | 1.00 | 0.63 | 0.71 | 0.93 |
| ADRB3 | 0 | 2 | 0 | 0 | 0.03 | 0.04 | 0.28 | 0.97 | 0.97 | 1.00 | 0.03 | 0.05 | 0.26 |
| ADRM1 | 0 | 2 | 0 | 0 | 0.02 | 0.03 | 0.24 | 0.97 | 0.97 | 1.00 | 0.03 | 0.04 | 0.22 |
| AF1Q | 0 | 1 | 0 | 0 | 0.59 | 0.70 | 0.95 | 0.97 | 0.97 | 1.00 | 0.64 | 0.72 | 0.95 |
| AGR2 | 0 | 1 | 0 | 0 | 0.55 | 0.66 | 0.95 | 0.97 | 0.97 | 1.00 | 0.60 | 0.69 | 0.94 |
| AKAP4 | 0 | 1 | 0 | 0 | 0.59 | 0.69 | 0.92 | 0.97 | 0.97 | 1.00 | 0.63 | 0.71 | 0.93 |
| AKAP8 | 1 | 1 | 0 | 0 | 0.01 | 0.06 | 0.23 | 0.97 | 0.97 | 1.00 | 0.08 | 0.16 | 0.39 |
| AKAP8L | 0 | 1 | 0 | 0 | 0.54 | 0.65 | 0.91 | 0.97 | 0.97 | 1.00 | 0.59 | 0.68 | 0.92 |
| AKT2 | 0 | 0 | 0 | 1 | 0.95 | 0.97 | 1.00 | 0.25 | 0.30 | 0.72 | 0.20 | 0.27 | 0.73 |
| ALDH3A1 | 0 | 0 | 0 | 1 | 0.95 | 0.97 | 1.00 | 0.25 | 0.30 | 0.72 | 0.20 | 0.27 | 0.73 |
| ALDH3A2 | 0 | 0 | 0 | 1 | 0.95 | 0.97 | 1.00 | 0.23 | 0.27 | 0.70 | 0.18 | 0.24 | 0.71 |
| ALDOC | 0 | 1 | 0 | 0 | 0.59 | 0.70 | 0.95 | 0.97 | 0.97 | 1.00 | 0.64 | 0.72 | 0.95 |
| ALG8 | 0 | 1 | 0 | 0 | 0.55 | 0.66 | 0.95 | 0.97 | 0.97 | 1.00 | 0.60 | 0.68 | 0.94 |
| ALKBH5 | 0 | 1 | 0 | 0 | 0.53 | 0.64 | 0.94 | 0.97 | 0.97 | 1.00 | 0.57 | 0.66 | 0.94 |
| AMOTL1 | 0 | 1 | 0 | 0 | 0.51 | 0.62 | 0.89 | 0.97 | 0.97 | 1.00 | 0.56 | 0.64 | 0.91 |
| AMPD1 | 0 | 1 | 1 | 0 | 0.56 | 0.67 | 0.91 | 0.25 | 0.42 | 0.51 | 0.09 | 0.14 | 0.17 |
| ANKRD27 | 0 | 1 | 0 | 0 | 0.52 | 0.63 | 0.90 | 0.97 | 0.97 | 1.00 | 0.57 | 0.66 | 0.91 |
| ANP32E | 0 | 1 | 0 | 0 | 0.57 | 0.68 | 0.95 | 0.97 | 0.97 | 1.00 | 0.62 | 0.70 | 0.95 |
| ANXA9 | 0 | 2 | 0 | 0 | 0.02 | 0.03 | 0.24 | 0.97 | 0.97 | 1.00 | 0.03 | 0.04 | 0.23 |
| AP4B1 | 0 | 1 | 0 | 0 | 0.58 | 0.68 | 0.92 | 0.97 | 0.97 | 1.00 | 0.62 | 0.70 | 0.93 |
| APLN | 0 | 1 | 0 | 0 | 0.54 | 0.65 | 0.94 | 0.97 | 0.97 | 1.00 | 0.59 | 0.67 | 0.94 |
| APOBEC2 | 0 | 1 | 0 | 0 | 0.58 | 0.69 | 0.95 | 0.97 | 0.97 | 1.00 | 0.63 | 0.71 | 0.95 |
| AQP10 | 0 | 1 | 0 | 0 | 0.58 | 0.69 | 0.95 | 0.97 | 0.97 | 1.00 | 0.63 | 0.71 | 0.95 |
| ARF6 | 0 | 1 | 0 | 0 | 0.59 | 0.70 | 0.95 | 0.97 | 0.97 | 1.00 | 0.64 | 0.72 | 0.95 |
| ARFGAP1 | 0 | 0 | 0 | 1 | 0.95 | 0.97 | 1.00 | 0.20 | 0.25 | 0.67 | 0.16 | 0.22 | 0.68 |
| ARFRP1 | 1 | 0 | 0 | 1 | 0.07 | 0.35 | 0.90 | 0.19 | 0.23 | 0.64 | 0.01 | 0.01 | 0.12 |
| ARGBP2 | 0 | 1 | 0 | 0 | 0.48 | 0.59 | 0.88 | 0.97 | 0.97 | 1.00 | 0.52 | 0.61 | 0.90 |
| ARID3C | 0 | 1 | 0 | 0 | 0.58 | 0.69 | 0.95 | 0.97 | 0.97 | 1.00 | 0.63 | 0.71 | 0.95 |
| ARL10C | 0 | 1 | 0 | 0 | 0.56 | 0.67 | 0.95 | 0.97 | 0.97 | 1.00 | 0.61 | 0.69 | 0.94 |
| ASH2L | 0 | 2 | 0 | 0 | 0.02 | 0.04 | 0.17 | 0.97 | 0.97 | 1.00 | 0.03 | 0.04 | 0.19 |
| ATPAF2 | 0 | 1 | 0 | 0 | 0.57 | 0.68 | 0.95 | 0.97 | 0.97 | 1.00 | 0.62 | 0.70 | 0.95 |
| BAG4 | 0 | 2 | 0 | 0 | 0.02 | 0.04 | 0.26 | 0.97 | 0.97 | 1.00 | 0.03 | 0.04 | 0.25 |
| BAIAP3 | 0 | 1 | 0 | 0 | 0.55 | 0.66 | 0.91 | 0.97 | 0.97 | 1.00 | 0.60 | 0.68 | 0.92 |
| BCAS2 | 0 | 1 | 1 | 0 | 0.58 | 0.69 | 0.95 | 0.24 | 0.42 | 0.50 | 0.10 | 0.15 | 0.18 |
| BCMP11 | 0 | 1 | 0 | 0 | 0.57 | 0.68 | 0.95 | 0.97 | 0.97 | 1.00 | 0.62 | 0.70 | 0.95 |
| BHLHB2 | 0 | 1 | 0 | 0 | 0.58 | 0.69 | 0.95 | 0.97 | 0.97 | 1.00 | 0.63 | 0.71 | 0.95 |
| BIRC7 | 0 | 1 | 0 | 1 | 0.55 | 0.66 | 0.95 | 0.17 | 0.21 | 0.62 | 0.01 | 0.02 | 0.10 |
| BLM | 0 | 0 | 0 | 1 | 0.95 | 0.97 | 0.99 | 0.11 | 0.14 | 0.50 | 0.09 | 0.12 | 0.44 |
| BLP1 | 0 | 2 | 0 | 0 | 0.03 | 0.04 | 0.28 | 0.97 | 0.97 | 1.00 | 0.03 | 0.05 | 0.26 |
| BMP15 | 0 | 1 | 0 | 0 | 0.58 | 0.69 | 0.95 | 0.97 | 0.97 | 1.00 | 0.63 | 0.71 | 0.95 |
| BNIPL | 0 | 1 | 0 | 0 | 0.57 | 0.68 | 0.95 | 0.97 | 0.97 | 1.00 | 0.62 | 0.70 | 0.95 |
| BOP1 | 0 | 1 | 0 | 0 | 0.53 | 0.64 | 0.94 | 0.97 | 0.97 | 1.00 | 0.58 | 0.67 | 0.94 |
| BRD4 | 0 | 1 | 0 | 0 | 0.56 | 0.67 | 0.91 | 0.97 | 0.97 | 1.00 | 0.61 | 0.69 | 0.93 |
| BRF2 | 0 | 2 | 0 | 0 | 0.02 | 0.04 | 0.26 | 0.97 | 0.97 | 1.00 | 0.03 | 0.04 | 0.25 |
| BTG3 | 0 | 1 | 0 | 0 | 0.55 | 0.66 | 0.95 | 0.97 | 0.97 | 1.00 | 0.60 | 0.68 | 0.94 |
| BYSL | 0 | 1 | 0 | 1 | 0.56 | 0.67 | 0.95 | 0.14 | 0.18 | 0.57 | 0.01 | 0.01 | 0.09 |
| BZRPL1 | 0 | 1 | 0 | 0 | 0.59 | 0.70 | 0.95 | 0.97 | 0.97 | 1.00 | 0.64 | 0.72 | 0.95 |
| C10orf120 | 0 | 0 | 0 | 1 | 0.95 | 0.97 | 1.00 | 0.25 | 0.30 | 0.73 | 0.20 | 0.27 | 0.73 |
| C10orf56 | 1 | 1 | 0 | 0 | 0.00 | 0.03 | 0.46 | 0.97 | 0.97 | 1.00 | 0.05 | 0.09 | 0.62 |
| C11orf13 | 0 | 0 | 0 | 1 | 0.95 | 0.97 | 1.00 | 0.20 | 0.25 | 0.67 | 0.16 | 0.22 | 0.68 |
| C11orf23 | 0 | 2 | 0 | 0 | 0.95 | 0.97 | 0.99 | 0.97 | 0.97 | 1.00 | 0.96 | 0.97 | 0.99 |

FIG. 11A

| Gene | | | | | | | | | | | | |
|---|---|---|---|---|---|---|---|---|---|---|---|---|
| C11orf31 | 0 | 1 | 0 | 0 | 0.58 | 0.69 | 0.95 | 0.97 | 0.97 | 1.00 | 0.63 | 0.71 | 0.95 |
| C12orf14 | 0 | 0 | 0 | 1 | 0.95 | 0.97 | 1.00 | 0.26 | 0.31 | 0.74 | 0.21 | 0.28 | 0.74 |
| C12orf28 | 0 | 1 | 0 | 0 | 0.56 | 0.67 | 0.95 | 0.97 | 0.97 | 1.00 | 0.60 | 0.69 | 0.94 |
| C14orf104 | 0 | 1 | 0 | 0 | 0.58 | 0.68 | 0.95 | 0.97 | 0.97 | 1.00 | 0.63 | 0.71 | 0.95 |
| C14orf151 | 0 | 1 | 0 | 0 | 0.53 | 0.64 | 0.94 | 0.97 | 0.97 | 1.00 | 0.58 | 0.67 | 0.94 |
| C14orf173 | 0 | 1 | 0 | 0 | 0.57 | 0.68 | 0.95 | 0.97 | 0.97 | 1.00 | 0.62 | 0.70 | 0.95 |
| C16orf28 | 0 | 1 | 0 | 0 | 0.57 | 0.68 | 0.95 | 0.97 | 0.97 | 1.00 | 0.62 | 0.70 | 0.95 |
| C17orf32 | 0 | 1 | 0 | 0 | 0.58 | 0.69 | 0.95 | 0.97 | 0.97 | 1.00 | 0.63 | 0.71 | 0.95 |
| C17orf37 | 0 | 4 | 0 | 1 | 0.95 | 0.97 | 1.00 | 0.97 | 0.97 | 1.00 | 0.96 | 0.97 | 1.00 |
| C17orf39 | 0 | 1 | 0 | 0 | 0.55 | 0.66 | 0.95 | 0.97 | 0.97 | 1.00 | 0.60 | 0.68 | 0.94 |
| C19orf12 | 0 | 4 | 0 | 0 | 0.95 | 0.97 | 1.00 | 0.97 | 0.97 | 1.00 | 0.96 | 0.97 | 1.00 |
| C19orf2 | 0 | 1 | 0 | 1 | 0.95 | 0.97 | 1.00 | 0.97 | 0.97 | 1.00 | 0.96 | 0.97 | 1.00 |
| C1orf178 | 0 | 1 | 0 | 0 | 0.57 | 0.68 | 0.95 | 0.97 | 0.97 | 1.00 | 0.62 | 0.70 | 0.95 |
| C1orf32 | 0 | 1 | 0 | 0 | 0.55 | 0.66 | 0.91 | 0.97 | 0.97 | 1.00 | 0.60 | 0.68 | 0.92 |
| C1QDC1 | 0 | 0 | 0 | 1 | 0.95 | 0.97 | 0.99 | 0.22 | 0.26 | 0.69 | 0.18 | 0.24 | 0.63 |
| C1QTNF8 | 0 | 1 | 0 | 0 | 0.57 | 0.68 | 0.95 | 0.97 | 0.97 | 1.00 | 0.62 | 0.70 | 0.95 |
| C20orf149 | 0 | 0 | 0 | 1 | 0.95 | 0.97 | 1.00 | 0.20 | 0.25 | 0.67 | 0.16 | 0.22 | 0.68 |
| C20orf177 | 1 | 1 | 0 | 0 | 0.01 | 0.07 | 0.24 | 0.97 | 0.97 | 1.00 | 0.08 | 0.17 | 0.41 |
| C20orf58 | 0 | 1 | 0 | 1 | 0.55 | 0.66 | 0.95 | 0.17 | 0.21 | 0.62 | 0.01 | 0.02 | 0.10 |
| C20orf85 | 0 | 1 | 0 | 0 | 0.58 | 0.68 | 0.95 | 0.97 | 0.97 | 1.00 | 0.63 | 0.71 | 0.95 |
| C20orf86 | 0 | 1 | 0 | 0 | 0.56 | 0.67 | 0.95 | 0.97 | 0.97 | 1.00 | 0.61 | 0.69 | 0.94 |
| C21orf91 | 0 | 1 | 0 | 0 | 0.54 | 0.65 | 0.94 | 0.97 | 0.97 | 1.00 | 0.59 | 0.67 | 0.94 |
| C2orf19 | 0 | 1 | 0 | 0 | 0.57 | 0.68 | 0.95 | 0.97 | 0.97 | 1.00 | 0.62 | 0.70 | 0.95 |
| C6 | 0 | 1 | 0 | 0 | 0.51 | 0.62 | 0.90 | 0.97 | 0.97 | 1.00 | 0.56 | 0.65 | 0.91 |
| C6orf108 | 0 | 1 | 0 | 0 | 0.59 | 0.70 | 0.95 | 0.97 | 0.97 | 1.00 | 0.64 | 0.72 | 0.95 |
| C6orf109 | 0 | 1 | 0 | 0 | 0.59 | 0.70 | 0.95 | 0.97 | 0.97 | 1.00 | 0.64 | 0.72 | 0.95 |
| C6orf130 | 0 | 1 | 0 | 0 | 0.58 | 0.68 | 0.95 | 0.97 | 0.97 | 1.00 | 0.62 | 0.70 | 0.95 |
| C6orf153 | 0 | 1 | 0 | 0 | 0.59 | 0.70 | 0.95 | 0.97 | 0.97 | 1.00 | 0.64 | 0.72 | 0.95 |
| C6orf154 | 0 | 1 | 0 | 0 | 0.59 | 0.69 | 0.95 | 0.97 | 0.97 | 1.00 | 0.63 | 0.71 | 0.95 |
| C6orf206 | 0 | 1 | 0 | 0 | 0.58 | 0.68 | 0.95 | 0.97 | 0.97 | 1.00 | 0.63 | 0.71 | 0.95 |
| C6orf49 | 0 | 1 | 0 | 1 | 0.59 | 0.70 | 0.95 | 0.20 | 0.25 | 0.67 | 0.02 | 0.02 | 0.14 |
| C7 | 0 | 1 | 0 | 0 | 0.49 | 0.60 | 0.89 | 0.97 | 0.97 | 1.00 | 0.54 | 0.63 | 0.91 |
| C8orf1 | 0 | 1 | 0 | 0 | 0.57 | 0.68 | 0.95 | 0.97 | 0.97 | 1.00 | 0.62 | 0.70 | 0.95 |
| C8orf4 | 0 | 2 | 0 | 0 | 0.03 | 0.04 | 0.28 | 0.97 | 0.97 | 1.00 | 0.03 | 0.05 | 0.26 |
| C9orf165 | 0 | 1 | 0 | 0 | 0.58 | 0.69 | 0.95 | 0.97 | 0.97 | 1.00 | 0.63 | 0.71 | 0.95 |
| C9orf23 | 0 | 1 | 0 | 0 | 0.59 | 0.70 | 0.95 | 0.97 | 0.97 | 1.00 | 0.64 | 0.72 | 0.95 |
| C9orf24 | 0 | 1 | 0 | 0 | 0.56 | 0.67 | 0.95 | 0.97 | 0.97 | 1.00 | 0.61 | 0.69 | 0.94 |
| C9orf25 | 0 | 1 | 0 | 0 | 0.55 | 0.66 | 0.94 | 0.97 | 0.97 | 1.00 | 0.60 | 0.68 | 0.94 |
| C9orf48 | 0 | 1 | 0 | 0 | 0.58 | 0.69 | 0.92 | 0.97 | 0.97 | 1.00 | 0.63 | 0.71 | 0.93 |
| CABLES2 | 0 | 2 | 0 | 0 | 0.02 | 0.03 | 0.20 | 0.97 | 0.97 | 1.00 | 0.02 | 0.03 | 0.19 |
| CACNA1H | 1 | 1 | 0 | 0 | 0.01 | 0.09 | 0.19 | 0.97 | 0.97 | 1.00 | 0.07 | 0.19 | 0.33 |
| CACNB1 | 0 | 3 | 1 | 0 | 0.95 | 0.97 | 1.00 | 0.25 | 0.42 | 0.51 | 0.59 | 0.69 | 0.75 |
| CALB1 | 0 | 1 | 0 | 0 | 0.58 | 0.68 | 0.95 | 0.97 | 0.97 | 1.00 | 0.63 | 0.71 | 0.95 |
| CAPN12 | 0 | 0 | 0 | 1 | 0.95 | 0.97 | 0.99 | 0.25 | 0.30 | 0.73 | 0.20 | 0.27 | 0.67 |
| CARD6 | 0 | 1 | 0 | 0 | 0.57 | 0.68 | 0.92 | 0.97 | 0.97 | 1.00 | 0.62 | 0.70 | 0.93 |
| CASC3 | 0 | 3 | 0 | 1 | 0.95 | 0.97 | 0.99 | 0.97 | 0.97 | 1.00 | 0.96 | 0.97 | 0.99 |
| CASP14 | 0 | 1 | 0 | 0 | 0.56 | 0.67 | 0.95 | 0.97 | 0.97 | 1.00 | 0.61 | 0.69 | 0.94 |
| CASP3 | 0 | 1 | 0 | 0 | 0.57 | 0.68 | 0.95 | 0.97 | 0.97 | 1.00 | 0.62 | 0.70 | 0.95 |
| CAT | 0 | 0 | 0 | 1 | 0.95 | 0.97 | 1.00 | 0.14 | 0.17 | 0.56 | 0.11 | 0.15 | 0.57 |
| CBX3 | 0 | 1 | 0 | 0 | 0.56 | 0.67 | 0.95 | 0.97 | 0.97 | 1.00 | 0.61 | 0.69 | 0.94 |
| CCDC49 | 0 | 2 | 0 | 0 | 0.95 | 0.97 | 1.00 | 0.97 | 0.97 | 1.00 | 0.96 | 0.97 | 1.00 |
| CCNB3 | 0 | 1 | 1 | 0 | 0.56 | 0.67 | 0.91 | 0.25 | 0.42 | 0.51 | 0.09 | 0.14 | 0.17 |
| CCND1 | 0 | 3 | 0 | 0 | 0.00 | 0.00 | 0.00 | 0.97 | 0.97 | 1.00 | 0.00 | 0.00 | 0.00 |
| CCND3 | 0 | 1 | 0 | 1 | 0.58 | 0.69 | 0.95 | 0.19 | 0.23 | 0.64 | 0.01 | 0.02 | 0.13 |
| CCNE1 | 0 | 4 | 0 | 1 | 0.00 | 0.00 | 0.00 | 0.19 | 0.23 | 0.64 | 0.00 | 0.00 | 0.00 |
| CCR7 | 0 | 1 | 0 | 0 | 0.95 | 0.97 | 1.00 | 0.97 | 0.97 | 1.00 | 0.96 | 0.97 | 1.00 |
| CCT2 | 0 | 1 | 0 | 0 | 0.57 | 0.68 | 0.95 | 0.97 | 0.97 | 1.00 | 0.62 | 0.70 | 0.95 |
| CD37 | 0 | 0 | 0 | 1 | 0.95 | 0.97 | 1.00 | 0.20 | 0.25 | 0.67 | 0.16 | 0.22 | 0.68 |
| CD44 | 0 | 0 | 0 | 1 | 0.95 | 0.97 | 0.99 | 0.07 | 0.09 | 0.39 | 0.06 | 0.08 | 0.33 |
| CDC42SE1 | 0 | 1 | 0 | 0 | 0.59 | 0.69 | 0.95 | 0.97 | 0.97 | 1.00 | 0.63 | 0.71 | 0.95 |
| CDC6 | 0 | 2 | 0 | 0 | 0.95 | 0.97 | 1.00 | 0.97 | 0.97 | 1.00 | 0.96 | 0.97 | 1.00 |
| CDH26 | 0 | 1 | 0 | 0 | 0.52 | 0.63 | 0.90 | 0.97 | 0.97 | 1.00 | 0.57 | 0.66 | 0.92 |
| CDX2 | 0 | 0 | 0 | 1 | 0.95 | 0.97 | 1.00 | 0.26 | 0.31 | 0.74 | 0.21 | 0.28 | 0.74 |
| CIB1 | 0 | 0 | 0 | 1 | 0.95 | 0.97 | 1.00 | 0.20 | 0.25 | 0.67 | 0.16 | 0.22 | 0.68 |
| CITED4 | 0 | 1 | 0 | 0 | 0.57 | 0.68 | 0.95 | 0.97 | 0.97 | 1.00 | 0.62 | 0.70 | 0.95 |
| CKLFSF5 | 0 | 1 | 0 | 0 | 0.57 | 0.68 | 0.95 | 0.97 | 0.97 | 1.00 | 0.62 | 0.70 | 0.95 |
| CLCN5 | 0 | 1 | 0 | 0 | 0.59 | 0.69 | 0.92 | 0.97 | 0.97 | 1.00 | 0.63 | 0.71 | 0.93 |
| CLCN7 | 0 | 1 | 0 | 0 | 0.50 | 0.61 | 0.89 | 0.97 | 0.97 | 1.00 | 0.55 | 0.64 | 0.91 |
| CLDN14 | 0 | 1 | 0 | 0 | 0.59 | 0.70 | 0.95 | 0.97 | 0.97 | 1.00 | 0.64 | 0.72 | 0.95 |
| CLNS1A | 0 | 1 | 0 | 0 | 0.58 | 0.68 | 0.95 | 0.97 | 0.97 | 1.00 | 0.63 | 0.71 | 0.95 |

FIG. 11B

| | | | | | | | | | | | | | |
|---|---|---|---|---|---|---|---|---|---|---|---|---|---|
| CNGA3 | 0 | 1 | 0 | 0 | 0.52 | 0.63 | 0.90 | 0.97 | 0.97 | 1.00 | 0.57 | 0.66 | 0.91 |
| CNOT2 | 0 | 1 | 0 | 0 | 0.49 | 0.61 | 0.93 | 0.97 | 0.97 | 1.00 | 0.54 | 0.63 | 0.93 |
| CNTF | 0 | 1 | 0 | 0 | 0.58 | 0.69 | 0.95 | 0.97 | 0.97 | 1.00 | 0.63 | 0.71 | 0.95 |
| CNTFR | 0 | 1 | 0 | 0 | 0.55 | 0.66 | 0.95 | 0.97 | 0.97 | 1.00 | 0.60 | 0.68 | 0.94 |
| CNTN1 | 0 | 1 | 1 | 0 | 0.42 | 0.53 | 0.85 | 0.25 | 0.43 | 0.51 | 0.05 | 0.08 | 0.10 |
| COX4I2 | 0 | 0 | 0 | 1 | 0.95 | 0.97 | 1.00 | 0.25 | 0.30 | 0.73 | 0.20 | 0.27 | 0.73 |
| CPSF1 | 0 | 1 | 0 | 0 | 0.56 | 0.67 | 0.91 | 0.97 | 0.97 | 1.00 | 0.61 | 0.69 | 0.93 |
| CPT1A | 0 | 2 | 0 | 0 | 0.95 | 0.97 | 0.99 | 0.97 | 0.97 | 1.00 | 0.96 | 0.97 | 0.99 |
| CPXCR1 | 0 | 1 | 0 | 0 | 0.58 | 0.68 | 0.95 | 0.97 | 0.97 | 1.00 | 0.62 | 0.70 | 0.95 |
| CRIP3 | 0 | 1 | 0 | 0 | 0.59 | 0.69 | 0.95 | 0.97 | 0.97 | 1.00 | 0.63 | 0.71 | 0.95 |
| CRK7 | 0 | 4 | 0 | 1 | 0.95 | 0.97 | 0.99 | 0.97 | 0.97 | 1.00 | 0.96 | 0.97 | 0.99 |
| CRP | 0 | 1 | 0 | 0 | 0.59 | 0.70 | 0.95 | 0.97 | 0.97 | 1.00 | 0.64 | 0.72 | 0.95 |
| CRTC3 | 0 | 0 | 0 | 1 | 0.95 | 0.97 | 1.00 | 0.10 | 0.12 | 0.46 | 0.08 | 0.11 | 0.47 |
| CRYBA1 | 0 | 1 | 0 | 0 | 0.59 | 0.69 | 0.95 | 0.97 | 0.97 | 1.00 | 0.63 | 0.71 | 0.95 |
| CSDE1 | 0 | 1 | 0 | 0 | 0.54 | 0.65 | 0.91 | 0.97 | 0.97 | 1.00 | 0.59 | 0.68 | 0.92 |
| CSF3 | 0 | 2 | 0 | 1 | 0.95 | 0.97 | 1.00 | 0.97 | 0.97 | 1.00 | 0.96 | 0.97 | 1.00 |
| CT45-1 | 0 | 1 | 0 | 0 | 0.57 | 0.68 | 0.95 | 0.97 | 0.97 | 1.00 | 0.62 | 0.70 | 0.95 |
| CT45-5 | 0 | 1 | 0 | 0 | 0.57 | 0.68 | 0.95 | 0.97 | 0.97 | 1.00 | 0.62 | 0.70 | 0.95 |
| CTEN | 0 | 1 | 1 | 0 | 0.95 | 0.97 | 0.99 | 0.25 | 0.42 | 0.51 | 0.59 | 0.69 | 0.74 |
| CTMP | 0 | 2 | 0 | 0 | 0.02 | 0.04 | 0.25 | 0.97 | 0.97 | 1.00 | 0.03 | 0.04 | 0.24 |
| CTNND1 | 1 | 1 | 0 | 0 | 0.01 | 0.06 | 0.21 | 0.97 | 0.97 | 1.00 | 0.07 | 0.15 | 0.37 |
| CTTN | 0 | 2 | 0 | 0 | 0.95 | 0.97 | 1.00 | 0.97 | 0.97 | 1.00 | 0.96 | 0.97 | 1.00 |
| CUL7 | 0 | 1 | 0 | 0 | 0.58 | 0.69 | 0.92 | 0.97 | 0.97 | 1.00 | 0.63 | 0.71 | 0.93 |
| CUZD1 | 0 | 0 | 0 | 1 | 0.95 | 0.97 | 1.00 | 0.26 | 0.31 | 0.74 | 0.21 | 0.28 | 0.74 |
| CXADR | 0 | 1 | 0 | 0 | 0.48 | 0.59 | 0.93 | 0.97 | 0.97 | 1.00 | 0.52 | 0.61 | 0.92 |
| CXCL3 | 0 | 1 | 0 | 0 | 0.58 | 0.69 | 0.95 | 0.97 | 0.97 | 1.00 | 0.63 | 0.71 | 0.95 |
| CXCL5 | 0 | 1 | 0 | 0 | 0.59 | 0.70 | 0.95 | 0.97 | 0.97 | 1.00 | 0.64 | 0.72 | 0.95 |
| CXorf48 | 0 | 1 | 0 | 0 | 0.55 | 0.66 | 0.95 | 0.97 | 0.97 | 1.00 | 0.60 | 0.68 | 0.94 |
| CXX1 | 0 | 1 | 0 | 0 | 0.57 | 0.68 | 0.95 | 0.97 | 0.97 | 1.00 | 0.62 | 0.70 | 0.95 |
| CYC1 | 0 | 2 | 0 | 0 | 0.02 | 0.03 | 0.23 | 0.97 | 0.97 | 1.00 | 0.03 | 0.04 | 0.22 |
| CYHR1 | 0 | 1 | 0 | 0 | 0.57 | 0.68 | 0.95 | 0.97 | 0.97 | 1.00 | 0.62 | 0.70 | 0.95 |
| CYP4F3 | 0 | 1 | 0 | 0 | 0.55 | 0.66 | 0.94 | 0.97 | 0.97 | 1.00 | 0.60 | 0.68 | 0.94 |
| CYP4F8 | 0 | 1 | 0 | 0 | 0.53 | 0.64 | 0.94 | 0.97 | 0.97 | 1.00 | 0.58 | 0.66 | 0.94 |
| DCLRE1B | 0 | 1 | 0 | 0 | 0.58 | 0.69 | 0.95 | 0.97 | 0.97 | 1.00 | 0.63 | 0.71 | 0.95 |
| DCTN3 | 0 | 1 | 0 | 0 | 0.58 | 0.68 | 0.95 | 0.97 | 0.97 | 1.00 | 0.63 | 0.71 | 0.95 |
| DDHD2 | 0 | 2 | 0 | 0 | 0.02 | 0.04 | 0.17 | 0.97 | 0.97 | 1.00 | 0.03 | 0.04 | 0.20 |
| DDX11 | 0 | 0 | 0 | 1 | 0.95 | 0.97 | 0.99 | 0.25 | 0.30 | 0.73 | 0.20 | 0.27 | 0.67 |
| DDX26B | 0 | 1 | 0 | 0 | 0.54 | 0.65 | 0.94 | 0.97 | 0.97 | 1.00 | 0.59 | 0.67 | 0.94 |
| DECR1 | 0 | 1 | 0 | 0 | 0.55 | 0.65 | 0.94 | 0.97 | 0.97 | 1.00 | 0.59 | 0.68 | 0.94 |
| DEFB115 | 0 | 0 | 0 | 1 | 0.95 | 0.97 | 1.00 | 0.26 | 0.31 | 0.74 | 0.21 | 0.28 | 0.74 |
| DEFB116 | 0 | 0 | 0 | 1 | 0.95 | 0.97 | 1.00 | 0.24 | 0.29 | 0.72 | 0.20 | 0.26 | 0.73 |
| DEFB118 | 0 | 0 | 0 | 1 | 0.95 | 0.97 | 1.00 | 0.26 | 0.31 | 0.74 | 0.21 | 0.28 | 0.74 |
| DEFB119 | 0 | 0 | 0 | 1 | 0.95 | 0.97 | 1.00 | 0.25 | 0.30 | 0.72 | 0.20 | 0.27 | 0.73 |
| DEFB121 | 0 | 0 | 0 | 1 | 0.95 | 0.97 | 1.00 | 0.26 | 0.31 | 0.74 | 0.21 | 0.28 | 0.74 |
| DEFB123 | 0 | 0 | 0 | 1 | 0.95 | 0.97 | 1.00 | 0.25 | 0.30 | 0.72 | 0.20 | 0.27 | 0.73 |
| DEFB124 | 0 | 0 | 0 | 1 | 0.95 | 0.97 | 1.00 | 0.26 | 0.31 | 0.74 | 0.21 | 0.28 | 0.74 |
| DGAT1 | 0 | 1 | 0 | 0 | 0.57 | 0.68 | 0.95 | 0.97 | 0.97 | 1.00 | 0.62 | 0.70 | 0.95 |
| DKFZp761 | 0 | 1 | 0 | 0 | 0.59 | 0.69 | 0.95 | 0.97 | 0.97 | 1.00 | 0.63 | 0.71 | 0.95 |
| DKKL1 | 0 | 0 | 0 | 1 | 0.95 | 0.97 | 1.00 | 0.16 | 0.20 | 0.60 | 0.13 | 0.17 | 0.61 |
| DMBT1 | 0 | 0 | 0 | 1 | 0.95 | 0.97 | 0.99 | 0.26 | 0.31 | 0.74 | 0.21 | 0.28 | 0.69 |
| DNAI1 | 0 | 1 | 0 | 0 | 0.52 | 0.64 | 0.90 | 0.97 | 0.97 | 1.00 | 0.57 | 0.66 | 0.92 |
| DOCK11 | 0 | 1 | 0 | 0 | 0.46 | 0.58 | 0.88 | 0.97 | 0.97 | 1.00 | 0.51 | 0.60 | 0.89 |
| DPM1 | 0 | 1 | 0 | 0 | 0.56 | 0.67 | 0.95 | 0.97 | 0.97 | 1.00 | 0.61 | 0.69 | 0.94 |
| DRG2 | 0 | 1 | 0 | 0 | 0.53 | 0.64 | 0.94 | 0.97 | 0.97 | 1.00 | 0.58 | 0.66 | 0.94 |
| DYM | 0 | 1 | 0 | 0 | 0.39 | 0.50 | 0.90 | 0.97 | 0.97 | 1.00 | 0.44 | 0.53 | 0.89 |
| DYRK1B | 0 | 0 | 0 | 1 | 0.95 | 0.97 | 0.99 | 0.25 | 0.30 | 0.73 | 0.20 | 0.27 | 0.67 |
| ECH1 | 0 | 0 | 0 | 1 | 0.95 | 0.97 | 1.00 | 0.23 | 0.28 | 0.71 | 0.19 | 0.25 | 0.72 |
| ECOP | 0 | 0 | 0 | 1 | 0.95 | 0.97 | 1.00 | 0.97 | 0.97 | 1.00 | 0.96 | 0.97 | 1.00 |
| EDEM1 | 1 | 1 | 0 | 0 | 0.01 | 0.06 | 0.22 | 0.97 | 0.97 | 1.00 | 0.08 | 0.16 | 0.39 |
| EEF1A2 | 0 | 0 | 0 | 1 | 0.95 | 0.97 | 1.00 | 0.19 | 0.23 | 0.64 | 0.15 | 0.20 | 0.65 |
| EGFL9 | 0 | 1 | 0 | 0 | 0.58 | 0.69 | 0.95 | 0.97 | 0.97 | 1.00 | 0.63 | 0.71 | 0.95 |
| EGFR | 0 | 0 | 0 | 2 | 0.95 | 0.97 | 0.99 | 0.00 | 0.00 | 0.01 | 0.00 | 0.00 | 0.01 |
| EHF | 0 | 0 | 0 | 1 | 0.95 | 0.97 | 1.00 | 0.16 | 0.20 | 0.61 | 0.13 | 0.18 | 0.62 |
| EIF4EBP1 | 0 | 2 | 0 | 0 | 0.03 | 0.04 | 0.28 | 0.97 | 0.97 | 1.00 | 0.03 | 0.05 | 0.26 |
| ELF5 | 0 | 0 | 0 | 1 | 0.95 | 0.97 | 1.00 | 0.14 | 0.17 | 0.56 | 0.11 | 0.15 | 0.57 |
| ELOVL5 | 0 | 1 | 0 | 0 | 0.58 | 0.68 | 0.95 | 0.97 | 0.97 | 1.00 | 0.62 | 0.70 | 0.95 |
| EME2 | 0 | 1 | 0 | 1 | 0.57 | 0.68 | 0.95 | 0.20 | 0.25 | 0.67 | 0.01 | 0.02 | 0.13 |
| EMR2 | 0 | 1 | 0 | 0 | 0.52 | 0.63 | 0.90 | 0.97 | 0.97 | 1.00 | 0.57 | 0.65 | 0.91 |
| EN2 | 0 | 1 | 0 | 0 | 0.56 | 0.67 | 0.95 | 0.97 | 0.97 | 1.00 | 0.61 | 0.69 | 0.94 |
| ENSA | 0 | 1 | 0 | 0 | 0.57 | 0.68 | 0.95 | 0.97 | 0.97 | 1.00 | 0.62 | 0.70 | 0.95 |

FIG. 11C

| | | | | | | | | | | | | | |
|---|---|---|---|---|---|---|---|---|---|---|---|---|---|
| EPPB9 | 0 | 0 | 0 | 2 | 0.95 | 0.97 | 1.00 | 0.00 | 0.00 | 0.01 | 0.00 | 0.00 | 0.01 |
| EPS8L1 | 0 | 0 | 0 | 1 | 0.95 | 0.97 | 0.99 | 0.16 | 0.20 | 0.60 | 0.13 | 0.17 | 0.54 |
| ERBB2 | 0 | 4 | 0 | 1 | 0.00 | 0.00 | 0.00 | 0.26 | 0.31 | 0.73 | 0.00 | 0.00 | 0.00 |
| EVX1 | 0 | 1 | 0 | 0 | 0.57 | 0.68 | 0.95 | 0.97 | 0.97 | 1.00 | 0.62 | 0.70 | 0.95 |
| EXOSC3 | 1 | 1 | 0 | 0 | 0.01 | 0.04 | 0.56 | 0.97 | 0.97 | 1.00 | 0.08 | 0.14 | 0.71 |
| EXOSC4 | 0 | 2 | 0 | 0 | 0.02 | 0.03 | 0.24 | 0.97 | 0.97 | 1.00 | 0.03 | 0.04 | 0.22 |
| F2RL3 | 0 | 1 | 0 | 0 | 0.56 | 0.67 | 0.95 | 0.97 | 0.97 | 1.00 | 0.61 | 0.69 | 0.94 |
| FADD | 0 | 3 | 0 | 0 | 0.95 | 0.97 | 1.00 | 0.97 | 0.97 | 1.00 | 0.96 | 0.97 | 1.00 |
| FAM78B | 0 | 1 | 0 | 0 | 0.49 | 0.60 | 0.93 | 0.97 | 0.97 | 1.00 | 0.54 | 0.63 | 0.93 |
| FBL | 0 | 0 | 0 | 1 | 0.95 | 0.97 | 1.00 | 0.24 | 0.28 | 0.71 | 0.19 | 0.25 | 0.72 |
| FBXL20 | 0 | 4 | 0 | 0 | 0.95 | 0.97 | 1.00 | 0.97 | 0.97 | 1.00 | 0.96 | 0.97 | 1.00 |
| FBXL6 | 0 | 1 | 0 | 0 | 0.56 | 0.67 | 0.95 | 0.97 | 0.97 | 1.00 | 0.61 | 0.69 | 0.94 |
| FBXO17 | 0 | 0 | 0 | 1 | 0.95 | 0.97 | 1.00 | 0.26 | 0.31 | 0.73 | 0.21 | 0.28 | 0.74 |
| FBXO27 | 0 | 0 | 0 | 1 | 0.95 | 0.97 | 1.00 | 0.26 | 0.31 | 0.74 | 0.21 | 0.28 | 0.74 |
| FBXO47 | 0 | 2 | 0 | 0 | 0.95 | 0.97 | 1.00 | 0.97 | 0.97 | 1.00 | 0.96 | 0.97 | 1.00 |
| FBXO9 | 0 | 1 | 0 | 0 | 0.57 | 0.67 | 0.95 | 0.97 | 0.97 | 1.00 | 0.61 | 0.70 | 0.94 |
| FCGBP | 0 | 0 | 0 | 1 | 0.95 | 0.97 | 0.80 | 0.23 | 0.28 | 0.70 | 0.18 | 0.25 | 0.08 |
| FES | 0 | 0 | 0 | 1 | 0.95 | 0.97 | 0.99 | 0.20 | 0.25 | 0.67 | 0.16 | 0.22 | 0.61 |
| FGF19 | 0 | 3 | 0 | 0 | 0.95 | 0.97 | 1.00 | 0.97 | 0.97 | 1.00 | 0.96 | 0.97 | 1.00 |
| FGF3 | 0 | 3 | 0 | 0 | 0.95 | 0.97 | 1.00 | 0.97 | 0.97 | 1.00 | 0.96 | 0.97 | 1.00 |
| FGF4 | 0 | 3 | 0 | 0 | 0.95 | 0.97 | 1.00 | 0.97 | 0.97 | 1.00 | 0.96 | 0.97 | 1.00 |
| FGFR1 | 0 | 2 | 0 | 0 | 0.02 | 0.04 | 0.24 | 0.97 | 0.97 | 1.00 | 0.03 | 0.04 | 0.23 |
| FGFR2 | 1 | 0 | 0 | 1 | 0.12 | 0.49 | 0.80 | 0.19 | 0.24 | 0.66 | 0.01 | 0.02 | 0.07 |
| FGIF | 0 | 1 | 0 | 0 | 0.57 | 0.68 | 0.95 | 0.97 | 0.97 | 1.00 | 0.62 | 0.70 | 0.95 |
| FHL1 | 0 | 1 | 0 | 0 | 0.56 | 0.67 | 0.95 | 0.97 | 0.97 | 1.00 | 0.61 | 0.69 | 0.94 |
| FKBP9L | 0 | 0 | 0 | 1 | 0.95 | 0.97 | 1.00 | 0.97 | 0.97 | 1.00 | 0.96 | 0.97 | 1.00 |
| FLCN | 0 | 1 | 0 | 0 | 0.55 | 0.66 | 0.91 | 0.97 | 0.97 | 1.00 | 0.60 | 0.68 | 0.92 |
| FLG | 0 | 1 | 0 | 0 | 0.58 | 0.69 | 0.95 | 0.97 | 0.97 | 1.00 | 0.63 | 0.71 | 0.95 |
| FLG2 | 1 | 1 | 0 | 0 | 0.00 | 0.02 | 0.13 | 0.97 | 0.97 | 1.00 | 0.07 | 0.09 | 0.26 |
| FLII | 0 | 1 | 0 | 0 | 0.56 | 0.67 | 0.91 | 0.97 | 0.97 | 1.00 | 0.61 | 0.69 | 0.93 |
| FLJ11200 | 0 | 1 | 0 | 0 | 0.55 | 0.66 | 0.95 | 0.97 | 0.97 | 1.00 | 0.60 | 0.69 | 0.94 |
| FLJ11280 | 0 | 1 | 0 | 0 | 0.58 | 0.69 | 0.95 | 0.97 | 0.97 | 1.00 | 0.63 | 0.71 | 0.95 |
| FLJ13265 | 0 | 0 | 0 | 1 | 0.95 | 0.97 | 1.00 | 0.25 | 0.30 | 0.73 | 0.20 | 0.27 | 0.73 |
| FLJ14904 | 0 | 1 | 0 | 0 | 0.55 | 0.66 | 0.95 | 0.97 | 0.97 | 1.00 | 0.60 | 0.69 | 0.94 |
| FLJ16165 | 0 | 0 | 0 | 1 | 0.95 | 0.97 | 1.00 | 0.22 | 0.27 | 0.69 | 0.18 | 0.24 | 0.70 |
| FLJ20519 | 0 | 1 | 0 | 0 | 0.59 | 0.70 | 0.95 | 0.97 | 0.97 | 1.00 | 0.64 | 0.72 | 0.95 |
| FLJ21168 | 0 | 1 | 0 | 0 | 0.59 | 0.70 | 0.95 | 0.97 | 0.97 | 1.00 | 0.64 | 0.72 | 0.95 |
| FLJ23441 | 0 | 1 | 0 | 0 | 0.52 | 0.63 | 0.94 | 0.97 | 0.97 | 1.00 | 0.57 | 0.66 | 0.93 |
| FLJ23467 | 0 | 1 | 0 | 0 | 0.59 | 0.70 | 0.95 | 0.97 | 0.97 | 1.00 | 0.64 | 0.72 | 0.95 |
| FLJ25006 | 0 | 1 | 0 | 0 | 0.59 | 0.70 | 0.95 | 0.97 | 0.97 | 1.00 | 0.64 | 0.72 | 0.95 |
| FLJ31196 | 0 | 0 | 0 | 1 | 0.95 | 0.97 | 1.00 | 0.24 | 0.29 | 0.71 | 0.19 | 0.26 | 0.72 |
| FLJ33167 | 0 | 1 | 0 | 0 | 0.56 | 0.67 | 0.95 | 0.97 | 0.97 | 1.00 | 0.61 | 0.69 | 0.94 |
| FLJ33860 | 0 | 1 | 0 | 0 | 0.59 | 0.70 | 0.95 | 0.97 | 0.97 | 1.00 | 0.64 | 0.72 | 0.95 |
| FLJ36840 | 0 | 1 | 0 | 0 | 0.59 | 0.70 | 0.95 | 0.97 | 0.97 | 1.00 | 0.64 | 0.72 | 0.95 |
| FLJ36888 | 0 | 0 | 0 | 1 | 0.95 | 0.97 | 1.00 | 0.25 | 0.30 | 0.73 | 0.20 | 0.27 | 0.73 |
| FLJ37099 | 0 | 1 | 0 | 0 | 0.57 | 0.68 | 0.92 | 0.97 | 0.97 | 1.00 | 0.62 | 0.70 | 0.93 |
| FLJ37538 | 0 | 1 | 0 | 0 | 0.57 | 0.68 | 0.92 | 0.97 | 0.97 | 1.00 | 0.62 | 0.70 | 0.93 |
| FLJ39501 | 0 | 1 | 0 | 0 | 0.53 | 0.64 | 0.94 | 0.97 | 0.97 | 1.00 | 0.57 | 0.66 | 0.94 |
| FLJ40243 | 0 | 1 | 0 | 0 | 0.47 | 0.58 | 0.88 | 0.97 | 0.97 | 1.00 | 0.52 | 0.61 | 0.90 |
| FLJ40365 | 0 | 1 | 0 | 0 | 0.54 | 0.65 | 0.94 | 0.97 | 0.97 | 1.00 | 0.59 | 0.68 | 0.94 |
| FLJ40504 | 0 | 1 | 0 | 0 | 0.56 | 0.67 | 0.95 | 0.97 | 0.97 | 1.00 | 0.61 | 0.69 | 0.94 |
| FLJ41484 | 0 | 0 | 0 | 1 | 0.95 | 0.97 | 1.00 | 0.20 | 0.24 | 0.67 | 0.16 | 0.22 | 0.67 |
| FLJ42258 | 0 | 3 | 0 | 0 | 0.95 | 0.97 | 1.00 | 0.97 | 0.97 | 1.00 | 0.96 | 0.97 | 1.00 |
| FLJ42486 | 0 | 1 | 0 | 0 | 0.56 | 0.67 | 0.95 | 0.97 | 0.97 | 1.00 | 0.61 | 0.69 | 0.94 |
| FLJ43582 | 0 | 2 | 0 | 0 | 0.02 | 0.03 | 0.24 | 0.97 | 0.97 | 1.00 | 0.03 | 0.04 | 0.22 |
| FLJ43826 | 0 | 2 | 0 | 0 | 0.95 | 0.97 | 1.00 | 0.97 | 0.97 | 1.00 | 0.96 | 0.97 | 1.00 |
| FLJ43855 | 0 | 0 | 0 | 1 | 0.95 | 0.97 | 1.00 | 0.26 | 0.31 | 0.74 | 0.21 | 0.28 | 0.74 |
| FLJ44060 | 0 | 0 | 0 | 1 | 0.95 | 0.97 | 1.00 | 0.97 | 0.97 | 1.00 | 0.96 | 0.97 | 1.00 |
| FLJ44790 | 0 | 2 | 0 | 0 | 0.02 | 0.03 | 0.22 | 0.97 | 0.97 | 1.00 | 0.02 | 0.03 | 0.21 |
| FLJ44861 | 0 | 0 | 0 | 1 | 0.95 | 0.97 | 1.00 | 0.18 | 0.22 | 0.64 | 0.15 | 0.20 | 0.65 |
| FLJ44894 | 0 | 1 | 0 | 0 | 0.55 | 0.66 | 0.94 | 0.97 | 0.97 | 1.00 | 0.60 | 0.68 | 0.94 |
| FLJ45721 | 0 | 1 | 0 | 0 | 0.55 | 0.66 | 0.95 | 0.97 | 0.97 | 1.00 | 0.60 | 0.68 | 0.94 |
| FLJ45744 | 0 | 1 | 0 | 0 | 0.59 | 0.70 | 0.95 | 0.97 | 0.97 | 1.00 | 0.64 | 0.72 | 0.95 |
| FLJ45909 | 0 | 0 | 0 | 1 | 0.95 | 0.97 | 1.00 | 0.26 | 0.31 | 0.74 | 0.21 | 0.28 | 0.74 |
| FLJ45974 | 0 | 0 | 0 | 1 | 0.95 | 0.97 | 1.00 | 0.97 | 0.97 | 1.00 | 0.96 | 0.97 | 1.00 |
| FLJ46247 | 0 | 1 | 0 | 0 | 0.55 | 0.66 | 0.91 | 0.97 | 0.97 | 1.00 | 0.60 | 0.68 | 0.92 |
| FLT3 | 0 | 0 | 0 | 1 | 0.95 | 0.97 | 0.99 | 0.19 | 0.23 | 0.64 | 0.15 | 0.20 | 0.59 |
| FOXA2 | 0 | 0 | 0 | 1 | 0.95 | 0.97 | 1.00 | 0.26 | 0.31 | 0.74 | 0.21 | 0.28 | 0.74 |
| FOXH1 | 0 | 1 | 0 | 0 | 0.57 | 0.68 | 0.95 | 0.97 | 0.97 | 1.00 | 0.62 | 0.70 | 0.95 |
| FOXN1 | 0 | 1 | 0 | 0 | 0.56 | 0.67 | 0.95 | 0.97 | 0.97 | 1.00 | 0.61 | 0.70 | 0.94 |

FIG. 11D

| | | | | | | | | | | | | | |
|---|---|---|---|---|---|---|---|---|---|---|---|---|---|
| FOXP4 | 1 | 1 | 0 | 1 | 0.01 | 0.08 | 0.21 | 0.15 | 0.18 | 0.58 | 0.00 | 0.00 | 0.00 |
| FOXR2 | 0 | 2 | 0 | 0 | 0.03 | 0.04 | 0.28 | 0.97 | 0.97 | 1.00 | 0.03 | 0.05 | 0.26 |
| FRS2 | 0 | 1 | 0 | 0 | 0.52 | 0.63 | 0.94 | 0.97 | 0.97 | 1.00 | 0.56 | 0.65 | 0.93 |
| FRS3 | 0 | 1 | 0 | 1 | 0.59 | 0.70 | 0.95 | 0.20 | 0.25 | 0.67 | 0.02 | 0.02 | 0.14 |
| FURIN | 0 | 0 | 0 | 1 | 0.95 | 0.97 | 0.99 | 0.20 | 0.25 | 0.67 | 0.16 | 0.22 | 0.61 |
| FUT4 | 0 | 1 | 0 | 0 | 0.57 | 0.68 | 0.95 | 0.97 | 0.97 | 1.00 | 0.62 | 0.70 | 0.95 |
| GAB2 | 0 | 1 | 0 | 0 | 0.50 | 0.61 | 0.89 | 0.97 | 0.97 | 1.00 | 0.54 | 0.63 | 0.91 |
| GABRA5 | 0 | 1 | 0 | 0 | 0.54 | 0.65 | 0.94 | 0.97 | 0.97 | 1.00 | 0.59 | 0.67 | 0.94 |
| GAGE1 | 0 | 1 | 0 | 0 | 0.59 | 0.70 | 0.95 | 0.97 | 0.97 | 1.00 | 0.64 | 0.72 | 0.95 |
| GAGE2 | 0 | 1 | 0 | 0 | 0.59 | 0.70 | 0.95 | 0.97 | 0.97 | 1.00 | 0.64 | 0.72 | 0.95 |
| GAGE4 | 0 | 1 | 0 | 0 | 0.59 | 0.70 | 0.95 | 0.97 | 0.97 | 1.00 | 0.64 | 0.72 | 0.95 |
| GAL | 0 | 2 | 0 | 0 | 0.95 | 0.97 | 1.00 | 0.97 | 0.97 | 1.00 | 0.96 | 0.97 | 1.00 |
| GALP | 0 | 1 | 0 | 0 | 0.55 | 0.66 | 0.95 | 0.97 | 0.97 | 1.00 | 0.60 | 0.68 | 0.94 |
| GALT | 0 | 1 | 0 | 0 | 0.59 | 0.70 | 0.95 | 0.97 | 0.97 | 1.00 | 0.64 | 0.72 | 0.95 |
| GAS6 | 0 | 0 | 0 | 1 | 0.95 | 0.97 | 0.99 | 0.14 | 0.17 | 0.56 | 0.11 | 0.15 | 0.50 |
| GCLC | 0 | 1 | 0 | 0 | 0.52 | 0.63 | 0.94 | 0.97 | 0.97 | 1.00 | 0.57 | 0.66 | 0.93 |
| GCM1 | 0 | 1 | 0 | 0 | 0.57 | 0.67 | 0.95 | 0.97 | 0.97 | 1.00 | 0.61 | 0.70 | 0.94 |
| GFER | 0 | 1 | 0 | 0 | 0.57 | 0.68 | 0.95 | 0.97 | 0.97 | 1.00 | 0.62 | 0.70 | 0.95 |
| GJC1 | 0 | 2 | 0 | 0 | 0.95 | 0.97 | 1.00 | 0.97 | 0.97 | 1.00 | 0.96 | 0.97 | 1.00 |
| GNA14 | 0 | 1 | 0 | 0 | 0.38 | 0.50 | 0.90 | 0.97 | 0.97 | 1.00 | 0.43 | 0.52 | 0.89 |
| GNMT | 0 | 1 | 0 | 0 | 0.59 | 0.70 | 0.95 | 0.97 | 0.97 | 1.00 | 0.64 | 0.72 | 0.95 |
| GNPTG | 0 | 1 | 0 | 0 | 0.56 | 0.67 | 0.95 | 0.97 | 0.97 | 1.00 | 0.61 | 0.69 | 0.94 |
| GOT1L1 | 0 | 2 | 0 | 0 | 0.03 | 0.04 | 0.28 | 0.97 | 0.97 | 1.00 | 0.03 | 0.05 | 0.26 |
| GPAA1 | 0 | 2 | 0 | 0 | 0.02 | 0.03 | 0.24 | 0.97 | 0.97 | 1.00 | 0.03 | 0.04 | 0.22 |
| GPBP1 | 0 | 1 | 1 | 0 | 0.56 | 0.67 | 0.95 | 0.24 | 0.42 | 0.51 | 0.09 | 0.14 | 0.17 |
| GPR124 | 0 | 2 | 1 | 0 | 0.02 | 0.03 | 0.12 | 0.25 | 0.42 | 0.51 | 0.00 | 0.00 | 0.00 |
| GPR172A | 0 | 1 | 0 | 0 | 0.57 | 0.68 | 0.95 | 0.97 | 0.97 | 1.00 | 0.62 | 0.70 | 0.95 |
| GPR83 | 0 | 1 | 0 | 0 | 0.55 | 0.66 | 0.94 | 0.97 | 0.97 | 1.00 | 0.60 | 0.68 | 0.94 |
| GPT | 0 | 1 | 0 | 0 | 0.56 | 0.67 | 0.95 | 0.97 | 0.97 | 1.00 | 0.61 | 0.69 | 0.94 |
| GRB7 | 0 | 4 | 0 | 1 | 0.95 | 0.97 | 1.00 | 0.97 | 0.97 | 1.00 | 0.96 | 0.97 | 1.00 |
| GRINA | 0 | 2 | 0 | 0 | 0.02 | 0.03 | 0.24 | 0.97 | 0.97 | 1.00 | 0.03 | 0.04 | 0.22 |
| GSDM1 | 0 | 3 | 0 | 1 | 0.95 | 0.97 | 1.00 | 0.97 | 0.97 | 1.00 | 0.96 | 0.97 | 1.00 |
| GSDML | 1 | 4 | 0 | 1 | 0.12 | 0.48 | 0.80 | 0.97 | 0.97 | 1.00 | 0.54 | 0.73 | 0.90 |
| GSH1 | 0 | 0 | 0 | 1 | 0.95 | 0.97 | 1.00 | 0.26 | 0.31 | 0.74 | 0.21 | 0.28 | 0.74 |
| GSPT2 | 0 | 1 | 0 | 0 | 0.59 | 0.70 | 0.92 | 0.97 | 0.97 | 1.00 | 0.64 | 0.72 | 0.93 |
| GSTA1 | 0 | 1 | 0 | 0 | 0.58 | 0.69 | 0.95 | 0.97 | 0.97 | 1.00 | 0.63 | 0.71 | 0.95 |
| GSTA2 | 0 | 1 | 0 | 0 | 0.58 | 0.69 | 0.95 | 0.97 | 0.97 | 1.00 | 0.63 | 0.71 | 0.95 |
| GSTA3 | 0 | 1 | 0 | 0 | 0.58 | 0.69 | 0.95 | 0.97 | 0.97 | 1.00 | 0.63 | 0.71 | 0.95 |
| GSTA4 | 0 | 1 | 0 | 0 | 0.55 | 0.66 | 0.95 | 0.97 | 0.97 | 1.00 | 0.60 | 0.69 | 0.94 |
| GSTA5 | 0 | 1 | 0 | 0 | 0.59 | 0.69 | 0.95 | 0.97 | 0.97 | 1.00 | 0.63 | 0.71 | 0.95 |
| GTPBP2 | 0 | 1 | 0 | 0 | 0.59 | 0.70 | 0.92 | 0.97 | 0.97 | 1.00 | 0.64 | 0.72 | 0.93 |
| GUCA1A | 0 | 1 | 0 | 1 | 0.58 | 0.69 | 0.95 | 0.20 | 0.24 | 0.66 | 0.01 | 0.02 | 0.14 |
| GUCA1B | 0 | 1 | 0 | 1 | 0.58 | 0.69 | 0.95 | 0.20 | 0.24 | 0.66 | 0.01 | 0.02 | 0.14 |
| HAS2 | 0 | 1 | 0 | 0 | 0.57 | 0.67 | 0.95 | 0.97 | 0.97 | 1.00 | 0.61 | 0.70 | 0.94 |
| HBXAP | 0 | 1 | 0 | 0 | 0.53 | 0.64 | 0.90 | 0.97 | 0.97 | 1.00 | 0.58 | 0.67 | 0.92 |
| HCG9 | 0 | 1 | 0 | 0 | 0.58 | 0.68 | 0.95 | 0.97 | 0.97 | 1.00 | 0.62 | 0.70 | 0.95 |
| HCP1 | 0 | 1 | 0 | 0 | 0.57 | 0.68 | 0.95 | 0.97 | 0.97 | 1.00 | 0.62 | 0.70 | 0.95 |
| HEAB | 0 | 1 | 0 | 0 | 0.59 | 0.70 | 0.95 | 0.97 | 0.97 | 1.00 | 0.64 | 0.72 | 0.95 |
| HIPK1 | 0 | 1 | 0 | 0 | 0.57 | 0.68 | 0.92 | 0.97 | 0.97 | 1.00 | 0.62 | 0.70 | 0.93 |
| HIPK4 | 0 | 0 | 0 | 1 | 0.95 | 0.97 | 0.99 | 0.24 | 0.29 | 0.72 | 0.20 | 0.26 | 0.66 |
| HIST3H3 | 0 | 1 | 0 | 0 | 0.57 | 0.68 | 0.95 | 0.97 | 0.97 | 1.00 | 0.62 | 0.70 | 0.95 |
| HLA-A | 0 | 1 | 0 | 0 | 0.59 | 0.70 | 0.95 | 0.97 | 0.97 | 1.00 | 0.64 | 0.72 | 0.95 |
| HM13 | 1 | 0 | 0 | 1 | 0.12 | 0.48 | 0.80 | 0.23 | 0.28 | 0.71 | 0.01 | 0.03 | 0.08 |
| HNRPA2B | 0 | 1 | 0 | 0 | 0.56 | 0.66 | 0.95 | 0.97 | 0.97 | 1.00 | 0.60 | 0.69 | 0.94 |
| HNRPL | 0 | 0 | 0 | 1 | 0.95 | 0.97 | 1.00 | 0.24 | 0.29 | 0.72 | 0.20 | 0.26 | 0.72 |
| HOXA1 | 0 | 1 | 0 | 0 | 0.57 | 0.67 | 0.95 | 0.97 | 0.97 | 1.00 | 0.61 | 0.70 | 0.94 |
| HOXA10 | 0 | 1 | 0 | 0 | 0.57 | 0.68 | 0.95 | 0.97 | 0.97 | 1.00 | 0.62 | 0.70 | 0.95 |
| HOXA11 | 0 | 1 | 0 | 0 | 0.56 | 0.67 | 0.95 | 0.97 | 0.97 | 1.00 | 0.61 | 0.69 | 0.94 |
| HOXA13 | 0 | 1 | 0 | 0 | 0.57 | 0.68 | 0.95 | 0.97 | 0.97 | 1.00 | 0.62 | 0.70 | 0.95 |
| HOXA2 | 0 | 1 | 0 | 0 | 0.57 | 0.68 | 0.95 | 0.97 | 0.97 | 1.00 | 0.62 | 0.70 | 0.95 |
| HOXA3 | 2 | 1 | 0 | 0 | 0.00 | 0.01 | 0.12 | 0.97 | 0.97 | 1.00 | 0.06 | 0.08 | 0.26 |
| HOXA4 | 1 | 1 | 0 | 0 | 0.01 | 0.06 | 0.22 | 0.97 | 0.97 | 1.00 | 0.08 | 0.16 | 0.38 |
| HOXA5 | 0 | 1 | 0 | 0 | 0.55 | 0.66 | 0.95 | 0.97 | 0.97 | 1.00 | 0.60 | 0.68 | 0.94 |
| HOXA6 | 0 | 1 | 0 | 0 | 0.57 | 0.68 | 0.95 | 0.97 | 0.97 | 1.00 | 0.62 | 0.70 | 0.95 |
| HOXA7 | 0 | 1 | 0 | 0 | 0.56 | 0.67 | 0.95 | 0.97 | 0.97 | 1.00 | 0.61 | 0.69 | 0.94 |
| HOXA9 | 0 | 1 | 0 | 0 | 0.57 | 0.68 | 0.95 | 0.97 | 0.97 | 1.00 | 0.62 | 0.70 | 0.95 |
| HRH3 | 0 | 2 | 0 | 0 | 0.02 | 0.03 | 0.24 | 0.97 | 0.97 | 1.00 | 0.03 | 0.04 | 0.22 |
| HSF1 | 0 | 1 | 0 | 0 | 0.57 | 0.68 | 0.95 | 0.97 | 0.97 | 1.00 | 0.62 | 0.70 | 0.95 |
| HSPC148 | 0 | 1 | 0 | 0 | 0.56 | 0.67 | 0.95 | 0.97 | 0.97 | 1.00 | 0.61 | 0.69 | 0.94 |
| HTR2A | 0 | 1 | 0 | 0 | 0.47 | 0.58 | 0.92 | 0.97 | 0.97 | 1.00 | 0.51 | 0.61 | 0.92 |

FIG. 11E

| | | | | | | | | | | | | | |
|---|---|---|---|---|---|---|---|---|---|---|---|---|---|
| HTRA4 | 0 | 2 | 0 | 0 | 0.02 | 0.04 | 0.26 | 0.97 | 0.97 | 1.00 | 0.03 | 0.04 | 0.24 |
| ICK | 0 | 1 | 0 | 0 | 0.55 | 0.66 | 0.95 | 0.97 | 0.97 | 1.00 | 0.60 | 0.68 | 0.94 |
| ID1 | 0 | 0 | 0 | 1 | 0.95 | 0.97 | 1.00 | 0.26 | 0.31 | 0.74 | 0.21 | 0.28 | 0.74 |
| ID4 | 0 | 1 | 0 | 0 | 0.59 | 0.70 | 0.95 | 0.97 | 0.97 | 1.00 | 0.64 | 0.72 | 0.95 |
| IFT20 | 0 | 1 | 0 | 0 | 0.59 | 0.70 | 0.95 | 0.97 | 0.97 | 1.00 | 0.64 | 0.72 | 0.95 |
| IGFBP4 | 0 | 1 | 0 | 0 | 0.95 | 0.97 | 1.00 | 0.97 | 0.97 | 1.00 | 0.96 | 0.97 | 1.00 |
| IGHMBP2 | 0 | 2 | 0 | 0 | 0.95 | 0.97 | 0.99 | 0.97 | 0.97 | 1.00 | 0.96 | 0.97 | 0.99 |
| IGSF10 | 0 | 1 | 0 | 0 | 0.55 | 0.66 | 0.21 | 0.97 | 0.97 | 1.00 | 0.60 | 0.68 | 0.37 |
| IL13RA1 | 0 | 1 | 0 | 0 | 0.54 | 0.65 | 0.94 | 0.97 | 0.97 | 1.00 | 0.59 | 0.68 | 0.94 |
| IL17E | 0 | 1 | 0 | 0 | 0.56 | 0.67 | 0.95 | 0.97 | 0.97 | 1.00 | 0.61 | 0.69 | 0.94 |
| IL28A | 0 | 0 | 0 | 1 | 0.95 | 0.97 | 1.00 | 0.26 | 0.31 | 0.74 | 0.21 | 0.28 | 0.74 |
| IL28B | 0 | 0 | 0 | 1 | 0.95 | 0.97 | 1.00 | 0.26 | 0.31 | 0.74 | 0.21 | 0.28 | 0.74 |
| ILVBL | 0 | 1 | 0 | 0 | 0.56 | 0.66 | 0.91 | 0.97 | 0.97 | 1.00 | 0.60 | 0.69 | 0.93 |
| INDO | 0 | 2 | 0 | 0 | 0.02 | 0.04 | 0.26 | 0.97 | 0.97 | 1.00 | 0.03 | 0.04 | 0.25 |
| INPP4A | 0 | 1 | 0 | 0 | 0.54 | 0.65 | 0.91 | 0.97 | 0.97 | 1.00 | 0.58 | 0.67 | 0.92 |
| INTS4 | 0 | 1 | 0 | 0 | 0.53 | 0.64 | 0.90 | 0.97 | 0.97 | 1.00 | 0.57 | 0.66 | 0.92 |
| IPF1 | 0 | 0 | 0 | 1 | 0.95 | 0.97 | 1.00 | 0.25 | 0.30 | 0.73 | 0.20 | 0.27 | 0.73 |
| IQGAP1 | 0 | 0 | 0 | 1 | 0.95 | 0.97 | 0.99 | 0.10 | 0.13 | 0.48 | 0.08 | 0.11 | 0.42 |
| IRS2 | 0 | 0 | 1 | 1 | 0.95 | 0.97 | 0.99 | 0.00 | 0.00 | 0.01 | 0.01 | 0.01 | 0.01 |
| JMJD2D | 0 | 1 | 0 | 0 | 0.56 | 0.67 | 0.95 | 0.97 | 0.97 | 1.00 | 0.61 | 0.69 | 0.94 |
| KCNG1 | 0 | 1 | 0 | 0 | 0.58 | 0.69 | 0.95 | 0.97 | 0.97 | 1.00 | 0.63 | 0.71 | 0.95 |
| KCNJ11 | 0 | 1 | 0 | 0 | 0.58 | 0.68 | 0.95 | 0.97 | 0.97 | 1.00 | 0.62 | 0.70 | 0.95 |
| KCNMB4 | 0 | 1 | 0 | 0 | 0.48 | 0.60 | 0.93 | 0.97 | 0.97 | 1.00 | 0.53 | 0.62 | 0.92 |
| KCTD14 | 0 | 1 | 0 | 0 | 0.59 | 0.70 | 0.95 | 0.97 | 0.97 | 1.00 | 0.64 | 0.72 | 0.95 |
| KIAA0100 | 0 | 1 | 0 | 0 | 0.58 | 0.69 | 0.92 | 0.97 | 0.97 | 1.00 | 0.63 | 0.71 | 0.93 |
| KIAA0240 | 0 | 1 | 0 | 0 | 0.57 | 0.68 | 0.92 | 0.97 | 0.97 | 1.00 | 0.62 | 0.70 | 0.93 |
| KIAA0590 | 0 | 1 | 0 | 0 | 0.47 | 0.58 | 0.88 | 0.97 | 0.97 | 1.00 | 0.51 | 0.61 | 0.90 |
| KIAA0683 | 0 | 1 | 0 | 0 | 0.54 | 0.65 | 0.91 | 0.97 | 0.97 | 1.00 | 0.59 | 0.68 | 0.92 |
| KIAA1161 | 1 | 1 | 0 | 0 | 0.01 | 0.05 | 0.69 | 0.97 | 0.97 | 1.00 | 0.08 | 0.14 | 0.80 |
| KIAA1441 | 0 | 1 | 0 | 0 | 0.58 | 0.69 | 0.92 | 0.97 | 0.97 | 1.00 | 0.63 | 0.71 | 0.93 |
| KIAA1688 | 0 | 1 | 0 | 0 | 0.54 | 0.65 | 0.91 | 0.97 | 0.97 | 1.00 | 0.59 | 0.67 | 0.92 |
| KIAA1875 | 0 | 2 | 1 | 0 | 0.02 | 0.03 | 0.15 | 0.25 | 0.43 | 0.50 | 0.00 | 0.00 | 0.00 |
| KIFC2 | 0 | 1 | 0 | 0 | 0.57 | 0.68 | 0.92 | 0.97 | 0.97 | 1.00 | 0.62 | 0.70 | 0.93 |
| KLF8 | 0 | 1 | 0 | 0 | 0.55 | 0.66 | 0.95 | 0.97 | 0.97 | 1.00 | 0.60 | 0.68 | 0.94 |
| KLHDC1 | 0 | 1 | 0 | 0 | 0.56 | 0.67 | 0.95 | 0.97 | 0.97 | 1.00 | 0.60 | 0.69 | 0.94 |
| KLHDC2 | 0 | 1 | 0 | 0 | 0.59 | 0.70 | 0.95 | 0.97 | 0.97 | 1.00 | 0.64 | 0.72 | 0.95 |
| KLHDC3 | 0 | 1 | 0 | 0 | 0.58 | 0.69 | 0.95 | 0.97 | 0.97 | 1.00 | 0.63 | 0.71 | 0.95 |
| KM-HN-1 | 0 | 1 | 0 | 0 | 0.54 | 0.65 | 0.91 | 0.97 | 0.97 | 1.00 | 0.58 | 0.67 | 0.92 |
| KNSL8 | 0 | 1 | 0 | 0 | 0.59 | 0.70 | 0.92 | 0.97 | 0.97 | 1.00 | 0.64 | 0.72 | 0.93 |
| KNTC2 | 0 | 1 | 0 | 0 | 0.55 | 0.66 | 0.91 | 0.97 | 0.97 | 1.00 | 0.60 | 0.68 | 0.92 |
| KRT24 | 0 | 1 | 0 | 0 | 0.95 | 0.97 | 1.00 | 0.97 | 0.97 | 1.00 | 0.96 | 0.97 | 1.00 |
| KRT25A | 0 | 1 | 0 | 0 | 0.95 | 0.97 | 1.00 | 0.97 | 0.97 | 1.00 | 0.96 | 0.97 | 1.00 |
| KRT25B | 0 | 1 | 0 | 0 | 0.95 | 0.97 | 1.00 | 0.97 | 0.97 | 1.00 | 0.96 | 0.97 | 1.00 |
| KRT25C | 0 | 1 | 0 | 0 | 0.95 | 0.97 | 1.00 | 0.97 | 0.97 | 1.00 | 0.96 | 0.97 | 1.00 |
| LAMA5 | 0 | 2 | 0 | 0 | 0.01 | 0.02 | 0.00 | 0.97 | 0.97 | 1.00 | 0.02 | 0.02 | 0.01 |
| LANCL2 | 0 | 0 | 0 | 2 | 0.95 | 0.97 | 1.00 | 0.97 | 0.97 | 1.00 | 0.96 | 0.97 | 1.00 |
| LASP1 | 0 | 2 | 0 | 0 | 0.95 | 0.97 | 1.00 | 0.97 | 0.97 | 1.00 | 0.96 | 0.97 | 1.00 |
| LASS2 | 0 | 1 | 0 | 0 | 0.58 | 0.69 | 0.95 | 0.97 | 0.97 | 1.00 | 0.63 | 0.71 | 0.95 |
| LETM2 | 0 | 2 | 0 | 0 | 0.03 | 0.04 | 0.27 | 0.97 | 0.97 | 1.00 | 0.03 | 0.04 | 0.26 |
| LGALS4 | 0 | 0 | 0 | 1 | 0.95 | 0.97 | 1.00 | 0.25 | 0.30 | 0.73 | 0.20 | 0.27 | 0.73 |
| LGALS7 | 0 | 0 | 0 | 1 | 0.95 | 0.97 | 1.00 | 0.26 | 0.31 | 0.74 | 0.21 | 0.28 | 0.74 |
| LLGL1 | 0 | 1 | 0 | 0 | 0.55 | 0.66 | 0.91 | 0.97 | 0.97 | 1.00 | 0.60 | 0.68 | 0.92 |
| LOC11365 | 0 | 1 | 0 | 0 | 0.57 | 0.68 | 0.95 | 0.97 | 0.97 | 1.00 | 0.62 | 0.70 | 0.95 |
| LOC11612 | 0 | 1 | 0 | 0 | 0.59 | 0.70 | 0.95 | 0.97 | 0.97 | 1.00 | 0.64 | 0.72 | 0.95 |
| LOC11623 | 0 | 1 | 0 | 0 | 0.59 | 0.70 | 0.95 | 0.97 | 0.97 | 1.00 | 0.64 | 0.72 | 0.95 |
| LOC14799 | 0 | 1 | 0 | 0 | 0.54 | 0.65 | 0.91 | 0.97 | 0.97 | 1.00 | 0.59 | 0.68 | 0.92 |
| LOC15857 | 0 | 1 | 0 | 0 | 0.59 | 0.70 | 0.95 | 0.97 | 0.97 | 1.00 | 0.64 | 0.72 | 0.95 |
| LOC16313 | 0 | 0 | 0 | 1 | 0.95 | 0.97 | 1.00 | 0.26 | 0.31 | 0.73 | 0.21 | 0.28 | 0.74 |
| LOC16935 | 0 | 2 | 0 | 0 | 0.02 | 0.03 | 0.20 | 0.97 | 0.97 | 1.00 | 0.02 | 0.03 | 0.18 |
| LOC19639 | 0 | 0 | 0 | 1 | 0.95 | 0.97 | 1.00 | 0.23 | 0.28 | 0.71 | 0.19 | 0.25 | 0.72 |
| LOC22007 | 0 | 1 | 0 | 0 | 0.59 | 0.70 | 0.95 | 0.97 | 0.97 | 1.00 | 0.64 | 0.72 | 0.95 |
| LOC28321 | 0 | 1 | 0 | 0 | 0.55 | 0.66 | 0.95 | 0.97 | 0.97 | 1.00 | 0.60 | 0.68 | 0.94 |
| LOC28395 | 0 | 1 | 0 | 0 | 0.57 | 0.67 | 0.95 | 0.97 | 0.97 | 1.00 | 0.61 | 0.70 | 0.94 |
| LOC28432 | 0 | 0 | 0 | 1 | 0.95 | 0.97 | 1.00 | 0.26 | 0.31 | 0.74 | 0.21 | 0.28 | 0.74 |
| LOC28475 | 0 | 1 | 0 | 0 | 0.55 | 0.66 | 0.95 | 0.97 | 0.97 | 1.00 | 0.60 | 0.69 | 0.94 |
| LOC34060 | 0 | 1 | 0 | 0 | 0.59 | 0.70 | 0.95 | 0.97 | 0.97 | 1.00 | 0.64 | 0.72 | 0.95 |
| LOC34289 | 0 | 0 | 0 | 1 | 0.95 | 0.97 | 1.00 | 0.26 | 0.31 | 0.74 | 0.21 | 0.28 | 0.74 |
| LOC39063 | 0 | 0 | 0 | 1 | 0.95 | 0.97 | 1.00 | 0.17 | 0.21 | 0.62 | 0.14 | 0.19 | 0.63 |
| LOC39066 | 0 | 1 | 0 | 0 | 0.53 | 0.64 | 0.94 | 0.97 | 0.97 | 1.00 | 0.58 | 0.67 | 0.94 |
| LOC39112 | 0 | 1 | 0 | 0 | 0.58 | 0.69 | 0.95 | 0.97 | 0.97 | 1.00 | 0.63 | 0.71 | 0.95 |

FIG. 11F

| Gene | C1 | C2 | C3 | C4 | V1 | V2 | V3 | V4 | V5 | V6 | V7 | V8 | V9 |
|---|---|---|---|---|---|---|---|---|---|---|---|---|---|
| LOC40025 | 0 | 1 | 0 | 0 | 0.56 | 0.67 | 0.95 | 0.97 | 0.97 | 1.00 | 0.61 | 0.69 | 0.94 |
| LOC44009 | 0 | 0 | 0 | 1 | 0.95 | 0.97 | 1.00 | 0.25 | 0.30 | 0.72 | 0.20 | 0.27 | 0.73 |
| LOC44115 | 0 | 1 | 0 | 0 | 0.59 | 0.70 | 0.95 | 0.97 | 0.97 | 1.00 | 0.64 | 0.72 | 0.95 |
| LOC44242 | 0 | 1 | 0 | 0 | 0.59 | 0.70 | 0.95 | 0.97 | 0.97 | 1.00 | 0.64 | 0.72 | 0.95 |
| LOC51236 | 0 | 2 | 0 | 0 | 0.02 | 0.03 | 0.24 | 0.97 | 0.97 | 1.00 | 0.03 | 0.04 | 0.22 |
| LOC90167 | 0 | 1 | 0 | 0 | 0.55 | 0.66 | 0.91 | 0.97 | 0.97 | 1.00 | 0.60 | 0.68 | 0.92 |
| LOC90321 | 0 | 0 | 0 | 1 | 0.95 | 0.97 | 1.00 | 0.15 | 0.18 | 0.58 | 0.12 | 0.16 | 0.59 |
| LPXN | 0 | 1 | 0 | 0 | 0.57 | 0.68 | 0.95 | 0.97 | 0.97 | 1.00 | 0.62 | 0.70 | 0.95 |
| Lrp2bp | 0 | 1 | 0 | 0 | 0.59 | 0.70 | 0.95 | 0.97 | 0.97 | 1.00 | 0.64 | 0.72 | 0.95 |
| LRRC10 | 0 | 1 | 0 | 0 | 0.59 | 0.70 | 0.95 | 0.97 | 0.97 | 1.00 | 0.64 | 0.72 | 0.95 |
| LRRC14 | 0 | 1 | 0 | 0 | 0.57 | 0.68 | 0.95 | 0.97 | 0.97 | 1.00 | 0.62 | 0.70 | 0.95 |
| LRRC24 | 0 | 1 | 0 | 0 | 0.57 | 0.68 | 0.95 | 0.97 | 0.97 | 1.00 | 0.62 | 0.70 | 0.95 |
| LRRC48 | 0 | 1 | 0 | 0 | 0.57 | 0.67 | 0.95 | 0.97 | 0.97 | 1.00 | 0.61 | 0.70 | 0.94 |
| LRRK2 | 0 | 1 | 0 | 0 | 0.35 | 0.46 | 0.10 | 0.97 | 0.97 | 1.00 | 0.39 | 0.48 | 0.20 |
| LSM1 | 0 | 2 | 0 | 0 | 0.02 | 0.04 | 0.26 | 0.97 | 0.97 | 1.00 | 0.03 | 0.04 | 0.24 |
| MAC30 | 0 | 1 | 0 | 0 | 0.59 | 0.70 | 0.95 | 0.97 | 0.97 | 1.00 | 0.64 | 0.72 | 0.95 |
| MAD2L1BP | 0 | 1 | 0 | 0 | 0.59 | 0.70 | 0.95 | 0.97 | 0.97 | 1.00 | 0.64 | 0.72 | 0.95 |
| MADP-1 | 0 | 1 | 0 | 0 | 0.56 | 0.67 | 0.95 | 0.97 | 0.97 | 1.00 | 0.61 | 0.69 | 0.94 |
| MAF1 | 0 | 2 | 0 | 0 | 0.02 | 0.03 | 0.24 | 0.97 | 0.97 | 1.00 | 0.03 | 0.04 | 0.22 |
| MAGED1 | 0 | 1 | 0 | 0 | 0.59 | 0.70 | 0.92 | 0.97 | 0.97 | 1.00 | 0.64 | 0.72 | 0.93 |
| MAGED4 | 0 | 1 | 0 | 0 | 0.59 | 0.70 | 0.95 | 0.97 | 0.97 | 1.00 | 0.64 | 0.72 | 0.95 |
| MAGEH1 | 0 | 2 | 0 | 0 | 0.03 | 0.04 | 0.28 | 0.97 | 0.97 | 1.00 | 0.03 | 0.05 | 0.26 |
| MAP3K10 | 0 | 0 | 0 | 1 | 0.95 | 0.97 | 0.99 | 0.23 | 0.28 | 0.71 | 0.19 | 0.25 | 0.65 |
| MAPK7 | 0 | 0 | 0 | 1 | 0.95 | 0.97 | 0.99 | 0.20 | 0.25 | 0.67 | 0.16 | 0.22 | 0.61 |
| MCART1 | 1 | 1 | 0 | 0 | 0.01 | 0.05 | 0.57 | 0.97 | 0.97 | 1.00 | 0.08 | 0.14 | 0.72 |
| MCEE | 0 | 1 | 0 | 0 | 0.55 | 0.66 | 0.95 | 0.97 | 0.97 | 1.00 | 0.60 | 0.69 | 0.94 |
| MCL1 | 0 | 1 | 0 | 0 | 0.57 | 0.68 | 0.95 | 0.97 | 0.97 | 1.00 | 0.62 | 0.70 | 0.95 |
| MDFI | 0 | 1 | 0 | 1 | 0.55 | 0.66 | 0.94 | 0.14 | 0.17 | 0.56 | 0.01 | 0.01 | 0.08 |
| MEA | 0 | 1 | 0 | 0 | 0.59 | 0.70 | 0.95 | 0.97 | 0.97 | 1.00 | 0.64 | 0.72 | 0.95 |
| MED19 | 0 | 1 | 0 | 0 | 0.59 | 0.70 | 0.95 | 0.97 | 0.97 | 1.00 | 0.64 | 0.72 | 0.95 |
| MED9 | 0 | 1 | 0 | 0 | 0.56 | 0.67 | 0.95 | 0.97 | 0.97 | 1.00 | 0.61 | 0.69 | 0.94 |
| METTL4 | 0 | 1 | 0 | 0 | 0.55 | 0.66 | 0.95 | 0.97 | 0.97 | 1.00 | 0.60 | 0.68 | 0.94 |
| MFAP4 | 0 | 0 | 0 | 1 | 0.95 | 0.97 | 1.00 | 0.20 | 0.25 | 0.67 | 0.16 | 0.22 | 0.68 |
| MGAT2 | 0 | 1 | 0 | 0 | 0.59 | 0.70 | 0.95 | 0.97 | 0.97 | 1.00 | 0.64 | 0.72 | 0.95 |
| MGAT4A | 0 | 1 | 0 | 0 | 0.52 | 0.63 | 0.94 | 0.97 | 0.97 | 1.00 | 0.56 | 0.65 | 0.93 |
| MGC13168 | 0 | 1 | 0 | 0 | 0.56 | 0.67 | 0.95 | 0.97 | 0.97 | 1.00 | 0.61 | 0.69 | 0.94 |
| MGC20579 | 0 | 0 | 0 | 1 | 0.95 | 0.97 | 1.00 | 0.13 | 0.16 | 0.54 | 0.10 | 0.14 | 0.55 |
| MGC20741 | 0 | 1 | 0 | 1 | 0.58 | 0.69 | 0.95 | 0.19 | 0.23 | 0.64 | 0.01 | 0.02 | 0.13 |
| MGC21416 | 0 | 1 | 0 | 0 | 0.59 | 0.70 | 0.95 | 0.97 | 0.97 | 1.00 | 0.64 | 0.72 | 0.95 |
| MGC24039 | 0 | 0 | 0 | 1 | 0.95 | 0.97 | 0.99 | 0.17 | 0.21 | 0.63 | 0.14 | 0.19 | 0.57 |
| MGC24381 | 0 | 1 | 0 | 0 | 0.56 | 0.67 | 0.95 | 0.97 | 0.97 | 1.00 | 0.61 | 0.69 | 0.94 |
| MGC26733 | 0 | 1 | 1 | 0 | 0.41 | 0.52 | 0.85 | 0.25 | 0.43 | 0.51 | 0.05 | 0.08 | 0.10 |
| MGC27005 | 0 | 1 | 0 | 0 | 0.57 | 0.68 | 0.95 | 0.97 | 0.97 | 1.00 | 0.62 | 0.70 | 0.95 |
| MGC29891 | 0 | 1 | 0 | 0 | 0.58 | 0.68 | 0.95 | 0.97 | 0.97 | 1.00 | 0.62 | 0.70 | 0.95 |
| MGC33530 | 0 | 0 | 0 | 1 | 0.95 | 0.97 | 1.00 | 0.97 | 0.97 | 1.00 | 0.96 | 0.97 | 1.00 |
| MGC33962 | 0 | 0 | 0 | 1 | 0.95 | 0.97 | 1.00 | 0.26 | 0.31 | 0.74 | 0.21 | 0.28 | 0.74 |
| MGC39606 | 0 | 1 | 0 | 0 | 0.57 | 0.68 | 0.95 | 0.97 | 0.97 | 1.00 | 0.62 | 0.70 | 0.95 |
| MGC45562 | 0 | 1 | 0 | 0 | 0.95 | 0.97 | 1.00 | 0.97 | 0.97 | 1.00 | 0.96 | 0.97 | 1.00 |
| MGC50559 | 0 | 0 | 0 | 1 | 0.95 | 0.97 | 1.00 | 0.24 | 0.29 | 0.72 | 0.20 | 0.26 | 0.72 |
| MGC52110 | 0 | 1 | 0 | 0 | 0.58 | 0.69 | 0.95 | 0.97 | 0.97 | 1.00 | 0.63 | 0.71 | 0.95 |
| MGC5356 | 0 | 0 | 0 | 1 | 0.95 | 0.97 | 1.00 | 0.20 | 0.25 | 0.67 | 0.16 | 0.22 | 0.68 |
| MGC70857 | 0 | 1 | 0 | 0 | 0.57 | 0.68 | 0.95 | 0.97 | 0.97 | 1.00 | 0.62 | 0.70 | 0.95 |
| MGC72001 | 0 | 1 | 0 | 0 | 0.56 | 0.67 | 0.95 | 0.97 | 0.97 | 1.00 | 0.61 | 0.69 | 0.94 |
| MGC75360 | 0 | 0 | 0 | 1 | 0.95 | 0.97 | 1.00 | 0.20 | 0.24 | 0.66 | 0.16 | 0.21 | 0.67 |
| MGC9850 | 0 | 0 | 0 | 1 | 0.95 | 0.97 | 1.00 | 0.19 | 0.23 | 0.65 | 0.15 | 0.20 | 0.66 |
| MLLT6 | 0 | 2 | 0 | 0 | 0.95 | 0.97 | 0.99 | 0.97 | 0.97 | 1.00 | 0.96 | 0.97 | 0.99 |
| MLSTD2 | 0 | 1 | 0 | 0 | 0.58 | 0.68 | 0.95 | 0.97 | 0.97 | 1.00 | 0.62 | 0.70 | 0.95 |
| MMRP19 | 0 | 0 | 0 | 1 | 0.95 | 0.97 | 1.00 | 0.14 | 0.17 | 0.56 | 0.11 | 0.15 | 0.57 |
| MOCS3 | 0 | 1 | 0 | 0 | 0.59 | 0.70 | 0.95 | 0.97 | 0.97 | 1.00 | 0.64 | 0.72 | 0.95 |
| MOSPD1 | 1 | 1 | 0 | 0 | 0.00 | 0.04 | 0.54 | 0.97 | 0.97 | 1.00 | 0.06 | 0.12 | 0.69 |
| MPHOSPH | 0 | 1 | 0 | 0 | 0.55 | 0.66 | 0.94 | 0.97 | 0.97 | 1.00 | 0.60 | 0.68 | 0.94 |
| MRCL3 | 0 | 2 | 0 | 0 | 0.03 | 0.04 | 0.28 | 0.97 | 0.97 | 1.00 | 0.03 | 0.05 | 0.26 |
| MRE11A | 2 | 1 | 0 | 0 | 0.00 | 0.01 | 0.06 | 0.97 | 0.97 | 1.00 | 0.05 | 0.06 | 0.16 |
| MRGPRD | 0 | 2 | 0 | 0 | 0.95 | 0.97 | 1.00 | 0.97 | 0.97 | 1.00 | 0.96 | 0.97 | 1.00 |
| MRGPRF | 0 | 2 | 0 | 0 | 0.95 | 0.97 | 1.00 | 0.97 | 0.97 | 1.00 | 0.96 | 0.97 | 1.00 |
| MRLC2 | 0 | 1 | 0 | 0 | 0.59 | 0.70 | 0.95 | 0.97 | 0.97 | 1.00 | 0.64 | 0.72 | 0.95 |
| MRPL2 | 0 | 1 | 0 | 0 | 0.59 | 0.70 | 0.95 | 0.97 | 0.97 | 1.00 | 0.64 | 0.72 | 0.95 |
| MRPL21 | 0 | 2 | 0 | 0 | 0.95 | 0.97 | 1.00 | 0.97 | 0.97 | 1.00 | 0.96 | 0.97 | 1.00 |
| MRPS10 | 0 | 1 | 0 | 1 | 0.59 | 0.70 | 0.95 | 0.20 | 0.25 | 0.67 | 0.02 | 0.02 | 0.14 |
| MRPS12 | 0 | 0 | 0 | 1 | 0.95 | 0.97 | 1.00 | 0.26 | 0.31 | 0.74 | 0.21 | 0.28 | 0.74 |

FIG. 11G

| | | | | | | | | | | | | | |
|---|---|---|---|---|---|---|---|---|---|---|---|---|---|
| MRPS17 | 0 | 0 | 0 | 1 | 0.95 | 0.97 | 1.00 | 0.97 | 0.97 | 1.00 | 0.96 | 0.97 | 1.00 |
| MRPS18A | 0 | 1 | 0 | 0 | 0.57 | 0.68 | 0.95 | 0.97 | 0.97 | 1.00 | 0.62 | 0.70 | 0.95 |
| MRPS34 | 0 | 1 | 0 | 1 | 0.57 | 0.68 | 0.95 | 0.20 | 0.25 | 0.67 | 0.01 | 0.02 | 0.13 |
| MST4 | 0 | 1 | 0 | 0 | 0.55 | 0.66 | 0.94 | 0.97 | 0.97 | 1.00 | 0.60 | 0.68 | 0.94 |
| MTBP | 0 | 1 | 0 | 0 | 0.55 | 0.66 | 0.91 | 0.97 | 0.97 | 1.00 | 0.60 | 0.68 | 0.92 |
| MTL5 | 1 | 2 | 0 | 0 | 0.12 | 0.48 | 0.80 | 0.97 | 0.97 | 1.00 | 0.54 | 0.73 | 0.90 |
| MYC | 0 | 0 | 0 | 2 | 0.95 | 0.97 | 1.00 | 0.00 | 0.00 | 0.01 | 0.00 | 0.00 | 0.01 |
| MYEOV | 0 | 3 | 0 | 0 | 0.95 | 0.97 | 1.00 | 0.97 | 0.97 | 1.00 | 0.96 | 0.97 | 1.00 |
| MYO15A | 0 | 1 | 0 | 0 | 0.50 | 0.61 | 0.18 | 0.97 | 0.97 | 1.00 | 0.55 | 0.64 | 0.32 |
| MYOM1 | 0 | 1 | 0 | 0 | 0.42 | 0.54 | 0.86 | 0.97 | 0.97 | 1.00 | 0.47 | 0.56 | 0.88 |
| NAGK | 0 | 1 | 0 | 0 | 0.56 | 0.67 | 0.95 | 0.97 | 0.97 | 1.00 | 0.61 | 0.70 | 0.94 |
| NBS1 | 0 | 1 | 0 | 0 | 0.54 | 0.65 | 0.91 | 0.97 | 0.97 | 1.00 | 0.59 | 0.67 | 0.92 |
| NCR2 | 0 | 1 | 0 | 0 | 0.54 | 0.65 | 0.94 | 0.97 | 0.97 | 1.00 | 0.59 | 0.67 | 0.94 |
| NDUFB10 | 0 | 1 | 0 | 0 | 0.55 | 0.66 | 0.95 | 0.97 | 0.97 | 1.00 | 0.60 | 0.68 | 0.94 |
| NDUFC2 | 0 | 1 | 0 | 0 | 0.58 | 0.69 | 0.95 | 0.97 | 0.97 | 1.00 | 0.63 | 0.71 | 0.95 |
| NEK8 | 0 | 1 | 0 | 0 | 0.59 | 0.69 | 0.92 | 0.97 | 0.97 | 1.00 | 0.63 | 0.71 | 0.93 |
| NEUGRIN | 0 | 0 | 1 | 1 | 0.95 | 0.97 | 1.00 | 0.00 | 0.01 | 0.01 | 0.01 | 0.02 | 0.02 |
| NEUROD2 | 0 | 4 | 0 | 1 | 0.95 | 0.97 | 1.00 | 0.97 | 0.97 | 1.00 | 0.96 | 0.97 | 1.00 |
| NFE2L3 | 0 | 1 | 0 | 0 | 0.54 | 0.65 | 0.91 | 0.97 | 0.97 | 1.00 | 0.59 | 0.68 | 0.92 |
| NFKBIB | 0 | 0 | 0 | 1 | 0.95 | 0.97 | 1.00 | 0.24 | 0.29 | 0.72 | 0.20 | 0.26 | 0.72 |
| NFKBIL2 | 0 | 1 | 0 | 0 | 0.51 | 0.63 | 0.90 | 0.97 | 0.97 | 1.00 | 0.56 | 0.65 | 0.91 |
| NFYA | 0 | 1 | 0 | 0 | 0.57 | 0.68 | 0.95 | 0.97 | 0.97 | 1.00 | 0.62 | 0.70 | 0.95 |
| NME3 | 0 | 1 | 0 | 1 | 0.57 | 0.68 | 0.95 | 0.20 | 0.25 | 0.67 | 0.01 | 0.02 | 0.13 |
| NOTCH3 | 0 | 1 | 0 | 0 | 0.52 | 0.63 | 0.19 | 0.97 | 0.97 | 1.00 | 0.57 | 0.66 | 0.34 |
| NOXO1 | 0 | 1 | 0 | 0 | 0.57 | 0.68 | 0.95 | 0.97 | 0.97 | 1.00 | 0.62 | 0.70 | 0.95 |
| NR1D1 | 0 | 2 | 0 | 1 | 0.95 | 0.97 | 0.99 | 0.97 | 0.97 | 1.00 | 0.96 | 0.97 | 0.99 |
| NRAS | 0 | 1 | 0 | 0 | 0.58 | 0.69 | 0.95 | 0.97 | 0.97 | 1.00 | 0.63 | 0.71 | 0.95 |
| NRIP1 | 0 | 1 | 0 | 0 | 0.56 | 0.67 | 0.91 | 0.97 | 0.97 | 1.00 | 0.61 | 0.69 | 0.93 |
| NSE2 | 0 | 1 | 0 | 1 | 0.59 | 0.70 | 0.95 | 0.20 | 0.25 | 0.67 | 0.02 | 0.02 | 0.14 |
| NUCB2 | 0 | 1 | 0 | 0 | 0.55 | 0.65 | 0.94 | 0.97 | 0.97 | 1.00 | 0.59 | 0.68 | 0.94 |
| NUDT10 | 0 | 1 | 0 | 0 | 0.58 | 0.69 | 0.95 | 0.97 | 0.97 | 1.00 | 0.63 | 0.71 | 0.95 |
| NUDT2 | 0 | 1 | 0 | 0 | 0.59 | 0.70 | 0.95 | 0.97 | 0.97 | 1.00 | 0.64 | 0.72 | 0.95 |
| NUFIP2 | 1 | 1 | 0 | 0 | 0.01 | 0.07 | 0.22 | 0.97 | 0.97 | 1.00 | 0.08 | 0.17 | 0.38 |
| OCRL | 0 | 1 | 0 | 0 | 0.54 | 0.65 | 0.91 | 0.97 | 0.97 | 1.00 | 0.59 | 0.68 | 0.92 |
| OLFML3 | 0 | 1 | 0 | 0 | 0.59 | 0.69 | 0.95 | 0.97 | 0.97 | 1.00 | 0.63 | 0.71 | 0.95 |
| OPHN1 | 0 | 1 | 0 | 0 | 0.46 | 0.58 | 0.88 | 0.97 | 0.97 | 1.00 | 0.51 | 0.60 | 0.90 |
| OPLAH | 0 | 2 | 0 | 0 | 0.02 | 0.03 | 0.15 | 0.97 | 0.97 | 1.00 | 0.03 | 0.04 | 0.18 |
| OPRS1 | 0 | 1 | 0 | 0 | 0.59 | 0.70 | 0.95 | 0.97 | 0.97 | 1.00 | 0.64 | 0.72 | 0.95 |
| OR10Q1 | 0 | 1 | 0 | 0 | 0.59 | 0.70 | 0.95 | 0.97 | 0.97 | 1.00 | 0.64 | 0.72 | 0.95 |
| OR1I1 | 0 | 1 | 0 | 0 | 0.55 | 0.66 | 0.94 | 0.97 | 0.97 | 1.00 | 0.60 | 0.68 | 0.94 |
| OR1S1 | 1 | 1 | 0 | 0 | 0.01 | 0.05 | 0.68 | 0.97 | 0.97 | 1.00 | 0.08 | 0.15 | 0.79 |
| OR1S2 | 0 | 1 | 0 | 0 | 0.59 | 0.70 | 0.95 | 0.97 | 0.97 | 1.00 | 0.64 | 0.72 | 0.95 |
| OR5B12 | 0 | 1 | 0 | 0 | 0.58 | 0.69 | 0.95 | 0.97 | 0.97 | 1.00 | 0.63 | 0.71 | 0.95 |
| OR5B17 | 0 | 1 | 0 | 0 | 0.59 | 0.70 | 0.95 | 0.97 | 0.97 | 1.00 | 0.64 | 0.72 | 0.95 |
| OR5B2 | 0 | 1 | 0 | 0 | 0.58 | 0.69 | 0.95 | 0.97 | 0.97 | 1.00 | 0.63 | 0.71 | 0.95 |
| OR5B21 | 0 | 1 | 0 | 0 | 0.59 | 0.70 | 0.95 | 0.97 | 0.97 | 1.00 | 0.64 | 0.72 | 0.95 |
| OR5B3 | 0 | 1 | 0 | 0 | 0.56 | 0.67 | 0.95 | 0.97 | 0.97 | 1.00 | 0.61 | 0.69 | 0.94 |
| OR6Q1 | 0 | 1 | 0 | 0 | 0.58 | 0.68 | 0.95 | 0.97 | 0.97 | 1.00 | 0.62 | 0.70 | 0.95 |
| OR7A10 | 0 | 1 | 0 | 0 | 0.56 | 0.67 | 0.95 | 0.97 | 0.97 | 1.00 | 0.61 | 0.69 | 0.94 |
| OR7A17 | 0 | 1 | 0 | 0 | 0.57 | 0.68 | 0.95 | 0.97 | 0.97 | 1.00 | 0.62 | 0.70 | 0.95 |
| OR7A5 | 0 | 1 | 0 | 0 | 0.56 | 0.67 | 0.95 | 0.97 | 0.97 | 1.00 | 0.61 | 0.69 | 0.94 |
| OR7C1 | 0 | 1 | 0 | 0 | 0.56 | 0.67 | 0.95 | 0.97 | 0.97 | 1.00 | 0.61 | 0.69 | 0.94 |
| OR7C2 | 0 | 1 | 0 | 0 | 0.57 | 0.68 | 0.95 | 0.97 | 0.97 | 1.00 | 0.62 | 0.70 | 0.95 |
| OR9I1 | 0 | 1 | 0 | 0 | 0.59 | 0.70 | 0.95 | 0.97 | 0.97 | 1.00 | 0.64 | 0.72 | 0.95 |
| OR9Q1 | 0 | 1 | 0 | 0 | 0.44 | 0.55 | 0.92 | 0.97 | 0.97 | 1.00 | 0.49 | 0.58 | 0.91 |
| OR9Q2 | 1 | 1 | 0 | 0 | 0.01 | 0.05 | 0.69 | 0.97 | 0.97 | 1.00 | 0.08 | 0.14 | 0.80 |
| ORAOV1 | 0 | 3 | 0 | 0 | 0.95 | 0.97 | 1.00 | 0.97 | 0.97 | 1.00 | 0.96 | 0.97 | 1.00 |
| ORMDL3 | 0 | 4 | 0 | 1 | 0.95 | 0.97 | 1.00 | 0.97 | 0.97 | 1.00 | 0.96 | 0.97 | 1.00 |
| OSBPL2 | 0 | 2 | 0 | 0 | 0.02 | 0.02 | 0.18 | 0.97 | 0.97 | 1.00 | 0.02 | 0.03 | 0.17 |
| PAGE1 | 0 | 1 | 0 | 0 | 0.59 | 0.70 | 0.95 | 0.97 | 0.97 | 1.00 | 0.64 | 0.72 | 0.95 |
| PAGE4 | 0 | 1 | 0 | 0 | 0.59 | 0.70 | 0.95 | 0.97 | 0.97 | 1.00 | 0.64 | 0.72 | 0.95 |
| PAK4 | 0 | 0 | 0 | 1 | 0.95 | 0.97 | 0.99 | 0.24 | 0.29 | 0.72 | 0.20 | 0.26 | 0.66 |
| PARC | 0 | 1 | 0 | 0 | 0.55 | 0.66 | 0.21 | 0.97 | 0.97 | 1.00 | 0.60 | 0.68 | 0.37 |
| PARD6A | 0 | 0 | 0 | 1 | 0.95 | 0.97 | 1.00 | 0.20 | 0.25 | 0.67 | 0.16 | 0.22 | 0.68 |
| PARD6B | 0 | 1 | 0 | 0 | 0.56 | 0.67 | 0.95 | 0.97 | 0.97 | 1.00 | 0.61 | 0.69 | 0.94 |
| PARP10 | 0 | 2 | 0 | 0 | 0.02 | 0.03 | 0.14 | 0.97 | 0.97 | 1.00 | 0.02 | 0.03 | 0.17 |
| PCDH7 | 0 | 1 | 0 | 0 | 0.58 | 0.69 | 0.23 | 0.97 | 0.97 | 1.00 | 0.63 | 0.71 | 0.40 |
| PCGF2 | 0 | 2 | 0 | 0 | 0.95 | 0.97 | 1.00 | 0.97 | 0.97 | 1.00 | 0.96 | 0.97 | 1.00 |
| PCK1 | 0 | 1 | 0 | 0 | 0.56 | 0.67 | 0.91 | 0.97 | 0.97 | 1.00 | 0.61 | 0.69 | 0.93 |
| PDCD5 | 0 | 1 | 0 | 0 | 0.58 | 0.68 | 0.95 | 0.97 | 0.97 | 1.00 | 0.63 | 0.71 | 0.95 |

FIG. 11H

| | | | | | | | | | | | | |
|---|---|---|---|---|---|---|---|---|---|---|---|---|
| PDHX | 0 | 0 | 0 | 1 | 0.95 | 0.97 | 1.00 | 0.12 | 0.15 | 0.53 | 0.10 | 0.14 | 0.54 |
| PDLIM3 | 0 | 1 | 0 | 0 | 0.56 | 0.67 | 0.95 | 0.97 | 0.97 | 1.00 | 0.61 | 0.69 | 0.94 |
| PDZRN4 | 0 | 1 | 1 | 0 | 0.39 | 0.50 | 0.84 | 0.25 | 0.43 | 0.51 | 0.05 | 0.07 | 0.09 |
| PEMT | 0 | 1 | 0 | 0 | 0.50 | 0.61 | 0.93 | 0.97 | 0.97 | 1.00 | 0.55 | 0.64 | 0.93 |
| PERLD1 | 0 | 4 | 0 | 1 | 0.95 | 0.97 | 1.00 | 0.97 | 0.97 | 1.00 | 0.96 | 0.97 | 1.00 |
| PEX6 | 0 | 1 | 0 | 0 | 0.57 | 0.68 | 0.92 | 0.97 | 0.97 | 1.00 | 0.62 | 0.70 | 0.93 |
| PF4 | 0 | 1 | 0 | 0 | 0.59 | 0.70 | 0.95 | 0.97 | 0.97 | 1.00 | 0.64 | 0.72 | 0.95 |
| PFN2 | 0 | 1 | 0 | 0 | 0.57 | 0.68 | 0.95 | 0.97 | 0.97 | 1.00 | 0.62 | 0.70 | 0.95 |
| PGC | 0 | 1 | 0 | 1 | 0.58 | 0.69 | 0.95 | 0.19 | 0.23 | 0.64 | 0.01 | 0.02 | 0.13 |
| PGLYRP2 | 0 | 1 | 0 | 0 | 0.55 | 0.66 | 0.91 | 0.97 | 0.97 | 1.00 | 0.60 | 0.68 | 0.92 |
| PIGS | 1 | 1 | 0 | 0 | 0.01 | 0.07 | 0.23 | 0.97 | 0.97 | 1.00 | 0.08 | 0.17 | 0.40 |
| PIGX | 0 | 1 | 0 | 0 | 0.58 | 0.68 | 0.95 | 0.97 | 0.97 | 1.00 | 0.62 | 0.70 | 0.95 |
| PIK3C2A | 0 | 1 | 0 | 0 | 0.56 | 0.67 | 0.91 | 0.97 | 0.97 | 1.00 | 0.61 | 0.70 | 0.93 |
| PIK4CB | 0 | 1 | 0 | 0 | 0.56 | 0.67 | 0.91 | 0.97 | 0.97 | 1.00 | 0.60 | 0.69 | 0.93 |
| PIP5K1A | 0 | 1 | 0 | 0 | 0.58 | 0.68 | 0.95 | 0.97 | 0.97 | 1.00 | 0.63 | 0.71 | 0.95 |
| PIP5K2B | 0 | 2 | 0 | 0 | 0.95 | 0.97 | 1.00 | 0.97 | 0.97 | 1.00 | 0.96 | 0.97 | 1.00 |
| PKIA | 0 | 1 | 0 | 0 | 0.59 | 0.70 | 0.95 | 0.97 | 0.97 | 1.00 | 0.64 | 0.72 | 0.95 |
| PLD3 | 0 | 0 | 0 | 1 | 0.95 | 0.97 | 1.00 | 0.25 | 0.30 | 0.72 | 0.20 | 0.27 | 0.73 |
| PLEC1 | 0 | 1 | 2 | 0 | 0.52 | 0.63 | 0.19 | 0.24 | 0.39 | 0.51 | 0.08 | 0.11 | 0.10 |
| PLEKHA1 | 0 | 0 | 0 | 1 | 0.95 | 0.97 | 1.00 | 0.22 | 0.27 | 0.69 | 0.18 | 0.24 | 0.70 |
| PLEKHA7 | 0 | 1 | 0 | 0 | 0.37 | 0.48 | 0.83 | 0.97 | 0.97 | 1.00 | 0.42 | 0.51 | 0.85 |
| PLEKHA9 | 0 | 1 | 0 | 0 | 0.57 | 0.68 | 0.95 | 0.97 | 0.97 | 1.00 | 0.62 | 0.70 | 0.95 |
| PLEKHF1 | 0 | 4 | 0 | 0 | 0.95 | 0.97 | 1.00 | 0.97 | 0.97 | 1.00 | 0.96 | 0.97 | 1.00 |
| PLXDC1 | 0 | 2 | 0 | 0 | 0.95 | 0.97 | 1.00 | 0.97 | 0.97 | 1.00 | 0.96 | 0.97 | 1.00 |
| PNMT | 0 | 4 | 0 | 1 | 0.95 | 0.97 | 1.00 | 0.97 | 0.97 | 1.00 | 0.96 | 0.97 | 1.00 |
| POGK | 0 | 1 | 0 | 0 | 0.59 | 0.70 | 0.95 | 0.97 | 0.97 | 1.00 | 0.64 | 0.72 | 0.95 |
| POLDIP2 | 0 | 1 | 0 | 0 | 0.59 | 0.70 | 0.95 | 0.97 | 0.97 | 1.00 | 0.64 | 0.72 | 0.95 |
| POLE2 | 0 | 1 | 0 | 0 | 0.56 | 0.67 | 0.95 | 0.97 | 0.97 | 1.00 | 0.61 | 0.69 | 0.94 |
| POLH | 1 | 1 | 0 | 0 | 0.01 | 0.09 | 0.23 | 0.97 | 0.97 | 1.00 | 0.08 | 0.20 | 0.40 |
| POLR1C | 0 | 1 | 0 | 0 | 0.57 | 0.68 | 0.95 | 0.97 | 0.97 | 1.00 | 0.62 | 0.70 | 0.95 |
| POLR1D | 0 | 0 | 0 | 1 | 0.95 | 0.97 | 1.00 | 0.26 | 0.31 | 0.74 | 0.21 | 0.28 | 0.74 |
| POP4 | 0 | 2 | 0 | 0 | 0.95 | 0.97 | 1.00 | 0.97 | 0.97 | 1.00 | 0.96 | 0.97 | 1.00 |
| PPAPDC1E | 0 | 2 | 0 | 0 | 0.03 | 0.04 | 0.28 | 0.97 | 0.97 | 1.00 | 0.03 | 0.05 | 0.26 |
| PPARBP | 0 | 4 | 0 | 0 | 0.95 | 0.97 | 0.99 | 0.97 | 0.97 | 1.00 | 0.96 | 0.97 | 0.99 |
| PPBP | 0 | 1 | 0 | 0 | 0.59 | 0.70 | 0.95 | 0.97 | 0.97 | 1.00 | 0.64 | 0.72 | 0.95 |
| PPFIA1 | 0 | 2 | 0 | 0 | 0.95 | 0.97 | 0.99 | 0.97 | 0.97 | 1.00 | 0.96 | 0.97 | 0.99 |
| PPHLN1 | 1 | 1 | 0 | 0 | 0.01 | 0.04 | 0.18 | 0.97 | 0.97 | 1.00 | 0.06 | 0.11 | 0.32 |
| PPIF | 0 | 1 | 0 | 0 | 0.56 | 0.67 | 0.95 | 0.97 | 0.97 | 1.00 | 0.61 | 0.69 | 0.94 |
| PPIL5 | 0 | 1 | 0 | 0 | 0.58 | 0.69 | 0.95 | 0.97 | 0.97 | 1.00 | 0.63 | 0.71 | 0.95 |
| PPP1R16A | 0 | 1 | 0 | 0 | 0.57 | 0.68 | 0.95 | 0.97 | 0.97 | 1.00 | 0.62 | 0.70 | 0.95 |
| PPP1R1B | 0 | 4 | 0 | 1 | 0.95 | 0.97 | 1.00 | 0.97 | 0.97 | 1.00 | 0.96 | 0.97 | 1.00 |
| PPP1R3D | 0 | 1 | 0 | 0 | 0.59 | 0.70 | 0.95 | 0.97 | 0.97 | 1.00 | 0.64 | 0.72 | 0.95 |
| PPP2R5D | 0 | 1 | 0 | 0 | 0.55 | 0.66 | 0.91 | 0.97 | 0.97 | 1.00 | 0.60 | 0.69 | 0.92 |
| PPP4R1 | 0 | 1 | 0 | 0 | 0.50 | 0.62 | 0.89 | 0.97 | 0.97 | 1.00 | 0.55 | 0.64 | 0.91 |
| PPP4R1L | 0 | 1 | 0 | 0 | 0.53 | 0.64 | 0.94 | 0.97 | 0.97 | 1.00 | 0.57 | 0.66 | 0.94 |
| PRIC285 | 0 | 0 | 0 | 1 | 0.95 | 0.97 | 0.99 | 0.16 | 0.20 | 0.60 | 0.13 | 0.17 | 0.54 |
| PRICKLE1 | 0 | 1 | 0 | 0 | 0.55 | 0.66 | 0.91 | 0.97 | 0.97 | 1.00 | 0.60 | 0.68 | 0.92 |
| PRMT6 | 0 | 1 | 0 | 0 | 0.58 | 0.69 | 0.95 | 0.97 | 0.97 | 1.00 | 0.63 | 0.71 | 0.95 |
| PROCA1 | 0 | 1 | 0 | 0 | 0.58 | 0.69 | 0.95 | 0.97 | 0.97 | 1.00 | 0.63 | 0.71 | 0.95 |
| PRUNE | 0 | 1 | 0 | 0 | 0.55 | 0.66 | 0.95 | 0.97 | 0.97 | 1.00 | 0.60 | 0.69 | 0.94 |
| PRX | 0 | 0 | 0 | 1 | 0.95 | 0.97 | 1.00 | 0.25 | 0.30 | 0.73 | 0.21 | 0.27 | 0.74 |
| PSMB3 | 0 | 2 | 0 | 0 | 0.95 | 0.97 | 1.00 | 0.97 | 0.97 | 1.00 | 0.96 | 0.97 | 1.00 |
| PSMC3 | 0 | 1 | 0 | 0 | 0.57 | 0.67 | 0.95 | 0.97 | 0.97 | 1.00 | 0.61 | 0.70 | 0.94 |
| PSMC4 | 0 | 0 | 0 | 1 | 0.95 | 0.97 | 1.00 | 0.24 | 0.29 | 0.72 | 0.20 | 0.26 | 0.72 |
| PSMD3 | 0 | 2 | 0 | 1 | 0.95 | 0.97 | 1.00 | 0.97 | 0.97 | 1.00 | 0.96 | 0.97 | 1.00 |
| PSMD4 | 0 | 1 | 0 | 0 | 0.59 | 0.69 | 0.95 | 0.97 | 0.97 | 1.00 | 0.63 | 0.71 | 0.95 |
| PTCRA | 0 | 1 | 0 | 0 | 0.58 | 0.69 | 0.95 | 0.97 | 0.97 | 1.00 | 0.63 | 0.71 | 0.95 |
| PTD015 | 0 | 1 | 0 | 0 | 0.57 | 0.68 | 0.95 | 0.97 | 0.97 | 1.00 | 0.62 | 0.70 | 0.95 |
| PTK6 | 0 | 0 | 0 | 1 | 0.95 | 0.97 | 1.00 | 0.20 | 0.25 | 0.67 | 0.16 | 0.22 | 0.68 |
| PTK7 | 0 | 1 | 0 | 0 | 0.51 | 0.62 | 0.89 | 0.97 | 0.97 | 1.00 | 0.56 | 0.64 | 0.91 |
| PTPN1 | 0 | 1 | 0 | 0 | 0.52 | 0.63 | 0.94 | 0.97 | 0.97 | 1.00 | 0.57 | 0.66 | 0.93 |
| PTPN22 | 0 | 1 | 0 | 0 | 0.56 | 0.67 | 0.95 | 0.97 | 0.97 | 1.00 | 0.60 | 0.69 | 0.94 |
| PTPRB | 0 | 1 | 0 | 0 | 0.45 | 0.56 | 0.87 | 0.97 | 0.97 | 1.00 | 0.50 | 0.59 | 0.89 |
| PTPRR | 0 | 1 | 0 | 0 | 0.33 | 0.44 | 0.88 | 0.97 | 0.97 | 1.00 | 0.38 | 0.47 | 0.87 |
| PVR | 0 | 1 | 0 | 0 | 0.57 | 0.68 | 0.95 | 0.97 | 0.97 | 1.00 | 0.62 | 0.70 | 0.95 |
| PYY2 | 0 | 1 | 0 | 0 | 0.59 | 0.70 | 0.95 | 0.97 | 0.97 | 1.00 | 0.64 | 0.72 | 0.95 |
| RAB11FIP | 0 | 2 | 0 | 0 | 0.02 | 0.03 | 0.14 | 0.97 | 0.97 | 1.00 | 0.02 | 0.03 | 0.16 |
| RAB22A | 0 | 1 | 0 | 0 | 0.53 | 0.64 | 0.94 | 0.97 | 0.97 | 1.00 | 0.58 | 0.67 | 0.94 |
| RAB34 | 0 | 1 | 0 | 0 | 0.59 | 0.70 | 0.95 | 0.97 | 0.97 | 1.00 | 0.64 | 0.72 | 0.95 |
| RAB3IP | 0 | 1 | 0 | 0 | 0.54 | 0.65 | 0.94 | 0.97 | 0.97 | 1.00 | 0.59 | 0.67 | 0.94 |

FIG. 11I

| | | | | | | | | | | | | | |
|---|---|---|---|---|---|---|---|---|---|---|---|---|---|
| RAI1 | 0 | 1 | 0 | 0 | 0.55 | 0.66 | 0.91 | 0.97 | 0.97 | 1.00 | 0.60 | 0.68 | 0.92 |
| RALBP1 | 0 | 1 | 0 | 0 | 0.52 | 0.63 | 0.94 | 0.97 | 0.97 | 1.00 | 0.57 | 0.66 | 0.93 |
| RAPGEFL' | 0 | 3 | 0 | 1 | 0.95 | 0.97 | 1.00 | 0.97 | 0.97 | 1.00 | 0.96 | 0.97 | 1.00 |
| RARA | 0 | 2 | 0 | 0 | 0.95 | 0.97 | 1.00 | 0.97 | 0.97 | 1.00 | 0.96 | 0.97 | 1.00 |
| RASA3 | 0 | 0 | 0 | 1 | 0.95 | 0.97 | 0.99 | 0.09 | 0.12 | 0.45 | 0.07 | 0.10 | 0.39 |
| RASD1 | 0 | 1 | 0 | 0 | 0.57 | 0.68 | 0.95 | 0.97 | 0.97 | 1.00 | 0.62 | 0.70 | 0.95 |
| RBM3 | 0 | 1 | 0 | 0 | 0.59 | 0.70 | 0.95 | 0.97 | 0.97 | 1.00 | 0.64 | 0.72 | 0.95 |
| RDS | 0 | 1 | 0 | 0 | 0.55 | 0.66 | 0.95 | 0.97 | 0.97 | 1.00 | 0.60 | 0.69 | 0.94 |
| RECQL4 | 0 | 1 | 0 | 0 | 0.57 | 0.68 | 0.92 | 0.97 | 0.97 | 1.00 | 0.62 | 0.70 | 0.93 |
| REM1 | 0 | 0 | 0 | 1 | 0.95 | 0.97 | 1.00 | 0.24 | 0.29 | 0.72 | 0.20 | 0.26 | 0.72 |
| RFX5 | 0 | 1 | 0 | 0 | 0.59 | 0.70 | 0.95 | 0.97 | 0.97 | 1.00 | 0.64 | 0.72 | 0.95 |
| RG9MTD3 | 0 | 1 | 0 | 0 | 0.57 | 0.68 | 0.95 | 0.97 | 0.97 | 1.00 | 0.62 | 0.70 | 0.95 |
| RHOD | 0 | 1 | 0 | 0 | 0.58 | 0.69 | 0.95 | 0.97 | 0.97 | 1.00 | 0.63 | 0.71 | 0.95 |
| RIPK2 | 0 | 1 | 0 | 0 | 0.54 | 0.65 | 0.94 | 0.97 | 0.97 | 1.00 | 0.59 | 0.67 | 0.94 |
| RNF13 | 0 | 1 | 0 | 0 | 0.51 | 0.63 | 0.94 | 0.97 | 0.97 | 1.00 | 0.56 | 0.65 | 0.93 |
| RNF151 | 0 | 1 | 0 | 0 | 0.57 | 0.68 | 0.95 | 0.97 | 0.97 | 1.00 | 0.62 | 0.70 | 0.95 |
| RPESP | 0 | 2 | 0 | 0 | 0.02 | 0.03 | 0.21 | 0.97 | 0.97 | 1.00 | 0.02 | 0.03 | 0.20 |
| RPL19 | 0 | 3 | 0 | 0 | 0.95 | 0.97 | 1.00 | 0.97 | 0.97 | 1.00 | 0.96 | 0.97 | 1.00 |
| RPL23 | 0 | 2 | 0 | 0 | 0.95 | 0.97 | 1.00 | 0.97 | 0.97 | 1.00 | 0.96 | 0.97 | 1.00 |
| RPL23A | 0 | 1 | 0 | 0 | 0.59 | 0.70 | 0.95 | 0.97 | 0.97 | 1.00 | 0.64 | 0.72 | 0.95 |
| RPL36AL | 0 | 1 | 0 | 0 | 0.59 | 0.70 | 0.95 | 0.97 | 0.97 | 1.00 | 0.64 | 0.72 | 0.95 |
| RPL37 | 0 | 1 | 0 | 0 | 0.59 | 0.70 | 0.95 | 0.97 | 0.97 | 1.00 | 0.64 | 0.72 | 0.95 |
| RPL7 | 0 | 1 | 0 | 0 | 0.58 | 0.69 | 0.95 | 0.97 | 0.97 | 1.00 | 0.63 | 0.71 | 0.95 |
| RPL7L1 | 0 | 1 | 0 | 0 | 0.58 | 0.68 | 0.95 | 0.97 | 0.97 | 1.00 | 0.63 | 0.71 | 0.95 |
| RPS13 | 0 | 1 | 0 | 0 | 0.58 | 0.69 | 0.95 | 0.97 | 0.97 | 1.00 | 0.63 | 0.71 | 0.95 |
| RPS2 | 0 | 1 | 0 | 0 | 0.57 | 0.68 | 0.95 | 0.97 | 0.97 | 1.00 | 0.62 | 0.70 | 0.95 |
| RPS21 | 0 | 2 | 0 | 0 | 0.02 | 0.03 | 0.22 | 0.97 | 0.97 | 1.00 | 0.02 | 0.03 | 0.21 |
| RPS29 | 0 | 1 | 0 | 0 | 0.59 | 0.70 | 0.95 | 0.97 | 0.97 | 1.00 | 0.64 | 0.72 | 0.95 |
| RPS5 | 0 | 0 | 0 | 1 | 0.95 | 0.97 | 1.00 | 0.20 | 0.25 | 0.67 | 0.16 | 0.22 | 0.68 |
| RRAGB | 0 | 2 | 0 | 0 | 0.02 | 0.04 | 0.26 | 0.97 | 0.97 | 1.00 | 0.03 | 0.04 | 0.25 |
| RTBDN | 0 | 1 | 0 | 0 | 0.56 | 0.66 | 0.95 | 0.97 | 0.97 | 1.00 | 0.60 | 0.69 | 0.94 |
| RXRG | 0 | 1 | 0 | 0 | 0.49 | 0.61 | 0.93 | 0.97 | 0.97 | 1.00 | 0.54 | 0.63 | 0.93 |
| S100A10 | 0 | 1 | 0 | 0 | 0.59 | 0.70 | 0.95 | 0.97 | 0.97 | 1.00 | 0.64 | 0.72 | 0.95 |
| S100A11 | 0 | 1 | 0 | 0 | 0.59 | 0.70 | 0.95 | 0.97 | 0.97 | 1.00 | 0.64 | 0.72 | 0.95 |
| SAGE1 | 0 | 1 | 0 | 0 | 0.55 | 0.66 | 0.91 | 0.97 | 0.97 | 1.00 | 0.60 | 0.68 | 0.92 |
| SAMSN1 | 0 | 1 | 0 | 0 | 0.42 | 0.54 | 0.91 | 0.97 | 0.97 | 1.00 | 0.47 | 0.56 | 0.91 |
| SARM1 | 0 | 1 | 0 | 0 | 0.58 | 0.68 | 0.92 | 0.97 | 0.97 | 1.00 | 0.62 | 0.70 | 0.93 |
| SARS2 | 0 | 0 | 0 | 1 | 0.95 | 0.97 | 1.00 | 0.25 | 0.30 | 0.72 | 0.20 | 0.27 | 0.73 |
| SB145 | 0 | 1 | 0 | 0 | 0.58 | 0.68 | 0.95 | 0.97 | 0.97 | 1.00 | 0.63 | 0.71 | 0.95 |
| SCAP2 | 0 | 1 | 0 | 0 | 0.47 | 0.58 | 0.92 | 0.97 | 0.97 | 1.00 | 0.51 | 0.61 | 0.92 |
| SCNM1 | 0 | 1 | 0 | 0 | 0.59 | 0.70 | 0.95 | 0.97 | 0.97 | 1.00 | 0.64 | 0.72 | 0.95 |
| SCRT1 | 0 | 1 | 0 | 0 | 0.57 | 0.68 | 0.95 | 0.97 | 0.97 | 1.00 | 0.62 | 0.70 | 0.95 |
| SDCCAG1 | 0 | 1 | 0 | 0 | 0.58 | 0.69 | 0.92 | 0.97 | 0.97 | 1.00 | 0.63 | 0.71 | 0.93 |
| SDF2 | 0 | 1 | 0 | 0 | 0.59 | 0.70 | 0.95 | 0.97 | 0.97 | 1.00 | 0.64 | 0.72 | 0.95 |
| SEC61G | 0 | 0 | 0 | 1 | 0.95 | 0.97 | 1.00 | 0.97 | 0.97 | 1.00 | 0.96 | 0.97 | 1.00 |
| SEMA6C | 0 | 1 | 0 | 0 | 0.58 | 0.69 | 0.92 | 0.97 | 0.97 | 1.00 | 0.63 | 0.71 | 0.93 |
| SESN3 | 0 | 1 | 0 | 0 | 0.52 | 0.63 | 0.94 | 0.97 | 0.97 | 1.00 | 0.57 | 0.66 | 0.93 |
| SETDB1 | 0 | 1 | 0 | 0 | 0.57 | 0.68 | 0.95 | 0.97 | 0.97 | 1.00 | 0.62 | 0.70 | 0.95 |
| SFTPA1 | 0 | 1 | 0 | 0 | 0.57 | 0.68 | 0.95 | 0.97 | 0.97 | 1.00 | 0.62 | 0.70 | 0.95 |
| SFTPA2 | 0 | 1 | 0 | 0 | 0.57 | 0.68 | 0.95 | 0.97 | 0.97 | 1.00 | 0.62 | 0.70 | 0.95 |
| SFTPD | 0 | 1 | 0 | 0 | 0.54 | 0.65 | 0.94 | 0.97 | 0.97 | 1.00 | 0.59 | 0.67 | 0.94 |
| SHANK2 | 0 | 2 | 0 | 0 | 0.95 | 0.97 | 0.99 | 0.97 | 0.97 | 1.00 | 0.96 | 0.97 | 0.99 |
| SHARPIN | 0 | 2 | 0 | 0 | 0.02 | 0.03 | 0.24 | 0.97 | 0.97 | 1.00 | 0.03 | 0.04 | 0.22 |
| SHMT1 | 0 | 1 | 0 | 0 | 0.56 | 0.66 | 0.95 | 0.97 | 0.97 | 1.00 | 0.60 | 0.69 | 0.94 |
| SIRT2 | 0 | 0 | 0 | 1 | 0.95 | 0.97 | 1.00 | 0.23 | 0.28 | 0.71 | 0.19 | 0.25 | 0.72 |
| SKI | 0 | 1 | 0 | 0 | 0.47 | 0.58 | 0.88 | 0.97 | 0.97 | 1.00 | 0.52 | 0.61 | 0.90 |
| SLAMF8 | 0 | 1 | 0 | 0 | 0.57 | 0.67 | 0.95 | 0.97 | 0.97 | 1.00 | 0.61 | 0.70 | 0.94 |
| SLC13A2 | 0 | 1 | 0 | 0 | 0.57 | 0.68 | 0.95 | 0.97 | 0.97 | 1.00 | 0.62 | 0.70 | 0.95 |
| SLC1A6 | 0 | 1 | 0 | 0 | 0.53 | 0.64 | 0.94 | 0.97 | 0.97 | 1.00 | 0.58 | 0.66 | 0.94 |
| SLC22A7 | 0 | 1 | 0 | 0 | 0.59 | 0.70 | 0.92 | 0.97 | 0.97 | 1.00 | 0.64 | 0.72 | 0.93 |
| SLC25A4 | 0 | 1 | 0 | 0 | 0.59 | 0.70 | 0.95 | 0.97 | 0.97 | 1.00 | 0.64 | 0.72 | 0.95 |
| SLC39A4 | 0 | 1 | 0 | 0 | 0.56 | 0.67 | 0.91 | 0.97 | 0.97 | 1.00 | 0.61 | 0.69 | 0.93 |
| SLC9A6 | 0 | 1 | 0 | 0 | 0.57 | 0.68 | 0.95 | 0.97 | 0.97 | 1.00 | 0.62 | 0.70 | 0.95 |
| SMAF1 | 0 | 1 | 0 | 0 | 0.59 | 0.70 | 0.95 | 0.97 | 0.97 | 1.00 | 0.64 | 0.72 | 0.95 |
| SMAP | 0 | 1 | 0 | 0 | 0.59 | 0.70 | 0.95 | 0.97 | 0.97 | 1.00 | 0.64 | 0.72 | 0.95 |
| SMARCA1 | 0 | 1 | 0 | 0 | 0.54 | 0.65 | 0.91 | 0.97 | 0.97 | 1.00 | 0.59 | 0.68 | 0.92 |
| SMARCE1 | 0 | 1 | 0 | 0 | 0.95 | 0.97 | 1.00 | 0.97 | 0.97 | 1.00 | 0.96 | 0.97 | 1.00 |
| SMCR7 | 0 | 1 | 0 | 0 | 0.57 | 0.68 | 0.95 | 0.97 | 0.97 | 1.00 | 0.62 | 0.70 | 0.95 |
| SMCR8 | 0 | 1 | 0 | 0 | 0.54 | 0.65 | 0.91 | 0.97 | 0.97 | 1.00 | 0.59 | 0.68 | 0.92 |
| SNIP | 0 | 1 | 0 | 0 | 0.95 | 0.97 | 0.99 | 0.97 | 0.97 | 1.00 | 0.96 | 0.97 | 0.99 |

FIG. 11J

| | | | | | | | | | | | | |
|---|---|---|---|---|---|---|---|---|---|---|---|---|
| SNX10 | 0 | 1 | 0 | 0 | 0.52 | 0.63 | 0.94 | 0.97 | 0.97 | 1.00 | 0.57 | 0.66 | 0.93 |
| SNX25 | 1 | 1 | 0 | 0 | 0.01 | 0.07 | 0.16 | 0.97 | 0.97 | 1.00 | 0.06 | 0.15 | 0.30 |
| SPAG5 | 0 | 1 | 0 | 0 | 0.59 | 0.70 | 0.92 | 0.97 | 0.97 | 1.00 | 0.64 | 0.72 | 0.93 |
| SPATC1 | 0 | 2 | 0 | 0 | 0.02 | 0.03 | 0.24 | 0.97 | 0.97 | 1.00 | 0.03 | 0.04 | 0.22 |
| SREBF1 | 0 | 1 | 0 | 0 | 0.56 | 0.67 | 0.91 | 0.97 | 0.97 | 1.00 | 0.61 | 0.69 | 0.93 |
| SRF | 0 | 1 | 0 | 0 | 0.57 | 0.68 | 0.95 | 0.97 | 0.97 | 1.00 | 0.62 | 0.70 | 0.95 |
| SRMS | 0 | 0 | 0 | 1 | 0.95 | 0.97 | 1.00 | 0.16 | 0.20 | 0.60 | 0.13 | 0.17 | 0.61 |
| SRP46 | 0 | 1 | 0 | 0 | 0.57 | 0.68 | 0.95 | 0.97 | 0.97 | 1.00 | 0.62 | 0.70 | 0.95 |
| STAC2 | 0 | 3 | 0 | 0 | 0.95 | 0.97 | 1.00 | 0.97 | 0.97 | 1.00 | 0.96 | 0.97 | 1.00 |
| STAF42 | 0 | 1 | 0 | 0 | 0.57 | 0.68 | 0.95 | 0.97 | 0.97 | 1.00 | 0.62 | 0.70 | 0.95 |
| STAR | 0 | 2 | 0 | 0 | 0.03 | 0.04 | 0.28 | 0.97 | 0.97 | 1.00 | 0.03 | 0.05 | 0.26 |
| STARD3 | 0 | 4 | 0 | 1 | 0.95 | 0.97 | 1.00 | 0.97 | 0.97 | 1.00 | 0.96 | 0.97 | 1.00 |
| STCH | 0 | 1 | 0 | 0 | 0.54 | 0.65 | 0.94 | 0.97 | 0.97 | 1.00 | 0.59 | 0.68 | 0.94 |
| STIM2 | 0 | 1 | 0 | 0 | 0.50 | 0.62 | 0.89 | 0.97 | 0.97 | 1.00 | 0.55 | 0.64 | 0.91 |
| SUCNR1 | 0 | 1 | 0 | 0 | 0.59 | 0.70 | 0.95 | 0.97 | 0.97 | 1.00 | 0.64 | 0.72 | 0.95 |
| SUPT6H | 0 | 1 | 0 | 0 | 0.59 | 0.70 | 0.92 | 0.97 | 0.97 | 1.00 | 0.64 | 0.72 | 0.93 |
| SYCP1 | 0 | 1 | 0 | 0 | 0.53 | 0.64 | 0.90 | 0.97 | 0.97 | 1.00 | 0.58 | 0.67 | 0.92 |
| SYCP2 | 0 | 1 | 0 | 0 | 0.58 | 0.69 | 0.92 | 0.97 | 0.97 | 1.00 | 0.63 | 0.71 | 0.93 |
| SYNGR3 | 0 | 1 | 0 | 0 | 0.56 | 0.67 | 0.95 | 0.97 | 0.97 | 1.00 | 0.61 | 0.69 | 0.94 |
| SYT12 | 0 | 1 | 0 | 0 | 0.59 | 0.69 | 0.95 | 0.97 | 0.97 | 1.00 | 0.63 | 0.71 | 0.95 |
| SYT6 | 0 | 1 | 0 | 0 | 0.45 | 0.56 | 0.92 | 0.97 | 0.97 | 1.00 | 0.50 | 0.59 | 0.91 |
| TACC1 | 0 | 2 | 0 | 0 | 0.02 | 0.03 | 0.14 | 0.97 | 0.97 | 1.00 | 0.02 | 0.03 | 0.17 |
| TAOK1 | 0 | 1 | 0 | 0 | 0.53 | 0.64 | 0.90 | 0.97 | 0.97 | 1.00 | 0.58 | 0.67 | 0.92 |
| TBCC | 0 | 1 | 0 | 0 | 0.59 | 0.70 | 0.95 | 0.97 | 0.97 | 1.00 | 0.64 | 0.72 | 0.95 |
| TBL3 | 0 | 1 | 0 | 0 | 0.56 | 0.67 | 0.91 | 0.97 | 0.97 | 1.00 | 0.61 | 0.69 | 0.93 |
| TBN | 0 | 1 | 0 | 1 | 0.53 | 0.64 | 0.94 | 0.12 | 0.15 | 0.53 | 0.01 | 0.01 | 0.07 |
| TCAP | 0 | 4 | 0 | 1 | 0.95 | 0.97 | 1.00 | 0.97 | 0.97 | 1.00 | 0.96 | 0.97 | 1.00 |
| TCFL1 | 1 | 1 | 0 | 0 | 0.01 | 0.07 | 0.23 | 0.97 | 0.97 | 1.00 | 0.08 | 0.17 | 0.40 |
| TCHHL1 | 0 | 1 | 0 | 0 | 0.59 | 0.70 | 0.92 | 0.97 | 0.97 | 1.00 | 0.64 | 0.72 | 0.93 |
| TEAD2 | 0 | 0 | 0 | 1 | 0.95 | 0.97 | 1.00 | 0.20 | 0.25 | 0.67 | 0.16 | 0.22 | 0.68 |
| TERF1 | 0 | 2 | 0 | 0 | 0.02 | 0.03 | 0.22 | 0.97 | 0.97 | 1.00 | 0.02 | 0.03 | 0.21 |
| TFEB | 0 | 1 | 0 | 1 | 0.58 | 0.69 | 0.95 | 0.19 | 0.23 | 0.64 | 0.01 | 0.02 | 0.13 |
| TFRC | 0 | 1 | 0 | 0 | 0.57 | 0.68 | 0.92 | 0.97 | 0.97 | 1.00 | 0.62 | 0.70 | 0.93 |
| THOC1 | 0 | 1 | 0 | 0 | 0.55 | 0.66 | 0.91 | 0.97 | 0.97 | 1.00 | 0.60 | 0.68 | 0.92 |
| THRA | 0 | 2 | 0 | 1 | 0.95 | 0.97 | 1.00 | 0.97 | 0.97 | 1.00 | 0.96 | 0.97 | 1.00 |
| THRAP4 | 0 | 2 | 0 | 1 | 0.95 | 0.97 | 0.99 | 0.97 | 0.97 | 1.00 | 0.96 | 0.97 | 0.99 |
| THRSP | 0 | 1 | 0 | 0 | 0.59 | 0.70 | 0.95 | 0.97 | 0.97 | 1.00 | 0.64 | 0.72 | 0.95 |
| TIP39 | 0 | 0 | 0 | 1 | 0.95 | 0.97 | 1.00 | 0.20 | 0.25 | 0.67 | 0.16 | 0.22 | 0.68 |
| TJP4 | 0 | 1 | 0 | 0 | 0.59 | 0.70 | 0.95 | 0.97 | 0.97 | 1.00 | 0.64 | 0.72 | 0.95 |
| TMEM14A | 0 | 1 | 0 | 0 | 0.59 | 0.70 | 0.95 | 0.97 | 0.97 | 1.00 | 0.64 | 0.72 | 0.95 |
| TMEM16A | 0 | 3 | 0 | 0 | 0.95 | 0.97 | 0.99 | 0.97 | 0.97 | 1.00 | 0.96 | 0.97 | 0.99 |
| TMEM32 | 0 | 1 | 0 | 0 | 0.57 | 0.68 | 0.95 | 0.97 | 0.97 | 1.00 | 0.62 | 0.70 | 0.95 |
| TMEM75 | 0 | 0 | 0 | 1 | 0.95 | 0.97 | 1.00 | 0.97 | 0.97 | 1.00 | 0.96 | 0.97 | 1.00 |
| TMEPAI | 0 | 1 | 0 | 0 | 0.51 | 0.62 | 0.94 | 0.97 | 0.97 | 1.00 | 0.56 | 0.64 | 0.93 |
| TMOD4 | 0 | 1 | 0 | 0 | 0.59 | 0.70 | 0.95 | 0.97 | 0.97 | 1.00 | 0.64 | 0.72 | 0.95 |
| TMX2 | 0 | 1 | 0 | 0 | 0.59 | 0.70 | 0.95 | 0.97 | 0.97 | 1.00 | 0.64 | 0.72 | 0.95 |
| TNFAIP1 | 0 | 1 | 0 | 0 | 0.59 | 0.70 | 0.95 | 0.97 | 0.97 | 1.00 | 0.64 | 0.72 | 0.95 |
| TNFRSF6E | 0 | 0 | 0 | 1 | 0.95 | 0.97 | 1.00 | 0.20 | 0.25 | 0.67 | 0.16 | 0.22 | 0.68 |
| TNRC5 | 0 | 1 | 0 | 0 | 0.57 | 0.68 | 0.95 | 0.97 | 0.97 | 1.00 | 0.62 | 0.70 | 0.95 |
| TOM1L2 | 0 | 1 | 0 | 0 | 0.53 | 0.64 | 0.94 | 0.97 | 0.97 | 1.00 | 0.58 | 0.66 | 0.94 |
| TOP2A | 0 | 1 | 0 | 0 | 0.95 | 0.97 | 0.99 | 0.97 | 0.97 | 1.00 | 0.96 | 0.97 | 0.99 |
| TOP3A | 0 | 1 | 0 | 0 | 0.54 | 0.65 | 0.91 | 0.97 | 0.97 | 1.00 | 0.59 | 0.67 | 0.92 |
| TP53TG3 | 0 | 0 | 0 | 1 | 0.95 | 0.97 | 1.00 | 0.26 | 0.31 | 0.74 | 0.21 | 0.28 | 0.74 |
| TPCN2 | 0 | 2 | 0 | 0 | 0.95 | 0.97 | 0.99 | 0.97 | 0.97 | 1.00 | 0.96 | 0.97 | 0.99 |
| TPSAB1 | 0 | 1 | 0 | 0 | 0.57 | 0.68 | 0.95 | 0.97 | 0.97 | 1.00 | 0.62 | 0.70 | 0.95 |
| TPSB2 | 0 | 1 | 0 | 0 | 0.57 | 0.68 | 0.95 | 0.97 | 0.97 | 1.00 | 0.62 | 0.70 | 0.95 |
| TPSD1 | 0 | 1 | 0 | 0 | 0.56 | 0.67 | 0.95 | 0.97 | 0.97 | 1.00 | 0.61 | 0.69 | 0.94 |
| TPSG1 | 0 | 1 | 0 | 0 | 0.57 | 0.68 | 0.95 | 0.97 | 0.97 | 1.00 | 0.62 | 0.70 | 0.95 |
| TRAF4 | 0 | 1 | 0 | 0 | 0.59 | 0.70 | 0.95 | 0.97 | 0.97 | 1.00 | 0.64 | 0.72 | 0.95 |
| TREM1 | 1 | 1 | 0 | 0 | 0.00 | 0.01 | 0.12 | 0.97 | 0.97 | 1.00 | 0.06 | 0.08 | 0.25 |
| TREM2 | 0 | 1 | 0 | 0 | 0.59 | 0.70 | 0.95 | 0.97 | 0.97 | 1.00 | 0.64 | 0.72 | 0.95 |
| TREML1 | 1 | 1 | 0 | 0 | 0.01 | 0.07 | 0.24 | 0.97 | 0.97 | 1.00 | 0.08 | 0.17 | 0.41 |
| TREML2 | 0 | 1 | 0 | 0 | 0.57 | 0.68 | 0.95 | 0.97 | 0.97 | 1.00 | 0.62 | 0.70 | 0.95 |
| TREML4 | 0 | 1 | 0 | 0 | 0.56 | 0.67 | 0.95 | 0.97 | 0.97 | 1.00 | 0.61 | 0.69 | 0.94 |
| TRERF1 | 0 | 1 | 0 | 1 | 0.54 | 0.65 | 0.91 | 0.13 | 0.16 | 0.54 | 0.01 | 0.01 | 0.05 |
| TRIM11 | 0 | 1 | 0 | 0 | 0.56 | 0.67 | 0.95 | 0.97 | 0.97 | 1.00 | 0.61 | 0.69 | 0.94 |
| TRIM17 | 0 | 1 | 0 | 0 | 0.56 | 0.67 | 0.95 | 0.97 | 0.97 | 1.00 | 0.61 | 0.69 | 0.94 |
| TRIM33 | 0 | 1 | 0 | 0 | 0.54 | 0.65 | 0.91 | 0.97 | 0.97 | 1.00 | 0.59 | 0.67 | 0.92 |
| TRPA1 | 0 | 1 | 0 | 0 | 0.48 | 0.60 | 0.89 | 0.97 | 0.97 | 1.00 | 0.53 | 0.62 | 0.90 |
| TSHB | 0 | 1 | 0 | 0 | 0.59 | 0.70 | 0.95 | 0.97 | 0.97 | 1.00 | 0.64 | 0.72 | 0.95 |

FIG. 11K

| | | | | | | | | | | | | | |
|---|---|---|---|---|---|---|---|---|---|---|---|---|---|
| TSPAN2 | 0 | 1 | 0 | 0 | 0.49 | 0.60 | 0.93 | 0.97 | 0.97 | 1.00 | 0.54 | 0.63 | 0.93 |
| TTBK1 | 0 | 1 | 0 | 0 | 0.54 | 0.65 | 0.91 | 0.97 | 0.97 | 1.00 | 0.59 | 0.68 | 0.92 |
| TTLL13 | 0 | 0 | 0 | 1 | 0.95 | 0.97 | 1.00 | 0.19 | 0.23 | 0.64 | 0.15 | 0.20 | 0.65 |
| UBAP1 | 0 | 1 | 0 | 0 | 0.57 | 0.68 | 0.95 | 0.97 | 0.97 | 1.00 | 0.62 | 0.70 | 0.95 |
| UBE2I | 1 | 1 | 0 | 0 | 0.01 | 0.04 | 0.67 | 0.97 | 0.97 | 1.00 | 0.07 | 0.13 | 0.78 |
| UBQLN2 | 0 | 1 | 0 | 0 | 0.57 | 0.68 | 0.95 | 0.97 | 0.97 | 1.00 | 0.62 | 0.70 | 0.95 |
| UBR2 | 0 | 2 | 0 | 0 | 0.02 | 0.02 | 0.11 | 0.97 | 0.97 | 1.00 | 0.02 | 0.03 | 0.13 |
| UCK2 | 0 | 1 | 0 | 0 | 0.49 | 0.61 | 0.93 | 0.97 | 0.97 | 1.00 | 0.54 | 0.63 | 0.93 |
| ULK2 | 0 | 0 | 0 | 1 | 0.95 | 0.97 | 0.99 | 0.21 | 0.25 | 0.68 | 0.17 | 0.23 | 0.62 |
| UNC119 | 0 | 1 | 0 | 0 | 0.59 | 0.70 | 0.95 | 0.97 | 0.97 | 1.00 | 0.64 | 0.72 | 0.95 |
| UNC50 | 0 | 1 | 0 | 0 | 0.59 | 0.69 | 0.95 | 0.97 | 0.97 | 1.00 | 0.63 | 0.71 | 0.95 |
| UNC5CL | 0 | 1 | 0 | 0 | 0.58 | 0.69 | 0.95 | 0.97 | 0.97 | 1.00 | 0.63 | 0.71 | 0.95 |
| UNKL | 0 | 1 | 0 | 0 | 0.55 | 0.66 | 0.91 | 0.97 | 0.97 | 1.00 | 0.60 | 0.68 | 0.92 |
| UNQ6469 | 0 | 1 | 0 | 0 | 0.58 | 0.69 | 0.95 | 0.97 | 0.97 | 1.00 | 0.63 | 0.71 | 0.95 |
| UQCRFS1 | 0 | 1 | 0 | 0 | 0.95 | 0.97 | 1.00 | 0.97 | 0.97 | 1.00 | 0.96 | 0.97 | 1.00 |
| USH1C | 0 | 1 | 0 | 0 | 0.48 | 0.59 | 0.88 | 0.97 | 0.97 | 1.00 | 0.53 | 0.62 | 0.90 |
| USP14 | 0 | 1 | 0 | 0 | 0.55 | 0.66 | 0.94 | 0.97 | 0.97 | 1.00 | 0.60 | 0.68 | 0.94 |
| USP49 | 0 | 1 | 0 | 1 | 0.56 | 0.67 | 0.95 | 0.15 | 0.18 | 0.58 | 0.01 | 0.01 | 0.09 |
| USP51 | 0 | 2 | 0 | 0 | 0.03 | 0.04 | 0.28 | 0.97 | 0.97 | 1.00 | 0.03 | 0.05 | 0.26 |
| VEGF | 0 | 1 | 0 | 0 | 0.56 | 0.67 | 0.95 | 0.97 | 0.97 | 1.00 | 0.61 | 0.69 | 0.94 |
| VMD2L3 | 0 | 1 | 0 | 0 | 0.50 | 0.61 | 0.93 | 0.97 | 0.97 | 1.00 | 0.55 | 0.64 | 0.93 |
| VPS13A | 0 | 1 | 1 | 0 | 0.47 | 0.58 | 0.16 | 0.25 | 0.43 | 0.51 | 0.07 | 0.10 | 0.08 |
| VPS28 | 0 | 1 | 0 | 0 | 0.57 | 0.68 | 0.95 | 0.97 | 0.97 | 1.00 | 0.62 | 0.70 | 0.95 |
| VTN | 0 | 1 | 0 | 0 | 0.59 | 0.70 | 0.95 | 0.97 | 0.97 | 1.00 | 0.64 | 0.72 | 0.95 |
| WDR32 | 0 | 1 | 0 | 0 | 0.57 | 0.68 | 0.95 | 0.97 | 0.97 | 1.00 | 0.62 | 0.70 | 0.95 |
| WDR40A | 0 | 1 | 0 | 0 | 0.55 | 0.66 | 0.95 | 0.97 | 0.97 | 1.00 | 0.60 | 0.69 | 0.94 |
| WDR44 | 0 | 1 | 0 | 0 | 0.54 | 0.65 | 0.91 | 0.97 | 0.97 | 1.00 | 0.58 | 0.67 | 0.92 |
| WHSC1L1 | 0 | 2 | 0 | 0 | 0.03 | 0.04 | 0.18 | 0.97 | 0.97 | 1.00 | 0.03 | 0.05 | 0.21 |
| WIRE | 0 | 2 | 0 | 1 | 0.95 | 0.97 | 1.00 | 0.97 | 0.97 | 1.00 | 0.96 | 0.97 | 1.00 |
| XPO1 | 0 | 1 | 0 | 0 | 0.57 | 0.68 | 0.92 | 0.97 | 0.97 | 1.00 | 0.62 | 0.70 | 0.93 |
| XPO5 | 1 | 1 | 0 | 0 | 0.01 | 0.10 | 0.21 | 0.97 | 0.97 | 1.00 | 0.08 | 0.21 | 0.37 |
| YAF2 | 0 | 1 | 0 | 0 | 0.51 | 0.62 | 0.94 | 0.97 | 0.97 | 1.00 | 0.56 | 0.65 | 0.93 |
| ZBP1 | 0 | 1 | 0 | 0 | 0.56 | 0.67 | 0.95 | 0.97 | 0.97 | 1.00 | 0.61 | 0.69 | 0.94 |
| ZCCHC12 | 0 | 1 | 0 | 0 | 0.57 | 0.68 | 0.95 | 0.97 | 0.97 | 1.00 | 0.62 | 0.70 | 0.95 |
| ZCCHC7 | 0 | 1 | 0 | 0 | 0.50 | 0.61 | 0.93 | 0.97 | 0.97 | 1.00 | 0.55 | 0.64 | 0.93 |
| ZDHHC5 | 0 | 1 | 0 | 0 | 0.57 | 0.68 | 0.92 | 0.97 | 0.97 | 1.00 | 0.62 | 0.70 | 0.93 |
| ZFP91 | 0 | 1 | 0 | 0 | 0.55 | 0.65 | 0.91 | 0.97 | 0.97 | 1.00 | 0.59 | 0.68 | 0.92 |
| ZGPAT | 0 | 0 | 0 | 1 | 0.95 | 0.97 | 0.99 | 0.16 | 0.20 | 0.60 | 0.13 | 0.17 | 0.54 |
| ZMYND11 | 0 | 1 | 0 | 0 | 0.56 | 0.67 | 0.91 | 0.97 | 0.97 | 1.00 | 0.61 | 0.69 | 0.93 |
| ZNF155 | 0 | 0 | 1 | 1 | 0.95 | 0.97 | 1.00 | 0.00 | 0.01 | 0.01 | 0.01 | 0.02 | 0.02 |
| ZNF179 | 0 | 0 | 0 | 1 | 0.95 | 0.97 | 1.00 | 0.20 | 0.25 | 0.67 | 0.16 | 0.22 | 0.68 |
| ZNF221 | 0 | 0 | 0 | 1 | 0.95 | 0.97 | 1.00 | 0.20 | 0.24 | 0.66 | 0.16 | 0.21 | 0.67 |
| ZNF318 | 1 | 1 | 0 | 0 | 0.01 | 0.09 | 0.22 | 0.97 | 0.97 | 1.00 | 0.08 | 0.19 | 0.38 |
| ZNF444 | 0 | 1 | 0 | 0 | 0.55 | 0.66 | 0.95 | 0.97 | 0.97 | 1.00 | 0.60 | 0.68 | 0.94 |
| ZNF449 | 0 | 1 | 0 | 0 | 0.56 | 0.66 | 0.95 | 0.97 | 0.97 | 1.00 | 0.60 | 0.69 | 0.94 |
| ZNF480 | 0 | 0 | 1 | 1 | 0.95 | 0.97 | 1.00 | 0.00 | 0.00 | 0.01 | 0.01 | 0.02 | 0.02 |
| ZNF528 | 0 | 0 | 0 | 1 | 0.95 | 0.97 | 1.00 | 0.16 | 0.19 | 0.60 | 0.13 | 0.17 | 0.61 |
| ZNF546 | 1 | 0 | 0 | 1 | 0.13 | 0.62 | 0.80 | 0.26 | 0.31 | 0.73 | 0.01 | 0.05 | 0.09 |
| ZNF598 | 0 | 1 | 0 | 0 | 0.55 | 0.66 | 0.91 | 0.97 | 0.97 | 1.00 | 0.60 | 0.68 | 0.92 |
| ZNF610 | 0 | 0 | 0 | 1 | 0.95 | 0.97 | 1.00 | 0.17 | 0.20 | 0.61 | 0.13 | 0.18 | 0.62 |
| ZNF713 | 0 | 0 | 0 | 1 | 0.95 | 0.97 | 1.00 | 0.97 | 0.97 | 1.00 | 0.96 | 0.97 | 1.00 |
| ZNF75 | 0 | 1 | 0 | 0 | 0.56 | 0.67 | 0.95 | 0.97 | 0.97 | 1.00 | 0.61 | 0.69 | 0.94 |
| ZNFN1A3 | 0 | 4 | 0 | 1 | 0.95 | 0.97 | 1.00 | 0.97 | 0.97 | 1.00 | 0.96 | 0.97 | 1.00 |
| ZPBP2 | 0 | 4 | 0 | 1 | 0.95 | 0.97 | 1.00 | 0.97 | 0.97 | 1.00 | 0.96 | 0.97 | 1.00 |
| ZSCAN5 | 0 | 1 | 1 | 0 | 0.57 | 0.68 | 0.95 | 0.10 | 0.25 | 0.50 | 0.07 | 0.10 | 0.18 |
| ZWINT | 0 | 1 | 0 | 0 | 0.58 | 0.68 | 0.95 | 0.97 | 0.97 | 1.00 | 0.62 | 0.70 | 0.95 |

* Passenger probability rates are provided for each tissue type as well as a total combined value, incorporating alterations from both tumor types. Three prior passenger mutation rates (high, medium and low) were used in these calculations and shown above (see SI Methods for additional information). Passenger genes co-amplified with known oncogenes CCND1, ERBB2, CCNE1, EGFR, or MYC are listed above, but their amplifications are not used to calculate passenger probabilities.

FIG. 11L

SI Table 5. Homozygously deleted genes in breast and colorectal cancers

| Gene | Breast Mutations | Breast Deletions | Colon Mutations | Colon Deletions | Passenger Probability ||||||||
|---|---|---|---|---|---|---|---|---|---|---|---|---|
| | | | | | Breast ||| Colon ||| Both tumor types combined |||
| | | | | | Low | Medium | High | Low | Medium | High | Low | Medium | High |
| AADAC | 0 | 1 | 0 | 0 | 0.56 | 0.67 | 0.95 | 0.97 | 0.97 | 1.00 | 0.61 | 0.69 | 0.94 |
| ABR | 0 | 1 | 0 | 0 | 0.72 | 0.80 | 0.95 | 0.97 | 0.97 | 1.00 | 0.75 | 0.81 | 0.96 |
| AK3 | 0 | 0 | 0 | 1 | 0.95 | 0.97 | 1.00 | 0.55 | 0.61 | 0.91 | 0.48 | 0.58 | 0.91 |
| ALG6 | 0 | 0 | 0 | 1 | 0.95 | 0.97 | 1.00 | 0.54 | 0.60 | 0.90 | 0.48 | 0.57 | 0.91 |
| ALPK2 | 0 | 0 | 0 | 1 | 0.95 | 0.97 | 0.99 | 0.65 | 0.71 | 0.94 | 0.58 | 0.67 | 0.92 |
| ANGPTL3 | 0 | 0 | 0 | 1 | 0.95 | 0.97 | 1.00 | 0.49 | 0.55 | 0.88 | 0.42 | 0.52 | 0.89 |
| APG4C | 0 | 0 | 0 | 1 | 0.95 | 0.97 | 1.00 | 0.53 | 0.60 | 0.90 | 0.47 | 0.56 | 0.90 |
| ARFIP2 | 0 | 1 | 0 | 0 | 0.48 | 0.59 | 0.93 | 0.97 | 0.97 | 1.00 | 0.53 | 0.62 | 0.92 |
| ASTN2 | 1 | 1 | 0 | 0 | 0.07 | 0.32 | 0.65 | 0.96 | 0.97 | 1.00 | 0.33 | 0.54 | 0.78 |
| ATAD1 | 0 | 1 | 1 | 1 | 0.95 | 0.97 | 1.00 | 0.25 | 0.42 | 0.50 | 0.59 | 0.69 | 0.74 |
| ATP10A | 1 | 1 | 0 | 0 | 0.03 | 0.15 | 0.41 | 0.97 | 0.97 | 1.00 | 0.17 | 0.32 | 0.60 |
| ATP8A1 | 0 | 0 | 0 | 1 | 0.95 | 0.97 | 0.99 | 0.66 | 0.71 | 0.94 | 0.59 | 0.67 | 0.92 |
| BACH | 0 | 0 | 0 | 1 | 0.95 | 0.97 | 1.00 | 0.52 | 0.58 | 0.89 | 0.45 | 0.54 | 0.90 |
| BNC2 | 0 | 1 | 0 | 0 | 0.76 | 0.83 | 0.96 | 0.97 | 0.97 | 1.00 | 0.79 | 0.85 | 0.97 |
| BVES | 0 | 1 | 0 | 0 | 0.51 | 0.62 | 0.94 | 0.97 | 0.97 | 1.00 | 0.55 | 0.64 | 0.93 |
| C10orf116 | 0 | 1 | 0 | 0 | 0.47 | 0.59 | 0.93 | 0.97 | 0.97 | 1.00 | 0.52 | 0.61 | 0.92 |
| C10orf59 | 0 | 0 | 0 | 1 | 0.95 | 0.97 | 1.00 | 0.97 | 0.97 | 1.00 | 0.95 | 0.97 | 1.00 |
| C14orf150 | 0 | 1 | 0 | 0 | 0.47 | 0.59 | 0.93 | 0.97 | 0.97 | 1.00 | 0.52 | 0.61 | 0.92 |
| C1orf141 | 0 | 0 | 0 | 1 | 0.95 | 0.97 | 1.00 | 0.52 | 0.58 | 0.89 | 0.45 | 0.54 | 0.90 |
| C1orf168 | 0 | 0 | 0 | 1 | 0.95 | 0.97 | 0.99 | 0.61 | 0.67 | 0.92 | 0.54 | 0.63 | 0.90 |
| C1orf41 | 0 | 1 | 0 | 0 | 0.53 | 0.64 | 0.94 | 0.97 | 0.97 | 1.00 | 0.58 | 0.66 | 0.94 |
| C6orf54 | 0 | 0 | 0 | 1 | 0.95 | 0.97 | 1.00 | 0.49 | 0.55 | 0.88 | 0.42 | 0.52 | 0.89 |
| C8A | 0 | 0 | 0 | 1 | 0.95 | 0.97 | 1.00 | 0.54 | 0.61 | 0.90 | 0.48 | 0.57 | 0.91 |
| C9orf11 | 0 | 1 | 0 | 0 | 0.95 | 0.97 | 1.00 | 0.97 | 0.97 | 1.00 | 0.96 | 0.97 | 1.00 |
| C9orf39 | 0 | 1 | 0 | 0 | 0.73 | 0.81 | 0.96 | 0.97 | 0.97 | 1.00 | 0.76 | 0.82 | 0.96 |
| C9orf72 | 0 | 1 | 0 | 0 | 0.95 | 0.97 | 1.00 | 0.97 | 0.97 | 1.00 | 0.96 | 0.97 | 1.00 |
| C9orf82 | 0 | 1 | 0 | 0 | 0.95 | 0.97 | 1.00 | 0.97 | 0.97 | 1.00 | 0.96 | 0.97 | 1.00 |
| CABLES1 | 0 | 0 | 0 | 1 | 0.95 | 0.97 | 1.00 | 0.56 | 0.62 | 0.91 | 0.49 | 0.58 | 0.91 |
| CART1 | 0 | 0 | 0 | 1 | 0.95 | 0.97 | 1.00 | 0.48 | 0.54 | 0.88 | 0.41 | 0.50 | 0.88 |
| CASK | 0 | 1 | 0 | 0 | 0.57 | 0.68 | 0.92 | 0.97 | 0.97 | 1.00 | 0.61 | 0.70 | 0.93 |
| CCBE1 | 0 | 0 | 0 | 2 | 0.95 | 0.96 | 1.00 | 0.06 | 0.08 | 0.34 | 0.04 | 0.06 | 0.33 |
| CDCA2 | 0 | 1 | 0 | 0 | 0.55 | 0.66 | 0.91 | 0.97 | 0.97 | 1.00 | 0.60 | 0.68 | 0.92 |
| CDH1 | 0 | 2 | 0 | 1 | 0.03 | 0.04 | 0.19 | 0.54 | 0.60 | 0.90 | 0.00 | 0.00 | 0.01 |
| CDH20 | 2 | 0 | 0 | 2 | 0.01 | 0.10 | 0.53 | 0.02 | 0.02 | 0.12 | 0.00 | 0.00 | 0.00 |
| CDH3 | 0 | 2 | 0 | 0 | 0.02 | 0.04 | 0.16 | 0.97 | 0.97 | 1.00 | 0.03 | 0.04 | 0.19 |
| CDKN2A | 0 | 6 | 0 | 0 | 0.00 | 0.00 | 0.00 | 0.97 | 0.97 | 1.00 | 0.00 | 0.00 | 0.00 |
| CDKN2B | 0 | 5 | 0 | 0 | 0.95 | 0.97 | 1.00 | 0.97 | 0.97 | 1.00 | 0.96 | 0.97 | 1.00 |
| CENTG2 | 0 | 1 | 0 | 0 | 0.78 | 0.85 | 0.97 | 0.97 | 0.97 | 1.00 | 0.80 | 0.85 | 0.97 |
| CHD5 | 2 | 0 | 0 | 1 | 0.01 | 0.13 | 0.66 | 0.55 | 0.61 | 0.90 | 0.04 | 0.05 | 0.17 |
| CHST7 | 0 | 1 | 0 | 0 | 0.47 | 0.59 | 0.93 | 0.97 | 0.97 | 1.00 | 0.52 | 0.61 | 0.92 |
| CNKSR2 | 0 | 1 | 1 | 0 | 0.55 | 0.66 | 0.91 | 0.25 | 0.42 | 0.50 | 0.09 | 0.13 | 0.16 |
| COMMD9 | 0 | 1 | 0 | 0 | 0.49 | 0.60 | 0.93 | 0.97 | 0.97 | 1.00 | 0.54 | 0.62 | 0.93 |
| CPLX4 | 0 | 0 | 0 | 2 | 0.95 | 0.97 | 1.00 | 0.01 | 0.01 | 0.08 | 0.01 | 0.01 | 0.08 |
| CRIM1 | 0 | 1 | 0 | 0 | 0.74 | 0.82 | 0.96 | 0.97 | 0.97 | 1.00 | 0.77 | 0.83 | 0.97 |
| CSMD1 | 1 | 3 | 3 | 0 | 0.03 | 0.24 | 0.42 | 0.01 | 0.05 | 0.31 | 0.01 | 0.06 | 0.16 |
| CXorf33 | 0 | 1 | 0 | 0 | 0.49 | 0.60 | 0.93 | 0.97 | 0.97 | 1.00 | 0.54 | 0.63 | 0.93 |
| CXorf36 | 0 | 1 | 0 | 0 | 0.54 | 0.65 | 0.94 | 0.97 | 0.97 | 1.00 | 0.59 | 0.67 | 0.94 |
| CXorf43 | 0 | 1 | 0 | 0 | 0.57 | 0.67 | 0.95 | 0.97 | 0.97 | 1.00 | 0.61 | 0.69 | 0.94 |
| CYP2A13 | 0 | 0 | 0 | 1 | 0.95 | 0.97 | 1.00 | 0.49 | 0.56 | 0.89 | 0.43 | 0.52 | 0.89 |
| CYP2J2 | 0 | 0 | 0 | 1 | 0.95 | 0.97 | 1.00 | 0.53 | 0.59 | 0.90 | 0.46 | 0.55 | 0.90 |
| CYP4V2 | 0 | 1 | 0 | 0 | 0.57 | 0.67 | 0.95 | 0.97 | 0.97 | 1.00 | 0.61 | 0.69 | 0.94 |
| DAB1 | 0 | 0 | 0 | 1 | 0.95 | 0.96 | 1.00 | 0.73 | 0.78 | 0.96 | 0.67 | 0.74 | 0.96 |
| DGCR6 | 0 | 1 | 0 | 0 | 0.52 | 0.63 | 0.94 | 0.97 | 0.97 | 1.00 | 0.57 | 0.66 | 0.93 |
| DIAPH3 | 0 | 1 | 0 | 0 | 0.60 | 0.70 | 0.92 | 0.97 | 0.97 | 1.00 | 0.64 | 0.72 | 0.93 |
| DLC1 | 0 | 0 | 0 | 1 | 0.94 | 0.96 | 0.99 | 0.79 | 0.82 | 0.97 | 0.72 | 0.79 | 0.95 |
| DMD | 2 | 1 | 2 | 0 | 0.02 | 0.13 | 0.58 | 0.11 | 0.35 | 0.46 | 0.05 | 0.18 | 0.44 |
| DMRTA1 | 0 | 3 | 1 | 0 | 0.95 | 0.97 | 1.00 | 0.25 | 0.42 | 0.50 | 0.59 | 0.69 | 0.74 |
| DNAH9 | 2 | 0 | 0 | 3 | 0.01 | 0.10 | 0.65 | 0.97 | 0.97 | 1.00 | 0.46 | 0.51 | 0.81 |
| DNAJC6 | 0 | 0 | 1 | 1 | 0.95 | 0.97 | 0.99 | 0.02 | 0.04 | 0.05 | 0.07 | 0.11 | 0.14 |
| DOCK5 | 0 | 1 | 0 | 0 | 0.70 | 0.79 | 0.95 | 0.97 | 0.97 | 1.00 | 0.74 | 0.80 | 0.96 |
| DOCK7 | 0 | 0 | 0 | 1 | 0.95 | 0.97 | 0.99 | 0.55 | 0.61 | 0.91 | 0.48 | 0.57 | 0.88 |
| DUSP21 | 0 | 1 | 1 | 0 | 0.47 | 0.59 | 0.93 | 0.25 | 0.42 | 0.50 | 0.07 | 0.10 | 0.13 |
| EFHC2 | 0 | 1 | 0 | 0 | 0.58 | 0.69 | 0.92 | 0.97 | 0.97 | 1.00 | 0.63 | 0.71 | 0.93 |

FIG. 12A

| Gene | | | | | | | | | | | | | |
|---|---|---|---|---|---|---|---|---|---|---|---|---|---|
| EFNA5 | 0 | 1 | 0 | 0 | 0.77 | 0.84 | 0.98 | 0.97 | 0.97 | 1.00 | 0.80 | 0.85 | 0.98 |
| EIF2C2 | 0 | 1 | 0 | 0 | 0.66 | 0.76 | 0.94 | 0.97 | 0.97 | 1.00 | 0.70 | 0.77 | 0.95 |
| ELAVL2 | 0 | 3 | 0 | 0 | 0.95 | 0.97 | 1.00 | 0.97 | 0.97 | 1.00 | 0.96 | 0.97 | 1.00 |
| EMILIN2 | 0 | 1 | 0 | 0 | 0.62 | 0.72 | 0.93 | 0.97 | 0.97 | 1.00 | 0.66 | 0.74 | 0.94 |
| ENC1 | 0 | 2 | 0 | 0 | 0.01 | 0.02 | 0.17 | 0.97 | 0.97 | 1.00 | 0.02 | 0.03 | 0.16 |
| ENTPD4 | 0 | 1 | 0 | 0 | 0.55 | 0.66 | 0.95 | 0.97 | 0.97 | 1.00 | 0.60 | 0.68 | 0.94 |
| ESPN | 0 | 0 | 0 | 1 | 0.95 | 0.97 | 0.99 | 0.47 | 0.53 | 0.87 | 0.40 | 0.49 | 0.84 |
| F11 | 0 | 1 | 0 | 0 | 0.56 | 0.67 | 0.95 | 0.97 | 0.97 | 1.00 | 0.61 | 0.69 | 0.94 |
| FAM27L | 0 | 1 | 0 | 1 | 0.47 | 0.59 | 0.93 | 0.46 | 0.52 | 0.87 | 0.03 | 0.04 | 0.26 |
| FAT | 0 | 2 | 0 | 0 | 0.06 | 0.09 | 0.01 | 0.97 | 0.97 | 1.00 | 0.07 | 0.10 | 0.03 |
| FBXL17 | 0 | 2 | 0 | 0 | 0.17 | 0.24 | 0.74 | 0.97 | 0.97 | 1.00 | 0.19 | 0.25 | 0.72 |
| FBXO42 | 0 | 1 | 0 | 0 | 0.58 | 0.69 | 0.92 | 0.97 | 0.97 | 1.00 | 0.63 | 0.71 | 0.93 |
| FHIT | 0 | 0 | 0 | 1 | 0.94 | 0.96 | 1.00 | 0.88 | 0.91 | 0.98 | 0.82 | 0.87 | 0.98 |
| FHOD3 | 2 | 0 | 1 | 1 | 0.01 | 0.12 | 0.64 | 0.04 | 0.09 | 0.12 | 0.02 | 0.05 | 0.15 |
| FLJ10884 | 0 | 0 | 0 | 1 | 0.95 | 0.97 | 0.99 | 0.52 | 0.58 | 0.90 | 0.46 | 0.55 | 0.87 |
| FLJ10986 | 0 | 0 | 0 | 1 | 0.95 | 0.97 | 1.00 | 0.68 | 0.74 | 0.94 | 0.62 | 0.70 | 0.95 |
| FLJ11506 | 0 | 0 | 0 | 1 | 0.95 | 0.97 | 1.00 | 0.51 | 0.57 | 0.89 | 0.44 | 0.54 | 0.90 |
| FLJ16323 | 0 | 2 | 0 | 0 | 0.95 | 0.97 | 1.00 | 0.97 | 0.97 | 1.00 | 0.96 | 0.97 | 1.00 |
| FLJ20315 | 0 | 0 | 0 | 1 | 0.95 | 0.97 | 0.99 | 0.53 | 0.60 | 0.90 | 0.47 | 0.56 | 0.88 |
| FLJ20344 | 0 | 1 | 0 | 0 | 0.48 | 0.59 | 0.93 | 0.97 | 0.97 | 1.00 | 0.52 | 0.61 | 0.92 |
| FLJ23129 | 0 | 0 | 0 | 1 | 0.95 | 0.97 | 1.00 | 0.56 | 0.62 | 0.91 | 0.49 | 0.58 | 0.91 |
| FLJ23311 | 0 | 1 | 0 | 0 | 0.51 | 0.62 | 0.89 | 0.97 | 0.97 | 1.00 | 0.55 | 0.64 | 0.91 |
| FLJ23560 | 0 | 0 | 0 | 1 | 0.95 | 0.97 | 1.00 | 0.46 | 0.52 | 0.87 | 0.39 | 0.48 | 0.87 |
| FLJ25801 | 0 | 1 | 0 | 0 | 0.54 | 0.65 | 0.94 | 0.97 | 0.97 | 1.00 | 0.59 | 0.67 | 0.94 |
| FLJ31810 | 0 | 1 | 0 | 0 | 0.95 | 0.97 | 1.00 | 0.97 | 0.97 | 1.00 | 0.96 | 0.97 | 1.00 |
| FLJ32096 | 0 | 0 | 0 | 1 | 0.95 | 0.97 | 1.00 | 0.46 | 0.52 | 0.87 | 0.39 | 0.48 | 0.87 |
| FLJ35709 | 0 | 1 | 0 | 0 | 0.51 | 0.62 | 0.94 | 0.97 | 0.97 | 1.00 | 0.55 | 0.64 | 0.93 |
| FLJ36980 | 0 | 0 | 0 | 1 | 0.95 | 0.97 | 1.00 | 0.54 | 0.60 | 0.90 | 0.47 | 0.56 | 0.91 |
| FLJ40873 | 0 | 0 | 0 | 1 | 0.95 | 0.97 | 1.00 | 0.53 | 0.59 | 0.90 | 0.46 | 0.55 | 0.90 |
| FLJ41327 | 0 | 1 | 0 | 0 | 0.52 | 0.63 | 0.94 | 0.97 | 0.97 | 1.00 | 0.57 | 0.66 | 0.93 |
| FLJ43080 | 0 | 1 | 0 | 0 | 0.68 | 0.77 | 0.97 | 0.97 | 0.97 | 1.00 | 0.71 | 0.78 | 0.96 |
| FLJ44894 | 0 | 1 | 0 | 0 | 0.54 | 0.65 | 0.94 | 0.97 | 0.97 | 1.00 | 0.59 | 0.67 | 0.94 |
| FLJ45212 | 0 | 1 | 0 | 0 | 0.47 | 0.59 | 0.93 | 0.97 | 0.97 | 1.00 | 0.52 | 0.61 | 0.92 |
| FLJ45337 | 0 | 0 | 0 | 1 | 0.95 | 0.97 | 1.00 | 0.63 | 0.68 | 0.93 | 0.56 | 0.65 | 0.93 |
| FLJ45455 | 1 | 0 | 0 | 1 | 0.11 | 0.47 | 0.79 | 0.97 | 0.97 | 1.00 | 0.51 | 0.71 | 0.89 |
| FLJ46380 | 0 | 0 | 0 | 1 | 0.95 | 0.97 | 1.00 | 0.46 | 0.52 | 0.87 | 0.39 | 0.48 | 0.87 |
| FNDC1 | 0 | 1 | 3 | 0 | 0.59 | 0.70 | 0.92 | 0.04 | 0.09 | 0.50 | 0.07 | 0.08 | 0.19 |
| FOXD3 | 0 | 0 | 0 | 1 | 0.95 | 0.97 | 1.00 | 0.49 | 0.55 | 0.88 | 0.42 | 0.52 | 0.89 |
| FRMD1 | 0 | 0 | 0 | 1 | 0.95 | 0.97 | 1.00 | 0.54 | 0.61 | 0.90 | 0.48 | 0.57 | 0.91 |
| FUNDC1 | 0 | 1 | 0 | 0 | 0.49 | 0.60 | 0.93 | 0.97 | 0.97 | 1.00 | 0.54 | 0.62 | 0.93 |
| FUT9 | 0 | 1 | 0 | 0 | 0.47 | 0.59 | 0.93 | 0.97 | 0.97 | 1.00 | 0.52 | 0.61 | 0.92 |
| FXC1 | 0 | 1 | 0 | 0 | 0.48 | 0.59 | 0.93 | 0.97 | 0.97 | 1.00 | 0.53 | 0.62 | 0.92 |
| GLRA3 | 0 | 0 | 0 | 1 | 0.95 | 0.97 | 1.00 | 0.65 | 0.71 | 0.94 | 0.58 | 0.67 | 0.94 |
| GLUD1 | 0 | 1 | 0 | 0 | 0.51 | 0.62 | 0.94 | 0.97 | 0.97 | 1.00 | 0.55 | 0.64 | 0.93 |
| GOLGA3 | 0 | 1 | 0 | 0 | 0.58 | 0.69 | 0.92 | 0.97 | 0.97 | 1.00 | 0.63 | 0.71 | 0.93 |
| GPHN | 0 | 0 | 0 | 1 | 0.95 | 0.97 | 0.99 | 0.63 | 0.69 | 0.93 | 0.56 | 0.65 | 0.91 |
| GPR153 | 0 | 0 | 0 | 1 | 0.95 | 0.97 | 1.00 | 0.46 | 0.52 | 0.87 | 0.39 | 0.48 | 0.87 |
| GRIA3 | 0 | 1 | 0 | 0 | 0.71 | 0.79 | 0.95 | 0.97 | 0.97 | 1.00 | 0.74 | 0.81 | 0.96 |
| GRIK2 | 1 | 1 | 0 | 0 | 0.04 | 0.25 | 0.50 | 0.96 | 0.97 | 1.00 | 0.22 | 0.44 | 0.67 |
| GRM5 | 0 | 0 | 0 | 1 | 0.95 | 0.96 | 0.99 | 0.75 | 0.79 | 0.96 | 0.68 | 0.76 | 0.95 |
| GRP | 0 | 0 | 0 | 2 | 0.95 | 0.97 | 1.00 | 0.01 | 0.01 | 0.06 | 0.01 | 0.01 | 0.06 |
| HACE1 | 0 | 1 | 0 | 0 | 0.55 | 0.66 | 0.91 | 0.97 | 0.97 | 1.00 | 0.60 | 0.68 | 0.92 |
| HES2 | 0 | 0 | 0 | 1 | 0.95 | 0.97 | 1.00 | 0.46 | 0.52 | 0.87 | 0.39 | 0.48 | 0.87 |
| HES3 | 0 | 0 | 0 | 1 | 0.95 | 0.97 | 1.00 | 0.46 | 0.52 | 0.87 | 0.39 | 0.48 | 0.87 |
| HGNT-IV-H | 0 | 0 | 0 | 1 | 0.95 | 0.97 | 1.00 | 0.46 | 0.52 | 0.87 | 0.39 | 0.48 | 0.87 |
| HOOK1 | 1 | 0 | 0 | 1 | 0.13 | 0.57 | 0.80 | 0.51 | 0.58 | 0.89 | 0.04 | 0.11 | 0.24 |
| HPGD | 0 | 0 | 0 | 1 | 0.95 | 0.97 | 1.00 | 0.54 | 0.60 | 0.90 | 0.48 | 0.57 | 0.91 |
| HRH4 | 0 | 0 | 0 | 1 | 0.95 | 0.97 | 1.00 | 0.51 | 0.58 | 0.89 | 0.45 | 0.54 | 0.90 |
| ICMT | 0 | 0 | 0 | 1 | 0.95 | 0.97 | 1.00 | 0.47 | 0.53 | 0.87 | 0.40 | 0.49 | 0.88 |
| IFNA1 | 0 | 2 | 0 | 0 | 0.95 | 0.97 | 1.00 | 0.97 | 0.97 | 1.00 | 0.96 | 0.97 | 1.00 |
| IFNA10 | 0 | 2 | 0 | 0 | 0.95 | 0.97 | 1.00 | 0.97 | 0.97 | 1.00 | 0.96 | 0.97 | 1.00 |
| IFNA13 | 0 | 2 | 0 | 0 | 0.95 | 0.97 | 1.00 | 0.97 | 0.97 | 1.00 | 0.96 | 0.97 | 1.00 |
| IFNA14 | 0 | 2 | 0 | 0 | 0.95 | 0.97 | 1.00 | 0.97 | 0.97 | 1.00 | 0.96 | 0.97 | 1.00 |
| IFNA16 | 0 | 2 | 0 | 0 | 0.95 | 0.97 | 1.00 | 0.97 | 0.97 | 1.00 | 0.96 | 0.97 | 1.00 |
| IFNA17 | 0 | 2 | 0 | 0 | 0.95 | 0.97 | 1.00 | 0.97 | 0.97 | 1.00 | 0.96 | 0.97 | 1.00 |
| IFNA2 | 1 | 2 | 0 | 0 | 0.09 | 0.38 | 0.97 | 0.97 | 0.97 | 1.00 | 0.52 | 0.67 | 0.98 |
| IFNA21 | 0 | 2 | 0 | 0 | 0.95 | 0.97 | 1.00 | 0.97 | 0.97 | 1.00 | 0.96 | 0.97 | 1.00 |
| IFNA4 | 0 | 2 | 0 | 0 | 0.95 | 0.97 | 1.00 | 0.97 | 0.97 | 1.00 | 0.96 | 0.97 | 1.00 |

FIG. 12B

| | | | | | | | | | | | | | |
|---|---|---|---|---|---|---|---|---|---|---|---|---|---|
| IFNA5 | 0 | 2 | 0 | 0 | 0.95 | 0.97 | 1.00 | 0.97 | 0.97 | 1.00 | 0.96 | 0.97 | 1.00 |
| IFNA6 | 0 | 2 | 0 | 0 | 0.95 | 0.97 | 1.00 | 0.97 | 0.97 | 1.00 | 0.96 | 0.97 | 1.00 |
| IFNA7 | 0 | 2 | 0 | 0 | 0.95 | 0.97 | 1.00 | 0.97 | 0.97 | 1.00 | 0.96 | 0.97 | 1.00 |
| IFNA8 | 0 | 2 | 0 | 0 | 0.95 | 0.97 | 1.00 | 0.97 | 0.97 | 1.00 | 0.96 | 0.97 | 1.00 |
| IFNB1 | 1 | 1 | 0 | 0 | 0.04 | 0.22 | 0.67 | 0.97 | 0.97 | 1.00 | 0.49 | 0.59 | 0.83 |
| IFNE1 | 0 | 2 | 0 | 0 | 0.95 | 0.97 | 1.00 | 0.97 | 0.97 | 1.00 | 0.96 | 0.97 | 1.00 |
| IFNK | 0 | 1 | 0 | 0 | 0.95 | 0.97 | 1.00 | 0.97 | 0.97 | 1.00 | 0.96 | 0.97 | 1.00 |
| IFNW1 | 0 | 1 | 0 | 0 | 0.95 | 0.97 | 1.00 | 0.97 | 0.97 | 1.00 | 0.96 | 0.97 | 1.00 |
| IFT74 | 0 | 1 | 0 | 0 | 0.95 | 0.97 | 1.00 | 0.97 | 0.97 | 1.00 | 0.96 | 0.97 | 1.00 |
| IL12RB2 | 0 | 0 | 0 | 1 | 0.95 | 0.97 | 0.99 | 0.54 | 0.60 | 0.90 | 0.47 | 0.56 | 0.88 |
| IL23R | 0 | 0 | 0 | 1 | 0.95 | 0.97 | 1.00 | 0.60 | 0.66 | 0.92 | 0.53 | 0.62 | 0.92 |
| IMPACT | 0 | 0 | 0 | 1 | 0.95 | 0.97 | 1.00 | 0.53 | 0.59 | 0.90 | 0.46 | 0.55 | 0.90 |
| INADL | 0 | 0 | 0 | 1 | 0.95 | 0.97 | 0.99 | 0.72 | 0.76 | 0.95 | 0.65 | 0.73 | 0.94 |
| INPP1 | 0 | 1 | 0 | 0 | 0.56 | 0.67 | 0.95 | 0.97 | 0.97 | 1.00 | 0.61 | 0.69 | 0.94 |
| INSL5 | 0 | 0 | 0 | 1 | 0.95 | 0.97 | 1.00 | 0.49 | 0.55 | 0.88 | 0.42 | 0.52 | 0.89 |
| ITGB3BP | 0 | 0 | 0 | 1 | 0.95 | 0.97 | 1.00 | 0.52 | 0.58 | 0.89 | 0.45 | 0.54 | 0.90 |
| ITM2B | 0 | 1 | 0 | 0 | 0.53 | 0.64 | 0.94 | 0.97 | 0.97 | 1.00 | 0.58 | 0.66 | 0.94 |
| JAK1 | 0 | 0 | 0 | 1 | 0.95 | 0.97 | 0.99 | 0.60 | 0.66 | 0.92 | 0.53 | 0.62 | 0.90 |
| KCNAB2 | 0 | 0 | 0 | 1 | 0.95 | 0.97 | 1.00 | 0.51 | 0.57 | 0.89 | 0.44 | 0.53 | 0.89 |
| KCNQ4 | 0 | 1 | 0 | 0 | 0.59 | 0.70 | 0.92 | 0.97 | 0.97 | 1.00 | 0.64 | 0.72 | 0.93 |
| KCTD9 | 0 | 1 | 0 | 0 | 0.54 | 0.65 | 0.94 | 0.97 | 0.97 | 1.00 | 0.58 | 0.67 | 0.94 |
| KIAA0427 | 2 | 0 | 0 | 1 | 0.01 | 0.09 | 0.52 | 0.75 | 0.80 | 0.96 | 0.08 | 0.10 | 0.24 |
| KIAA0720 | 0 | 0 | 0 | 1 | 0.95 | 0.97 | 0.99 | 0.47 | 0.53 | 0.87 | 0.40 | 0.49 | 0.84 |
| KIAA0802 | 0 | 1 | 0 | 0 | 0.70 | 0.78 | 0.95 | 0.97 | 0.97 | 1.00 | 0.73 | 0.80 | 0.96 |
| KIAA1456 | 0 | 0 | 0 | 1 | 0.95 | 0.97 | 1.00 | 0.52 | 0.58 | 0.89 | 0.45 | 0.54 | 0.90 |
| KIAA1468 | 0 | 0 | 1 | 2 | 0.95 | 0.97 | 0.99 | 0.00 | 0.00 | 0.00 | 0.00 | 0.00 | 0.00 |
| KIAA1573 | 0 | 0 | 0 | 1 | 0.95 | 0.97 | 0.99 | 0.56 | 0.62 | 0.91 | 0.49 | 0.58 | 0.89 |
| KIAA1799 | 0 | 0 | 0 | 1 | 0.95 | 0.97 | 1.00 | 0.52 | 0.58 | 0.89 | 0.45 | 0.54 | 0.90 |
| KIF25 | 0 | 0 | 0 | 1 | 0.95 | 0.97 | 1.00 | 0.51 | 0.58 | 0.89 | 0.45 | 0.54 | 0.90 |
| KLHL9 | 0 | 2 | 0 | 0 | 0.95 | 0.97 | 1.00 | 0.97 | 0.97 | 1.00 | 0.96 | 0.97 | 1.00 |
| KLKB1 | 0 | 1 | 0 | 0 | 0.57 | 0.68 | 0.95 | 0.97 | 0.97 | 1.00 | 0.62 | 0.70 | 0.95 |
| KRT1B | 0 | 1 | 0 | 0 | 0.55 | 0.66 | 0.95 | 0.97 | 0.97 | 1.00 | 0.60 | 0.68 | 0.94 |
| LDLRAD3 | 0 | 1 | 0 | 0 | 0.77 | 0.84 | 0.98 | 0.97 | 0.97 | 1.00 | 0.80 | 0.85 | 0.98 |
| LECT1 | 0 | 1 | 0 | 0 | 0.53 | 0.64 | 0.94 | 0.97 | 0.97 | 1.00 | 0.57 | 0.66 | 0.94 |
| LEPR | 0 | 0 | 0 | 1 | 0.95 | 0.97 | 0.99 | 0.55 | 0.61 | 0.91 | 0.48 | 0.57 | 0.88 |
| LEPROT | 0 | 0 | 0 | 1 | 0.95 | 0.97 | 1.00 | 0.51 | 0.57 | 0.89 | 0.44 | 0.53 | 0.89 |
| LIN28B | 0 | 1 | 0 | 0 | 0.53 | 0.64 | 0.94 | 0.97 | 0.97 | 1.00 | 0.58 | 0.67 | 0.94 |
| LMAN1 | 0 | 0 | 0 | 2 | 0.95 | 0.97 | 1.00 | 0.01 | 0.01 | 0.07 | 0.01 | 0.01 | 0.07 |
| LOC115645 | 0 | 1 | 0 | 0 | 0.52 | 0.63 | 0.94 | 0.97 | 0.97 | 1.00 | 0.57 | 0.66 | 0.93 |
| LOC148213 | 0 | 1 | 0 | 0 | 0.53 | 0.64 | 0.94 | 0.97 | 0.97 | 1.00 | 0.58 | 0.66 | 0.94 |
| LOC163782 | 0 | 0 | 0 | 1 | 0.95 | 0.97 | 0.99 | 0.57 | 0.63 | 0.91 | 0.50 | 0.59 | 0.89 |
| LOC440337 | 0 | 0 | 0 | 1 | 0.95 | 0.97 | 1.00 | 0.48 | 0.54 | 0.88 | 0.41 | 0.51 | 0.88 |
| LOC91431 | 0 | 1 | 0 | 0 | 0.55 | 0.66 | 0.91 | 0.97 | 0.97 | 1.00 | 0.59 | 0.68 | 0.92 |
| LPIN2 | 0 | 1 | 0 | 0 | 0.56 | 0.67 | 0.91 | 0.97 | 0.97 | 1.00 | 0.60 | 0.69 | 0.92 |
| LRRC19 | 0 | 1 | 0 | 0 | 0.95 | 0.97 | 1.00 | 0.97 | 0.97 | 1.00 | 0.96 | 0.97 | 1.00 |
| LRRIQ1 | 0 | 0 | 0 | 1 | 0.95 | 0.97 | 0.99 | 0.50 | 0.56 | 0.89 | 0.43 | 0.53 | 0.86 |
| MALT1 | 0 | 0 | 0 | 2 | 0.95 | 0.97 | 0.99 | 0.01 | 0.02 | 0.09 | 0.01 | 0.01 | 0.07 |
| MANEA | 1 | 1 | 0 | 0 | 0.01 | 0.05 | 0.17 | 0.97 | 0.97 | 1.00 | 0.06 | 0.12 | 0.31 |
| MAOA | 1 | 1 | 0 | 0 | 0.00 | 0.01 | 0.10 | 0.97 | 0.97 | 1.00 | 0.05 | 0.07 | 0.21 |
| MAOB | 0 | 1 | 0 | 0 | 0.52 | 0.63 | 0.94 | 0.97 | 0.97 | 1.00 | 0.56 | 0.65 | 0.93 |
| MAP2K4 | 0 | 0 | 0 | 3 | 0.95 | 0.97 | 1.00 | 0.00 | 0.00 | 0.00 | 0.00 | 0.00 | 0.00 |
| MC4R | 0 | 0 | 0 | 2 | 0.95 | 0.97 | 1.00 | 0.01 | 0.01 | 0.06 | 0.01 | 0.01 | 0.06 |
| METT5D1 | 0 | 1 | 0 | 0 | 0.54 | 0.65 | 0.94 | 0.97 | 0.97 | 1.00 | 0.58 | 0.67 | 0.94 |
| MGC34837 | 1 | 0 | 0 | 1 | 0.10 | 0.48 | 0.80 | 0.59 | 0.65 | 0.92 | 0.05 | 0.12 | 0.30 |
| MGC35130 | 0 | 0 | 0 | 1 | 0.95 | 0.97 | 1.00 | 0.54 | 0.60 | 0.90 | 0.47 | 0.56 | 0.91 |
| MGC40168 | 0 | 0 | 0 | 1 | 0.95 | 0.97 | 1.00 | 0.46 | 0.52 | 0.87 | 0.39 | 0.48 | 0.87 |
| MGC4399 | 0 | 1 | 0 | 0 | 0.55 | 0.65 | 0.94 | 0.97 | 0.97 | 1.00 | 0.59 | 0.68 | 0.94 |
| MIER1 | 0 | 0 | 0 | 1 | 0.95 | 0.97 | 1.00 | 0.51 | 0.58 | 0.89 | 0.45 | 0.54 | 0.90 |
| MINPP1 | 0 | 1 | 0 | 1 | 0.95 | 0.97 | 1.00 | 0.97 | 0.97 | 1.00 | 0.96 | 0.97 | 1.00 |
| MLLT4 | 0 | 0 | 0 | 1 | 0.95 | 0.97 | 0.99 | 0.56 | 0.62 | 0.91 | 0.49 | 0.58 | 0.89 |
| MMRN2 | 0 | 1 | 1 | 0 | 0.51 | 0.62 | 0.89 | 0.25 | 0.43 | 0.50 | 0.07 | 0.11 | 0.14 |
| MOBKL2B | 0 | 1 | 0 | 0 | 0.95 | 0.97 | 1.00 | 0.97 | 0.97 | 1.00 | 0.96 | 0.97 | 1.00 |
| MSRA | 0 | 0 | 0 | 1 | 0.94 | 0.96 | 1.00 | 0.80 | 0.83 | 0.97 | 0.73 | 0.80 | 0.97 |
| MTAP | 0 | 4 | 0 | 0 | 0.95 | 0.97 | 1.00 | 0.97 | 0.97 | 1.00 | 0.96 | 0.97 | 1.00 |
| MTNR1A | 0 | 1 | 0 | 0 | 0.55 | 0.66 | 0.95 | 0.97 | 0.97 | 1.00 | 0.60 | 0.68 | 0.94 |
| MTUS1 | 0 | 1 | 0 | 0 | 0.75 | 0.82 | 0.96 | 0.97 | 0.97 | 1.00 | 0.78 | 0.83 | 0.97 |
| MYO3B | 0 | 0 | 0 | 1 | 0.94 | 0.96 | 0.99 | 0.79 | 0.83 | 0.97 | 0.73 | 0.80 | 0.96 |
| MYO9A | 0 | 1 | 0 | 0 | 0.67 | 0.76 | 0.31 | 0.97 | 0.97 | 1.00 | 0.71 | 0.78 | 0.49 |

FIG. 12C

| | | | | | | | | | | | | | |
|---|---|---|---|---|---|---|---|---|---|---|---|---|---|
| MYOCD | 0 | 0 | 0 | 1 | 0.95 | 0.97 | 0.99 | 0.97 | 0.97 | 1.00 | 0.96 | 0.97 | 0.99 |
| NAP1L1 | 0 | 0 | 0 | 1 | 0.95 | 0.97 | 1.00 | 0.48 | 0.54 | 0.88 | 0.42 | 0.51 | 0.88 |
| NDP | 0 | 1 | 0 | 0 | 0.50 | 0.61 | 0.93 | 0.97 | 0.97 | 1.00 | 0.54 | 0.63 | 0.93 |
| NEDD4L | 0 | 0 | 0 | 1 | 0.94 | 0.96 | 0.99 | 0.76 | 0.80 | 0.96 | 0.69 | 0.76 | 0.95 |
| NELL1 | 0 | 1 | 1 | 0 | 0.90 | 0.93 | 0.99 | 0.23 | 0.40 | 0.48 | 0.38 | 0.49 | 0.55 |
| NFIA | 0 | 0 | 0 | 1 | 0.95 | 0.97 | 1.00 | 0.71 | 0.76 | 0.95 | 0.64 | 0.72 | 0.95 |
| NR3C2 | 0 | 1 | 1 | 0 | 0.76 | 0.83 | 0.96 | 0.24 | 0.42 | 0.50 | 0.20 | 0.27 | 0.33 |
| NRXN3 | 1 | 0 | 0 | 1 | 0.13 | 0.59 | 0.78 | 0.84 | 0.87 | 0.98 | 0.16 | 0.39 | 0.58 |
| NTS | 0 | 0 | 0 | 1 | 0.95 | 0.97 | 1.00 | 0.46 | 0.52 | 0.87 | 0.40 | 0.49 | 0.88 |
| OLFM4 | 0 | 1 | 0 | 0 | 0.55 | 0.66 | 0.95 | 0.97 | 0.97 | 1.00 | 0.60 | 0.68 | 0.94 |
| OMA1 | 0 | 0 | 1 | 1 | 0.95 | 0.97 | 1.00 | 0.01 | 0.01 | 0.04 | 0.04 | 0.05 | 0.10 |
| OR3A3 | 0 | 0 | 0 | 1 | 0.95 | 0.97 | 1.00 | 0.47 | 0.53 | 0.87 | 0.40 | 0.49 | 0.88 |
| OR4C6 | 0 | 1 | 0 | 0 | 0.52 | 0.63 | 0.94 | 0.97 | 0.97 | 1.00 | 0.57 | 0.66 | 0.93 |
| OR4S2 | 0 | 1 | 0 | 0 | 0.52 | 0.63 | 0.94 | 0.97 | 0.97 | 1.00 | 0.57 | 0.66 | 0.93 |
| OR51E2 | 0 | 0 | 0 | 1 | 0.95 | 0.97 | 1.00 | 0.50 | 0.56 | 0.89 | 0.43 | 0.53 | 0.89 |
| OSBPL1A | 0 | 0 | 0 | 1 | 0.95 | 0.97 | 0.99 | 0.66 | 0.72 | 0.94 | 0.60 | 0.68 | 0.92 |
| OSBPL8 | 0 | 0 | 0 | 1 | 0.95 | 0.97 | 0.99 | 0.55 | 0.61 | 0.91 | 0.48 | 0.57 | 0.88 |
| PAMCI | 0 | 0 | 0 | 1 | 0.95 | 0.97 | 1.00 | 0.50 | 0.56 | 0.89 | 0.43 | 0.53 | 0.89 |
| PAPSS2 | 0 | 1 | 0 | 1 | 0.95 | 0.97 | 1.00 | 0.97 | 0.97 | 1.00 | 0.96 | 0.97 | 1.00 |
| PCDH17 | 0 | 1 | 0 | 0 | 0.59 | 0.69 | 0.92 | 0.97 | 0.97 | 1.00 | 0.63 | 0.71 | 0.93 |
| PCDH8 | 1 | 1 | 0 | 0 | 0.01 | 0.05 | 0.17 | 0.97 | 0.97 | 1.00 | 0.05 | 0.12 | 0.30 |
| PCGF3 | 0 | 1 | 0 | 0 | 0.54 | 0.65 | 0.94 | 0.97 | 0.97 | 1.00 | 0.59 | 0.67 | 0.94 |
| PDE4B | 0 | 0 | 0 | 1 | 0.95 | 0.96 | 0.99 | 0.72 | 0.77 | 0.95 | 0.66 | 0.73 | 0.94 |
| PGM1 | 0 | 0 | 0 | 1 | 0.95 | 0.97 | 1.00 | 0.57 | 0.63 | 0.91 | 0.50 | 0.59 | 0.91 |
| PHLDA1 | 0 | 0 | 0 | 1 | 0.95 | 0.97 | 1.00 | 0.47 | 0.54 | 0.88 | 0.41 | 0.50 | 0.88 |
| PIK3R1 | 1 | 0 | 0 | 1 | 0.13 | 0.57 | 0.80 | 0.59 | 0.65 | 0.92 | 0.06 | 0.14 | 0.30 |
| PLAA | 0 | 1 | 0 | 0 | 0.95 | 0.97 | 1.00 | 0.97 | 0.97 | 1.00 | 0.96 | 0.97 | 1.00 |
| PLXDC2 | 0 | 1 | 0 | 0 | 0.84 | 0.89 | 0.99 | 0.96 | 0.97 | 1.00 | 0.86 | 0.90 | 0.99 |
| PMAIP1 | 0 | 0 | 0 | 2 | 0.95 | 0.97 | 1.00 | 0.01 | 0.01 | 0.06 | 0.01 | 0.01 | 0.06 |
| POF1B | 0 | 1 | 0 | 0 | 0.49 | 0.61 | 0.93 | 0.97 | 0.97 | 1.00 | 0.54 | 0.63 | 0.93 |
| POPDC3 | 0 | 1 | 0 | 0 | 0.47 | 0.59 | 0.93 | 0.97 | 0.97 | 1.00 | 0.52 | 0.61 | 0.92 |
| PPAP2B | 0 | 0 | 0 | 1 | 0.95 | 0.97 | 1.00 | 0.60 | 0.66 | 0.92 | 0.53 | 0.62 | 0.92 |
| PPP2R5E | 0 | 1 | 0 | 0 | 0.61 | 0.71 | 0.96 | 0.97 | 0.97 | 1.00 | 0.65 | 0.73 | 0.95 |
| PREP | 0 | 1 | 0 | 0 | 0.64 | 0.74 | 0.94 | 0.97 | 0.97 | 1.00 | 0.68 | 0.75 | 0.94 |
| PRKAA2 | 2 | 0 | 0 | 1 | 0.01 | 0.10 | 0.66 | 0.53 | 0.59 | 0.90 | 0.03 | 0.04 | 0.15 |
| PRODH | 1 | 1 | 0 | 0 | 0.01 | 0.07 | 0.24 | 0.97 | 0.97 | 1.00 | 0.08 | 0.17 | 0.40 |
| PROM1 | 0 | 1 | 0 | 0 | 0.66 | 0.76 | 0.94 | 0.97 | 0.97 | 1.00 | 0.70 | 0.77 | 0.95 |
| PSD3 | 0 | 2 | 0 | 0 | 0.40 | 0.52 | 0.85 | 0.96 | 0.97 | 1.00 | 0.43 | 0.53 | 0.86 |
| PSG5 | 0 | 1 | 0 | 0 | 0.52 | 0.63 | 0.94 | 0.97 | 0.97 | 1.00 | 0.57 | 0.66 | 0.93 |
| PTCHD3 | 0 | 1 | 0 | 0 | 0.58 | 0.69 | 0.95 | 0.97 | 0.97 | 1.00 | 0.63 | 0.71 | 0.95 |
| PTEN | 0 | 2 | 3 | 2 | 0.02 | 0.03 | 0.21 | 0.00 | 0.00 | 0.00 | 0.00 | 0.00 | 0.00 |
| PTPLAD2 | 0 | 1 | 0 | 0 | 0.95 | 0.97 | 1.00 | 0.97 | 0.97 | 1.00 | 0.96 | 0.97 | 1.00 |
| PXDNL | 0 | 1 | 0 | 0 | 0.77 | 0.84 | 0.98 | 0.97 | 0.97 | 1.00 | 0.79 | 0.85 | 0.98 |
| RAVER2 | 0 | 0 | 1 | 1 | 0.95 | 0.97 | 1.00 | 0.01 | 0.03 | 0.04 | 0.06 | 0.08 | 0.11 |
| RAX | 0 | 0 | 0 | 2 | 0.95 | 0.97 | 1.00 | 0.01 | 0.01 | 0.06 | 0.01 | 0.01 | 0.06 |
| RB1 | 0 | 1 | 0 | 0 | 0.57 | 0.67 | 0.92 | 0.97 | 0.97 | 1.00 | 0.61 | 0.69 | 0.93 |
| RHOJ | 0 | 1 | 0 | 0 | 0.60 | 0.70 | 0.95 | 0.97 | 0.97 | 1.00 | 0.64 | 0.72 | 0.95 |
| RNF152 | 0 | 0 | 0 | 2 | 0.95 | 0.97 | 1.00 | 0.01 | 0.01 | 0.06 | 0.01 | 0.01 | 0.06 |
| ROBO1 | 0 | 1 | 2 | 0 | 0.80 | 0.86 | 0.97 | 0.13 | 0.38 | 0.49 | 0.19 | 0.30 | 0.38 |
| ROBO2 | 0 | 1 | 1 | 0 | 0.82 | 0.88 | 0.97 | 0.24 | 0.42 | 0.49 | 0.26 | 0.35 | 0.41 |
| ROR1 | 1 | 0 | 0 | 1 | 0.11 | 0.47 | 0.79 | 0.72 | 0.77 | 0.95 | 0.09 | 0.18 | 0.43 |
| RP2 | 0 | 1 | 0 | 0 | 0.50 | 0.61 | 0.93 | 0.97 | 0.97 | 1.00 | 0.54 | 0.63 | 0.93 |
| RPL22 | 0 | 0 | 0 | 1 | 0.95 | 0.97 | 1.00 | 0.47 | 0.54 | 0.88 | 0.41 | 0.50 | 0.88 |
| RPS6KA6 | 0 | 1 | 0 | 0 | 0.52 | 0.63 | 0.94 | 0.97 | 0.97 | 1.00 | 0.57 | 0.65 | 0.93 |
| RSHL2 | 0 | 1 | 0 | 0 | 0.50 | 0.61 | 0.93 | 0.97 | 0.97 | 1.00 | 0.54 | 0.63 | 0.93 |
| RUNX1 | 0 | 1 | 0 | 0 | 0.76 | 0.84 | 0.98 | 0.97 | 0.97 | 1.00 | 0.79 | 0.84 | 0.98 |
| SAPS2 | 0 | 1 | 0 | 0 | 0.59 | 0.69 | 0.92 | 0.97 | 0.97 | 1.00 | 0.63 | 0.71 | 0.93 |
| SATL1 | 1 | 1 | 0 | 0 | 0.01 | 0.05 | 0.17 | 0.97 | 0.97 | 1.00 | 0.05 | 0.12 | 0.30 |
| SCEL | 0 | 0 | 0 | 1 | 0.95 | 0.97 | 0.99 | 0.55 | 0.61 | 0.91 | 0.48 | 0.57 | 0.88 |
| SCN1A | 0 | 1 | 1 | 0 | 0.58 | 0.69 | 0.92 | 0.25 | 0.42 | 0.50 | 0.10 | 0.14 | 0.18 |
| SEC11L3 | 0 | 0 | 0 | 2 | 0.95 | 0.97 | 1.00 | 0.01 | 0.01 | 0.08 | 0.01 | 0.01 | 0.09 |
| SGIP1 | 0 | 0 | 0 | 1 | 0.95 | 0.97 | 0.99 | 0.67 | 0.72 | 0.94 | 0.60 | 0.68 | 0.92 |
| SGK | 0 | 1 | 0 | 0 | 0.47 | 0.59 | 0.93 | 0.97 | 0.97 | 1.00 | 0.52 | 0.61 | 0.92 |
| SGPP1 | 0 | 1 | 0 | 0 | 0.49 | 0.61 | 0.93 | 0.97 | 0.97 | 1.00 | 0.54 | 0.63 | 0.93 |
| SH3GL2 | 0 | 1 | 0 | 0 | 0.78 | 0.85 | 0.98 | 0.97 | 0.97 | 1.00 | 0.81 | 0.86 | 0.98 |
| SLC25A37 | 0 | 1 | 0 | 0 | 0.60 | 0.70 | 0.96 | 0.97 | 0.97 | 1.00 | 0.64 | 0.72 | 0.95 |
| SLC2A12 | 0 | 1 | 0 | 0 | 0.58 | 0.68 | 0.95 | 0.97 | 0.97 | 1.00 | 0.62 | 0.70 | 0.95 |
| SLC35D1 | 0 | 0 | 0 | 1 | 0.95 | 0.97 | 1.00 | 0.53 | 0.59 | 0.90 | 0.46 | 0.56 | 0.90 |

FIG. 12D

| | | | | | | | | | | | | | |
|---|---|---|---|---|---|---|---|---|---|---|---|---|---|
| SLC6A15 | 0 | 0 | 0 | 1 | 0.95 | 0.97 | 1.00 | 0.49 | 0.55 | 0.88 | 0.42 | 0.51 | 0.89 |
| SLC9A7 | 0 | 1 | 0 | 0 | 0.54 | 0.65 | 0.91 | 0.97 | 0.97 | 1.00 | 0.58 | 0.67 | 0.92 |
| SLITRK1 | 0 | 1 | 0 | 0 | 0.52 | 0.63 | 0.94 | 0.97 | 0.97 | 1.00 | 0.57 | 0.66 | 0.93 |
| SMAD2 | 0 | 0 | 3 | 1 | 0.95 | 0.97 | 1.00 | 0.00 | 0.00 | 0.01 | 0.03 | 0.03 | 0.04 |
| SMAD3 | 0 | 0 | 2 | 1 | 0.95 | 0.97 | 1.00 | 0.00 | 0.01 | 0.06 | 0.05 | 0.07 | 0.15 |
| SMARCC1 | 0 | 1 | 0 | 0 | 0.61 | 0.71 | 0.93 | 0.97 | 0.97 | 1.00 | 0.65 | 0.73 | 0.94 |
| SNCG | 0 | 1 | 0 | 0 | 0.49 | 0.60 | 0.93 | 0.97 | 0.97 | 1.00 | 0.53 | 0.62 | 0.92 |
| SNTG1 | 0 | 1 | 0 | 0 | 0.69 | 0.78 | 0.97 | 0.97 | 0.97 | 1.00 | 0.73 | 0.79 | 0.97 |
| SSB1 | 0 | 1 | 0 | 0 | 0.50 | 0.61 | 0.93 | 0.97 | 0.97 | 1.00 | 0.54 | 0.63 | 0.93 |
| TACSTD2 | 0 | 0 | 0 | 1 | 0.95 | 0.97 | 1.00 | 0.50 | 0.56 | 0.89 | 0.43 | 0.52 | 0.89 |
| TAGAP | 0 | 1 | 0 | 0 | 0.50 | 0.61 | 0.89 | 0.97 | 0.97 | 1.00 | 0.55 | 0.64 | 0.91 |
| TDRD3 | 0 | 1 | 0 | 0 | 0.53 | 0.64 | 0.94 | 0.97 | 0.97 | 1.00 | 0.58 | 0.66 | 0.94 |
| TEK | 1 | 1 | 0 | 0 | 0.13 | 0.56 | 0.79 | 0.97 | 0.97 | 1.00 | 0.53 | 0.76 | 0.89 |
| TLR3 | 0 | 1 | 0 | 0 | 0.54 | 0.65 | 0.91 | 0.97 | 0.97 | 1.00 | 0.58 | 0.67 | 0.92 |
| TM2D1 | 0 | 0 | 0 | 1 | 0.95 | 0.97 | 1.00 | 0.52 | 0.58 | 0.89 | 0.45 | 0.54 | 0.90 |
| TMEM16E | 0 | 1 | 0 | 0 | 0.57 | 0.68 | 0.92 | 0.97 | 0.97 | 1.00 | 0.62 | 0.70 | 0.93 |
| TMEM16J | 0 | 1 | 0 | 0 | 0.56 | 0.67 | 0.91 | 0.97 | 0.97 | 1.00 | 0.61 | 0.69 | 0.93 |
| TNFRSF10/ | 0 | 0 | 0 | 1 | 0.95 | 0.97 | 1.00 | 0.54 | 0.60 | 0.90 | 0.47 | 0.57 | 0.91 |
| TNFRSF11/ | 0 | 0 | 0 | 2 | 0.95 | 0.97 | 0.99 | 0.02 | 0.02 | 0.13 | 0.01 | 0.02 | 0.11 |
| TNFRSF25 | 1 | 0 | 0 | 1 | 0.07 | 0.35 | 0.90 | 0.47 | 0.54 | 0.88 | 0.03 | 0.06 | 0.36 |
| TP53 | 18 | 0 | 18 | 1 | 0.00 | 0.00 | 0.00 | 0.00 | 0.00 | 0.00 | 0.00 | 0.00 | 0.00 |
| TRIM3 | 0 | 1 | 1 | 0 | 0.50 | 0.61 | 0.89 | 0.25 | 0.43 | 0.50 | 0.07 | 0.11 | 0.14 |
| TUBB4Q | 0 | 1 | 0 | 0 | 0.52 | 0.63 | 0.94 | 0.97 | 0.97 | 1.00 | 0.57 | 0.66 | 0.93 |
| TUSC1 | 0 | 2 | 0 | 0 | 0.95 | 0.97 | 1.00 | 0.97 | 0.97 | 1.00 | 0.96 | 0.97 | 1.00 |
| ULBP3 | 0 | 0 | 0 | 1 | 0.95 | 0.97 | 1.00 | 0.51 | 0.57 | 0.89 | 0.44 | 0.53 | 0.89 |
| USP1 | 0 | 0 | 0 | 1 | 0.95 | 0.97 | 0.99 | 0.49 | 0.55 | 0.88 | 0.42 | 0.52 | 0.86 |
| USP3 | 0 | 1 | 0 | 0 | 0.58 | 0.68 | 0.95 | 0.97 | 0.97 | 1.00 | 0.62 | 0.70 | 0.95 |
| UTX | 0 | 1 | 1 | 0 | 0.52 | 0.63 | 0.90 | 0.25 | 0.42 | 0.50 | 0.08 | 0.12 | 0.15 |
| WWOX | 0 | 1 | 0 | 0 | 0.91 | 0.94 | 0.99 | 0.96 | 0.97 | 1.00 | 0.92 | 0.94 | 0.99 |
| ZBTB7C | 0 | 0 | 0 | 1 | 0.95 | 0.97 | 0.99 | 0.52 | 0.58 | 0.89 | 0.45 | 0.54 | 0.87 |
| ZFP42 | 0 | 1 | 0 | 0 | 0.52 | 0.63 | 0.94 | 0.97 | 0.97 | 1.00 | 0.57 | 0.66 | 0.93 |
| ZNF100 | 0 | 1 | 0 | 0 | 0.53 | 0.64 | 0.94 | 0.97 | 0.97 | 1.00 | 0.58 | 0.67 | 0.94 |
| ZNF18 | 0 | 0 | 0 | 3 | 0.95 | 0.97 | 1.00 | 0.97 | 0.97 | 1.00 | 0.96 | 0.97 | 1.00 |
| ZNF254 | 0 | 1 | 0 | 0 | 0.54 | 0.65 | 0.94 | 0.97 | 0.97 | 1.00 | 0.59 | 0.67 | 0.94 |
| ZNF257 | 0 | 1 | 0 | 0 | 0.54 | 0.65 | 0.94 | 0.97 | 0.97 | 1.00 | 0.59 | 0.67 | 0.94 |
| ZNF43 | 0 | 1 | 1 | 0 | 0.52 | 0.63 | 0.94 | 0.22 | 0.39 | 0.50 | 0.08 | 0.11 | 0.15 |
| ZNF430 | 0 | 1 | 0 | 0 | 0.52 | 0.63 | 0.94 | 0.97 | 0.97 | 1.00 | 0.57 | 0.66 | 0.93 |
| ZNF431 | 0 | 1 | 0 | 0 | 0.53 | 0.64 | 0.94 | 0.97 | 0.97 | 1.00 | 0.58 | 0.67 | 0.94 |
| ZNF493 | 0 | 1 | 0 | 0 | 0.52 | 0.63 | 0.94 | 0.97 | 0.97 | 1.00 | 0.57 | 0.66 | 0.93 |
| ZNF521 | 0 | 0 | 2 | 1 | 0.95 | 0.97 | 0.99 | 0.00 | 0.01 | 0.07 | 0.06 | 0.08 | 0.17 |
| ZNF532 | 1 | 0 | 0 | 2 | 0.12 | 0.50 | 0.80 | 0.01 | 0.02 | 0.09 | 0.00 | 0.00 | 0.00 |
| ZNF539 | 0 | 1 | 0 | 0 | 0.54 | 0.65 | 0.94 | 0.97 | 0.97 | 1.00 | 0.59 | 0.67 | 0.94 |
| ZNF6 | 0 | 1 | 0 | 0 | 0.47 | 0.59 | 0.93 | 0.97 | 0.97 | 1.00 | 0.52 | 0.61 | 0.92 |
| ZNF626 | 0 | 1 | 0 | 0 | 0.53 | 0.64 | 0.94 | 0.97 | 0.97 | 1.00 | 0.58 | 0.67 | 0.94 |
| ZNF674 | 2 | 1 | 0 | 0 | 0.00 | 0.01 | 0.09 | 0.97 | 0.97 | 1.00 | 0.04 | 0.05 | 0.19 |
| ZNF675 | 0 | 1 | 0 | 0 | 0.52 | 0.63 | 0.94 | 0.97 | 0.97 | 1.00 | 0.57 | 0.66 | 0.93 |
| ZNF676 | 0 | 1 | 0 | 0 | 0.53 | 0.64 | 0.94 | 0.97 | 0.97 | 1.00 | 0.58 | 0.66 | 0.94 |
| ZNF708 | 0 | 1 | 0 | 0 | 0.54 | 0.65 | 0.94 | 0.97 | 0.97 | 1.00 | 0.59 | 0.67 | 0.94 |
| ZNF714 | 0 | 1 | 1 | 0 | 0.54 | 0.65 | 0.94 | 0.16 | 0.39 | 0.50 | 0.07 | 0.11 | 0.16 |
| ZNF85 | 0 | 1 | 0 | 0 | 0.54 | 0.65 | 0.94 | 0.97 | 0.97 | 1.00 | 0.59 | 0.67 | 0.94 |
| ZNF91 | 0 | 1 | 0 | 0 | 0.54 | 0.65 | 0.94 | 0.97 | 0.97 | 1.00 | 0.58 | 0.67 | 0.94 |
| ZNFN1A2 | 0 | 1 | 0 | 0 | 0.66 | 0.75 | 0.96 | 0.97 | 0.97 | 1.00 | 0.69 | 0.77 | 0.96 |

* Passenger probability rates are provided for each tissue type as well as a total combined value, incorporating alterations from both tumor types. Three prior passenger mutation rates (high, medium and low) were used in these calculations and shown above (see SI Methods for additional information). Passenger genes co-deleted with known tumor suppressor genes CDKN2A, PTEN, MAP2K4, or TP53 are listed above, but their deletions are not used to calculate passenger probabilities.

FIG. 12E

SI table 6. Pathways enriched for copy number alterations and point mutations

| Pathway | Pathway Database | Set Size | Breast | | | | Colon | | | |
|---|---|---|---|---|---|---|---|---|---|---|
| | | | Number of Mutations | Number of Deletions | Number of Amplifications | Q Value | Number of Mutations | Number of Deletions | Number of Amplifications | Q Value |
| A2BR signaling via G-alpha-q: Inhibition of TKR-specific PI3K activation (map 1a) 488 | MA | 6 | 6 | 0 | 0 | 2.08E-01 | 5 | 1 | 0 | 1.55E-01 |
| A2BR signaling via G-alpha-q: PRKCA - RSK & JNK specific pathways (map 2b) 491 | MA | 22 | 12 | 0 | 1 | 9.16E-04 | 22 | 1 | 1 | 1.39E-01 |
| A2BR signaling via G-alpha-q: PRKCB/G/Q specific pathways (map 3a) 493 | MA | 22 | 6 | 0 | 0 | 9.51E-02 | 3 | 0 | 1 | 4.80E-01 |
| A2BR signaling via G-alpha-q: PRKCE - RASGRP specific pathways (map 3b) 494 | MA | 18 | 12 | 0 | 0 | 8.87E-04 | 5 | 1 | 1 | 3.78E-01 |
| A2BR signaling via G-beta/gamma dimer. Activation of PH-domain proteins. (map 1) 484 | MA | 9 | 3 | 0 | 0 | 1.71E-01 | 0 | 0 | 0 | 5.96E-01 |
| actin cytoskeleton organization and biogenesis -613846463 | GO | 103 | 16 | 2 | 5 | 4.61E-02 | 22 | 2 | 0 | 4.15E-01 |
| actin filament organization -1442479876 | GO | 31 | 7 | 2 | 1 | 1.43E-01 | 1 | 0 | 0 | 5.96E-01 |
| actin filament severing -1362194210 | GO | 6 | 2 | 0 | 1 | 1.90E-01 | 1 | 0 | 0 | 1.92E-01 |
| actin filament-based movement -457359296 | GO | 16 | 6 | 0 | 1 | 5.64E-02 | 1 | 0 | 0 | 5.92E-01 |
| actin filament-based process -1936960890 | GO | 3 | 2 | 0 | 0 | 3.31E-01 | 3 | 0 | 0 | 1.18E-02 |
| activation of JNK activity -1853311838 | GO | 26 | 5 | 0 | 2 | 6.43E-02 | 0 | 0 | 3 | 5.66E-01 |
| adult heart development -1002770935 | GO | 10 | 5 | 0 | 0 | 1.57E-01 | 9 | 0 | 0 | 3.77E-01 |
| aging -1415412811 | GO | 34 | 6 | 6 | 1 | 8.58E-02 | 3 | 2 | 0 | 1.50E-01 |
| Anandamide biosynthesis and metabolism 2428 | MA | 20 | 7 | 0 | 1 | 1.46E-02 | 4 | 0 | 0 | 4.74E-01 |
| androgen receptor signaling pathway -1288723100 | GO | 28 | 3 | 1 | 8 | 1.85E-01 | 1 | 0 | 2 | 3.30E-01 |
| anterior/posterior pattern formation -1140404228 | GO | 43 | 5 | 0 | 5 | 1.57E-01 | 41 | 1 | 0 | 7.44E-02 |
| Apoptosis and survival_NGF activation of NF-kB 653 | MA | 33 | 13 | 0 | 0 | 7.40E-02 | 6 | 1 | 1 | 5.25E-01 |
| Apoptosis and survival_NGF signaling pathway 652 | MA | 22 | 11 | 0 | 1 | 6.35E-02 | 5 | 1 | 0 | 5.10E-01 |
| Apoptosis_Apoptosis mediated by external signals 141097 | GG | 150 | 17 | 4 | 3 | 2.96E-01 | 25 | 8 | 2 | 7.25E-02 |
| arginine biosynthetic process -969117670 | GO | 3 | 3 | 0 | 0 | 2.10E-02 | 0 | 0 | 0 | 5.96E-01 |
| arrestin mediated desensitization of G-protein coupled receptor protein signaling pathway -1130473540 | GO | 4 | 1 | 0 | 2 | 4.85E-02 | 0 | 0 | 0 | 4.29E-01 |
| artery morphogenesis -34974221 | GO | 6 | 2 | 0 | 0 | 3.97E-02 | 3 | 1 | 0 | 1.08E-02 |
| attachment of GPI anchor to protein -1434364319 | GO | 4 | 1 | 0 | 3 | 4.75E-02 | 0 | 0 | 0 | 7.89E-02 |
| axonal fasciculation -1539022840 | GO | 8 | 3 | 1 | 0 | 1.53E-02 | 2 | 0 | 0 | 3.01E-01 |
| B cell receptor signaling pathway -1484422901 | GO | 5 | 3 | 0 | 0 | 1.30E-01 | 0 | 0 | 0 | 5.96E-01 |
| behavioral response to pain -1016118538 | GO | 5 | 0 | 1 | 0 | 5.15E-01 | 1 | 0 | 0 | 1.38E-01 |
| beta-tubulin folding -2023989277 | GO | 5 | 0 | 1 | 1 | 1.37E-01 | 0 | 0 | 0 | 1.46E-01 |
| blastocyst development -1623841854 | GO | 8 | 2 | 0 | 0 | 1.67E-03 | 0 | 0 | 3 | 4.60E-02 |
| Blood coagulation_GPVI-dependent platelet activation 2449 | MA | 45 | 15 | 0 | 0 | 1.64E-01 | 9 | 1 | 0 | 5.96E-01 |
| blood vessel development -77768385 | GO | 30 | 4 | 0 | 0 | 3.20E-01 | 4 | 1 | 1 | 1.87E-01 |
| blood vessel remodeling -446919990 | GO | 18 | 7 | 0 | 1 | 7.47E-02 | 3 | 0 | 0 | 2.30E-01 |
| brain development -430097946 | GO | 103 | 10 | 2 | 7 | 1.52E-01 | 15 | 3 | 1 | 9.75E-02 |
| branching morphogenesis of a tube -1827134395 | GO | 22 | 5 | 0 | 4 | 1.69E-01 | 4 | 0 | 1 | 1.54E-01 |
| brown fat cell differentiation -1941172241 | GO | 6 | 0 | 0 | 3 | 2.00E-01 | 0 | 0 | 0 | 2.27E-01 |
| caspase activation -2143949465 | GO | 36 | 4 | 7 | 1 | 5.45E-02 | 4 | 2 | 2 | 1.64E-01 |
| Caspases activation via nuclear import 375 | MA | 21 | 21 | 0 | 4 | 1.70E-01 | 18 | 1 | 1 | 4.80E-01 |
| Catecholamine metabolism 860 | MA | 15 | 3 | 1 | 4 | 5.47E-02 | 0 | 1 | 2 | 3.30E-01 |
| cell adhesion -552545827 | GO | 501 | 69 | 16 | 17 | 5.04E-04 | 101 | 4 | 5 | 1.20E-03 |

FROM FIG. 13A

| | | | | | | | | | |
|---|---|---|---|---|---|---|---|---|---|
| Cell adhesion_Cadherins 141141 | GG | 210 | 20 | 8 | 7 | 3.84E-01 | 65 | 6 | 3 | 7.98E-03 |
| Cell adhesion_Cell junctions 141177 | GG | 155 | 19 | 5 | 4 | 3.61E-01 | 23 | 6 | 2 | 1.52E-01 |
| Cell adhesion_Cell-matrix interactions 141085 | GG | 158 | 20 | 1 | 10 | 1.20E-01 | 31 | 0 | 4 | 3.02E-02 |
| Cell adhesion_Chemokines and adhesion 716 | MA | 127 | 28 | 2 | 2 | 9.75E-02 | 22 | 3 | 3 | 4.85E-01 |
| Cell adhesion_ECM remodeling 717 | MA | 51 | 8 | 0 | 2 | 2.08E-01 | 13 | 0 | 3 | 1.49E-01 |
| Cell adhesion_Endothelial cell contacts by junctional mechanisms 745 | MA | 30 | 5 | 0 | 2 | 1.52E-01 | 2 | 1 | 0 | 3.57E-01 |
| Cell adhesion_Endothelial cell contacts by non-junctional mechanisms 727 | MA | 34 | 10 | 0 | 2 | 1.65E-02 | 9 | 0 | 0 | 1.45E-01 |
| Cell adhesion_Histamine H1 receptor signaling in the interruption of cell barrier integrity 2435 | MA | 78 | 18 | 2 | 4 | 7.03E-02 | 2 | 1 | 0 | 5.96E-01 |
| Cell adhesion_Integrin priming 141127 | GG | 113 | 22 | 2 | 4 | 1.40E-01 | 22 | 4 | 0 | 3.77E-01 |
| Cell adhesion_Integrin-mediated cell-matrix adhesion 141120 | GG | 205 | 39 | 0 | 13 | 3.34E-02 | 23 | 2 | 2 | 4.63E-01 |
| Cell adhesion_Plasmin signaling 637 | MA | 38 | 13 | 1 | 1 | 2.24E-02 | 13 | 1 | 1 | 7.52E-02 |
| Cell adhesion_Platelet aggregation 141160 | GG | 182 | 33 | 0 | 8 | 1.52E-01 | 21 | 2 | 0 | 5.05E-01 |
| Cell adhesion_Platelet-endothelium-leucocyte interactions 141174 | GG | 161 | 25 | 2 | 6 | 4.35E-02 | 25 | 0 | 5 | 1.40E-01 |
| Cell adhesion_PLAU signaling 677 | MA | 41 | 11 | 0 | 1 | 1.17E-01 | 6 | 2 | 2 | 3.76E-01 |
| Cell adhesion_Role of CDK5 in cell adhesion 2361 | MA | 12 | 3 | 2 | 4 | 1.42E-02 | 2 | 1 | 1 | 4.60E-02 |
| Cell adhesion_Synaptic contact 141185 | GG | 167 | 19 | 2 | 14 | 1.34E-01 | 15 | 0 | 0 | 4.25E-01 |
| cell aging -294078400 | GO | 15 | 20 | 6 | 0 | 1.36E-01 | 18 | 1 | 0 | 5.46E-01 |
| cell cycle -1352108539 | GO | 384 | 47 | 17 | 31 | 4.84E-02 | 72 | 5 | 10 | 6.20E-02 |
| cell cycle checkpoint -483595763 | GO | 16 | 5 | 7 | 1 | 4.36E-02 | 1 | 0 | 0 | 1.95E-01 |
| Cell cycle_ATM/ATR regulation of G2 / M checkpoint 441 | MA | 27 | 22 | 0 | 1 | 1.95E-01 | 19 | 1 | 1 | 5.92E-01 |
| Cell cycle_ATM/ATR regulation of G1/S checkpoint 426 | MA | 37 | 26 | 0 | 8 | 1.13E-04 | 18 | 2 | 6 | 5.82E-02 |
| Cell cycle_Brca1 as a transcription regulator 525 | MA | 26 | 22 | 1 | 4 | 1.58E-02 | 18 | 1 | 2 | 2.75E-01 |
| Cell cycle_Chromosome condensation in prometaphase 709 | MA | 26 | 4 | 0 | 4 | 1.83E-01 | 4 | 0 | 0 | 2.62E-01 |
| Cell cycle_DNA-damage-induced responses 651 | MA | 7 | 21 | 0 | 0 | 4.19E-02 | 18 | 1 | 0 | 5.51E-01 |
| Cell cycle_ESR1 regulation of G1/S transition 2620 | MA | 31 | 2 | 1 | 8 | 1.40E-01 | 5 | 0 | 3 | 2.10E-01 |
| Cell cycle_G1-S Growth factor regulation 141098 | GG | 153 | 19 | 13 | 21 | 3.59E-03 | 52 | 5 | 10 | 1.65E-03 |
| Cell cycle_G1-S Interleukin regulation 141063 | GG | 97 | 13 | 12 | 9 | 3.05E-02 | 10 | 5 | 7 | 8.28E-02 |
| Cell cycle_Nucleocytoplasmic transport of CDK/Cyclins 473 | MA | 18 | 2 | 0 | 9 | 6.90E-02 | 0 | 0 | 2 | 2.37E-01 |
| Cell cycle_Regulation of G1/S transition (part 1) 544 | MA | 57 | 5 | 12 | 9 | 7.40E-02 | 12 | 2 | 2 | 7.25E-02 |
| Cell cycle_Role of Nek in cell cycle regulation 731 | MA | 47 | 6 | 0 | 3 | 6.13E-01 | 10 | 1 | 0 | 1.24E-01 |
| Cell cycle_Role of NFBD1 in DNA damage response 650 | MA | 10 | 23 | 0 | 1 | 2.10E-02 | 19 | 1 | 0 | 1.46E-01 |
| cell differentiation -2007041962 | GO | 391 | 69 | 9 | 22 | 1.58E-02 | 54 | 5 | 5 | 4.05E-01 |
| cell division -2006020920 | GO | 171 | 11 | 2 | 26 | 3.97E-02 | 6 | 1 | 5 | 1.09E-01 |
| cell projection organization and biogenesis -1945193380 | GO | 21 | 6 | 0 | 3 | 1.65E-02 | 0 | 3 | 0 | 5.34E-01 |
| cell-cell adhesion -1469629106 | GO | 67 | 20 | 5 | 1 | 1.67E-03 | 6 | 1 | 3 | 5.96E-01 |
| cell-substrate junction assembly -97649409 | GO | 5 | 3 | 0 | 0 | 1.31E-01 | 3 | 0 | 0 | 9.75E-02 |
| cellular component organization and biogenesis -1650313226 | GO | 12 | 3 | 1 | 1 | 7.03E-02 | 3 | 1 | 0 | 5.97E-03 |
| cellular lipid metabolic process -1142222772 | GO | 5 | 1 | 0 | 2 | 1.03E-01 | 0 | 0 | 0 | 5.01E-01 |
| cellular sodium ion homeostasis -1009169423 | GO | 3 | 1 | 0 | 0 | 4.29E-02 | 0 | 1 | 0 | 3.34E-01 |
| central nervous system development -662867866 | GO | 97 | 27 | 4 | 4 | 3.80E-01 | 31 | 4 | 2 | 8.44E-02 |
| centrosome duplication -16257103 | GO | 5 | 3 | 0 | 0 | 1.39E-01 | 0 | 0 | 0 | 5.96E-01 |
| cerebellar Purkinje cell differentiation -1386705213 | GO | 7 | 0 | 0 | 0 | 6.13E-01 | 4 | 0 | 0 | 2.98E-02 |
| cholesterol transport -1002673459 | GO | 14 | 0 | 0 | 0 | 6.13E-01 | 6 | 1 | 0 | 7.96E-02 |
| chondroitin sulfate biosynthetic process -991222150 | GO | 6 | 0 | 1 | 0 | 2.48E-01 | 0 | 1 | 0 | 1.98E-01 |
| chromatin assembly or disassembly -7775406 | GO | 34 | 7 | 1 | 1 | 1.17E-01 | 2 | 1 | 0 | 4.25E-01 |
| chromatin-mediated maintenance of transcription -248235439 | GO | 4 | 2 | 0 | 0 | 1.03E-01 | 0 | 0 | 0 | 5.96E-01 |

FROM FIG. 13B

| | | | | | | | | | |
|---|---|---|---|---|---|---|---|---|---|
| ciliary or flagellar motility -900195991 | GO | 13 | 0 | 0 | 0 | 6.24E-01 | 9 | 0 | 0 | 5.14E-02 |
| cilium biogenesis -696213771 | GO | 6 | 4 | 0 | 0 | 1.71E-01 | 0 | 0 | 0 | 5.96E-01 |
| CoA biosynthesis 878 | MA | 16 | 0 | 0 | 0 | 6.30E-01 | 5 | 0 | 0 | 1.51E-01 |
| common-partner SMAD protein phosphorylation -705118067 | GO | 8 | 1 | 0 | 0 | 1.38E-01 | 5 | 2 | 0 | 2.71E-01 |
| cysteine metabolic process -1485519200 | GO | 5 | 0 | 0 | 1 | 4.73E-01 | 1 | 0 | 0 | 1.27E-01 |
| cytoplasmic sequestering of NF-kappaB -1337920917 | GO | 4 | 3 | 0 | 0 | 5.64E-02 | 0 | 0 | 0 | 5.96E-01 |
| cytoplasmic sequestering of transcription factor -1329821075 | GO | 7 | 2 | 0 | 2 | 3.81E-02 | 0 | 0 | 1 | 2.75E-01 |
| cytoskeletal anchoring -602941718 | GO | 9 | 8 | 1 | 1 | 4.50E-04 | 6 | 0 | 0 | 7.52E-02 |
| Cytoskeleton remodeling_Alpha-1A adrenergic receptor- dependent inhibition of PI3K 2395 | MA | 32 | 12 | 0 | 3 | 1.19E-01 | 5 | 1 | 0 | 5.39E-01 |
| Cytoskeleton remodeling_Cytoskeleton remodeling 714 | MA | 131 | 30 | 2 | 6 | 2.10E-02 | 22 | 4 | 2 | 3.77E-01 |
| Cytoskeleton remodeling_FAK signaling 449 | MA | 61 | 18 | 2 | 1 | 5.64E-02 | 15 | 3 | 1 | 4.95E-01 |
| Cytoskeleton remodeling_Integrin outside-in signaling 664 | MA | 65 | 18 | 0 | 4 | 1.48E-01 | 13 | 1 | 2 | 3.57E-01 |
| Cytoskeleton remodeling_Role Activin A in cytoskeleton remodeling 2492 | MA | 18 | 1 | 0 | 0 | 3.41E-01 | 10 | 5 | 0 | 3.85E-02 |
| Cytoskeleton remodeling_Role of PDGFs in cell migration 693 | MA | 20 | 7 | 1 | 0 | 1.61E-01 | 8 | 1 | 1 | 1.98E-02 |
| Cytoskeleton remodeling_TGF, WNT and cytoskeletal remodeling 715 | MA | 160 | 42 | 5 | 9 | 1.70E-01 | 40 | 3 | 2 | 3.22E-01 |
| Cytoskeleton_Actin filaments 141066 | GG | 178 | 39 | 2 | 10 | 7.03E-02 | 19 | 0 | 1 | 5.96E-01 |
| Cytoskeleton_Cytoplasmic microtubules 141118 | GG | 127 | 6 | 2 | 8 | 5.83E-01 | 16 | 4 | 2 | 1.00E-01 |
| Cytoskeleton_Regulation of cytoskeleton rearrangement 141123 | GG | 232 | 35 | 3 | 11 | 1.70E-01 | 27 | 4 | 2 | 4.21E-01 |
| defense response to bacterium -2060986632 | GO | 70 | 4 | 4 | 1 | 2.04E-01 | 9 | 0 | 7 | 9.24E-03 |
| detection of chemical stimulus involved in sensory perception of smell -33319143 | GO | 4 | 0 | 0 | 2 | 6.78E-02 | 1 | 0 | 0 | 9.85E-04 |
| Development_Glucocorticoid receptor signaling 410 | MA | 32 | 6 | 0 | 1 | 1.56E-01 | 2 | 1 | 0 | 5.96E-01 |
| Development_A2A receptor signaling 643 | MA | 56 | 13 | 0 | 1 | 1.48E-01 | 15 | 0 | 2 | 2.27E-01 |
| Development_ACM3 activation of astroglial cells proliferation 2645 | MA | 23 | 8 | 0 | 2 | 2.53E-01 | 8 | 1 | 0 | 5.17E-02 |
| Development_Angiopoietin - Tie2 signaling 532 | MA | 42 | 13 | 1 | 4 | 1.36E-01 | 5 | 1 | 2 | 5.96E-01 |
| Development_CNTF receptor signaling 2231 | MA | 33 | 7 | 0 | 2 | 3.38E-01 | 9 | 2 | 0 | 1.12E-02 |
| Development_Cross-talk VEGF an angiopoietin 1signaling 534 | MA | 24 | 8 | 1 | 0 | 1.65E-02 | 5 | 0 | 1 | 5.14E-02 |
| Development_EGF signaling pathway 443 | MA | 58 | 13 | 0 | 4 | 2.24E-02 | 9 | 4 | 7 | 1.26E-01 |
| Development_EGFR signaling via PIP3 692 | MA | 23 | 8 | 2 | 4 | 1.38E-03 | 12 | 6 | 5 | 8.79E-05 |
| Development_EGFR signaling via small GTPases 704 | MA | 34 | 6 | 0 | 5 | 1.15E-01 | 25 | 4 | 6 | 1.20E-03 |
| Development_EPO-induced PI3K/AKT pathway and Ca(2+) influx 739 | MA | 57 | 19 | 0 | 5 | 4.02E-02 | 15 | 1 | 1 | 1.54E-01 |
| Development_ERBB-family signaling 535 | MA | 44 | 13 | 0 | 8 | 1.47E-02 | 5 | 1 | 7 | 3.86E-01 |
| Development_FGF-family signaling 549 | MA | 30 | 11 | 0 | 12 | 4.35E-02 | 6 | 1 | 1 | 2.02E-01 |
| Development_FGFR signaling pathway 444 | MA | 50 | 13 | 0 | 3 | 7.03E-02 | 6 | 4 | 0 | 5.32E-01 |
| Development_GDNF family signaling 495 | MA | 53 | 14 | 0 | 2 | 2.24E-02 | 11 | 4 | 1 | 3.15E-01 |
| Development_Growth hormone signaling via PI3K/AKT and MAPK cascades 2253 | MA | 39 | 8 | 0 | 2 | 4.23E-01 | 9 | 1 | 1 | 1.98E-01 |
| Development_Heart development 141171 | GG | 112 | 14 | 2 | 8 | 3.61E-01 | 30 | 5 | 2 | 1.45E-01 |
| Development_Hemopoiesis, Erythropoietin pathway 141165 | GG | 146 | 28 | 0 | 14 | 1.99E-02 | 33 | 1 | 7 | 3.01E-01 |
| Development_IGF-RI signaling 540 | MA | 66 | 12 | 2 | 7 | 9.76E-02 | 12 | 3 | 4 | 1.49E-01 |
| Development_Leptin signaling via PI3K-dependent pathway 719 | MA | 48 | 12 | 0 | 5 | 1.40E-02 | 7 | 2 | 2 | 1.50E-01 |
| Development_Neurogenesis:Synaptogenesis 141089 | GG | 213 | 23 | 2 | 20 | 4.89E-01 | 28 | 2 | 2 | 1.55E-01 |
| Development_Neuromuscular junction 141054 | GG | 109 | 22 | 1 | 8 | 1.26E-01 | 48 | 0 | 1 | 5.96E-01 |
| Development_PDGF signaling via MAPK cascades 654 | MA | 37 | 8 | 0 | 1 | 4.13E-01 | 10 | 4 | 0 | 1.55E-01 |
| Development_PDGF signaling via STATs and NF-kB 635 | MA | 35 | 12 | 0 | 0 | 1.99E-02 | 5 | 2 | 3 | 3.90E-01 |
| Development_PIP3 signaling in cardiac myocytes 701 | MA | 67 | 9 | 2 | 8 | 1.76E-01 | 11 | 3 | 4 | 4.60E-02 |

FROM FIG. 13C

| Pathway | Type | | | | | | | | | |
|---|---|---|---|---|---|---|---|---|---|---|
| Development_Role Activin A in cell differentiation and proliferation 2482 | MA | 47 | 1 | 5 | 2 | 6.13E-01 | 13 | 2 | 2 | 9.75E-02 |
| Development_Skeletal muscle development 141077 | GG | 164 | 37 | 1 | 10 | 3.36E-02 | 29 | 1 | 1 | 4.37E-01 |
| Development_TPO in cell process 631 | MA | 45 | 7 | 0 | 3 | 5.35E-01 | 9 | 1 | 3 | 1.72E-01 |
| Development_Transcription regulation of granulocyte development 458 | MA | 40 | 2 | 1 | 4 | 6.10E-01 | 5 | 1 | 4 | 1.02E-01 |
| Development_VEGF signaling and activation 539 | MA | 40 | 15 | 0 | 0 | 4.45E-02 | 9 | 1 | 1 | 4.77E-01 |
| Development_VEGF signaling via VEGFR2 - generic cascades 533 | MA | 40 | 15 | 0 | 0 | 2.05E-02 | 12 | 1 | 1 | 2.06E-01 |
| Development_VEGF-family signaling 445 | MA | 37 | 9 | 0 | 1 | 4.10E-01 | 13 | 1 | 0 | 1.55E-01 |
| diet induced thermogenesis -1432371732 | GO | 4 | 0 | 0 | 2 | 7.47E-02 | 0 | 2 | 0 | 5.14E-02 |
| DNA damage response, signal transduction by p53 class mediator resulting in induction of apoptosis -425938156 | GO | 7 | 19 | 0 | 1 | 4.84E-02 | 18 | 1 | 0 | 2.61E-01 |
| DNA damage_Checkpoint 141148 | GG | 130 | 37 | 0 | 11 | 4.45E-02 | 24 | 2 | 7 | 4.38E-01 |
| DNA fragmentation during apoptosis -1711207303 | GO | 15 | 1 | 6 | 2 | 4.06E-02 | 1 | 0 | 3 | 2.18E-02 |
| DNA metabolic process -2101003070 | GO | 32 | 8 | 0 | 3 | 1.83E-01 | 2 | 0 | 0 | 5.96E-01 |
| DNA topological change -1048278752 | GO | 10 | 5 | 0 | 2 | 4.50E-04 | 0 | 0 | 0 | 5.96E-01 |
| early endosome to late endosome transport -1319957615 | GO | 5 | 3 | 0 | 1 | 1.03E-01 | 0 | 0 | 0 | 5.14E-01 |
| elevation of cytosolic calcium ion concentration during G-protein signaling, coupled to IP3 second messenger (phospholipase C activating) -534345072 | GO | 7 | 1 | 0 | 0 | 3.20E-01 | 3 | 1 | 0 | 3.16E-02 |
| embryonic organ development -1155643774 | GO | 4 | 0 | 0 | 0 | 6.13E-01 | 2 | 0 | 0 | 4.60E-02 |
| embryonic viscerocranium morphogenesis -1742672726 | GO | 4 | 2 | 0 | 1 | 2.45E-03 | 1 | 0 | 0 | 5.71E-02 |
| endosome organization and biogenesis -1860965674 | GO | 7 | 2 | 0 | 1 | 6.37E-02 | 1 | 0 | 0 | 3.01E-01 |
| energy reserve metabolic process -575338353 | GO | 8 | 0 | 0 | 2 | 1.03E-01 | 1 | 3 | 0 | 3.69E-03 |
| entrainment of circadian clock -817674890 | GO | 6 | 2 | 0 | 1 | 1.96E-01 | 1 | 0 | 0 | 2.22E-01 |
| ephrin receptor signaling pathway -23454986 | GO | 6 | 0 | 0 | 0 | 6.13E-01 | 3 | 0 | 0 | 1.75E-01 |
| epithelial cell differentiation -1079909866 | GO | 27 | 3 | 0 | 1 | 9.68E-02 | 4 | 0 | 3 | 2.49E-01 |
| epithelial cell proliferation -1145565213 | GO | 9 | 3 | 0 | 1 | 1.17E-01 | 0 | 0 | 1 | 3.61E-01 |
| equilibrioception -1679963697 | GO | 5 | 1 | 0 | 1 | 1.52E-01 | 3 | 0 | 0 | 1.26E-01 |
| ER overload response -687998334 | GO | 6 | 18 | 0 | 0 | 5.07E-01 | 19 | 1 | 0 | 1.46E-01 |
| establishment and/or maintenance of cell polarity -149409502 | GO | 20 | 4 | 2 | 1 | 3.30E-01 | 35 | 0 | 0 | 1.20E-01 |
| establishment of cellular localization -1943445715 | GO | 3 | 0 | 0 | 1 | 3.51E-01 | 1 | 0 | 0 | 2.09E-02 |
| establishment of epithelial cell polarity -181128603 | GO | 4 | 2 | 0 | 1 | 5.04E-02 | 4 | 0 | 0 | 5.71E-02 |
| establishment of synaptic specificity at neuromuscular junction -1859495799 | GO | 4 | 0 | 0 | 0 | 4.55E-01 | 1 | 1 | 0 | 5.71E-02 |
| FAS signaling cascades (short map) 417 | MA | 21 | 3 | 0 | 5 | 6.44E-02 | 0 | 3 | 1 | 3.15E-01 |
| female pregnancy -364569498 | GO | 50 | 2 | 1 | 4 | 2.79E-01 | 6 | 2 | 2 | 1.51E-01 |
| fibroblast growth factor receptor signaling pathway -1527475869 | GO | 15 | 2 | 0 | 4 | 4.45E-02 | 0 | 0 | 2 | 1.45E-01 |
| galactose metabolic process -1731439529 | GO | 7 | 2 | 0 | 1 | 6.21E-02 | 0 | 0 | 0 | 5.96E-01 |
| Galactose metabolism 821 | MA | 19 | 3 | 0 | 1 | 1.52E-01 | 2 | 1 | 0 | 2.70E-01 |
| generation of action potential -1357766322 | GO | 9 | 4 | 1 | 1 | 1.75E-02 | 1 | 0 | 0 | 3.77E-01 |
| Glutathione metabolism 896 | MA | 32 | 0 | 0 | 8 | 1.48E-01 | 0 | 0 | 0 | 1.62E-01 |
| glycogen catabolic process -1333887968 | GO | 4 | 2 | 0 | 0 | 6.43E-02 | 1 | 0 | 0 | 4.15E-01 |
| glycolipid transport -5583279 | GO | 5 | 2 | 0 | 1 | 1.13E-01 | 0 | 0 | 0 | 5.01E-01 |
| G-protein signaling_Cross-talk between Ras-family GTPases 408 | MA | 17 | 5 | 0 | 1 | 6.04E-01 | 9 | 0 | 0 | 4.60E-02 |
| G-protein signaling_G-Protein alpha-q signaling cascades 639 | MA | 49 | 15 | 0 | 0 | 1.39E-01 | 9 | 0 | 1 | 5.96E-01 |
| G-protein signaling_H-RAS regulation pathway 398 | MA | 32 | 8 | 1 | 0 | 3.47E-01 | 11 | 1 | 1 | 7.52E-02 |
| G-protein signaling_Regulation of CDC42 activity 389 | MA | 21 | 1 | 1 | 4 | 1.78E-01 | 0 | 0 | 0 | 3.57E-01 |
| hair cell differentiation -676960703 | GO | 4 | 3 | 0 | 0 | 3.78E-03 | 3 | 0 | 0 | 3.77E-01 |
| heparan sulfate proteoglycan metabolic process -338905318 | GO | 3 | 3 | 0 | 0 | 1.65E-02 | 0 | 0 | 0 | 5.96E-01 |
| HETE and HPETE biosynthesis and metabolism 892 | MA | 16 | 0 | 0 | 2 | 4.08E-01 | 1 | 1 | 0 | 1.96E-01 |

FROM FIG. 13D

| | | | | | | | | | |
|---|---|---|---|---|---|---|---|---|---|
| homophilic cell adhesion -2018894362 | GO | 127 | 13 | 10 | 2 | 3.06E-01 | 20 | 3 | 0 | 5.17E-02 |
| hyperosmotic response -643291399 | GO | 5 | 1 | 1 | 0 | 1.56E-01 | 0 | 0 | 0 | 4.95E-01 |
| I-kappaB phosphorylation -679604649 | GO | 5 | 2 | 0 | 0 | 1.86E-01 | 0 | 0 | 0 | 5.96E-01 |
| Immune response_Fc epsilon RI pathway 566 | MA | 69 | 16 | 0 | 1 | 7.68E-02 | 13 | 4 | 1 | 3.86E-01 |
| Immune response_IFN alpha/beta signaling pathway 429 | MA | 26 | 4 | 27 | 1 | 1.40E-01 | 0 | 1 | 0 | 5.96E-01 |
| Immune response_IL4 - antiapoptotic action 659 | MA | 36 | 10 | 0 | 0 | 1.44E-01 | 6 | 2 | 2 | 4.15E-01 |
| Immune response_IL4 signaling pathway 431 | MA | 41 | 11 | 0 | 0 | 6.13E-02 | 7 | 2 | 3 | 2.30E-01 |
| Immune response_IL9 signaling pathway 523 | MA | 30 | 12 | 0 | 0 | 5.52E-03 | 6 | 2 | 2 | 3.15E-01 |
| Immune response_MIF in innate immunity response 519 | MA | 53 | 27 | 0 | 1 | 5.47E-02 | 19 | 4 | 1 | 5.96E-01 |
| Immune response_MIF-JAB1 signaling 520 | MA | 21 | 4 | 0 | 5 | 5.64E-02 | 0 | 0 | 2 | 4.87E-01 |
| immune response_IL10 signaling pathway 531 | MA | 21 | 7 | 0 | 0 | 2.13E-01 | 7 | 2 | 1 | 1.03E-01 |
| Immune response_Signaling pathway mediated by IL-6 and IL-1 478 | MA | 31 | 6 | 0 | 0 | 1.76E-01 | 1 | 1 | 1 | 5.96E-01 |
| Immune response_Inhibitory action of Lipoxins on pro-inflammatory TNF-alpha signaling 2727 | MA | 41 | 11 | 0 | 4 | 1.10E-01 | 6 | 2 | 2 | 3.66E-01 |
| Immune_Phagocytosis 141163 | GG | 187 | 37 | 0 | 7 | 6.37E-02 | 19 | 1 | 1 | 5.96E-01 |
| Immune_Phagosome in antigen presentation 141124 | GG | 204 | 31 | 1 | 10 | 1.58E-01 | 15 | 1 | 4 | 5.96E-01 |
| induction of apoptosis -1544887085 | GO | 147 | 23 | 13 | 7 | 3.43E-01 | 31 | 6 | 2 | 1.24E-01 |
| induction of apoptosis by oxidative stress -1267605724 | GO | 6 | 1 | 1 | 1 | 1.95E-01 | 0 | 0 | 0 | 2.30E-01 |
| Inflammation_IFN-gamma signaling 141153 | GG | 105 | 22 | 1 | 4 | 5.64E-02 | 9 | 2 | 4 | 5.96E-01 |
| Inflammation_IgE signaling 141113 | GG | 131 | 30 | 0 | 5 | 5.47E-02 | 19 | 4 | 1 | 5.46E-01 |
| Inflammation_IL-10 anti-inflammatory response 141157 | GG | 72 | 16 | 0 | 6 | 2.10E-02 | 9 | 2 | 4 | 2.49E-01 |
| Inflammation_IL-2 signaling 141106 | GG | 88 | 18 | 3 | 0 | 1.18E-01 | 14 | 4 | 1 | 4.99E-01 |
| Inflammation_Innate inflammatory response 141173 | GG | 172 | 26 | 29 | 8 | 6.58E-02 | 11 | 1 | 2 | 5.96E-01 |
| Inflammation_Kallikrein-kinin system 141116 | GG | 175 | 32 | 2 | 4 | 1.95E-01 | 24 | 2 | 1 | 5.68E-01 |
| inner cell mass cell proliferation -167074679 | GO | 7 | 2 | 0 | 1 | 9.65E-03 | 0 | 0 | 1 | 2.75E-01 |
| inner ear morphogenesis -1671528044 | GO | 41 | 4 | 1 | 5 | 1.03E-01 | 5 | 0 | 1 | 7.25E-02 |
| insulin receptor signaling pathway -1356877082 | GO | 33 | 5 | 0 | 3 | 1.91E-01 | 2 | 1 | 1 | 4.05E-01 |
| intercellular junction assembly -1374404163 | GO | 10 | 4 | 0 | 1 | 1.37E-01 | 0 | 0 | 0 | 5.96E-01 |
| intra-Golgi vesicle-mediated transport -1197087893 | GO | 18 | 4 | 1 | 0 | 9.76E-02 | 2 | 0 | 0 | 4.23E-01 |
| lipid transport -966909428 | GO | 60 | 8 | 0 | 9 | 1.85E-01 | 6 | 2 | 1 | 3.26E-01 |
| lipoprotein transport -1706169113 | GO | 4 | 1 | 0 | 0 | 1.17E-01 | 1 | 1 | 0 | 5.43E-02 |
| lymphocyte differentiation -1238305505 | GO | 5 | 1 | 0 | 0 | 1.93E-01 | 0 | 0 | 1 | 4.47E-01 |
| male meiosis -1800817867 | GO | 7 | 3 | 0 | 0 | 7.03E-02 | 0 | 0 | 0 | 5.96E-01 |
| male meiosis I -199974762 | GO | 4 | 1 | 0 | 2 | 6.67E-02 | 0 | 0 | 0 | 4.47E-01 |
| MAPK cascade. Part I. Map 1. ERK-related pathways 505 | MA | 12 | 4 | 0 | 0 | 7.91E-02 | 0 | 0 | 1 | 5.96E-01 |
| MAPK cascade. Part I. Map 2. ERK-RPS/MKNK signaling 506 | MA | 22 | 7 | 0 | 0 | 2.10E-02 | 1 | 0 | 1 | 5.96E-01 |
| MAPK cascade. Part II, Map 1 - MAP4K2-4 - ERK5 & JNK pathway 499 | MA | 11 | 5 | 0 | 0 | 1.13E-02 | 0 | 0 | 1 | 5.96E-01 |
| MAPK cascade. Part II, Map 2 - MAP4K2-4 - ERK/JNK pathway; interaction with MEK1/2 503 | MA | 10 | 5 | 0 | 0 | 4.50E-03 | 0 | 0 | 1 | 5.96E-01 |
| MAPK cascade. Part III. JNK activating by MLK/LZK/MEKK signaling 508 | MA | 10 | 5 | 0 | 0 | 4.50E-03 | 0 | 0 | 1 | 5.96E-01 |
| MAPK cascade. Part IV. Map 1. Generic p38-MAPK cascade 509 | MA | 10 | 5 | 0 | 0 | 4.50E-03 | 0 | 0 | 1 | 5.96E-01 |
| meiosis -542134950 | GO | 38 | 5 | 0 | 7 | 6.07E-02 | 2 | 0 | 0 | 1.49E-01 |
| metabotropic glutamate receptor, phospholipase C activating pathway -2062420629 | GO | 3 | 0 | 0 | 0 | 3.84E-01 | 2 | 1 | 0 | 1.32E-02 |
| middle ear morphogenesis - 1744556616 | GO | 4 | 1 | 0 | 1 | 2.97E-03 | 1 | 0 | 2 | 6.82E-04 |
| mitotic metaphase -998361018 | GO | 6 | 2 | 0 | 1 | 1.90E-01 | 0 | 0 | 0 | 5.66E-01 |
| mitotic sister chromatid segregation -449579919 | GO | 10 | 0 | 0 | 2 | 1.95E-01 | 0 | 0 | 1 | 1.64E-01 |

FROM FIG. 13E

| | | | | | | | | | |
|---|---|---|---|---|---|---|---|---|---|
| Mo-molybdopterin cofactor biosynthetic process -411206268 | GO | 4 | 0 | 0 | 1 | 9.75E-02 | 0 | 1 | 0 | 6.24E-02 |
| multicellular organism growth -922607540 | GO | 8 | 2 | 0 | 1 | 8.71E-02 | 0 | 0 | 0 | 5.96E-01 |
| multicellular organismal development -528578425 | GO | 781 | 96 | 9 | 41 | 7.35E-02 | 84 | 11 | 9 | 1.27E-01 |
| myoblast fusion -618004434 | GO | 9 | 6 | 0 | 1 | 1.53E-02 | 0 | 0 | 1 | 3.68E-01 |
| negative regulation of angiogenesis -623466880 | GO | 22 | 4 | 1 | 1 | 9.76E-02 | 6 | 0 | 0 | 1.51E-01 |
| negative regulation of astrocyte differentiation -246047964 | GO | 4 | 1 | 0 | 1 | 9.68E-02 | 2 | 0 | 0 | 5.17E-02 |
| negative regulation of cell cycle -788931279 | GO | 105 | 23 | 16 | 5 | 1.48E-01 | 64 | 5 | 3 | 5.66E-04 |
| negative regulation of cell-matrix adhesion -821843213 | GO | 5 | 2 | 6 | 0 | 1.42E-02 | 2 | 1 | 0 | 3.69E-03 |
| negative regulation of cyclin-dependent protein kinase activity -731093535 | GO | 7 | 0 | 6 | 1 | 2.64E-01 | 33 | 0 | 0 | 3.85E-02 |
| negative regulation of DNA binding -1104540163 | GO | 5 | 1 | 0 | 1 | 1.40E-01 | 0 | 0 | 1 | 4.47E-01 |
| negative regulation of hydrolase activity -979514759 | GO | 6 | 0 | 0 | 0 | 3.06E-01 | 2 | 2 | 0 | 1.32E-02 |
| negative regulation of multicellular organism growth -1794478736 | GO | 7 | 1 | 0 | 3 | 4.45E-02 | 0 | 0 | 0 | 3.01E-01 |
| negative regulation of neuroblast proliferation -628297374 | GO | 5 | 20 | 0 | 0 | 1.42E-02 | 21 | 1 | 0 | 2.80E-03 |
| negative regulation of osteoclast differentiation -34309697 | GO | 8 | 2 | 2 | 0 | 1.42E-02 | 2 | 1 | 0 | 3.69E-03 |
| negative regulation of protein kinase activity -1232950652 | GO | 25 | 4 | 8 | 1 | 3.97E-02 | 2 | 0 | 0 | 2.61E-01 |
| negative regulation of Rac protein signal transduction -1944312683 | GO | 3 | 4 | 0 | 0 | 2.10E-02 | 3 | 0 | 0 | 1.28E-02 |
| negative regulation of synaptic transmission, glutamatergic -571308705 | GO | 4 | 0 | 0 | 1 | 4.05E-01 | 1 | 0 | 0 | 7.52E-02 |
| negative regulation of transcription -1612180416 | GO | 105 | 18 | 0 | 8 | 8.40E-02 | 9 | 2 | 6 | 1.81E-01 |
| nervous system development -985177928 | GO | 339 | 36 | 8 | 23 | 2.10E-01 | 35 | 3 | 2 | 1.72E-01 |
| neural tube development -1812068704 | GO | 4 | 1 | 0 | 0 | 4.55E-01 | 4 | 0 | 0 | 3.85E-02 |
| neurite development -1976621165 | GO | 23 | 0 | 2 | 2 | 6.13E-01 | 40 | 2 | 0 | 1.48E-01 |
| neuron adhesion -1297833140 | GO | 5 | 0 | 0 | 0 | 6.13E-01 | 3 | 0 | 0 | 9.75E-02 |
| neurotransmitter receptor metabolic process -391744984 | GO | 4 | 3 | 1 | 0 | 6.80E-02 | 2 | 0 | 0 | 3.77E-01 |
| opsonization -959203984 | GO | 4 | 0 | 0 | 0 | 6.13E-01 | 2 | 0 | 0 | 4.60E-02 |
| osteoblast differentiation -1265056083 | GO | 18 | 6 | 0 | 0 | 1.06E-01 | 3 | 0 | 0 | 5.96E-01 |
| ovulation -89364692 | GO | 3 | 1 | 0 | 1 | 1.99E-02 | 0 | 0 | 0 | 3.61E-01 |
| ovulation from ovarian follicle -249635567 | GO | 9 | 1 | 0 | 0 | 4.23E-01 | 6 | 1 | 0 | 7.98E-03 |
| p38-MAPK cascade activation via IGF1R and EGFR 501 | MA | 17 | 6 | 0 | 0 | 4.40E-01 | 9 | 4 | 0 | 3.69E-03 |
| parathyroid gland development -542291539 | GO | 4 | 3 | 0 | 1 | 4.84E-02 | 1 | 0 | 0 | 5.71E-02 |
| paraxial mesoderm morphogenesis -503969283 | GO | 3 | 0 | 0 | 0 | 4.88E-02 | 5 | 2 | 0 | 7.56E-03 |
| pattern specification process -1974918225 | GO | 63 | 4 | 0 | 9 | 1.36E-01 | 3 | 0 | 1 | 9.75E-02 |
| peptidyl-citrulline biosynthetic process from peptidyl-arginine -564196101 | GO | 5 | 2 | 0 | 0 | 1.39E-01 | 0 | 0 | 0 | 5.96E-01 |
| PH proteins and focal adhesion complex formation. Interaction with integrin receptors 686 | MA | 23 | 8 | 0 | 1 | 2.10E-02 | 2 | 1 | 0 | 5.44E-01 |
| PH proteins participation in different RTKs adaptor complexes formation and intermediation with focal adhesion complex. Part 1 685 | MA | 20 | 10 | 0 | 1 | 4.06E-02 | 5 | 1 | 0 | 4.66E-01 |
| PH proteins participation in RTKs adaptor complexes formation and intermediation with focal adhesion complex. Part 2 684 | MA | 21 | 10 | 0 | 1 | 5.04E-02 | 5 | 1 | 0 | 4.95E-01 |
| Phosphatidylinositol metabolism 855 | MA | 24 | 3 | 3 | 2 | 9.51E-02 | 6 | 2 | 0 | 2.22E-01 |
| phosphoenolpyruvate-dependent sugar phosphotransferase system -146070395 | GO | 6 | 0 | 0 | 0 | 6.13E-01 | 5 | 0 | 0 | 1.46E-01 |
| phosphoinositide-mediated signaling -2144439186 | GO | 43 | 9 | 0 | 9 | 4.84E-02 | 6 | 1 | 1 | 1.98E-01 |
| phospholipid transport -105811417 | GO | 18 | 5 | 1 | 0 | 4.46E-01 | 6 | 1 | 0 | 9.24E-03 |
| pigmentation -568542820 | GO | 24 | 5 | 0 | 1 | 4.40E-01 | 5 | 0 | 2 | 6.24E-02 |
| platelet-derived growth factor receptor signaling pathway -1283799075 | GO | 4 | 1 | 2 | 0 | 6.37E-02 | 3 | 2 | 0 | 3.77E-01 |
| Pleckstrin homology proteins interactions. Part III 679 | MA | 5 | 0 | 0 | 1 | 4.95E-01 | 18 | 0 | 0 | 3.69E-03 |
| Pleckstrin homology proteins interactions. Part V 694 | MA | 14 | 0 | 0 | 0 | 6.25E-01 | 7 | 0 | 0 | 8.59E-02 |

FROM FIG. 13F

| | | | | | | | | | |
|---|---|---|---|---|---|---|---|---|---|
| positive regulation of anti-apoptosis -1435289744 | GO | 15 | 2 | 0 | 2 | 3.84E-01 | 3 | 1 | 0 | 1.24E-01 |
| positive regulation of axonogenesis -1453841276 | GO | 9 | 2 | 2 | 0 | 3.35E-02 | 5 | 0 | 0 | 8.44E-02 |
| positive regulation of bone mineralization -72729965 | GO | 3 | 0 | 0 | 0 | 6.13E-01 | 3 | 0 | 0 | 1.18E-02 |
| positive regulation of cardiac muscle cell proliferation -617405374 | GO | 3 | 1 | 0 | 2 | 2.08E-02 | 0 | 0 | 1 | 1.76E-02 |
| positive regulation of cell migration -1563863907 | GO | 23 | 2 | 0 | 0 | 3.31E-01 | 1 | 2 | 3 | 1.55E-01 |
| positive regulation of cell proliferation -1793645288 | GO | 200 | 13 | 0 | 21 | 3.28E-01 | 24 | 5 | 10 | 1.45E-01 |
| positive regulation of cyclin-dependent protein kinase activity -162478261 | GO | 3 | 0 | 0 | 4 | 1.82E-02 | 0 | 0 | 1 | 1.76E-02 |
| positive regulation of DNA replication -803432389 | GO | 3 | 3 | 0 | 0 | 1.58E-02 | 0 | 0 | 0 | 5.96E-01 |
| positive regulation of fat cell differentiation -1751499095 | GO | 5 | 1 | 0 | 1 | 1.74E-01 | 0 | 0 | 0 | 5.01E-01 |
| positive regulation of innate immune response -1562258761 | GO | 5 | 2 | 2 | 0 | 1.06E-01 | 1 | 0 | 0 | 4.82E-01 |
| positive regulation of interferon-alpha biosynthetic process -262011939 | GO | 4 | 0 | 1 | 0 | 4.13E-01 | 3 | 0 | 0 | 7.98E-04 |
| positive regulation of interferon-beta biosynthetic process -1757116884 | GO | 4 | 0 | 1 | 0 | 4.13E-01 | 3 | 0 | 0 | 7.98E-04 |
| positive regulation of interferon-gamma biosynthetic process -1423714468 | GO | 11 | 0 | 1 | 0 | 6.13E-01 | 3 | 0 | 0 | 1.85E-01 |
| positive regulation of MAP kinase activity -290179819 | GO | 8 | 0 | 0 | 5 | 7.47E-02 | 17 | 0 | 3 | 2.80E-03 |
| positive regulation of MAPKKK cascade -1281980043 | GO | 12 | 1 | 0 | 7 | 5.07E-02 | 0 | 0 | 1 | 2.52E-01 |
| positive regulation of mesenchymal cell proliferation -1219206192 | GO | 6 | 1 | 0 | 2 | 2.04E-01 | 2 | 0 | 1 | 1.28E-02 |
| positive regulation of myoblast differentiation -263087633 | GO | 4 | 2 | 0 | 0 | 1.06E-01 | 2 | 1 | 0 | 4.60E-02 |
| positive regulation of phosphoinositide 3-kinase cascade -784380377 | GO | 3 | 0 | 0 | 5 | 1.82E-02 | 0 | 0 | 1 | 1.76E-02 |
| positive regulation of protein amino acid dephosphorylation -1019561265 | GO | 4 | 0 | 0 | 0 | 4.55E-01 | 3 | 1 | 0 | 4.60E-02 |
| positive regulation of protein amino acid phosphorylation -1450627351 | GO | 11 | 1 | 0 | 4 | 1.91E-01 | 1 | 0 | 1 | 1.75E-01 |
| positive regulation of protein kinase activity -1664988450 | GO | 15 | 4 | 0 | 0 | 1.74E-01 | 1 | 1 | 0 | 5.66E-01 |
| positive regulation of Rac protein signal transduction -1197144599 | GO | 4 | 1 | 0 | 1 | 9.51E-02 | 17 | 0 | 0 | 5.17E-02 |
| positive regulation of transcription factor import into nucleus -2098512704 | GO | 3 | 3 | 2 | 0 | 1.13E-04 | 2 | 2 | 0 | 1.05E-02 |
| positive regulation of transcription from RNA polymerase II promoter -769589989 | GO | 196 | 43 | 3 | 9 | 5.59E-02 | 32 | 4 | 5 | 5.13E-01 |
| positive regulation of transcription, DNA-dependent -1739655726 | GO | 95 | 25 | 2 | 8 | 1.18E-01 | 27 | 3 | 6 | 7.22E-02 |
| positive regulation of vasoconstriction -1479163174 | GO | 7 | 2 | 0 | 1 | 4.45E-02 | 0 | 0 | 0 | 5.96E-01 |
| potassium ion transport -1338626540 | GO | 145 | 9 | 3 | 6 | 5.07E-01 | 12 | 1 | 0 | 1.98E-01 |
| Proliferation_Positive regulation cell proliferation 141131 | GG | 195 | 14 | 0 | 15 | 4.55E-01 | 21 | 6 | 10 | 1.37E-01 |
| protein amino acid N-linked glycosylation -1502848963 | GO | 19 | 0 | 0 | 2 | 3.43E-01 | 3 | 1 | 1 | 8.67E-02 |
| protein amino acid phosphorylation -2002083056 | GO | 474 | 42 | 2 | 25 | 3.78E-01 | 51 | 7 | 15 | 1.45E-01 |
| protein export from nucleus -1853913917 | GO | 12 | 4 | 0 | 2 | 6.37E-02 | 0 | 0 | 0 | 5.09E-01 |
| protein insertion into membrane -1716508193 | GO | 5 | 1 | 0 | 0 | 1.52E-01 | 0 | 0 | 2 | 4.40E-01 |
| protein targeting to membrane -1355692229 | GO | 6 | 0 | 0 | 3 | 5.83E-01 | 1 | 1 | 0 | 1.67E-01 |
| proteolysis -142006563 | GO | 400 | 35 | 3 | 18 | 4.13E-01 | 55 | 3 | 3 | 2.32E-02 |
| Proteolysis_Connective tissue degradation 141086 | GG | 120 | 18 | 0 | 6 | 3.10E-01 | 25 | 0 | 1 | 9.09E-02 |
| purine ribonucleoside monophosphate biosynthetic process -390371389 | GO | 6 | 2 | 0 | 1 | 1.85E-01 | 2 | 0 | 0 | 1.67E-01 |
| pyrimidine dimer repair -889477112 | GO | 3 | 2 | 0 | 1 | 2.10E-02 | 0 | 0 | 0 | 3.59E-01 |
| receptor-mediated endocytosis -1416543536 | GO | 37 | 7 | 0 | 4 | 1.37E-01 | 9 | 0 | 0 | 1.98E-01 |
| Receptors. Part B. INSR- pleckstrin homology proteins interactions 688 | MA | 10 | 8 | 0 | 1 | 2.10E-02 | 6 | 1 | 0 | 1.95E-02 |
| Receptors. Part D. IL4R-pleckstrin homology proteins interactions 691 | MA | 8 | 6 | 0 | 0 | 3.39E-01 | 6 | 1 | 0 | 5.09E-02 |
| regulation of angiogenesis -272493130 | GO | 11 | 2 | 1 | 4 | 1.42E-02 | 2 | 0 | 3 | 2.03E-02 |
| regulation of ARF GTPase activity -1171561273 | GO | 21 | 8 | 1 | 0 | 5.47E-02 | 4 | 0 | 1 | 3.85E-02 |
| regulation of ARF protein signal transduction -663556509 | GO | 13 | 3 | 2 | 0 | 1.03E-01 | 2 | 0 | 0 | 2.96E-01 |
| regulation of binding -1945763488 | GO | 4 | 0 | 0 | 0 | 9.65E-03 | 5 | 2 | 1 | 4.04E-04 |
| regulation of caspase activity -1163943657 | GO | 6 | 0 | 2 | 1 | 1.83E-01 | 0 | 1 | 0 | 2.18E-01 |
| regulation of cell adhesion -89840565 | GO | 25 | 6 | 0 | 2 | 1.37E-01 | 5 | 1 | 0 | 3.99E-01 |

FROM FIG. 13G

| Term | Type | | | | | | | | |
|---|---|---|---|---|---|---|---|---|---|
| regulation of cell cycle -1053689556 | GO | 99 | 21 | 1 | 16 | 3.75E-01 | 39 | 2 | 6 | 1.74E-01 |
| regulation of cell migration -32885135 | GO | 30 | 8 | 1 | 4 | 1.47E-02 | 7 | 0 | 0 | 8.89E-02 |
| regulation of developmental process -1281503183 | GO | 3 | 4 | 0 | 0 | 2.10E-02 | 0 | 0 | 0 | 5.96E-01 |
| regulation of embryonic development -2117926109 | GO | 6 | 4 | 0 | 2 | 9.16E-04 | 5 | 0 | 0 | 1.76E-02 |
| regulation of epithelial cell proliferation -2069652354 | GO | 6 | 4 | 0 | 0 | 2.10E-02 | 2 | 1 | 0 | 5.03E-01 |
| regulation of fat cell differentiation -616853313 | GO | 4 | 2 | 0 | 1 | 5.47E-02 | 1 | 0 | 1 | 4.60E-02 |
| Regulation of lipid metabolism_Regulation of lipid metabolism by niacin and isoprenaline 742 | MA | 46 | 1 | 0 | 2 | 6.31E-01 | 11 | 0 | 0 | 1.98E-01 |
| regulation of long-term neuronal synaptic plasticity -963469962 | GO | 16 | 1 | 0 | 1 | 6.13E-01 | 20 | 0 | 0 | 1.45E-01 |
| regulation of metabolic process -1652923753 | GO | 6 | 0 | 0 | 0 | 3.07E-01 | 0 | 3 | 0 | 1.55E-01 |
| regulation of neuronal synaptic plasticity -1737819995 | GO | 18 | 5 | 0 | 3 | 8.76E-02 | 0 | 0 | 0 | 5.96E-01 |
| regulation of peptidyl-tyrosine phosphorylation -504349667 | GO | 8 | 1 | 0 | 0 | 3.84E-01 | 2 | 0 | 2 | 4.59E-02 |
| regulation of protein stability -1760401496 | GO | 6 | 0 | 8 | 0 | 1.56E-01 | 3 | 2 | 0 | 1.67E-01 |
| regulation of Rho protein signal transduction -22735490 | GO | 57 | 18 | 1 | 0 | 1.82E-02 | 28 | 0 | 0 | 1.32E-01 |
| regulation of S phase -1701242031 | GO | 3 | 4 | 0 | 0 | 1.47E-02 | 0 | 0 | 0 | 5.96E-01 |
| regulation of small GTPase mediated signal transduction -1403056627 | GO | 45 | 8 | 0 | 0 | 3.36E-01 | 8 | 0 | 2 | 1.64E-01 |
| regulation of steroid biosynthetic process -751374322 | GO | 4 | 1 | 0 | 2 | 5.61E-02 | 0 | 0 | 0 | 4.29E-01 |
| regulation of striated muscle development -432075468 | GO | 4 | 1 | 0 | 0 | 1.12E-01 | 4 | 1 | 0 | 3.62E-02 |
| regulation of synaptic transmission, GABAergic -1564880640 | GO | 4 | 1 | 0 | 1 | 9.51E-02 | 19 | 0 | 0 | 6.82E-04 |
| regulation of synaptic transmission, glutamatergic -1347909330 | GO | 4 | 0 | 0 | 0 | 6.13E-01 | 3 | 0 | 0 | 4.67E-02 |
| regulation of transcription, DNA-dependent -2079527498 | GO | 1681 | 155 | 41 | 76 | 1.13E-01 | 133 | 19 | 25 | 5.17E-02 |
| Reproduction_FSH-beta signaling pathway 141137 | GG | 204 | 26 | 2 | 15 | 9.12E-02 | 29 | 3 | 6 | 9.75E-02 |
| response to cold -549647509 | GO | 14 | 2 | 0 | 4 | 1.02E-01 | 1 | 0 | 0 | 1.27E-01 |
| response to exogenous dsRNA -993340016 | GO | 7 | 2 | 1 | 0 | 5.04E-02 | 0 | 0 | 0 | 5.92E-01 |
| response to gamma radiation -1175640644 | GO | 11 | 22 | 0 | 0 | 4.60E-02 | 18 | 1 | 0 | 5.96E-01 |
| response to iron ion -1535662249 | GO | 5 | 0 | 0 | 3 | 4.55E-01 | 1 | 0 | 0 | 1.45E-01 |
| retinal ganglion cell axon guidance -1825867090 | GO | 6 | 1 | 1 | 0 | 2.28E-01 | 1 | 0 | 0 | 1.98E-01 |
| RNA transport -1260438635 | GO | 3 | 3 | 0 | 0 | 2.01E-02 | 0 | 0 | 0 | 5.96E-01 |
| RNA-mediated gene silencing -374093643 | GO | 9 | 2 | 1 | 1 | 1.37E-01 | 0 | 0 | 0 | 3.77E-01 |
| Role of CARD-protein family in NF-kB regulation 698 | MA | 12 | 2 | 0 | 1 | 1.03E-01 | 1 | 2 | 0 | 2.29E-01 |
| rRNA processing -1829242755 | GO | 52 | 5 | 6 | 8 | 1.52E-01 | 1 | 0 | 1 | 3.57E-01 |
| ruffle organization and biogenesis -1886109443 | GO | 3 | 0 | 1 | 0 | 3.37E-01 | 1 | 0 | 0 | 1.85E-02 |
| S-adenosylhomocysteine metabolic process -2103922540 | GO | 10 | 0 | 0 | 2 | 1.96E-01 | 0 | 1 | 0 | 1.64E-01 |
| S-adenosylmethionine metabolic process -268280103 | GO | 10 | 0 | 0 | 2 | 1.96E-01 | 0 | 1 | 0 | 1.64E-01 |
| salivary gland development -1265246213 | GO | 4 | 0 | 0 | 2 | 3.86E-01 | 1 | 0 | 0 | 7.52E-02 |
| salivary gland morphogenesis -424124948 | GO | 6 | 1 | 0 | 2 | 2.04E-01 | 0 | 0 | 1 | 1.98E-01 |
| Serotonin - melatonin biosynthesis and metabolism 864 | MA | 16 | 4 | 1 | 2 | 1.63E-01 | 0 | 0 | 0 | 5.96E-01 |
| signal transduction -661461986 | GO | 1708 | 135 | 12 | 96 | 2.87E-01 | 156 | 26 | 18 | 1.52E-01 |
| Signal transduction_AKT signaling 554 | MA | 50 | 31 | 2 | 6 | 3.00E-03 | 28 | 4 | 4 | 2.09E-02 |
| Signal transduction_Androgen receptor signaling cross-talk 141076 | GG | 91 | 10 | 0 | 2 | 6.13E-01 | 20 | 2 | 3 | 4.60E-02 |
| Signal transduction_ERBB-family signaling 141134 | GG | 74 | 15 | 2 | 9 | 9.79E-03 | 30 | 6 | 9 | 3.02E-02 |
| Signal transduction_Insulin signaling 141070 | GG | 100 | 11 | 0 | 3 | 6.13E-01 | 16 | 1 | 2 | 1.98E-01 |
| Signal transduction_Leptin signaling 141155 | GG | 101 | 16 | 0 | 11 | 2.10E-02 | 14 | 2 | 2 | 1.54E-01 |
| Signal transduction_NOTCH signaling 141136 | GG | 197 | 46 | 2 | 11 | 1.79E-02 | 50 | 10 | 8 | 3.02E-02 |
| Signal transduction_PTEN pathway 676 | MA | 44 | 26 | 2 | 1 | 2.82E-01 | 28 | 4 | 2 | 1.52E-01 |
| Signal transduction_WNT signaling 141184 | GG | 183 | 12 | 3 | 8 | 6.13E-01 | 60 | 5 | 7 | 9.37E-02 |
| SMAD protein complex assembly -1772613411 | GO | 5 | 0 | 0 | 0 | 2.08E-01 | 5 | 2 | 0 | 7.52E-02 |

FROM FIG. 13H

| | | | | | | | | | |
|---|---|---|---|---|---|---|---|---|---|
| social behavior -976505965 | GO | 9 | 2 | 0 | 1 | 1.17E-01 | 2 | 0 | 0 | 3.51E-01 |
| somatic stem cell division -1956551075 | GO | 5 | 3 | 6 | 0 | 8.97E-02 | 0 | 0 | 0 | 4.95E-01 |
| spindle organization and biogenesis -981603555 | GO | 8 | 3 | 0 | 3 | 3.50E-04 | 0 | 0 | 0 | 9.75E-02 |
| steroid metabolic process -1662814541 | GO | 60 | 11 | 1 | 3 | 5.63E-02 | 10 | 2 | 0 | 1.15E-01 |
| striated muscle cell differentiation -636256116 | GO | 4 | 0 | 1 | 1 | 7.03E-02 | 17 | 0 | 0 | 7.98E-04 |
| striated muscle contraction -1591136223 | GO | 27 | 9 | 0 | 1 | 1.81E-01 | 8 | 0 | 0 | 5.96E-01 |
| surfactant homeostasis -872771821 | GO | 4 | 1 | 0 | 1 | 5.47E-02 | 2 | 0 | 0 | 5.58E-02 |
| sympathetic nervous system development -2067209709 | GO | 4 | 1 | 0 | 4 | 6.67E-02 | 2 | 0 | 1 | 4.08E-02 |
| synaptic transmission, GABAergic -472586611 | GO | 5 | 0 | 0 | 0 | 6.13E-01 | 3 | 0 | 0 | 1.19E-01 |
| synaptonemal complex assembly -757287430 | GO | 6 | 1 | 0 | 2 | 2.24E-02 | 0 | 0 | 0 | 2.49E-01 |
| T cell proliferation -1812244822 | GO | 10 | 2 | 0 | 3 | 3.57E-03 | 0 | 2 | 1 | 2.00E-02 |
| thyroid gland development -1296121775 | GO | 9 | 3 | 0 | 2 | 9.54E-02 | 1 | 0 | 0 | 1.20E-01 |
| tissue regeneration -1518962880 | GO | 29 | 7 | 0 | 1 | 1.03E-01 | 0 | 0 | 2 | 5.96E-01 |
| transcription -929449585 | GO | 1463 | 140 | 30 | 73 | 5.47E-02 | 112 | 17 | 28 | 1.27E-01 |
| transcription from RNA polymerase I promoter -52828037 | GO | 6 | 1 | 0 | 1 | 1.95E-01 | 0 | 0 | 0 | 5.66E-01 |
| Transcription_Assembly of RNA Polymerase II preinitiation complex on TATA-less promoters 673 | MA | 31 | 5 | 6 | 1 | 2.96E-01 | 5 | 0 | 2 | 1.73E-01 |
| Transcription_Receptor-mediated HIF regulation 416 | MA | 28 | 6 | 2 | 2 | 4.72E-01 | 11 | 3 | 0 | 3.89E-02 |
| Transcription_Role of heterochromatin protein 1 (HP1) family in transcriptional silencing 671 | MA | 39 | 5 | 0 | 6 | 3.39E-02 | 1 | 0 | 4 | 2.40E-01 |
| transcription-coupled nucleotide-excision repair -1802353278 | GO | 9 | 6 | 0 | 0 | 2.10E-02 | 2 | 0 | 0 | 5.96E-01 |
| Translation_Insulin regulation of protein synthesis 723 | MA | 50 | 8 | 0 | 2 | 5.90E-01 | 11 | 1 | 1 | 1.48E-01 |
| Translation_Regulation activity of EIF4F 496 | MA | 54 | 9 | 0 | 2 | 4.15E-01 | 11 | 4 | 2 | 9.75E-02 |
| transmembrane receptor protein tyrosine kinase signaling pathway -1070907330 | GO | 81 | 2 | 2 | 6 | 6.13E-01 | 15 | 0 | 4 | 8.44E-02 |
| transmembrane receptor protein tyrosine phosphatase signaling pathway -1683545553 | GO | 15 | 0 | 0 | 2 | 5.64E-01 | 6 | 0 | 0 | 3.02E-02 |
| Transmission of nerve impulse 141067 | GG | 212 | 15 | 3 | 15 | 5.52E-01 | 25 | 3 | 0 | 1.26E-01 |
| Transport_RAN regulation pathway 404 | MA | 40 | 12 | 0 | 2 | 1.31E-01 | 3 | 0 | 0 | 5.96E-01 |
| tryptophan catabolic process -414886310 | GO | 3 | 0 | 0 | 2 | 3.30E-01 | 1 | 0 | 0 | 2.09E-02 |
| Tyrosine metabolism p.1 (dopamine) 805 | MA | 15 | 4 | 1 | 4 | 1.45E-01 | 0 | 0 | 2 | 5.57E-01 |
| Tyrosine metabolism p.2 (melanin) 887 | MA | 22 | 6 | 1 | 0 | 1.76E-01 | 1 | 0 | 1 | 5.08E-01 |
| V(D)J recombination -1875586723 | GO | 4 | 0 | 0 | 0 | 6.13E-01 | 2 | 0 | 0 | 6.09E-02 |
| vitamin metabolic process -1190247353 | GO | 4 | 1 | 0 | 0 | 4.55E-01 | 4 | 0 | 0 | 4.82E-02 |

FIG. 13I

SI Table 7. Breast and colorectal cancer samples used in these analyses

| Sample | Tissue | Sample type | Copy Number Analysis | Illumina Array Type | Sequencing Analysis |
|---|---|---|---|---|---|
| B10C | Breast | Cell line | Illumina | 317k | Discovery |
| B11C | Breast | Cell line | Illumina | 317k | Discovery |
| B1C | Breast | Cell line | Illumina | 317k | Discovery |
| B2C | Breast | Cell line | Illumina | 317k | Discovery |
| B3C | Breast | Cell line | Illumina | 317k | Discovery |
| B4C | Breast | Cell line | Illumina | 317k | Discovery |
| B5C | Breast | Cell line | Illumina | 317k | Discovery |
| B6C | Breast | Cell line | Illumina | 317k | Discovery |
| B7C | Breast | Cell line | Illumina | 317k | Discovery |
| B8C | Breast | Cell line | Illumina | 550k | Discovery |
| B9C | Breast | Cell line | Illumina | 317k | Discovery |
| BT483 | Breast | Cell line | Illumina | 550k | N/A |
| MCF7 | Breast | Cell line | Illumina | 550k | N/A |
| MDAMB175VII | Breast | Cell line | Illumina | 550k | N/A |
| MDAMB231 | Breast | Cell line | Illumina | 550k | N/A |
| MDAMB415 | Breast | Cell line | Illumina | 550k | N/A |
| SKBR3 | Breast | Cell line | Illumina | 550k | N/A |
| T47D | Breast | Cell line | Illumina | 550k | N/A |
| UACC812 | Breast | Cell line | Illumina | 550k | N/A |
| UACC893 | Breast | Cell line | Illumina | 550k | N/A |
| ZR751 | Breast | Cell line | Illumina | 550k | N/A |
| ZR7530 | Breast | Cell line | Illumina | 550k | N/A |
| Bx10 | Breast | Xenograft | Illumina | 550k | N/A |
| Bx12 | Breast | Xenograft | Illumina | 550k | N/A |
| Bx13 | Breast | Xenograft | Illumina | 550k | N/A |
| Bx14 | Breast | Xenograft | Illumina | 550k | N/A |
| Bx15 | Breast | Xenograft | Illumina | 550k | N/A |
| Bx17 | Breast | Xenograft | Illumina | 550k | N/A |
| Bx19 | Breast | Xenograft | Illumina | 550k | N/A |
| Bx20 | Breast | Xenograft | Illumina | 550k | N/A |
| Bx22 | Breast | Xenograft | Illumina | 550k | N/A |
| Bx23 | Breast | Xenograft | Illumina | 550k | N/A |
| Bx24 | Breast | Xenograft | Illumina | 550k | N/A |
| Bx25 | Breast | Xenograft | Illumina | 550k | N/A |
| Bx26 | Breast | Xenograft | Illumina | 550k | N/A |
| Bx27 | Breast | Xenograft | Illumina | 550k | N/A |
| Bx28 | Breast | Xenograft | Illumina | 550k | N/A |
| Bx29 | Breast | Xenograft | Illumina | 550k | N/A |
| Bx30 | Breast | Xenograft | Illumina | 550k | N/A |
| Bx34 | Breast | Xenograft | Illumina | 550k | N/A |
| Bx35 | Breast | Xenograft | Illumina | 550k | N/A |
| Bx37 | Breast | Xenograft | Illumina | 550k | N/A |
| Bx38 | Breast | Xenograft | Illumina | 550k | N/A |
| Bx39 | Breast | Xenograft | Illumina | 550k | N/A |
| Bx8 | Breast | Xenograft | Illumina | 550k | N/A |
| Co108C | Colon | Cell line | Illumina | 317k | Discovery |
| Co109C | Colon | Cell line | Illumina | 550k | N/A |
| Co110C | Colon | Cell line | Illumina | 550k | N/A |
| Co111C | Colon | Cell line | Illumina | 550k | N/A |
| Co44C | Colon | Cell line | Illumina & DK | 317k | N/A |
| Co74C | Colon | Cell line | Illumina | 317k | Discovery |

FIG. 14A

| | | | | | |
|---|---|---|---|---|---|
| Co82C | Colon | Cell line | Illumina & DK | 550k | Validation |
| Co84C | Colon | Cell line | Illumina & DK | 317k | Validation |
| Co92C | Colon | Cell line | Illumina | 317k | Discovery |
| Co94C | Colon | Cell line | Illumina | 550k | Validation |
| Hx107 | Colon | Xenograft | Illumina | 550k | N/A |
| Hx110 | Colon | Xenograft | Illumina | 550k | N/A |
| Hx129 | Colon | Xenograft | Illumina | 550k | N/A |
| Hx130 | Colon | Xenograft | Illumina | 550k | N/A |
| Hx132 | Colon | Xenograft | Illumina | 550k | N/A |
| Hx134 | Colon | Xenograft | Illumina | 550k | N/A |
| Hx136 | Colon | Xenograft | Illumina | 550k | N/A |
| Hx152 | Colon | Xenograft | Illumina | 550k | N/A |
| Hx190 | Colon | Xenograft | Illumina | 550k | Validation |
| Mx03x | Colon | Xenograft | Illumina | 550k | Validation |
| Mx08x | Colon | Xenograft | Illumina | 550k | Validation |
| Mx22x | Colon | Xenograft | Illumina | 317k | Discovery |
| Mx26x | Colon | Xenograft | Illumina | 317k | Validation |
| Mx27x | Colon | Xenograft | Illumina | 317k | Discovery |
| Mx29x | Colon | Xenograft | Illumina | 550k | Validation |
| Mx30x | Colon | Xenograft | Illumina | 317k | Discovery |
| Mx31x | Colon | Xenograft | Illumina | 550k | Validation |
| Mx32x | Colon | Xenograft | Illumina | 317k | Discovery |
| Mx34x | Colon | Xenograft | Illumina | 550k | Validation |
| Mx35x | Colon | Xenograft | Illumina | 550k | Validation |
| Mx38x | Colon | Xenograft | Illumina | 317k | Discovery |
| Mx40x | Colon | Xenograft | Illumina | 550k | Validation |
| Mx41x | Colon | Xenograft | Illumina | 317k | Discovery |
| Mx42x | Colon | Xenograft | Illumina | 317k | Discovery |
| Mx43x | Colon | Xenograft | Illumina | 317k | Discovery |
| Mx45x | Colon | Xenograft | Illumina | 550k | Validation |
| Co37C | Colon | Cell line | DK | N/A | N/A |
| Co85C | Colon | Cell line | DK | N/A | N/A |
| Co90C | Colon | Cell line | DK | N/A | N/A |
| Co93C | Colon | Cell line | DK | N/A | N/A |
| M10-16 | Colon | Immunopurified tumor tissue | DK | N/A | N/A |
| M10-23 | Colon | Immunopurified tumor tissue | DK | N/A | N/A |
| M11-1 | Colon | Immunopurified tumor tissue | DK | N/A | N/A |
| M12-02 | Colon | Immunopurified tumor tissue | DK | N/A | N/A |
| M12-05 | Colon | Immunopurified tumor tissue | DK | N/A | N/A |
| M4-10 | Colon | Immunopurified tumor tissue | DK | N/A | N/A |
| M8-10 | Colon | Immunopurified tumor tissue | DK | N/A | N/A |
| M8-20 | Colon | Immunopurified tumor tissue | DK | N/A | N/A |
| M-JC1 | Colon | Immunopurified tumor tissue | DK | N/A | N/A |
| M-JC3 | Colon | Immunopurified tumor tissue | DK | N/A | N/A |
| M-JC-T4 | Colon | Immunopurified tumor tissue | DK | N/A | N/A |

FIG. 14B

INTEGRATED ANALYSES OF BREAST AND COLORECTAL CANCERS

The disclosed invention was made using funds from the U.S. government, particularly National Institutes of Health grants CA 043460, CA 057345, CA 062924, and CA 121113. The U.S. government therefore retains certain rights in the invention.

TECHNICAL FIELD OF THE INVENTION

This invention is related to the area of classifying, characterizing, detecting and diagnosing cancers. In particular, it relates to breast and colorectal cancers.

BACKGROUND OF THE INVENTION

It is well accepted that cancer is the result of the sequential mutations of oncogenes and tumor suppressor genes (1). Historically, the discovery of these genes has been accomplished through analyses of individual candidate genes chosen on the basis of functional or biologic data implicating them in the tumorigenic process. Recent advances in genomic technologies and bioinformatics have permitted simultaneous evaluation of many genes, thereby offering more comprehensive and unbiased information (2, 3). For example, the sequence of large families of genes, and even the human genes in the Reference Sequence (RefSeq) database, have been determined in subsets of human cancers (4, 5). However, the alterations detected by sequencing represent only one category of genetic change that occurs in human cancer. Other alterations include gains (amplifications) and losses (deletions) of discrete chromosomal sequences that occur during tumor progression. Dramatic amplifications of oncogenes such as ERBB2 (6) or MYC (7) and deletions of tumor suppressor genes such as CDKN2A (8), PTEN (9, 10) and SMAD4 (11) have demonstrated the importance of these mechanisms of genetic alteration in particular tumor types. A comprehensive picture of genetic alterations in human cancer should therefore include the integration of sequence based alterations together with copy number gains and losses.

Evaluations of copy number changes in cancers using a variety of array types have been previously reported (12). Several of the more recent studies employed oligonucleotide arrays capable of distinguishing >100,000 genomic loci in colon, breast lung, pancreatic, and skin cancers as well as certain leukemias (13-20). However, identification of focal, high copy amplifications or homozygous deletions (HDs) have infrequently been reported because many prior copy number analyses on arrays have used genomic DNA purified from primary tumors. Primary tumors contain varying proportions of non-neoplastic cells thereby reducing the apparent extent of amplification and obscuring focal amplifications—defined by the increased copy number of a small region of the genome—from simple gains of whole chromosome arms. Furthermore, HDs can be difficult to discern in primary tumors due to confounding hybridization signals from non-neoplastic cells (17).

Many of the problems encountered with primary tumor samples can be overcome by use of early passage cancer cell lines or xenografts which are devoid of human non-neoplastic cells. Previous studies have shown that the process of generating such in vitro or in vivo cultures is not associated with the development of additional genetic alterations (21). It is now widely recognized that HDs found in cell lines and xenografts represent true genetic alterations that are present in clonal fashion in primary tumors but are difficult to document in the latter because of contaminating non-neoplastic cells (22, 23).

There is a continuing need in the art for methods to characterize, classify, detect and diagnose breast and colorectal cancers.

SUMMARY OF THE INVENTION

According to one embodiment of the invention a method of characterizing a breast or colon tumor in a human is provided. A mutated pathway selected from those listed in Table 3 or SI Table 6 is determined in a breast or colon tumor by determining at least one somatic mutation in a gene in the pathway in a test sample relative to a normal sample of the human. The breast or colon tumor is assigned to a first group of breast or colon tumors that have a somatic mutation in at least one gene in said pathway.

According to another embodiment of the invention a method of detecting or diagnosing a breast or colon tumor or minimal residual disease of a breast or colon tumor or molecular relapse of a breast or colon tumor in a human is provided. A genomic amplification of at least one genomic region is determined in a test sample of a tumor or suspected tumor of the human. The genomic region is selected from the group consisting of those listed in SI Table 4 or Table 1. The human is identified as likely to have a breast or colon tumor, minimal residual disease, or molecular relapse of breast or colon tumor when the amplification is determined.

According to another embodiment a method is provided of detecting or diagnosing a breast or colon tumor or minimal residual disease of a breast or colon tumor or molecular relapse of a breast or colon tumor in a human. A genomic deletion of at least one genomic region is determined in a test sample of a tumor or suspected tumor of the human. The genomic region is selected from the group consisting of those listed in SI Table 5 or Table 2. The human is identified as likely to have a breast or colon tumor, minimal residual disease, or molecular relapse of breast or colon tumor when the homozygous deletion is determined.

These and other embodiments which will be apparent to those of skill in the art upon reading the specification provide the art with methods for detecting, classifying, characterizing and diagnosing breast and colorectal tumors.

BRIEF DESCRIPTION OF THE DRAWINGS

FIG. 2A indicates breast cancer alterations while FIG. 2B indicates colorectal cancer alterations. The telomere of the short arm of chromosome 1 is represented in the rear left corner of the green plane and ascending chromosomal positions continue in the direction of the arrow. Chromosomal positions that follow the front edge of the plane are continued at the back edge of the plane of the adjacent row and chromosomes are appended end to end. Peaks indicate the 60 highest-ranking candidate cancer genes for each tumor type, with peak heights reflecting the passenger probability scores. The yellow and blue peaks correspond to genes that are altered by copy number changes, while those altered only by point mutations are purple. The dots represent genes that were altered by copy number changes (red squares) or point mutations (white circles) in the B9C breast or Mx27 colorectal tumor samples. Altered genes participating in significant gene groups or pathways (FIG. 13; SI Table 6) are indicated as black circles or squares.

FIG. 5 (Table 1) Top candidate cancer genes in breast and colorectal cancer amplifications.

FIG. 6 (Table 2) Top candidate cancer genes in breast and colorectal cancer homozygous deletions.

FIG. 7A to 7B (Table 3) Candidate cancer pathways altered in breast and colorectal cancers.

FIG. 8 (SI Table 1) Comparison between Illumina™ array and Digital Karyotyping copy number analyses.

FIG. 9 (SI Table 2) Copy number changes detected by Digital Karyotyping in colorectal cancer FIG. 10A to 10Z (SI Table 3) Amplifications and homozygous deletions detected by Illumina™, arrays in breast and colorectal cancers FIG. 11A to 11L (SI Table 4) Amplified genes in breast and colorectal cancers.

FIG. 12A to 12E (SI Table 5) Homozygously deleted genes in breast and colorectal cancers.

FIG. 13A to 13I (SI Table 6) Pathways enriched for copy number alterations and point mutations.

FIG. 14A to 14B (SI Table 7) Breast and colorectal cancer samples used in these analyses.

DETAILED DESCRIPTION OF THE INVENTION

The inventors have developed means of diagnosing, classifying, characterizing, and detecting breast and colorectal tumors based on somatic mutations in genes in pathways, including point mutations, genomic amplifications, and genomic deletions.

Xenografts or cell lines derived from breast and colorectal cancers were examined to obtain high resolution analyses of copy number and nucleotide alterations. Tumors were evaluated with microarrays containing at least 317,000 SNP probes and selected samples were also evaluated with Digital Karyotyping (24). This latter method provides a highly quantitative measure of gene copy number and was used to validate the sensitivity and specificity of the microarray data. The sequences of the 18,191 genes from the RefSeq database previously determined for breast and colorectal cancers were integrated with these results, providing a genome-wide analysis of sequence and copy number alterations.

The integrated mutational analysis described here provides a global picture of the genetic alterations of breast and colorectal cancers. The combination of sequencing and copy number analysis at the whole genome level permits the identification of genes and pathways that may not be easily detected by either analysis alone. The analysis of point mutations can provide independent information that can help identify candidate target genes in regions of amplification or HD. As gene groups and pathways can be affected by sequence and copy number changes, a combined analysis can highlight the groups that are enriched for these somatic alterations.

The analysis of copy number changes can also provide general insights into the functional effects of point mutations. Single nucleotide substitutions in genes that are observed to be deleted are more likely to be inactivating, while substitutions in genes that are amplified are more likely to be activating. This was confirmed by the observation of HDs and point mutations in TP53, SMAD2, SMAD3, and PTEN all of which are thought to be tumor suppressors. If copy number changes faithfully reflect the overall effect of target genes, one would expect to infrequently see both amplifications and HDs of the same set of genes in human tumors. Accordingly, we observed an under-representation of genes that are homozygously deleted in one tumor and amplified in another (only two of the 1148 altered genes identified were altered by both amplification and HD ($p<0.01$, binomial test) and neither were considered good candidates by the integrated statistical analyses).

Figure 2A:
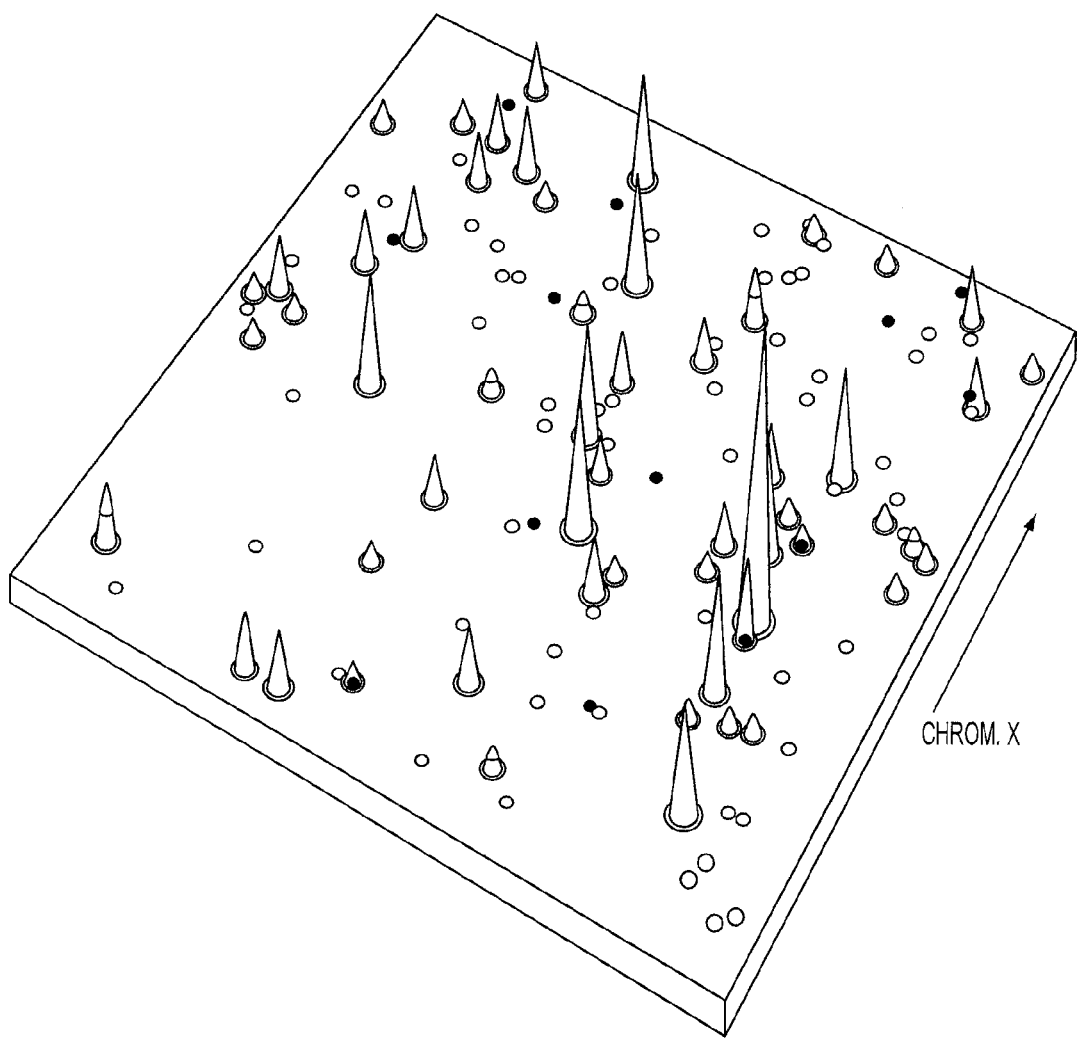
FIG. 2A-2B shows genomic landscape of a copy number and nucleotide alterations in two typical cancer samples.
Figure 2B:
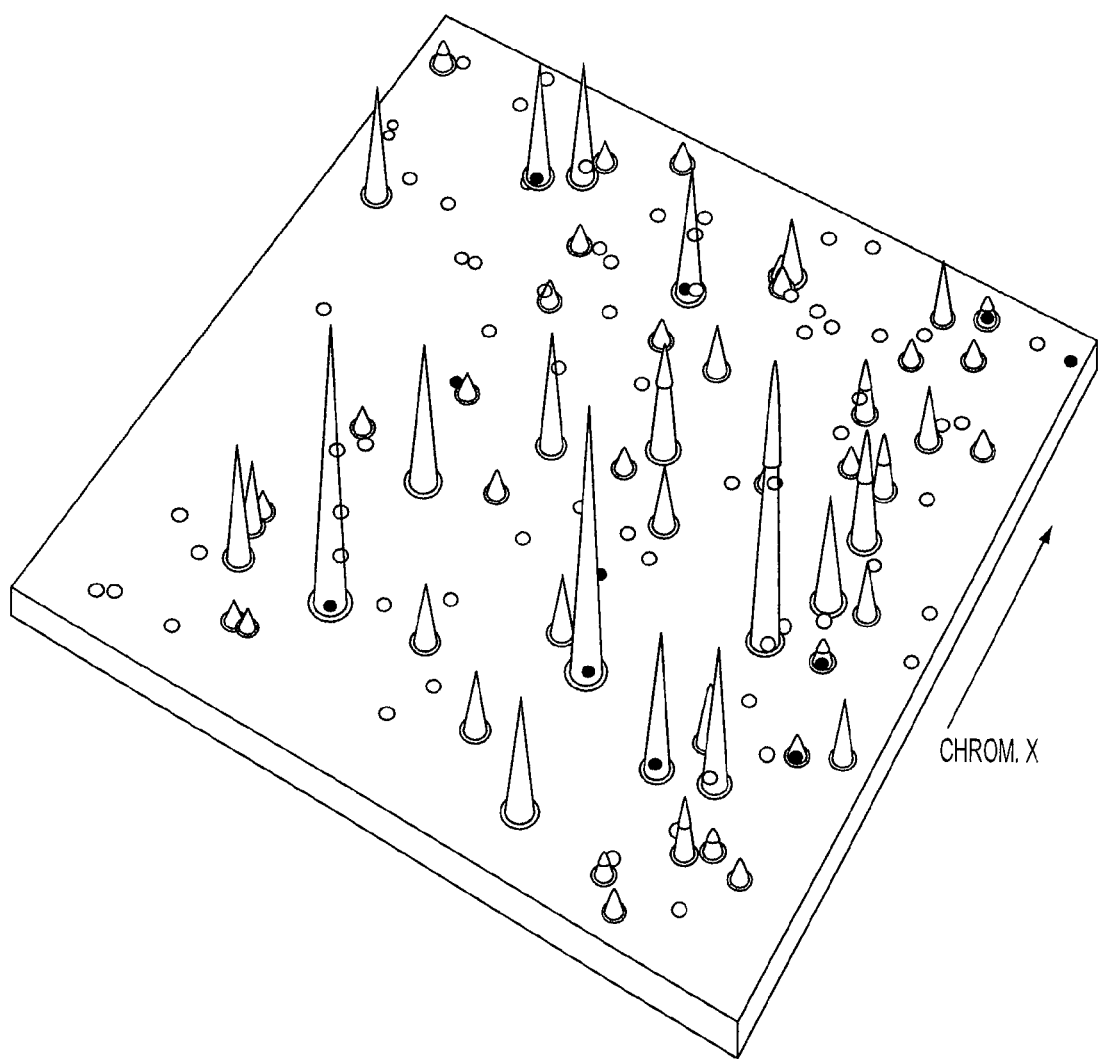
Figure 3:
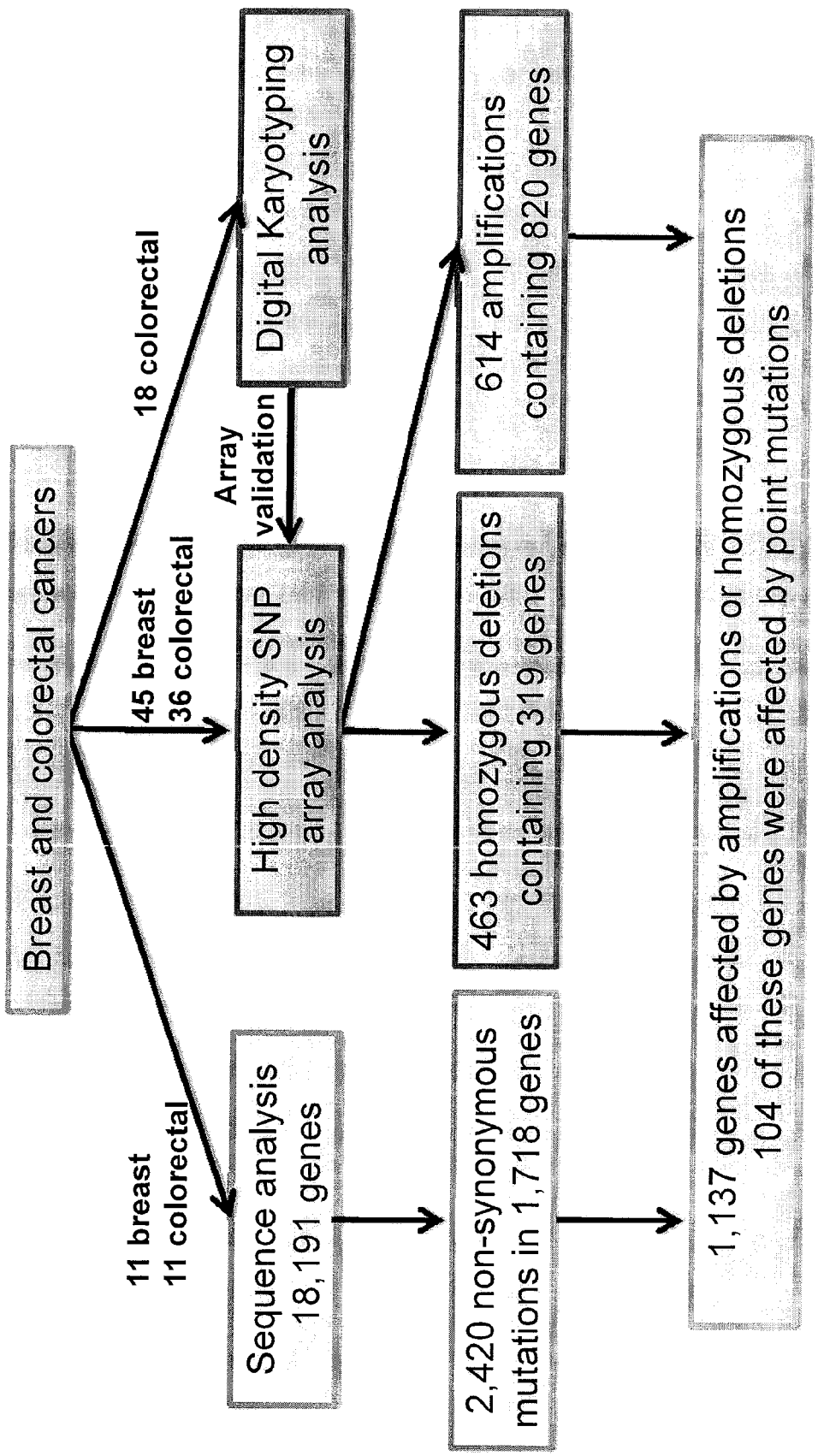
FIG. 3 (SI FIG. 1.) shows schematic of experimental approach for integration of copy number and sequence alterations in breast and colorectal cancers FIG. 4 (SI FIG. 2.) shows detection of amplifications and homozygous deletions using Illumina arrays and Digital Karyotyping. Digital Karyotyping results are shown in the top graphs, with the chromosomal coordinates indicated on the horizontal axis and the Digital Karyotyping tag density ratio indicated on the vertical axis. Illumina array results are shown in the bottom graphs, with the chromosomal coordinates indicated on the horizontal axis and the Log R Ratio indicated on the vertical axis. Digital Karyotyping data were used to validate the Illumina arrays and to develop approaches for sensitive and specific detection of focal amplifications and homozygous deletions.

In addition to identifying genes through the integrated analysis of point mutations and copy number changes, a number of issues arise from these studies that have implications for future large scale genomic analyses (36). One is that the complexity of genetic alterations in human cancer increases when considering both point alterations and copy number changes. In addition to a median of 84 and 76 genes altered by point mutation, breast and colorectal cancers have a median of 24 and 9 genes altered by a major copy number change. These observations support a view of the breast and colorectal cancer genomic landscape where a few commonly affected "gene mountains" are scattered among a much larger number of "gene hills" that are infrequently altered by either point mutation or copy number changes. An example of a cancer genome landscape that incorporates copy number changes, illustrated in FIG. 2, shows new gene mountains and hills that result from the combined analysis.

Though cancer genome landscapes are complex, they may be better understood by placing all genetic alterations within defined cellular pathways. Our analyses identified several converging gene pathways, including the ERBB2, EGFR and PI3K pathways, that were affected by copy number changes and point alterations in both breast and colorectal cancers. In addition, many pathways implicated in colorectal tumor progression (Notch, AKT, and MAPK) were enriched for alterations. Interestingly, many gene groups contained genes that were both amplified and others that were deleted, suggesting that different genes within the same group or pathway may be affected through alternate mechanisms. This is consistent with the observation that most signaling pathways contain both positive and negative regulators and alterations in any of these can lead to dysregulated signaling.

The copy number and sequence alterations reported here should be placed in the context of other analyses to reveal the full compendium of molecular changes in a tumor cell. One limitation of our approach is that the copy number analyses we performed may have missed very small regions (<20 kb) that were amplified or deleted. Use of arrays with higher numbers of SNPs or larger DK libraries generated using next generation sequencing approaches will help improve the sensitivity of these analyses. Additionally, the incorporation of approaches that detect structural changes (e.g. translocations) and epigenetic alterations will likely prove to be useful. Finally, as has been done with karyotypic abnormalities (37), it will be important to determine the timing of these alterations within each tumor type by analysis of additional tumor samples from different stages. In this regard, it should be noted that other methods of tumor isolation may not result in tumor DNA purity that will allow the sensitive and quantitative detection of copy number alterations afforded by our studies (38, 39).

The development of approaches to identify genetic alterations on a genome-wide scale has made the discovery of mutations the "easy" part of cancer gene discovery efforts. Functional studies to identify the culprits underlying the 1077 copy number changes discovered from our study would currently be impractical. The statistical techniques we developed highlight the best candidates for future functional studies, but it remains possible that specific loci are more likely to be altered by copy number changes than others because they are located near fragile sites or other hotspots for recombination (40). Therefore, these genetic analyses can only identify candidate genes that may play a role in cancer and do not definitively implicate any gene in the neoplastic process.

Several of the pathways identified affected a relatively high fraction of cancers and may be useful for cancer diagnosis or therapy. Alterations in signaling pathways of FGFR, EGFR, ERBB2 and PI3K were detected in nearly two thirds of breast and colorectal tumors that were comprehensively examined in this study. These data suggest that the ERBB2 inhibitors may be useful not only in breast cancer but also in selected colorectal cancer patients in combination with existing therapeutic agents. Additionally, a significant fraction of the breast tumors analyzed had genetic alterations in a process regulating DNA topology. Although TOP2A is co-amplified with ERBB2 and therefore does not represent the likely driver of this amplicon, alterations of TOP2A may still be of clinical utility. As higher doses of anthracyclines may improve clinical outcomes in breast cancer patients with TOP2A amplifications (41, 42), our observations suggest that the additional alterations that we identified could be used to select patients that may respond to topoisomerase-targeted therapies. In a similar fashion, tumor cells deficient in certain cellular processes as a result of HDs could be targeted pharmacologically through synthetic lethality. In a general sense, our discovery that a typical colorectal or breast cancer has 4 to 7 genes homozygously deleted suggests that further development of strategies targeting such HDs (43) could be widely applicable.

Mutations, including homozygous deletions, genomic amplifications, and point mutations can be determined by any means known in the art, including but not limited to the methods described below. Sequencing, digital karyotyping, and hybridization to SNP arrays, are non-limiting examples of techniques which can be used. DNA sequencing can be performed using any techniques which are known in the art, for example, based on chemical degradation, enzymatic synthesis, ligation, hybridization, etc. Enzymes which can be used include but are not limited to polymerases and ligases. Synthesized or degraded nucleic acids can be analyzed using techniques which separate molecules based on length or mass, for example. Sequence determinations can be performed manually or in an automated fashion. Some techniques which can be be exploited utilize radiolabeled or fluorescently labeled nucleotides. Single stranded oligonucleotides can be employed as probes or primers, both of which may hybridize to the analyte. Some methods utilize dideoxynucleotides which act as monomers and terminators of DNA synthesis.

Mutation, deletion, or amplification determination involves one or more ex vivo samples which are processed in order to analyze the genetic material (or sometimes the proteins encoded by the genetic material). Typically this involves purification or enrichment of nucleic acids and removal or de-enrichment of other cellular components, such as protein, lipid, carbohydrates. The nucleic acids are further reacted chemically or enzymatically to yield readily detectable products which correspond to the nucleic acids in the ex vivo samples. Determination of a somatic mutation is done by comparing a tumor sample or characteristic to a normal sample of the same individual. Differences can be observed and recorded by a human or a machine or a computer.

Changes in copy number of a genomic segment can be determined by any means known in the art. In one technique, fragments (enzymatically generated or random) are generated and ligated together to form a chain or concatenate. The concatenates can be sequenced, and underrepresented or overrepresented fragments of the genome can be noted. Alternatively genomic DNA fragments can be hybridized to an array of oligonucleotides and their relative prevalence scored. Such techniques may detect deletions or amplifications. Changes in copy number may be from diploid to homozygous deletion, or amplifications ranging from diploid to at least 5-, at least 6-, at least 7-, at least 8-, at least 9-, at least 10-, at least 15-, at least 20-, at least 25-fold of diploid.

Tumors or patients bearing tumors can be divided into or assigned to groups based on the presence or absence of a particular somatic mutation. The group with the mutation may optionally contain tumors with a particular mutation in a particular gene, tumors with mutations in a single gene, or tumors with mutations in a single pathway. Groups comprising tumors with mutations in a single gene or a single pathway may be the same or different types of mutations.

Groups that are divided on the basis of a mutation in a gene or in a pathway may be used to evaluate drugs or other therapeutic treatments. This permits the determination of groups which are susceptible or refractory to the treatment. Thus patients who are susceptible can be successfully treated, and patients who are refractory can avoid expensive, potentially hazardous, and ultimately ineffective treatments.

The mutations in genes and pathways, including point mutations, homozygous deletions, and amplifications, can also be used to detect or diagnose breast or colon tumors, or minimal residual disease of such tumors, or molecular relapse of such tumors. The mutations and genes and pathways which have been found are characteristic of these cancers and can be used to identify them in various stages of disease. Characteristic mutations are not necessarily present in all or even in a majority of tumors of the breast or colon.

Mutations found in tumors can be determined or confirmed by comparison to normal tissue. Somatic mutations are ones that occur in the tumor but are not found in normal tissue of the individual. Thus a comparison between tumor and normal can be used for identification and confirmation.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Optimization of Copy Number Analysis with Digital Karyotyping

Digital Karyotyping (DK) was used as a standard to develop criteria for assessing amplifications and HDs with Illumina high density SNP arrays. Analysis of DK libraries from 18 colorectal tumor samples identified a total of 21 amplification events, each containing relatively small chromosomal regions (41 kb to 2.3 Mb) with 12 to 186 copies per nucleus (SI Table 2). We also found 4 regions within the autosomal chromosomes where the tag density reached zero, representing HDs. As expected, we identified low-amplitude gains and losses of entire chromosomes, chromosomal arms, or other large genomic regions. We did not pursue these low-amplitude copy number changes as it is difficult to reliably identify candidate cancer genes from such large regions. To ensure that the copy number changes identified by DK were bona fide amplifications or HDs, we independently examined 12 alterations by quantitative PCR and confirmed the presence of the genomic alterations in every case examined.

We then directly compared DK data to those obtained through genomic hybridization of the same DNA samples to Illumina high density oligonucleotide arrays. The Illumina platform employs a two step procedure based on oligo hybridization and single base extension for analysis of genomic SNPs (25). The combination of these two steps leads to greater fidelity of SNP calls and decreases false hybridization signals. Using fluorescence intensity measurements we developed an approach to detect amplifications resulting in 12 or more copies per nucleus (6-fold or greater amplification compared to the diploid genome) as well as deletions of both copies of a gene (HDs) (see SI Methods).

Using this new approach, 14 amplification events and 3 HD events identified by DK in 3 representative tumor samples were detected by Illumina arrays (SI Table 1 and SI FIG. 2). In all cases, the genomic boundaries identified by both approaches were similar and within the resolution expected for both methods. The copy number of amplifications determined by DK was higher than those same regions identified by Illumina arrays. It is known that arrays underestimate the copy number of amplifications (26) and this was confirmed by real-time PCR for amplifications in SI Table 1. No additional copy number changes of the sizes expected to be detected by DK were identified by the microarray approach in these samples. We did identify 25 additional small HDs; all of these were <250 kb in length and would not have been possible to detect with DK given the number of tags analyzed (24). To independently validate such smaller HDs, we used PCR and Sanger sequencing to examine genes located within small HDs and found that in each case, multiple exons of each gene could not be amplified or sequenced. These results suggested that our approach for analysis of Illumina array data provided a sensitive and specific method for identification of amplifications and HDs, including relatively small alterations of either type.

Example 2

Detection of Amplifications and Homozygous Deletions

Figure 1:
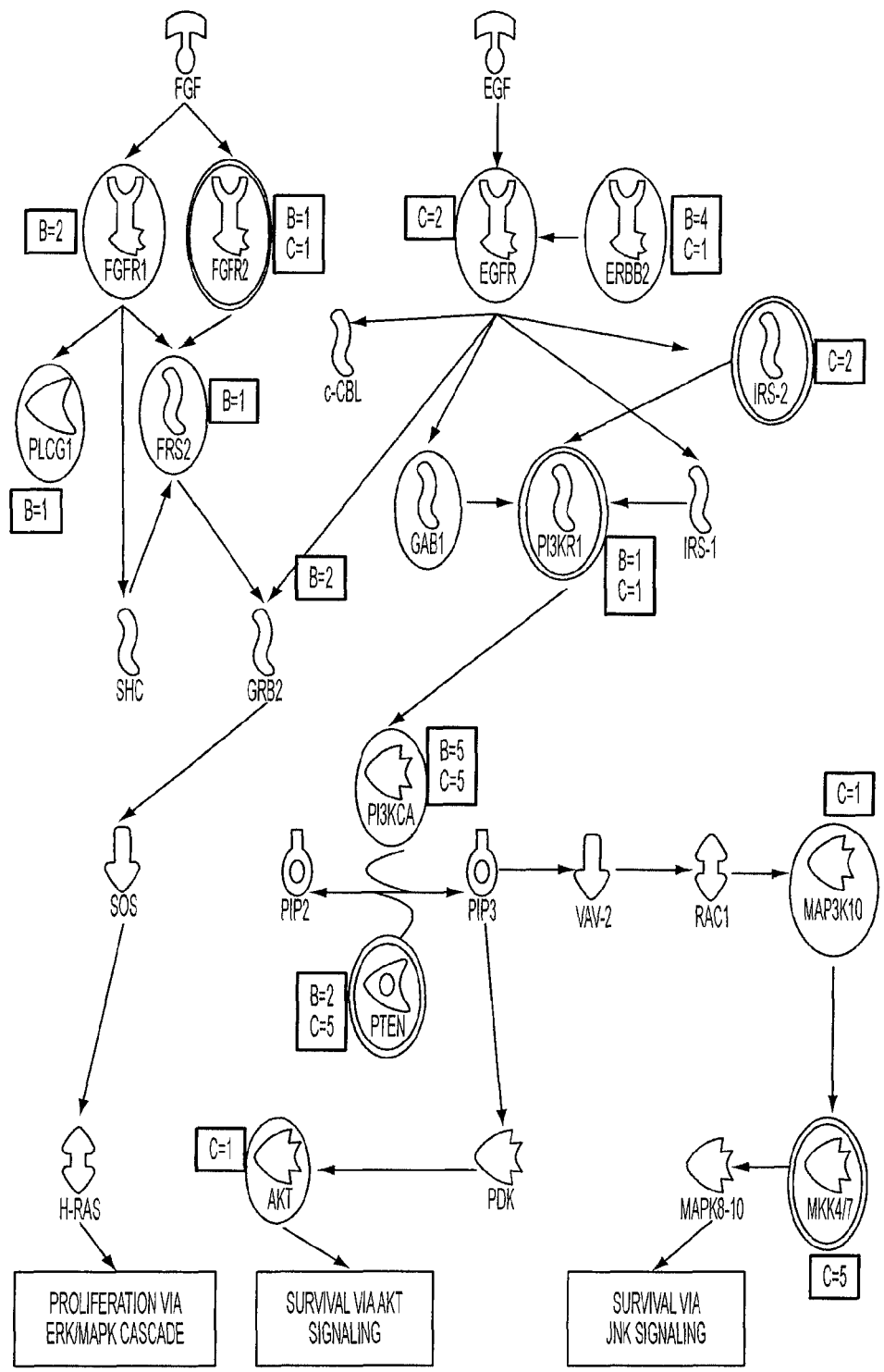
FIG. 1 shows alterations in the combined FGF, EGFR, ERBB2 and PI3K pathways. Genes affected by copy number alterations are circled in red, while those altered by point mutations are circled in blue. The number of breast (B) and colorectal (C) tumors containing alterations are indicated in boxes adjacent to each gene.

A total of 45 breast and 36 colorectal tumors were analyzed by Illumina arrays containing either ~317,000 or ~550,000 SNPs (SI FIG. 1). To determine the fraction of alterations that were likely to be somatic (i.e., tumor derived), we analyzed these regions in 23 matched normal samples. In the normal samples, no amplifications and only four distinct HDs were detected. We removed these alterations from further analysis, as well as those corresponding to known copy number variation in normal human cells (27, 28). Finally, we removed any copy number changes where the boundaries were identical in two or more samples, as these were likely to represent germline variants. Based on this conservative strategy, we estimated that >95% of the 614 amplifications and 463 HDs (SI Table 3) represented true somatic alterations.

Breast cancers contributed to a majority of the alterations identified, comprising 68% and 81% of the total HDs and amplifications, respectively. Individual colorectal and breast tumors had on average 7 and 18 copy number alterations, respectively. Each colorectal cancer had an average of 4 HDs and 3 amplifications. Breast cancers had on average 7 HDs and 11 amplifications. Several of the tumor samples contained copy number alterations that were separated by short non-amplified or deleted sequences, presumably reflecting the complex structure of these alterations (29, 30).

The copy number alterations observed encompassed on average 1.7 and 2.4 Mb of colorectal and breast haploid genomic sequence, respectively. Each HD affected the coding region of one gene on average, while an average amplicon contained two genes. The average numbers of protein-coding genes that were affected by either amplification or HD were 24 and 9 per breast and colorectal cancer, respectively.

Example 3

Genes Altered in More Than One Tumor

One of the main challenges in the analysis of somatic alterations in cancers involves the distinction between those changes which are selected for during tumorigenesis (driver alterations) from those that provide no selective advantage (passenger alterations). Even in regions that have multiple copy number alterations, this distinction can be particularly difficult because regions of amplification and HD can contain multiple genes, only a subset of which are presumably the underlying targets. We reasoned that the integration of copy number analyses with sequence data would help reveal the driver genes that were more likely to contain genetic alterations. To accomplish this integration, we developed a new statistical approach for determining whether the observed genetic alterations of any type in any gene were likely to reflect an underlying mutation frequency that was significantly higher than the passenger rate. To analyze the probability that a given gene would be involved in a copy number alteration, we made the conservative assumption that the frequency of all amplifications and HDs observed in each tumor type represented the passenger mutation frequency (i.e., we assumed that all copy number changes were passengers). The number of actual copy number alterations affecting each gene in all tumors was then compared to the simulated number of expected passenger alterations taking into account gene size, the distribution of SNP locations, and the frequency of passenger amplifications and HDs in breast and colorectal cancers.

We integrated these copy number analyses with the sequence data of the Sjöblom et al. and Wood et al studies (5, 31). In these studies, the protein coding sequences of 20,857 transcripts from the 18,191 genes in the RefSeq database were determined in 11 breast and 11 colorectal cancer samples, allowing detection of somatic sequence alterations. Genes containing somatic alterations were subsequently analyzed for mutations in additional tumors of the same type. In the current study, the same 22 breast and colorectal tumor samples were analyzed in parallel by Illumina arrays, together with additional samples of each tumor type (SI FIG. 1 and SI Table 7). To integrate these different mutational data for each tumor type, we combined the probability that a gene was a driver gene based on the type and frequency of point mutations previously observed with the probability that the gene was a driver based on the number of observed amplifications and HDs.

Table 1 lists the loci that were amplified in at least one tumor and had the highest probability of containing driver genes as determined by the combined mutation analysis (a complete list of amplifications is provided in SI Table 3 and amplified genes in SI Table 4). For genes to be considered potential targets of the amplification, the entire coding region of the gene was required to be contained within a focal amplicon. A few candidate genes in this list (e.g. CCNE1 (cyclin E) and ERBB2) were amplified in multiple tumors but were not found to be mutated by sequencing. The majority of candidate genes, however, harbored point mutations in some tumors and amplifications in others. The most striking aspect of this list of candidate genes is that only some of them had been implicated in cancer in the past. Of the 19 genes indicated in Table 1, only 8 had been previously implicated in tumorigenesis. The known cancer genes included MYC, ERBB2 (HER2/NEU), CCNE1, CCND1, EGFR, FGFR2, and IRS2, each of which had been shown to be amplified. In addition, MRE11, which was amplified in breast cancers, has been shown to be mutated in small fraction of colorectal cancers and is thought to play an essential role in maintaining chromosomal stability (32). Some genes were shown to be altered in both breast and colorectal cancers, with at least one of the tumors containing amplifications. Interestingly, among these genes, ERBB2 was found to be amplified in both breast and colorectal cancers, and FGFR2 was found to be mutated in breast cancers and amplified in colorectal cancers.

Table 2 similarly lists the loci that were homozygously deleted in at least one tumor and had the highest probability of containing drivers as determined by the combined mutation analysis (a complete list of HDs is provided in SI Table 3 and homozygously deleted genes in SI Table 5). For each of these genes, a portion of the coding region was affected by the HD. A number of genes previously known to be inactivated in colorectal or breast tumorigenesis, such as CDKN2A, PTEN, and TP53 are found in this list. We also identified genes, such as CHD5, MAP2K4, SMAD2, and SMAD3 that have been previously shown to be deleted in other tumor types, but not in colorectal or breast cancers. Finally, we discovered a number of genes not previously known to be affected by HD in any tumor type. For example, HDs as well as point mutations were found in OMA1 and ZNF521 in colorectal cancers and in MANEA, PCDH8, SATL1, and ZNF674 in breast cancers. During the course of preparing this manuscript, we identified through independent experimentation that PCDH8 is mutated and homozygously deleted in breast cancer (33). A number of genes that were less frequently altered in any one tumor type were shown to be affected at significant levels in both tumor types, including CDH20, FHOD3 and FNDC1.

Example 4

Pathways Enriched for Copy Number and Point Alterations

We examined whether groups of genes belonging to certain cellular processes or pathways were preferentially affected by genetic alterations. For this purpose, we developed a statistical approach that provided a probability that a pathway contained driver alterations, taking into account both the copy number changes and point mutations. This approach was similar to that described above for evaluating individual genes but in this case was applied to entire groups of genes involved in specific pathways or functional groups. Because the net effect of a pathway can be the same whether certain components are amplified or others deleted, all copy number alterations within a gene group were considered. The analysis was performed using three well-annotated GeneGo MetaCore databases: gene ontology (GO), canonical gene pathway maps (MA), and genes participating in defined cellular processes and networks (GG) (34). For each gene group, we considered whether the component genes were more likely to be affected by point mutations, amplifications, or HDs, as compared to all genes analyzed. Importantly, these analyses were based on analysis of the rankings of altered genes within each group using a modified version of gene set enrichment analysis (GSEA) (35), rather than the total number of mutations within individual groups. This approach limits the effects of single highly mutated genes and requires the involvement of multiple genes to score a pathway as significantly affected.

These analyses identified gene groups that were enriched for genetic alterations in these tumor types (Table 3). In particular, the EGFR and ERBB gene families were enriched for alterations. Interestingly, both of these signaling pathways involved various components of the PI3 kinase pathway, suggesting that the observed alterations may result in similar effects in these tumor cells (FIG. 1). A third of genes in these combined pathways were mutated by sequence alterations, amplifications, or HDs. Enrichment of alterations in other canonical gene groups including Notch and G1-S cell cycle transition pathways were also detected. The latter group included HDs of CDKN2A and CDKN2B genes as well as amplifications of cyclin D1, cyclin D3, and cyclin E3 genes in breast cancers. For all these gene groups, new genes were identified that had not previously been implicated by genetic alterations in these cellular processes. Finally, a variety of gene groups not previously known to be enriched for copy number changes in tumorigenesis were identified. These included genes implicated in cell-cell interaction and adhesion, including cadherins and metalloproteases, as well as other genes implicated in cellular interactions during early embryonic and neural development. As an example, in colorectal cancers, a total of 33 cadherin and protocadherin genes were detected as being affected by copy number or sequence changes. In breast cancers, there was also enrichment in genes implicated in DNA topological control, including alterations in a number of topoisomerases (TOP1, TOP2A, TOP2B and TOP3A) and helicases. All pathways showing significant enrichment for genetic alterations are listed in SI Table 6.

REFERENCES

The disclosure of each reference cited is expressly incorporated herein.
1. Vogelstein, B. & Kinzler, K. W. (2004) Cancer genes and the pathways they control. Nat Med 10:789-99.
2. Bardelli, A. & Velculescu, V. E. (2005) Mutational analysis of gene families in human cancer. Curr Opin Genet Dev 15:5-12.
3. Strausberg, R. L., Levy, S. & Rogers, Y. H. (2008) Emerging DNA sequencing technologies for human genomic medicine. Drug Discov Today 13:569-77.
4. Greenman, C., et al. (2007) Patterns of somatic mutation in human cancer genomes. Nature 446:153-8.
5. Wood, L. D., et al. (2007) The genomic landscapes of human breast and colorectal cancers. Science 318:1108-13.

6. Slamon, D. J., et al. (1987) Human breast cancer: correlation of relapse and survival with amplification of the HER-2/neu oncogene. Science 235:177-82.
7. Collins, S. & Groudine, M. (1982) Amplification of endogenous myc-related DNA sequences in a human myeloid leukaemia cell line. Nature 298:679-81.
8. Kamb, A., et al. (1994) A cell cycle regulator potentially involved in genesis of many tumor types. Science 264:436-40.
9. Li, J., et al. (1997) PTEN, a putative protein tyrosine phosphatase gene mutated in human brain, breast, and prostate cancer. Science 275:1943-7.
10. Steck, P. A., et al. (1997) Identification of a candidate tumour suppressor gene, MMAC1, at chromosome 10q23.3 that is mutated in multiple advanced cancers. Nat Genet 15:356-62.
11. Hahn, S. A., et al. (1996) Dpc4, a Candidate Tumor Suppressor Gene At Human Chromosome 18q21.1. Science 271:350-353.
12. Pinkel, D. & Albertson, D. G. (2005) Array comparative genomic hybridization and its applications in cancer. Nat Genet 37 Suppl:S11-7.
13. Camps, J., et al. (2008) Chromosomal breakpoints in primary colon cancer cluster at sites of structural variants in the genome. Cancer Res 68:1284-95.
14. Weir, B. A., et al. (2007) Characterizing the cancer genome in lung adenocarcinoma. Nature 450:893-8.
15. Haverty, P. M., et al. (2008) High-resolution genomic and expression analyses of copy number alterations in breast tumors. Genes Chromosomes Cancer 47:530-42.
16. Mullighan, C. G., et al. (2007) Genome-wide analysis of genetic alterations in acute lymphoblastic leukaemia. Nature 446:758-64.
17. Harada, T., et al. (2008) Genome-wide DNA copy number analysis in pancreatic cancer using high-density single nucleotide polymorphism arrays. Oncogene 27:1951-60.
18. Stark, M. & Hayward, N. (2007) Genome-wide loss of heterozygosity and copy number analysis in melanoma using high-density single-nucleotide polymorphism arrays. Cancer Res 67:2632-42.
19. Nagayama, K., et al. (2007) Homozygous deletion scanning of the lung cancer genome at a 100-kb resolution. Genes Chromosomes Cancer 46:1000-10.
20. Zhao, X., et al. (2005) Homozygous deletions and chromosome amplifications in human lung carcinomas revealed by single nucleotide polymorphism array analysis. Cancer Res 65:5561-70.
21. Jones, S., et al. (2008) Comparative lesion sequencing provides insights into tumor evolution. Proc Natl Acad Sci USA 105:4283-8.
22. Cairns, P., et al. (1995) Frequency of homozygous deletion at p16/CDKN2 in primary human tumours. Nat Genet 11:210-2.
23. Liggett, W. H., Jr. & Sidransky, D. (1998) Role of the p16 tumor suppressor gene in cancer. J Clin Oncol 16:1197-206.
24. Wang, T. L., et al. (2002) Digital karyotyping. Proc Natl Acad Sci USA 99:16156-61.
25. Steemers, F. J., et al. (2006) Whole-genome genotyping with the single-base extension assay. Nat Methods 3:31-3.
26. Peiffer, D. A., et al. (2006) High-resolution genomic profiling of chromosomal aberrations using Infinium whole-genome genotyping. Genome Res 16:1136-48.
27. Conrad, D. F., Andrews, T. D., Carter, N. P., Hurles, M. E. & Pritchard, J. K. (2006) A high-resolution survey of deletion polymorphism in the human genome. Nat Genet 38:75-81.
28. Sebat, J., et al. (2004) Large-scale copy number polymorphism in the human genome. Science 305:525-8.
29. Volik, S., et al. (2003) End-sequence profiling: sequence-based analysis of aberrant genomes. Proc Natl Acad Sci USA 100:7696-701.
30. Bignell, G. R., et al. (2007) Architectures of somatic genomic rearrangement in human cancer amplicons at sequence-level resolution. Genome Res 17:1296-303.
31. Sjoblom, T., et al. (2006) The consensus coding sequences of human breast and colorectal cancers. Science 314:268-74.
32. Wang, Z., et al. (2004) Three classes of genes mutated in colorectal cancers with chromosomal instability. Cancer Res 64:2998-3001.
33. Yu, J. S., et al. (2008) PCDH8, the human homolog of PAPC, is a candidate tumor suppressor of breast cancer. Oncogene.
34. Ekins, S., Nikolsky, Y., Bugrim, A., Kirillov, E. & Nikolskaya, T. (2007) Pathway mapping tools for analysis of high content data. Methods Mol Biol 356:319-50.
35. Subramanian, A., et al. (2005) Gene set enrichment analysis: a knowledge-based approach for interpreting genome-wide expression profiles. Proc Natl Acad Sci USA 102:15545-50.
36. Collins, F. S. & Barker, A. D. (2007) Mapping the cancer genome. Pinpointing the genes involved in cancer will help chart a new course across the complex landscape of human malignancies. Sci Am 296:50-7.
37. Hoglund, M., et al. (2002) Dissecting karyotypic patterns in colorectal tumors: two distinct but overlapping pathways in the adenoma-carcinoma transition. Cancer Res 62:5939-46.
38. Paez, J. G., et al. (2004) Genome coverage and sequence fidelity of phi29 polymerase-based multiple strand displacement whole genome amplification. Nucleic Acids Res 32:e71.
39. Arriola, E., et al. (2007) Evaluation of Phi29-based whole-genome amplification for microarray-based comparative genomic hybridisation. Lab Invest 87:75-83.
40. Popescu, N. C. (2004) Fragile sites and cancer genes on the short arm of chromosome 8. Lancet Oncol 5:77; discussion 77.
41. Tanner, M., et al. (2006) Topoisomerase IIalpha gene amplification predicts favorable treatment response to tailored and dose-escalated anthracycline-based adjuvant chemotherapy in HER-2/neu-amplified breast cancer: Scandinavian Breast Group Trial 9401. J Clin Oncol 24:2428-36.
42. Coon, J. S., et al. (2002) Amplification and overexpression of topoisomerase IIalpha predict response to anthracycline-based therapy in locally advanced breast cancer. Clin Cancer Res 8:1061-7.
43. Varshaysky, A. (2007) Targeting the absence: homozygous DNA deletions as immutable signposts for cancer therapy. Proc Natl Acad Sci USA 104:14935-40.
44. Leary, R. J., Cummins, J., Wang, T. L. & Velculescu, V. E. (2007) Digital karyotyping. Nat Protoc 2:1973-86.

Example 5

Materials and Methods

DNA samples from tumor derived xenografts and cell lines were obtained and purified. DK libraries were generated and analyzed as previously described (24, 44). The Illumina SNP arrays were used to analyze tumor samples. Bioinformatic analyses were used to determine focal amplifications and HDs. Statistical methods were employed to determine the likelihood that genetic alterations occurred at a frequency higher than the passenger rate, and to identify gene groups enriched for copy number and sequence alterations.

Clinical Samples and Cell Lines

DNA samples were obtained from xenografts and cell lines of ductal breast and colorectal carcinoma. Normal DNA samples were obtained from matched normal tissue or peripheral blood. Twenty two of the DNA samples include those used in the Discovery Screen of Sjöblom et al. and Wood et al. (1, 2). All tumor samples analyzed for copy number analyses are listed in SI Table 9. For the Illumina analyses, the colorectal cancer samples used were cell lines (10) or xenografts (26), each developed from a liver metastasis of a different patient. The breast cancer samples used were cell lines (22) and xenografts (23), each developed from a different patient. In addition, 11 colorectal cancer metastases (immunopurified using the BerEP4 antibody as previously described (3)) and 7 cell lines were analyzed by Digital Karyotyping analyses. Available clinical information for samples that were analyzed by copy number and sequence analyses is available in Table S2 of reference (2). All samples were obtained in accordance with the Health Insurance Portability and Accountability Act (HIPAA).

Digital Karyotyping

Digital Karyotyping libraries were constructed as previously described (4, 5). In brief, 17 bp tags of genomic DNA were generated using the NlaIII mapping and SacI fragmenting restriction enzymes. For each library, the experimental tags obtained were concatenated, cloned and sequenced. SAGE2002 software was used to extract the experimental tags from the sequencing data. The sequences of the experimental tags were compared to the predicted virtual tags extracted from the human genome reference sequence hg16 (NCBI Build 34, July 2003) and were visualized using the SageGenie DKView to identify potential alterations (http://cgap.nci.nih.gov/SAGE/DKViewHome). The coordinates of all identified alterations were translated to the human genome reference sequence hg17 (NCBI Build 35, May 2004) to allow comparison to Illumina data.

Homozygous deletions were identified using a sliding window size of 175 virtual tags (~700 kb in size). Windows with a tag density ratio (observed tags in window/expected tags in window) <0.01 were considered to represent putative homozygous deletions and were further examined. Regions of homozygous deletions were defined as containing no experimental tags and the boundaries were determined as the outermost virtual tags with no matching experimental tags.

Amplifications were identified using sliding windows of variable sizes, as the most accurate window size for detection and quantification of amplifications is the exact size of the altered region. Windows with tag density ratios ≥6 were considered to represent amplified regions. Boundaries of the amplified region are determined by the outermost tag contained in a window with a tag density ratio >3 or by the virtual tag position after which there is sharp decline in the observed experimental tags.

High Density SNP Arrays

The Illumina Infinium II Whole Genome Genotyping Assay employing the BeadChip platform was used to analyze tumor samples at 317,503 (317 k), 555,351 (550 k V1), or 561,466 (550 k V3) SNP loci from the Human HapMap collection. All SNP positions were based on hg17 (NCBI Build 35, May 2004) version of the human genome reference sequence. The genotyping assay is a two step procedure that is based on hybridization to a 50 nucleotide oligo, followed by a two-color fluorescent single base extension. The image files of fluorescence intensities were processed using Illumina BeadStation software to provide intensity values for each SNP position. For each SNP, the normalized experimental intensity value (R) was compared to the intensity values for that SNP from a training set of normal samples and represented as a ratio (called the "Log R Ratio") of log 2(Rexperimental/Rtraining set).

Bioinformatic Analysis of High Density SNP Array Data

Digital Karyotyping was used to inform and optimize the criteria for detection of focal homozygous deletions and high-copy amplifications using the Illumina arrays. Three colorectal cancer samples (Co44, Co82 and Co84) were assessed by Digital Karyotyping tag libraries as well as the Illumina arrays (SI Table 1). From these analyses criteria were developed to permit sensitive and specific detection of the Digital Karyotyping alterations using the Illumina platform as described below. These criteria were subsequently used to analyze an additional 46 breast and 33 colorectal cancers.

Detection of Homozygous Deletions

Homozygous deletions (HDs) were defined as two or more consecutive SNPs with a Log R Ratio value of ≤−2. The first and last SNPs of the identified HD region were considered to be the boundaries of the alteration for subsequent analyses. The deletion breakpoint would be expected to be located between the boundary deleted SNPs and adjacent non-deleted SNPs; use of the inner deleted SNP boundaries provides the most conservative approach as use of the outer boundaries may include non-deleted regions. To eliminate chip artifacts and potential copy number polymorphisms, we removed all HDs that were included in copy number polymorphism databases (6, 7). As these analyses showed that copy number polymorphisms had conserved boundaries, we also removed all observed HDs with identical boundaries that occurred in multiple samples. Adjacent homozygous deletions separated by one or two SNPs were considered to be part of the same alteration. Adjacent HDs were evaluated separately for the purposes of determining affected genes, but were counted as single entries in Table 2 and SI Table 5.

To identify genes affected by HDs, we compared the location of coding exons in the RefSeq and CCDS databases with the genomic coordinates of the observed HDs. Any gene with a portion of its coding region contained within a homozygous deletion was considered to be affected by the deletion.

Detection of Amplifications

High copy amplifications (i.e. >12 chromosomal copies as determined by Digital Karyotyping) were defined as regions having at least one SNP with a LogR ratio ≥1.4, at least one in ten SNPs with a LogR ratio ≥1, and an average LogR ratio of the entire region of ≥0.9. The boundaries of amplified regions were delimited by the outermost SNPs with LogR ratios ≥1. Similar to analyses of homozygous deletions, we removed all amplifications that had identical boundaries and occurred in multiple samples.

As focal amplifications are more likely to be useful in identifying specific target genes, a second set of criteria were used to remove large chromosomal regions or entire chromosomes that showed copy number gains. These large alterations, called "complex amplifications", were thus distinguished from small focal alterations, called "simple amplifications". Based on observations from Digital Karyotyping, several steps were used to identify and remove complex amplifications. First, amplifications >3 Mb in size and groups of nearby amplifications (within 1 Mb) that were also >3 Mb in size were considered complex. Amplifications or groups of amplifications that occurred at a frequency of ≥4 amplifications in a 10 Mb region, or ≥5 amplifications per chromosome were deemed to be complex. The amplifications remaining after these filtering steps were considered to be simple amplifications and were further examined. The complex regions were not included in subsequent statistical analyses but those containing candidate cancer genes are indicated in Table 1. To identify protein coding genes affected by amplifications, we compared the location of the start and stop positions of each gene within the RefSeq and CCDS databases with the genomic coordinates of the observed amplifications. As amplifications of a sub-genic region (i.e. containing only a fraction of a gene) are less likely to have a functional consequence, we focused our analyses on genes whose entire coding regions were included in the observed amplifications.

A number of genes co-amplified or co-deleted with known oncogenes (CCND1, ERBB2, CCNE1, EGFR, MYC) or tumor suppressors (CDKN2A, PTEN, MAP2K4, TP53) were considered "known passengers" and eliminated from further statistical analysis. However, for completeness, these known passengers were listed along with their respective copy number alterations in SI Tables 4 and 5. Copy number alterations of known passengers were also listed in SI Tables 6 and 7, but these alterations were not used to calculate the passenger probabilities listed in the same tables. Alterations of known passengers were also excluded from statistical analysis of pathways (SI Table 8).

Statistical Analysis of Deletions and Amplifications

For each of the genes involved in amplifications or deletions, we quantify the strength of the evidence that they may be drivers of carcinogenesis by reporting a driver probability, separately for amplifications and deletions. In each case, the passenger probability is an a posteriori probability that integrates information from the somatic mutation analysis of Wood et al. (2) with the data presented in this article. The passenger probabilities reported in Wood et al. (2) serve as a priori probabilities. These are available for three different scenarios of passenger mutation rates and results are presented separately for each. If a gene was not found to be mutated in Wood et al. (2) the prior passenger probability is set to the estimated proportion of passengers in the RefSeq set. Then, a likelihood ratio for "driver" versus "passenger" was evaluated using as evidence the number of samples in which a gene was found to be amplified (or deleted). Analysis is carried out separately by type of array, and then combined by multiplication of the relevant likelihood terms. The passenger term is the probability that the gene in question is amplified (deleted). For each sample, we begin by computing the probability that the observed amplifications (deletions) will include the gene in question by chance. Inclusion of all available SNPs is required for amplification, while any overlap of SNPs is sufficient for deletions. Specifically, if in a specific sample N SNPs are typed, and K amplifications are found, whose sizes, in terms of SNPs involved, are $A_1 \ldots A_K$, a gene with G SNPs will be included at random with probability $$(A_1-G+1)/N + \ldots + (A_K-G+1)/N$$

for amplifications and $$(A_1+G-1)/N + \ldots + (A_K+G-1)/N$$

for deletions.

We then compute the probability of the observed number of amplifications (deletions) assuming that the samples are independent but not identically distributed Bernoulli random variables, using the Thomas and Taub algorithm (8), as implemented in R by M. Newton. Our approach to evaluating the passenger probabilities provides an upper bound, as it assumes that all the deletions and amplifications observed only include passengers. The driver term of the likelihood ratio was approximated as for the passenger term, after multiplying the sample-specific passenger rates above by a gene-specific factor reflecting the increase (alternative hypothesis) of interest. This increase is estimated by the ratio between the empirical deletion rate of the gene and the expected deletion rate for that gene.

For each of the gene sets considered we quantify the strength of the evidence that they may include a higher-than-average proportion of driver genes. For each set, in a list of all the RefSeq genes sorted by a score combining information on mutations, amplifications and deletions, we compared the ranking of the genes contained in the set with the ranking of those outside, using the rank-sum test, as implemented by the Limma package in Bioconductor (9). Scores were obtained by adding three log likelihood ratios for mutations, amplifications and deletions. This combination approach makes an approximating assumption of independence of amplifications and deletions. In general, amplified genes cannot be deleted, so independence is technically violated. However, because of the relatively small number of dramatic amplification and deletions, this assumption is tenable for the purposes of gene set analysis. Inspection of the log likelihoods suggest that they are roughly linear in the number of events, supporting the validity of this approximation as a scoring system. The statistical significance of deviation from the null hypothesis of a random distribution was calculated using Limma and then corrected for multiplicity by the q-value method (10) as implemented in version 1.1 of the package "q-value".

Example 5

Methods References

1. Sjoblom, T., Jones, S., Wood, L. D., Parsons, D. W., Lin, J., Barber, T. D., Mandelker, D., Leary, R. J., Ptak, J., Silliman, N., Szabo, S., Buckhaults, P., Farrell, C., Meeh, P., Markowitz, S. D., Willis, J., Dawson, D., Willson, J. K., Gazdar, A. F., Hartigan, J., Wu, L., Liu, C., Parmigiani, G., Park, B. H., Bachman, K. E., Papadopoulos, N., Vogelstein, B., Kinzler, K. W. & Velculescu, V. E. (2006) The consensus coding sequences of human breast and colorectal cancers. Science 314:268-74.

2. Wood, L. D., Parsons, D. W., Jones, S., Lin, J., Sjoblom, T., Leary, R. J., Shen, D., Boca, S. M., Barber, T., Ptak, J., Silliman, N., Szabo, S., Dezso, Z., Ustyanksky, V., Nikolskaya, T., Nikolsky, Y., Karchin, R., Wilson, P. A., Kaminker, J. S., Zhang, Z., Croshaw, R., Willis, J., Dawson, D., Shipitsin, M., Willson, J. K., Sukumar, S., Polyak, K., Park, B. H., Pethiyagoda, C. L., Pant, P. V., Ballinger, D. G., Sparks, A. B., Hartigan, J., Smith, D. R., Suh, E., Papadopoulos, N., Buckhaults, P., Markowitz, S. D., Parmigiani, G., Kinzler, K. W., Velculescu, V. E. & Vogelstein, B. (2007) The genomic landscapes of human breast and colorectal cancers. Science 318:1108-13.

3. Saha, S., Bardelli, A., Buckhaults, P., Velculescu, V. E., Rago, C., St Croix, B., Romans, K. E., Choti, M. A., Lengauer, C., Kinzler, K. W. & Vogelstein, B. (2001) A phosphatase associated with metastasis of colorectal cancer. Science 294:1343-6.

4. Wang, T. L., Maierhofer, C., Speicher, M. R., Lengauer, C., Vogelstein, B., Kinzler, K. W. & Velculescu, V. E. (2002) Digital karyotyping. Proc Natl Acad Sci USA 99:16156-61.
5. Leary, R. J., Cummins, J., Wang, T. L. & Velculescu, V. E. (2007) Digital karyotyping. Nat Protoc 2:1973-86.
6. Conrad, D. F., Andrews, T. D., Carter, N. P., Hurles, M. E. & Pritchard, J. K. (2006) A high-resolution survey of deletion polymorphism in the human genome. Nat Genet 38:75-81.
7. Sebat, J., Lakshmi, B., Troge, J., Alexander, J., Young, J., Lundin, P., Maner, S., Massa, H., Walker, M., Chi, M., Navin, N., Lucito, R., Healy, J., Hicks, J., Ye, K., Reiner, A., Gilliam, T. C., Trask, B., Patterson, N., Zetterberg, A. & Wigler, M. (2004) Large-scale copy number polymorphism in the human genome. Science 305:525-8.
8. Thomas, M. A. & Taub, A. E. (1982) Calculating binomial probabilities when the trial probabilities are unequal. Journal of Statistical Computation and Simulation 14:125-131.
9. Smyth, G. K. (2005) in Bioinformatics and Computational Biology Solutions using R and Bioconductor, eds. Gentleman, V., Carey, S., Dudoit, R. & Irizarry, W. H. (Springer, New York), pp. 397-420.
10. Storey, J. D. & Tibshirani, R. (2003) Statistical significance for genomewide studies. Proc Natl Acad Sci USA 100:9440-5.

The invention claimed is:

1. A method of testing a test sample of a human, comprising testing and detecting in a test sample of a colon tumor or suspected colon tumor of the human, the presence of genomic amplification of neugrin.

2. The method of claim 1 wherein genomic amplification is detected by generating fragments of genomic DNA from the test sample, ligating the fragments into a concatenate, and sequencing the concatenate.

3. The method of claim 1 wherein genomic amplification is detected by hybridizing genomic DNA from the test sample to an array of oligonucleotides.

4. The method of claim 1 wherein the genomic amplification is at least 6-fold increased relative to a normal sample of the human.

* * * * *